(12) United States Patent
Lee et al.

(10) Patent No.: US 11,489,122 B1
(45) Date of Patent: Nov. 1, 2022

(54) COMPOUND AND ORGANIC LIGHT EMITTING DEVICE COMPRISING SAME

(71) Applicant: LG CHEM, LTD., Seoul (KR)

(72) Inventors: Woochul Lee, Daejeon (KR); Ki Dong Koo, Daejeon (KR); Dongheon Kim, Daejeon (KR); Ki Kon Lee, Daejeon (KR); Sujeong Geum, Daejeon (KR); Jung Min Yoon, Daejeon (KR); Kongkyeom Kim, Daejeon (KR); Hyungjin Lee, Daejeon (KR); Nansra Heo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 391 days.

(21) Appl. No.: 16/630,331

(22) PCT Filed: Jul. 9, 2018

(86) PCT No.: PCT/KR2018/007740
§ 371 (c)(1),
(2) Date: Jan. 10, 2020

(87) PCT Pub. No.: WO2019/017633
PCT Pub. Date: Jan. 24, 2019

(30) Foreign Application Priority Data

Jul. 18, 2017 (KR) .......................... 10-2017-0090829

(51) Int. Cl.
*H01L 51/00* (2006.01)
*C09K 11/06* (2006.01)
(Continued)

(52) U.S. Cl.
CPC ........ *H01L 51/0061* (2013.01); *C07C 211/61* (2013.01); *C07D 487/04* (2013.01); *C07D 493/04* (2013.01); *C07D 495/04* (2013.01);

*C09K 11/06* (2013.01); *H01L 51/006* (2013.01); *H01L 51/0052* (2013.01); *C07C 2603/54* (2017.05); *C09K 2211/1007* (2013.01); *C09K 2211/1011* (2013.01);
(Continued)

(58) Field of Classification Search
None
See application file for complete search history.

(56) References Cited

U.S. PATENT DOCUMENTS

| 9,012,040 B2 | 4/2015 | Kim et al. |
| 2004/0251816 A1 | 12/2004 | Leo et al. |
| 2010/0032658 A1 | 2/2010 | Lee et al. |
| 2015/0218184 A1 | 8/2015 | Kitamura et al. |

(Continued)

FOREIGN PATENT DOCUMENTS

| CN | 104513662 | 4/2015 |
| JP | 2015078169 | 4/2015 |

(Continued)

*Primary Examiner* — Jay Yang
(74) *Attorney, Agent, or Firm* — Dentons US LLP

(57) ABSTRACT

Provided is a compound of Formula 1:

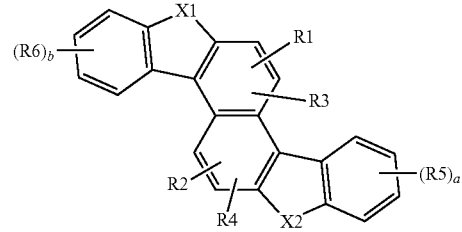

and an organic light emitting device including the same.

17 Claims, 1 Drawing Sheet

(51) Int. Cl.
*C07D 487/04* (2006.01)
*C07D 495/04* (2006.01)
*C07C 211/61* (2006.01)
*C07D 493/04* (2006.01)
*H01L 51/50* (2006.01)

(52) U.S. Cl.
CPC ............ *C09K 2211/1014* (2013.01); *C09K 2211/1018* (2013.01); *H01L 51/0056* (2013.01); *H01L 51/0058* (2013.01); *H01L 51/0072* (2013.01); *H01L 51/0073* (2013.01); *H01L 51/0074* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | |
|---|---|---|
| 2016/0276596 A1 | 9/2016 | Jang et al. |
| 2017/0155048 A1 | 6/2017 | Kim et al. |

FOREIGN PATENT DOCUMENTS

| | | |
|---|---|---|
| KR | 20100007780 | 1/2010 |
| KR | 20100106014 | 10/2010 |
| KR | 10-1115255 | 2/2012 |
| KR | 10-20130073700 | 7/2013 |
| KR | 10-20140023407 | 2/2014 |
| KR | 20140078096 | 6/2014 |
| KR | 20150070475 | 6/2015 |
| KR | 20150115649 | 10/2015 |
| KR | 20160090058 | 7/2016 |
| KR | 20170061768 | 6/2017 |
| WO | 2010110553 | 9/2010 |
| WO | 2015093814 | 6/2015 |

[Figure 1]
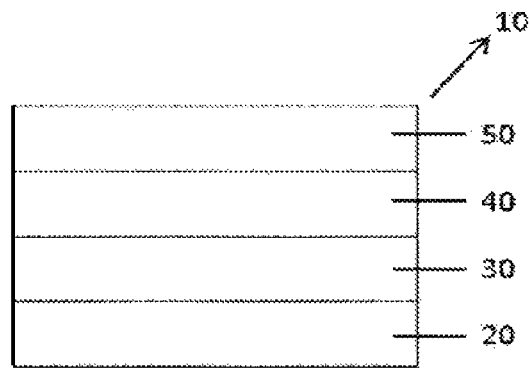
[Figure 2]
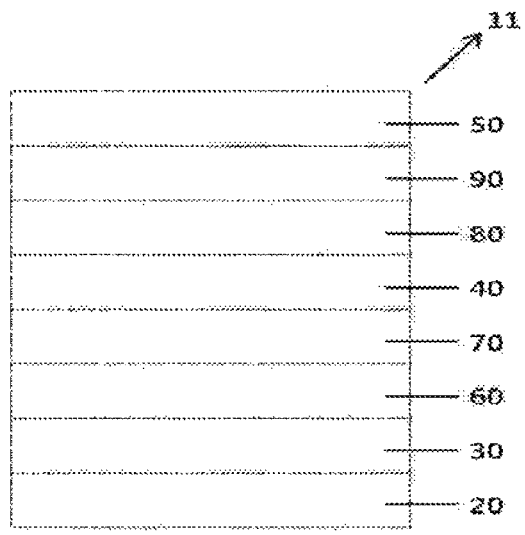

COMPOUND AND ORGANIC LIGHT EMITTING DEVICE COMPRISING SAME

CROSS-REFERENCE TO RELATED APPLICATIONS

This application is the National Stage Application of International Application No. PCT/KR2018/007740 filed on Jul. 9, 2018, which claims priority to and the benefit of Korean Patent Application No. 10-2017-0090829 filed in the Korean Intellectual Property Office on Jul. 18, 2017, the entire contents of which are incorporated herein by reference.

TECHNICAL FIELD

The present specification relates to a novel compound and an organic light emitting device including the same.

BACKGROUND

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer has in many cases a multi-layered structure composed of different materials in order to improve the efficiency and stability of the organic light emitting device, and for example, can be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

DETAILED DESCRIPTION

Technical Problem

The present specification provides a novel compound and an organic light emitting device including the same.

Technical Solution

An exemplary embodiment of the present specification provides a compound of the following Formula 1.

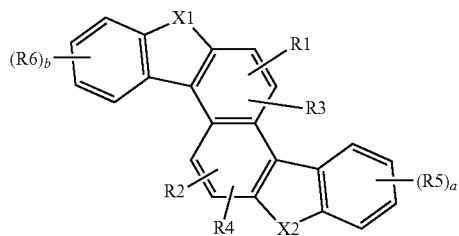

[Formula 1]

In Formula 1:

X1 and X2 are the same as or different from each other, and are each independently —O—, —S—, —C(R7R8)-, or —N(R9)-;

at least two of R1 to R4 are the same as or different from each other, and are each independently a group of the following Formula A;

groups which are not the following Formula A among R1 to R4 are the same as or different from each other, and are each independently hydrogen, deuterium, a substituted or unsubstituted alkyl group, a substituted or unsubstituted aryl group, or a substituted or unsubstituted heteroaryl group;

R5 and R6 are the same as or different from each other, and are each independently hydrogen, a substituted or unsubstituted alkyl group, a substituted or unsubstituted aryl group, or a substituted or unsubstituted heteroaryl group, or adjacent groups are bonded to each other to form a substituted or unsubstituted ring;

R7 to R9 are the same as or different from each other, and are each independently a substituted or unsubstituted alkyl group, a substituted or unsubstituted aryl group, or a substituted or unsubstituted heteroaryl group;

a and b are each an integer from 1 to 4;

when a and b are each 2 or more, two or more structures in the parenthesis are the same as or different from each other:

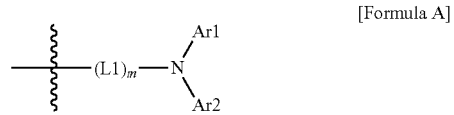

[Formula A]

wherein in Formula A:

L1 is a direct bond, a substituted or unsubstituted arylene group, or a substituted or unsubstituted heteroarylene group;

Ar1 and Ar2 are the same as or different from each other, and are each independently a substituted or unsubstituted aryl group or a substituted or unsubstituted heteroaryl group, or can be bonded to each other to form a substituted or unsubstituted ring;

m is an integer from 1 to 5;

when m is 2 or more, two or more L1's are the same as or different from each other, and

is a moiety boned to Formula 1.

Further, an exemplary embodiment of the present specification provides an organic light emitting device including: a first electrode; a second electrode provided to face the first electrode; and an organic material layer having one or more layers provided between the first electrode and the second electrode, in which one or more layers of the organic material layer include the compound of Formula 1.

Advantageous Effects

A compound according to an exemplary embodiment of the present specification can be used as a material for an organic material layer of an organic light emitting device, and it is possible to improve efficiency, achieve low driving voltage, and/or improve service life characteristics in the organic light emitting device by using the compound.

BRIEF DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

EXPLANATION OF REFERENCE NUMERALS AND SYMBOLS 10, 11: Organic light emitting device
20: Substrate
30: First electrode
40: Light emitting layer
50: Second electrode
60: Hole injection layer
70: Hole transport layer
80: Electron transport layer
90: Electron injection layer

BEST MODE

Hereinafter, the present specification will be described in more detail.

The present specification provides the compound of Formula 1.

According to an exemplary embodiment of the present specification, since the compound of Formula 1 forms a hexacyclic or more structure as a structure in which a tricyclic ring compound is fused, and uses, as a basic skeleton structure, a derivative into which a hetero element is introduced, as compared to an organic light emitting device using a chrysene (tetracyclic ring) derivative composed of only aryl in the related art, electrons easily move, and as the compound of Formula 1 includes the amine group Formula A as a substituent at specific positions such as R1 and R2 of Formula 1, holes easily move to an unshared electron pair of N, so that a movement between holes and electrons is balanced well, and as a result, an organic light emitting device including the compound of Formula 1 can have a low voltage, improved service life characteristics, and improved efficiency.

When one part "includes" one constituent element in the present specification, unless otherwise specifically described, this does not mean that another constituent element is excluded, but means that another constituent element can be further included.

When one member is disposed "on" another member in the present specification, this includes not only a case where the one member is brought into contact with another member, but also a case where still another member is present between the two members.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more are substituted, the two or more substituents can be the same as or different from each other.

In the present specification, the term "substituted or unsubstituted" means being substituted with one or two or more substituents selected from the group consisting of deuterium, a halogen group, a nitrile group, a nitro group, an imide group, an amide group, a carbonyl group, an ester group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, and a substituted or unsubstituted heterocyclic group or being substituted with a substituent to which two or more substituents are linked among the substituents exemplified above, or having no substituent. For example, "the substituent to which two or more substituents are linked" can be a biphenyl group. That is, the biphenyl group can also be an aryl group, and can be interpreted as a substituent to which two phenyl groups are linked.

In the present specification,

means a moiety bonded to another substituent or a bonding portion.

In the present specification, a halogen group can be fluorine, chlorine, bromine or iodine.

In the present specification, the number of carbon atoms of an imide group is not particularly limited, but is preferably 1 to 30. Specifically, the imide group can be a compound having the following structures, but is not limited thereto:

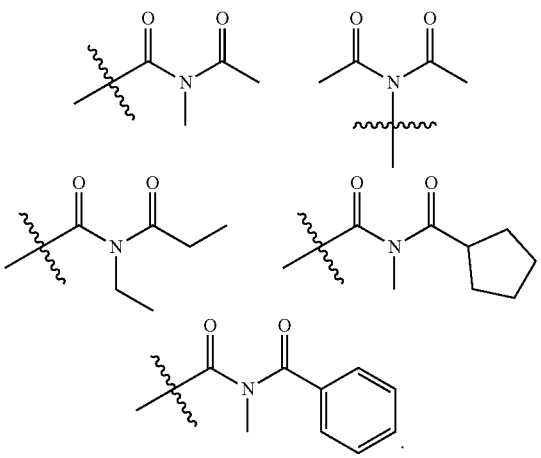

In the present specification, for an amide group, the nitrogen of the amide group can be substituted with hydrogen, a straight-chained, branched, or cyclic alkyl group having 1 to 30 carbon atoms, or an aryl group having 6 to 30 carbon atoms. Specifically, the amide group can be a compound having the following structural formulae, but is not limited thereto:

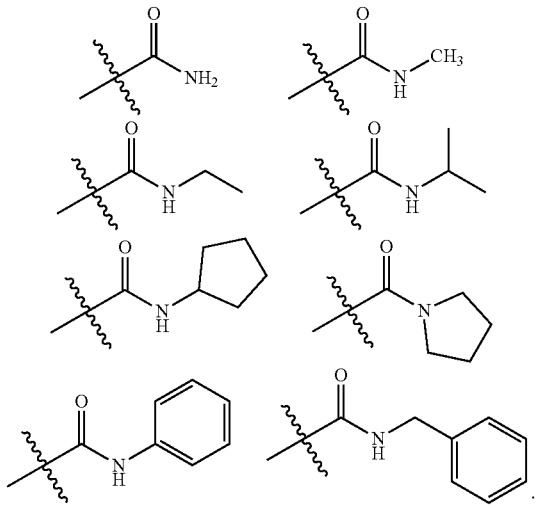

In the present specification, the number of carbon atoms of a carbonyl group is not particularly limited, but is preferably 1 to 30. Specifically, the carbonyl group can be a compound having the following structures, but is not limited thereto:

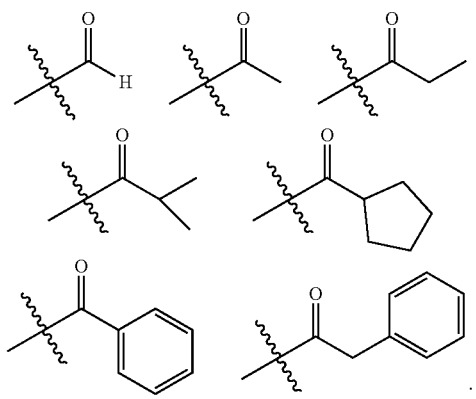

In the present specification, for an ester group, the oxygen of the ester group can be substituted with a straight-chained, branched, or cyclic alkyl group having 1 to 25 carbon atoms, or an aryl group having 6 to 30 carbon atoms. Specifically, the ester group can be a compound having the following structural formulae, but is not limited thereto:

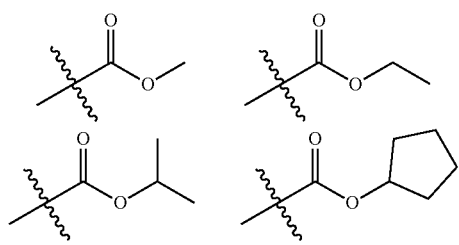

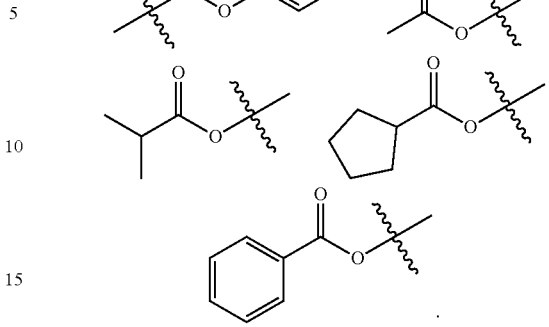

In the present specification, the alkyl group can be straight-chained or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclo-hexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group can be straight-chained, branched, or cyclic. The number of carbon atoms of the alkoxy group is not particularly limited, but is preferably 1 to 30. Specific examples thereof include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group can be selected from the group consisting of —NH$_2$; an alkylamine group; an N-alkylarylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, an N-phenylbiphenylamine group, an N-phenylnaphthylamine group, an N-biphenylnaphthylamine group, an N-naphthylfluorenylamine group, an N-phenyl-phenanthrenylamine group, an N-biphenylphenanthrenylamine group, an N-phenylfluorenylamine group, an N-phenyl terphenylamine group, an N-phenanthrenylfluorenylamine group, an N-biphenylfluorenylamine group, and the like, but are not limited thereto.

In the present specification, an N-alkylarylamine group means an amine group in which an alkyl group and an aryl group are substituted with N of the amine group.

In the present specification, an N-arylheteroaryl-amine group means an amine group in which an aryl group and a heteroaryl group are substituted with N of the amine group.

In the present specification, an N-alkylheteroarylamine group means an amine group in which an alkyl group and a heteroaryl group are substituted with N of the amine group.

In the present specification, examples of an alkylamine group include a substituted or unsubstituted monoalkylamine group or a substituted or unsubstituted dialkylamine group. The alkyl group in the alkylamine group can be a straight-chained or branched alkyl group. The alkylamine group including two or more alkyl groups can include a straight-chained alkyl group, a branched alkyl group, or both a straight-chained alkyl group and a branched alkyl group. For example, the alkyl group in the alkylamine group can be selected from the above-described examples of the alkyl group.

In the present specification, the alkyl group in the alkylamine group, the N-arylalkylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples are not limited thereto.

In the present specification, the alkenyl group can be straight-chained or branched, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)-vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group can be —$BR_{100}R_{101}$, and $R_{100}$ and $R_{101}$ are the same as or different from each other, and can be each independently selected from the group consisting of hydrogen, deuterium, halogen, a nitrile group, a substituted or unsubstituted monocyclic or polycyclic cycloalkyl group having 3 to 30 carbon atoms, a substituted or unsubstituted straight-chained or branched alkyl group having 1 to 30 carbon atoms, a substituted or unsubstituted monocyclic or polycyclic aryl group having 6 to 30 carbon atoms, and a substituted or unsubstituted monocyclic or polycyclic heteroaryl group having 2 to 30 carbon atoms.

In the present specification, specific examples of a phosphine oxide group include a diphenylphosphine oxide group, a dinaphthylphosphine oxide group, and the like, but are not limited thereto.

In the present specification, an aryl group is not particularly limited, but has preferably 6 to 30 carbon atoms, and the aryl group can be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a phenalenyl group, a perylenyl group, a chrysenyl group, a fluorenyl group, and the like, but are not limited thereto.

In the present specification, the fluorenyl group can be substituted, and adjacent substituents can be bonded to each other to form a ring.

When the fluorenyl group is substituted, the substituent can be

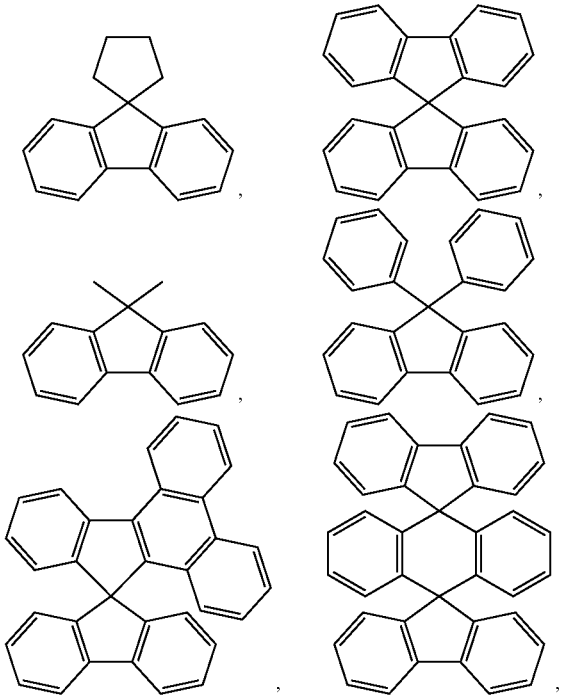

and the like. However, the fluorenyl group is not limited thereto.

In the present specification, the "adjacent" group can mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring can be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, examples of an arylamine group include a substituted or unsubstituted monoarylamine group or a substituted or unsubstituted diarylamine group. The aryl group in the arylamine group can be a monocyclic aryl group or a polycyclic aryl group. The arylamine group including two or more aryl groups can include a monocyclic aryl group, a polycyclic aryl group, or both a monocyclic aryl group and a polycyclic aryl group. For example, the aryl group in the arylamine group can be selected from the above-described examples of the aryl group.

In the present specification, a heteroaryl group includes one or more atoms other than carbon, that is, one or more heteroatoms, and specifically, the heteroatom can include one or more atoms selected from the group consisting of O, N, Se, S, and the like. The number of carbon atoms thereof is not particularly limited, but is preferably 2 to 30, and the heteroaryl group can be monocyclic or polycyclic. Examples of a heteroaryl group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolyl group, a quinoxalinyl group, a phthalazinyl group, a pyridopyrimidyl group, a pyridopyrazinyl group, a pyrazinopyrazinyl group, an isoquinolyl group, an indolyl group, a carbazolyl group, a benzoxazolyl group, a benzimidazolyl group, a benzo-thiazolyl group, a benzocarbazolyl group, a benzothiophene group, a dibenzothiophene group, a benzofuranyl group, a phenanthrolinyl group (phenanthroline), an isoxazolyl group, a thiadiazolyl group, a phenothiazinyl group, a dibenzo-furanyl group, and the like, but are not limited thereto.

In the present specification, examples of a heteroarylamine group include a substituted or unsubstituted monoheteroarylamine group or a substituted or unsubstituted diheteroarylamine group. The heteroarylamine group including two or more heteroaryl groups can include a monocyclic heteroaryl group, a polycyclic heteroaryl group, or both a monocyclic heteroaryl group and a polycyclic heteroaryl group. For example, the heteroaryl group in the heteroarylamine group can be selected from the above-described examples of the heteroaryl group.

In the present specification, examples of the heteroaryl group in the N-arylheteroarylamine group and the N-alkylheteroarylamine group are the same as the above-described examples of the heteroaryl group.

In the present specification, an arylene group means a group having two bonding positions in an aryl group, that is, a divalent group. The above-described description on the aryl group can be applied to the arylene group, except for a divalent arylene group.

In the present specification, a heteroarylene group means a group having two bonding positions in a heteroaryl group, that is, a divalent group. The above-described description on the heteroaryl group can be applied to the heteroarylene group, except for a divalent heteroarylene group.

In the present specification, in a substituted or unsubstituted ring formed by bonding adjacent groups, the "ring" means a substituted or unsubstituted hydrocarbon ring; or a substituted or unsubstituted hetero ring.

In the present specification, a hydrocarbon ring can be an aromatic ring, an aliphatic ring, or a fused ring of the aromatic ring and the aliphatic ring, and can be selected from the examples of the cycloalkyl group or the aryl group, except for the hydrocarbon ring which is not monovalent.

In the present specification, an aromatic ring can be monocyclic or polycyclic, and can be selected from the examples of the aryl group, except for the aromatic ring which is not monovalent.

In the present specification, a hetero ring includes one or more atoms other than carbon, that is, one or more heteroatoms, and specifically, the heteroatom can include one or more atoms selected from the group consisting of O, N, Se, S, and the like. The hetero ring can be monocyclic or polycyclic, can be an aromatic ring, an aliphatic ring, or a fused ring of the aromatic ring and the aliphatic ring, and can be selected from the examples of the heteroaryl group or the heterocyclic group, except for the hetero ring which is not monovalent.

According to an exemplary embodiment of the present specification, in Formula 1, adjacent R5's are bonded to each other to form a substituted or unsubstituted ring.

According to an exemplary embodiment of the present specification, in Formula 1, adjacent R5's are bonded to each other to form a substituted or unsubstituted aromatic ring.

According to an exemplary embodiment of the present specification, in Formula 1, adjacent R5's are bonded to each other to form a substituted or unsubstituted benzene ring.

According to an exemplary embodiment of the present specification, in Formula 1, adjacent R5's are bonded to each other to form a benzene ring.

According to an exemplary embodiment of the present specification, in Formula 1, adjacent R6's are bonded to each other to form a substituted or unsubstituted ring.

According to an exemplary embodiment of the present specification, in Formula 1, adjacent R6's are bonded to each other to form a substituted or unsubstituted aromatic ring.

According to an exemplary embodiment of the present specification, in Formula 1, adjacent R6's are bonded to each other to form a substituted or unsubstituted benzene ring.

According to an exemplary embodiment of the present specification, in Formula 1, adjacent R6's are bonded to each other to form a benzene ring.

According to an exemplary embodiment of the present specification, Formula 1 is any one of the following Formulae 1-1 to 1-3:

[Formula 1-1]

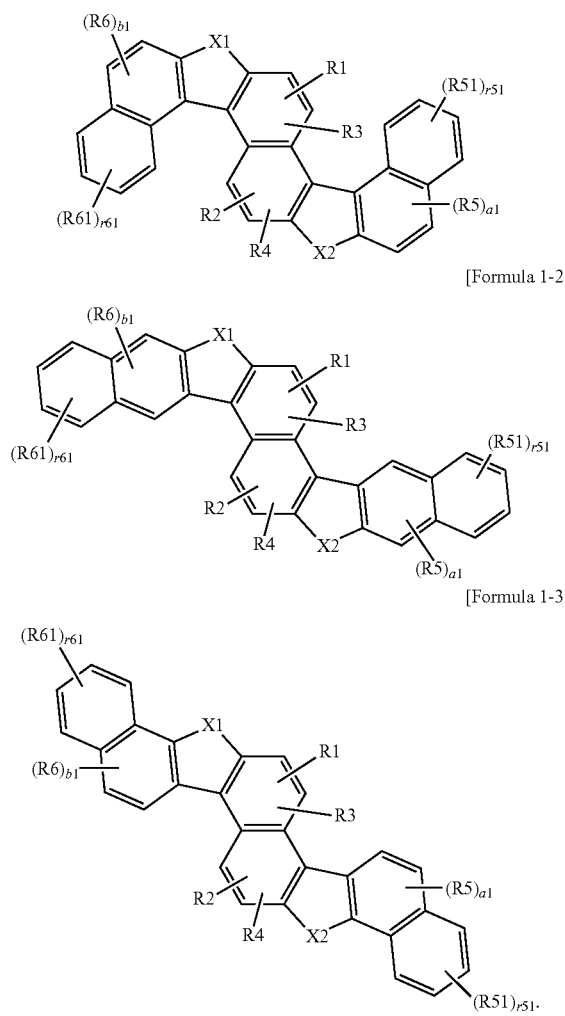

[Formula 1-2]

[Formula 1-3]

In Formulae 1-1 to 1-3:

the definitions of X1, X2, and R1 to R4 are the same as those described above;

R5, R6, R51, and R61 are the same as or different from each other, and are each independently hydrogen, deuterium, a substituted or unsubstituted alkyl group, a substituted or unsubstituted aryl group, or a substituted or unsubstituted heteroaryl group;

a1 and b1 are each 1 or 2;

r51 and r61 are each an integer from 1 to 4;

when a1 and b1 are each 2, the structures in the parenthesis are the same as or different from each other; and when r51 and r61 are each 2 or more, two or more structures in the parenthesis are the same as or different from each other.

According to an exemplary embodiment of the present specification, Formula 1 is any one of the following Formulae 1-4 to 1-7:

[Formula 1-4]

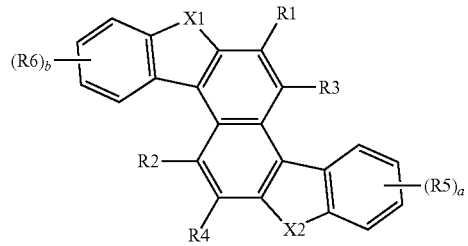

[Formula 1-5]

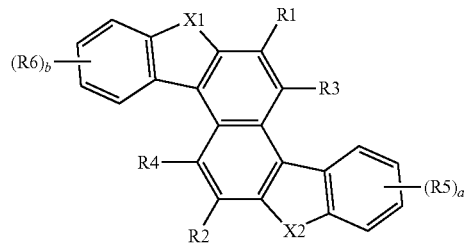

[Formula 1-6]

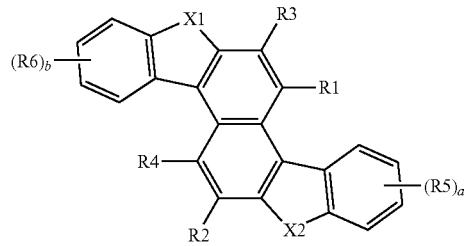

[Formula 1-7]

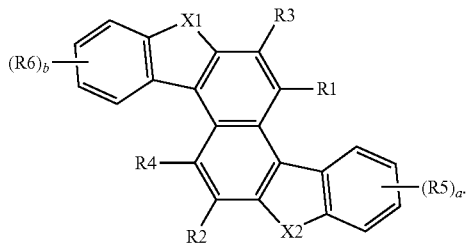

In Formulae 1-4 to 1-7:

the definitions of X1, X2, R5, R6, a, and b are the same as those defined in Formula 1;

R1 and R2 are the same as or different from each other, and are each independently a group of Formula A; and R3 and R4 are the same as or different from each other, and are each independently hydrogen, a substituted or unsubstituted alkyl group, a substituted or unsubstituted aryl group, or a substituted or unsubstituted heteroaryl group.

According to an exemplary embodiment of the present specification, Formula 1 is the following Formula 1-8:

[Formula 1-8]

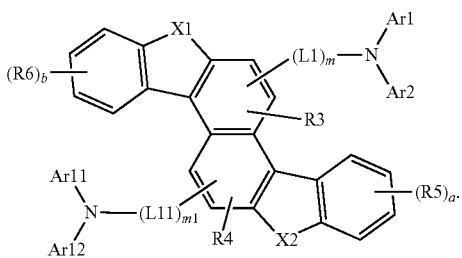

In Formula 1-8, the definitions of X1, X2, R5, R6, a, b, L1, m, Ar1, and Ar2 are the same as those described above;

R3 and R4 are the same as or different from each other, and are each independently hydrogen, deuterium, a substituted or unsubstituted alkyl group, a substituted or unsubstituted aryl group, or a substituted or unsubstituted heteroaryl group;

L11 is a direct bond, a substituted or unsubstituted arylene group, or a substituted or unsubstituted heteroarylene group;

Ar11 and Ar12 are the same as or different from each other, and are each independently a substituted or unsubstituted aryl group or a substituted or unsubstituted heteroaryl group, or can be bonded to each other to form a substituted or unsubstituted ring;

m1 is an integer from 1 to 5; and when m1 is 2 or more, two or more L11's are the same as or different from each other.

According to an exemplary embodiment of the present specification, Formula 1 is any one of the following Formulae 1-9 to 1-12:

[Formula 1-9]

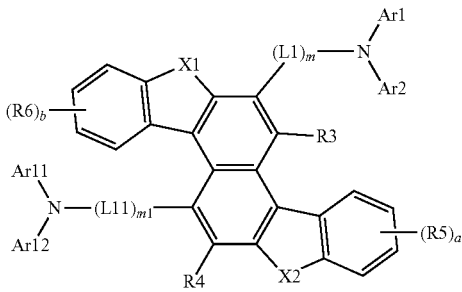

[Formula 1-10]

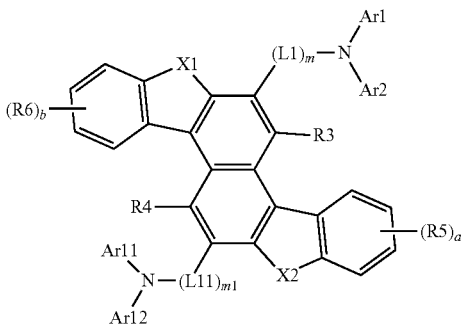

[Formula 1-11]

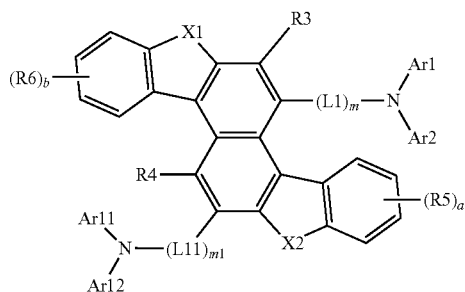

[Formula 1-12]

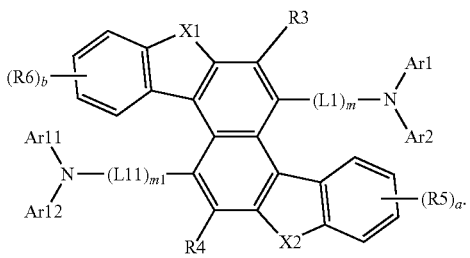

In Formulae 1-9 to 1-12:

the definitions of X1, X2, R5, R6, a, b, L1, m, Ar1, and Ar2 are the same as those described above;

R3 and R4 are the same as or different from each other, and are each independently hydrogen, deuterium, a substituted or unsubstituted alkyl group, a substituted or unsubstituted aryl group, or a substituted or unsubstituted heteroaryl group;

L11 is a direct bond, a substituted or unsubstituted arylene group, or a substituted or unsubstituted heteroarylene group;

Ar11 and Ar12 are the same as or different from each other, and are each independently a substituted or unsubstituted aryl group or a substituted or unsubstituted heteroaryl group, or can be bonded to each other to form a substituted or unsubstituted ring;

m1 is an integer from 1 to 5; and when m1 is 2 or more, two or more L11's are the same as or different from each other.

According to an exemplary embodiment of the present specification, Formula 1 is any one of the following Formulae 1-13 to 1-15:

[Formula 1-13]

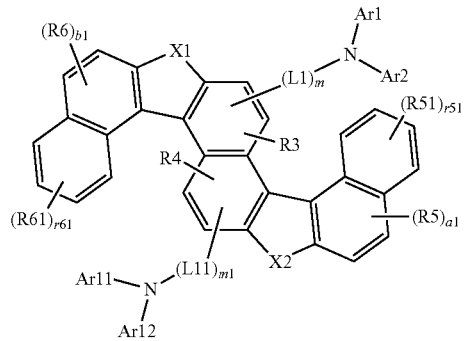

[Formula 1-14]

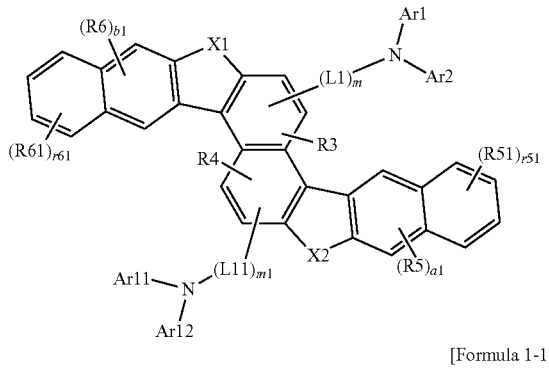

[Formula 1-15]

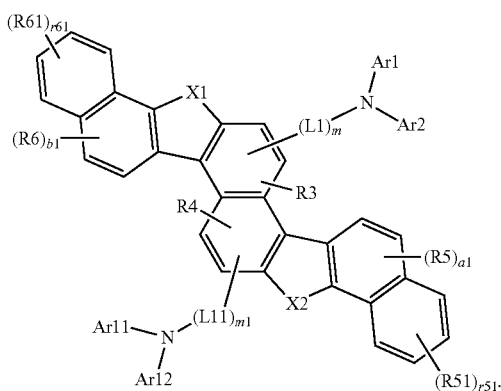

In Formulae 1-13 to 1-15:

the definitions of X1, X2, R3, R4, L1, m, Ar1, and Ar2 are the same as those described above;

R5, R6, R51, and R61 are the same as or different from each other, and are each independently hydrogen, deuterium, a substituted or unsubstituted alkyl group, a substituted or unsubstituted aryl group, or a substituted or unsubstituted heteroaryl group;

a1 and b1 are each 1 or 2;

r51 and r61 are each an integer from 1 to 4;

when a1 and b1 are each 2, the structures in the parenthesis are the same as or different from each other;

when r51 and r61 are each 2 or more, two or more structures in the parenthesis are the same as or different from each other;

L11 is a direct bond, a substituted or unsubstituted arylene group, or a substituted or unsubstituted heteroarylene group;

Ar11 and Ar12 are the same as or different from each other, and are each independently a substituted or unsubstituted aryl group or a substituted or unsubstituted heteroaryl group, or can be bonded to each other to form a substituted or unsubstituted ring;

m1 is an integer from 1 to 5; and when m1 is 2 or more, two or more L11's are the same as or different from each other.

According to an exemplary embodiment of the present specification, in Formula 1, X1 is O.

According to an exemplary embodiment of the present specification, in Formula 1, X1 is S.

According to an exemplary embodiment of the present specification, in Formula 1, X1 is —C(R7R8)-.

According to an exemplary embodiment of the present specification, in Formula 1, X1 is —N(R9)-.

According to an exemplary embodiment of the present specification, in Formula 1, X2 is O.

According to an exemplary embodiment of the present specification, in Formula 1, X2 is S.

According to an exemplary embodiment of the present specification, in Formula 1, X2 is —C(R7R8)-.

According to an exemplary embodiment of the present specification, in Formula 1, X2 is —N(R9)-.

According to an exemplary embodiment of the present specification, R7 to R9 are the same as or different from each other, and are each independently an alkyl group or an aryl group.

According to an exemplary embodiment of the present specification, R7 to R9 are the same as or different from each other, and are each independently a methyl group or a phenyl group.

According to an exemplary embodiment of the present specification, R3 to R6 are the same as or different from each other, and are each independently hydrogen, an alkyl group, or an aryl group.

In an exemplary embodiment of the present specification, R3 to R6 are the same as or different from each other, and are each independently hydrogen, a methyl group, an isopropyl group, a t-butyl group, a phenyl group, a biphenyl group, or a naphthyl group.

According to an exemplary embodiment of the present specification, R3 is hydrogen, an alkyl group, or an aryl group.

According to an exemplary embodiment of the present specification, R3 is hydrogen, a methyl group, an isopropyl group, a t-butyl group, a phenyl group, a biphenyl group, or a naphthyl group.

According to an exemplary embodiment of the present specification, R4 is hydrogen, an alkyl group, or an aryl group.

According to an exemplary embodiment of the present specification, R4 is hydrogen, a methyl group, an isopropyl group, a t-butyl group, a phenyl group, a biphenyl group; or a naphthyl group.

According to an exemplary embodiment of the present specification, a is 1.

According to an exemplary embodiment of the present specification, a is 2.

According to an exemplary embodiment of the present specification, a is 3.

According to an exemplary embodiment of the present specification, a is 4.

According to an exemplary embodiment of the present specification, b is 1.

According to an exemplary embodiment of the present specification, b is 2.

According to an exemplary embodiment of the present specification, b is 3.

According to an exemplary embodiment of the present specification, b is 4.

According to an exemplary embodiment of the present specification, a is 1, and R5 is hydrogen; an alkyl group; or an aryl group.

According to an exemplary embodiment of the present specification, a is 1, and R5 is hydrogen, a methyl group, an isopropyl group, a t-butyl group, a phenyl group; a biphenyl group; or a naphthyl group.

According to an exemplary embodiment of the present specification, a is 2, and R5 of 2 is hydrogen, an alkyl group, or an aryl group.

According to an exemplary embodiment of the present specification, a is 2, and R5 of 2 is hydrogen, a methyl group, an isopropyl group, a t-butyl group, a phenyl group, a biphenyl group, or a naphthyl group.

According to an exemplary embodiment of the present specification, a is 3, and R5 of 3 is hydrogen, an alkyl group, or an aryl group.

According to an exemplary embodiment of the present specification, a is 3, and R5 of 3 is hydrogen, a methyl group, an isopropyl group, a t-butyl group, a phenyl group, a biphenyl group, or a naphthyl group.

According to an exemplary embodiment of the present specification, a is 4, and R5 of 4 is hydrogen, an alkyl group, or an aryl group.

According to an exemplary embodiment of the present specification, a is 4, and R5 of 4 is hydrogen, a methyl group, an isopropyl group, a t-butyl group, a phenyl group, a biphenyl group; or a naphthyl group.

According to an exemplary embodiment of the present specification, b is 1, and R6 is hydrogen, an alkyl group, or an aryl group.

According to an exemplary embodiment of the present specification, b is 1, and R6 is hydrogen, a methyl group, an isopropyl group; a t-butyl group, a phenyl group, a biphenyl group, or a naphthyl group.

According to an exemplary embodiment of the present specification, b is 2, and R6 of 2 is hydrogen, an alkyl group, or an aryl group.

According to an exemplary embodiment of the present specification, b is 2, and R6 of 2 is hydrogen, a methyl group, an isopropyl group, a t-butyl group, a phenyl group, a biphenyl group, or a naphthyl group.

According to an exemplary embodiment of the present specification, b is 3, and R6 of 3 is hydrogen, an alkyl group, or an aryl group.

According to an exemplary embodiment of the present specification, b is 3, and R6 of 3 is hydrogen, a methyl group, an isopropyl group, a t-butyl group, a phenyl group; a biphenyl group, or a naphthyl group.

According to an exemplary embodiment of the present specification, b is 4, and R6 of 4 is hydrogen, an alkyl group, or an aryl group.

According to an exemplary embodiment of the present specification, b is 4, and R6 of 4 is hydrogen, a methyl group, an isopropyl group, a t-butyl group, a phenyl group, a biphenyl group, or a naphthyl group.

According to an exemplary embodiment of the present specification, L1 is a direct bond, or an arylene group.

According to an exemplary embodiment of the present specification, L1 is a direct bond, or a phenylene group.

According to an exemplary embodiment of the present specification, m is 1.

According to an exemplary embodiment of the present specification, L11 is a direct bond or an arylene group.

According to an exemplary embodiment of the present specification, L11 is a direct bond or a phenylene group.

According to an exemplary embodiment of the present specification, m1 is 1.

According to an exemplary embodiment of the present specification, Ar1 and Ar2 are the same as or different from each other, and are each independently an aryl group which is unsubstituted or substituted with a halogen group, an alkyl group, or an aryl group; or a heteroaryl group which is unsubstituted or substituted with an alkyl group, or an aryl group.

According to an exemplary embodiment of the present specification, Ar1 and Ar2 are the same as or different from each other, and are each independently a phenyl group which is unsubstituted or substituted with a halogen group, or an alkyl group, a biphenyl group which is unsubstituted or substituted with an alkyl group, a naphthyl group, a fluorenyl group which is unsubstituted or substituted with an alkyl group, a pyridyl group, a thiophene group which is unsubstituted or substituted with an aryl group, a dibenzofuran group which is unsubstituted or substituted with an alkyl group, or a carbazolyl group which is unsubstituted or substituted with an alkyl group, or an aryl group.

According to an exemplary embodiment of the present specification, Ar1 and Ar2 are the same as or different from each other, and are each independently a phenyl group which is unsubstituted or substituted with F, a methyl group, or a t-butyl group, a biphenyl group which is unsubstituted or substituted with a methyl group, a naphthyl group, a fluorenyl group which is unsubstituted or substituted with a methyl group, a pyridyl group, a thiophene group which is unsubstituted or substituted with a phenyl group, a dibenzofuran group which is unsubstituted or substituted with an i-propyl group, or a carbazolyl group which is unsubstituted or substituted with an ethyl group, or a phenyl group.

According to an exemplary embodiment of the present specification, Ar1 and Ar2 are bonded to each other to form a substituted or unsubstituted hetero ring.

According to an exemplary embodiment of the present specification, Ar1 and Ar2 are bonded to each other to form a hetero ring.

According to an exemplary embodiment of the present specification, Ar1 and Ar2 are bonded to each other to form a carbazole ring.

According to an exemplary embodiment of the present specification, Ar11 and Ar12 are the same as or different from each other, and are each independently an aryl group which is unsubstituted or substituted with a halogen group, an alkyl group, or an aryl group; or a heteroaryl group which is unsubstituted or substituted with an alkyl group, or an aryl group.

According to an exemplary embodiment of the present specification, Ar11 and Ar12 are the same as or different from each other, and are each independently a phenyl group which is unsubstituted or substituted with a halogen group, or an alkyl group, a biphenyl group which is unsubstituted or substituted with an alkyl group, a naphthyl group, a fluorenyl group which is unsubstituted or substituted with an alkyl group, a pyridyl group, a thiophene group which is unsubstituted or substituted with an aryl group, a dibenzofuran group which is unsubstituted or substituted with an alkyl group, or a carbazolyl group which is unsubstituted or substituted with an alkyl group, or an aryl group.

According to an exemplary embodiment of the present specification, Ar11 and Ar12 are the same as or different from each other, and are each independently a phenyl group which is unsubstituted or substituted with F, a methyl group, or a t-butyl group, a biphenyl group which is unsubstituted or substituted with a methyl group, a naphthyl group, a fluorenyl group which is unsubstituted or substituted with a methyl group, a pyridyl group, a thiophene group which is unsubstituted or substituted with a phenyl group, a dibenzofuran group which is unsubstituted or substituted with an i-propyl group, or a carbazolyl group which is unsubstituted or substituted with an ethyl group, or a phenyl group.

According to an exemplary embodiment of the present specification, Ar11 and Ar12 are bonded to each other to form a substituted or unsubstituted hetero ring.

According to an exemplary embodiment of the present specification, Ar11 and Ar12 are bonded to each other to form a hetero ring.

According to an exemplary embodiment of the present specification, Ar11 and Ar12 are bonded to each other to form a carbazole ring.
According to an exemplary embodiment of the present specification, Formula 1 is selected from the following compounds.
| Compound | X1 | X2 | R1 | R2 | R3 to R6 |
|---|---|---|---|---|---|
| 1-1 | O | O | 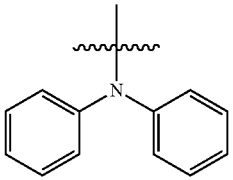 [SMILES: *N(c1ccccc1)c1ccccc1] | 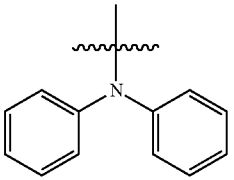 [SMILES: *N(c1ccccc1)c1ccccc1] | H |
| 1-2 | O | O | 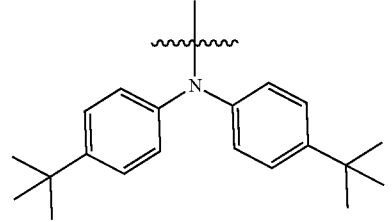 [SMILES: *N(c1ccc(C(C)(C)C)cc1)c1ccc(C(C)(C)C)cc1] | 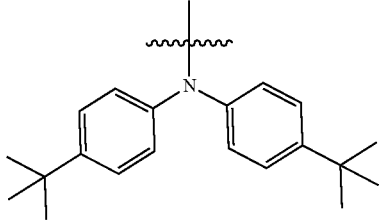 [SMILES: *N(c1ccc(C(C)(C)C)cc1)c1ccc(C(C)(C)C)cc1] | H |
| 1-3 | O | O | 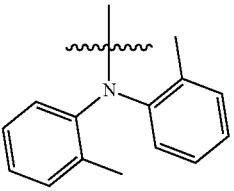 [SMILES: *N(c1ccccc1C)c1ccccc1C] | 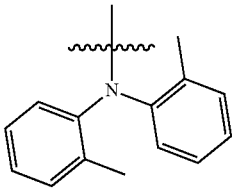 [SMILES: *N(c1ccccc1C)c1ccccc1C] | H |
| 1-4 | O | O | 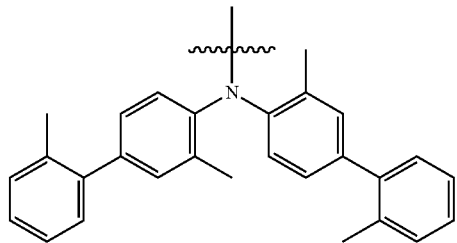 [SMILES: *N(c1ccc(-c2ccccc2C)cc1C)c1ccc(-c2ccccc2C)cc1C] | 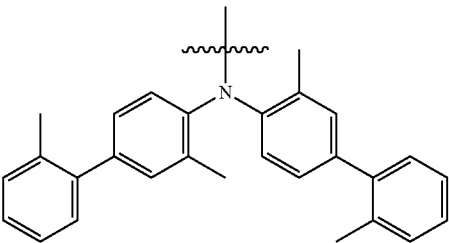 [SMILES: *N(c1ccc(-c2ccccc2C)cc1C)c1ccc(-c2ccccc2C)cc1C] | H |
| 1-5 | O | O | 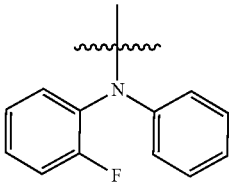 [SMILES: *N(c1ccccc1)c1ccccc1F] | 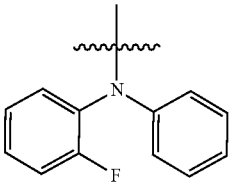 [SMILES: *N(c1ccccc1)c1ccccc1F] | H |
| 1-6 | O | O | 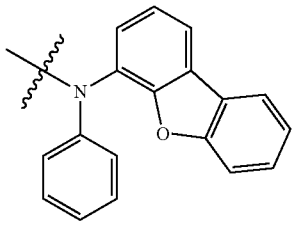 [SMILES: *N(c1ccccc1)c1cccc2c1oc1ccccc12] | 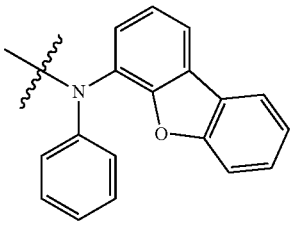 [SMILES: *N(c1ccccc1)c1cccc2c1oc1ccccc12] | H |

-continued

| Compound | X1 | X2 | R1 | R2 | R3 to R6 |
|---|---|---|---|---|---|
| 1-7 | O | O | (7-isopropyl-dibenzofuran-N-phenyl-amine) | (7-isopropyl-dibenzofuran-N-phenyl-amine) | H |
| 1-8 | O | O | N,N-bis(dibenzofuran-4-yl)amine | N,N-bis(dibenzofuran-4-yl)amine | H |
| 1-9 | O | O | N-(2-fluorophenyl)-N-(naphthalen-2-yl)amine | N-(2-fluorophenyl)-N-(naphthalen-2-yl)amine | H |
| 1-10 | O | O | N-phenyl-N-(pyridin-3-yl)amine | N-phenyl-N-(naphthalen-2-yl)amine | H |
| 1-11 | O | O | N,N-di(naphthalen-1-yl)amine | N,N-di(naphthalen-1-yl)amine | H |
| 1-12 | O | O | N-phenyl-N-(9,9-dimethylfluoren-4-yl)amine | N-phenyl-N-(9,9-dimethylfluoren-4-yl)amine | H |
| 1-13 | O | O | N-(dibenzofuran-2-yl)-N-(9,9-dimethylfluoren-4-yl)amine | N-(dibenzofuran-2-yl)-N-(9,9-dimethylfluoren-4-yl)amine | H |

-continued
| Compound | X1 | X2 | R1 | R2 | R3 to R6 |
|---|---|---|---|---|---|
| 1-14 | O | O | 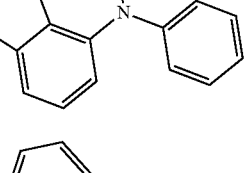 | 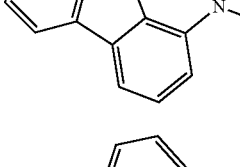 | H |
| 1-15 | O | O | 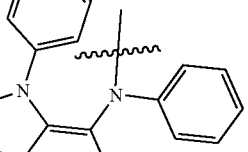 | 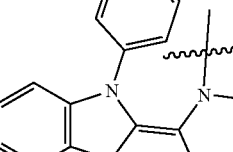 | H |
| 1-16 | O | O | 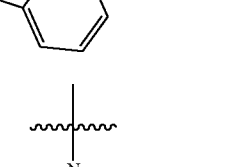 | 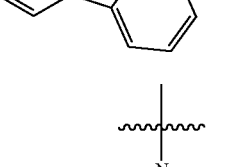 | H |
| 1-17 | O | O | 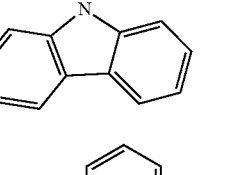 | 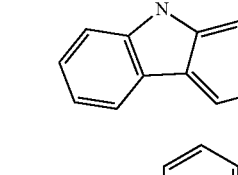 | H |
| 1-18 | O | O | 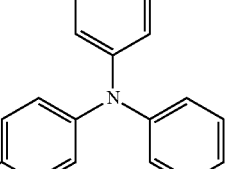 | 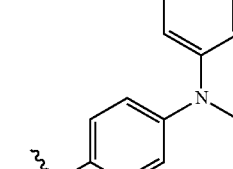 | H |
| 1-19 | O | O | 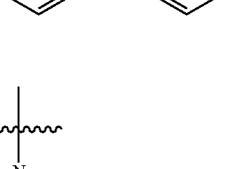 | 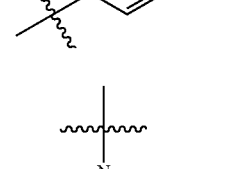 | H |
| 1-20 | O | O | 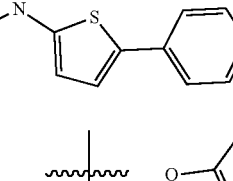 | 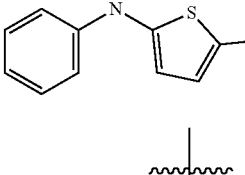 | H |

-continued

| Compound | X1 | X2 | R1 | R2 | R3 to R6 |
|---|---|---|---|---|---|
| 1-21 | O | O | N-phenyl-(3-tert-butylphenyl)amino | N-phenyl-(3-tert-butylphenyl)amino | H |
| 1-22 | O | O | N-(biphenyl-4-yl)-(dibenzofuran-2-yl)amino | N-(biphenyl-4-yl)-(dibenzofuran-2-yl)amino | H |
| 1-23 | O | O | N-(biphenyl-4-yl)-(dibenzofuran-4-yl)amino | N-(biphenyl-4-yl)-(dibenzofuran-4-yl)amino | H |

| Compound | X1 | X2 | R1 | R2 | R3 to R6 |
|---|---|---|---|---|---|
| 2-1 | S | S | diphenylamino | diphenylamino | H |
| 2-2 | S | S | bis(4-tert-butylphenyl)amino | bis(4-tert-butylphenyl)amino | H |

-continued
| Compound | X1 | X2 | R1 | R2 | R3 to R6 |
|---|---|---|---|---|---|
| 2-3 | S | S | 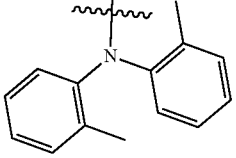 | 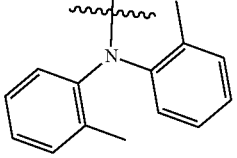 | H |
| 2-4 | S | S | 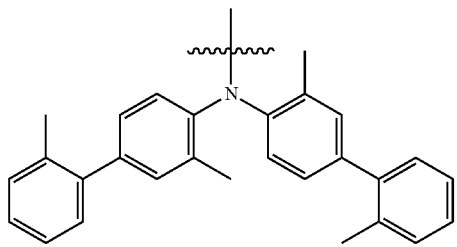 [SMILES: *N(c1ccc(-c2ccccc2C)cc1C)c1ccc(-c2ccccc2C)cc1C] | 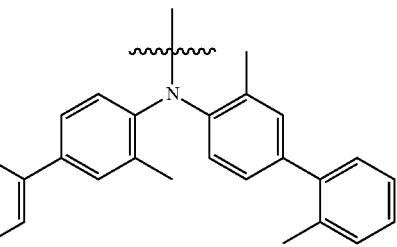 | H |
| 2-5 | S | S | 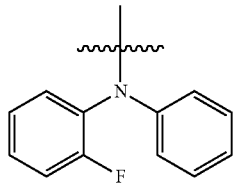 [SMILES: *N(c1ccccc1)c1ccccc1F] | 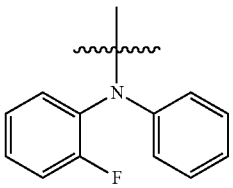 [SMILES: *N(c1ccccc1)c1ccccc1F] | H |
| 2-6 | S | S | 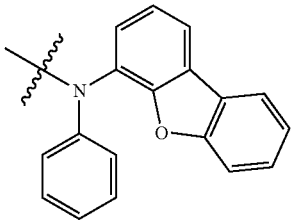 [SMILES: *N(c1ccccc1)c1cccc2c1oc1ccccc12] | 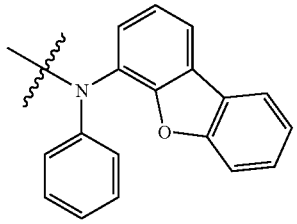 [SMILES: *N(c1ccccc1)c1cccc2c1oc1ccccc12] | H |
| 2-7 | S | S | 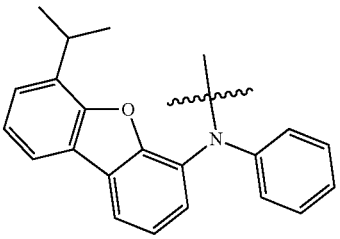 [SMILES: *N(c1ccccc1)c1cccc2c1oc1c(C(C)C)cccc12] | 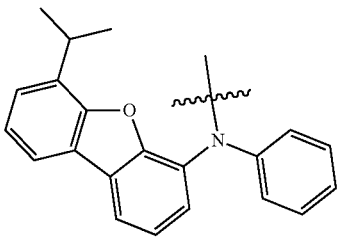 [SMILES: *N(c1ccccc1)c1cccc2c1oc1c(C(C)C)cccc12] | H |
| 2-8 | S | S | 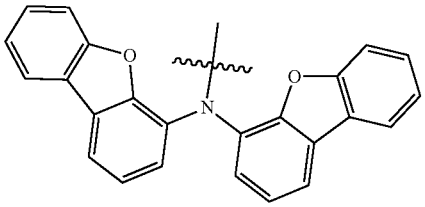 [SMILES: *N(c1cccc2c1oc1ccccc12)c1cccc2c1oc1ccccc12] | 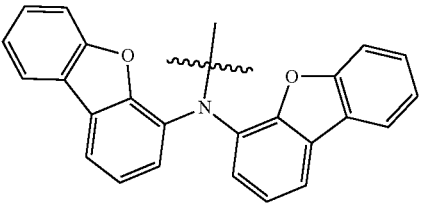 [SMILES: *N(c1cccc2c1oc1ccccc12)c1cccc2c1oc1ccccc12] | H |
| 2-9 | S | S | 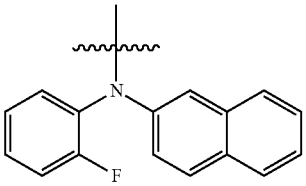 [SMILES: *N(c1ccc2ccccc2c1)c1ccccc1F] | 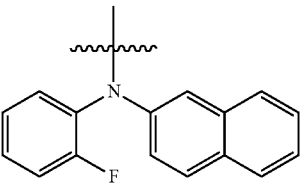 [SMILES: *N(c1ccc2ccccc2c1)c1ccccc1F] | H |

-continued

| Compound | X1 | X2 | R1 | R2 | R3 to R6 |
|---|---|---|---|---|---|
| 2-10 | S | S | N-phenyl-N-(pyridin-3-yl) | N-phenyl-N-(naphthalen-2-yl) | H |
| 2-11 | S | S | N,N-di(naphthalen-1-yl) | N,N-di(naphthalen-1-yl) | H |
| 2-12 | S | S | N-phenyl-N-(9,9-dimethylfluoren-1-yl) | N-phenyl-N-(9,9-dimethylfluoren-1-yl) | H |
| 2-13 | S | S | N-(dibenzofuran-2-yl)-N-(9,9-dimethylfluoren-1-yl) | N-(dibenzofuran-2-yl)-N-(9,9-dimethylfluoren-1-yl) | H |
| 2-14 | S | S | N-(9-ethylcarbazol-1-yl)-N-phenyl | N-(9-ethylcarbazol-1-yl)-N-phenyl | H |
| 2-15 | S | S | N-(9-phenylcarbazol-1-yl)-N-phenyl | N-(9-phenylcarbazol-1-yl)-N-phenyl | H |
| 2-16 | S | S | carbazol-9-yl | carbazol-9-yl | H |

-continued

| Compound | X1 | X2 | R1 | R2 | R3 to R6 |
|---|---|---|---|---|---|
| 2-17 | S | S | 4-(N-phenyl-N-phenylamino)phenyl | 4-(N-phenyl-N-phenylamino)phenyl | H |
| 2-18 | S | S | N-phenyl-N-(5-phenylthiophen-2-yl)amino | N-phenyl-N-(5-phenylthiophen-2-yl)amino | H |
| 2-19 | S | S | N-(dibenzofuran-2-yl)-N-(dibenzofuran-4-yl)amino | N-(dibenzofuran-2-yl)-N-(dibenzofuran-4-yl)amino | H |
| 2-20 | S | S | N-phenyl-N-(pyridin-3-yl)amino | N-phenyl-N-(pyridin-3-yl)amino | H |
| 2-21 | S | S | N-(4-tert-butylphenyl)-N-(dibenzofuran-1-yl)amino | N-(4-tert-butylphenyl)-N-(dibenzofuran-1-yl)amino | H |
| 2-22 | S | S | N-(4-tert-butylphenyl)-N-(naphthalen-1-yl)amino | N-(4-tert-butylphenyl)-N-(naphthalen-1-yl)amino | H |

| Compound | X1 | X2 | R1 |
|---|---|---|---|
| 3-1 | —N— | —N— | diphenylamino group |
| 3-2 | —N— | —N— | bis(4-tert-butylphenyl)amino group |
| 3-3 | —N— | —N— | di(o-tolyl)amino group |
| 3-4 | —N— | —N— | N,N-bis(2'-methyl-3-methylbiphenyl-4-yl)amino group |
| 3-5 | —N— | —N— | N-(2-fluorophenyl)-N-phenylamino group |
| 3-6 | —N— | —N— | N-phenyl-N-(dibenzofuran-2-yl)amino group |
| 3-7 | —N— | —N— | N-phenyl-N-(6-isopropyldibenzofuran-4-yl)amino group |

| | | | |
|---|---|---|---|
| 3-8 |  |  | 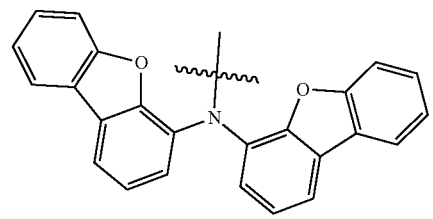 [SMILES: *N(c1cccc2c1oc1ccccc12)c1cccc2c1oc1ccccc12] |
| 3-9 |  |  | 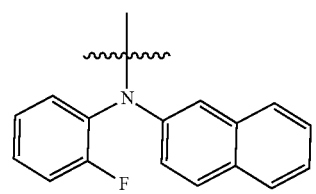 [SMILES: *N(c1ccc2ccccc2c1)c1ccccc1F] |
| 3-10 |  |  | 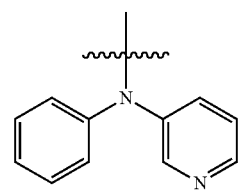 [SMILES: *N(c1ccccc1)c1cccnc1] |
| 3-11 |  |  | 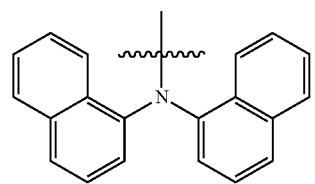 [SMILES: *N(c1cccc2ccccc12)c1cccc2ccccc12] |
| 3-12 |  |  | 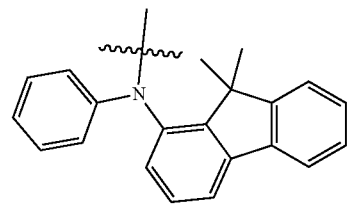 [SMILES: *N(c1ccccc1)c1cccc2c1C(C)(C)c1ccccc1-2] |
| 3-13 |  |  | 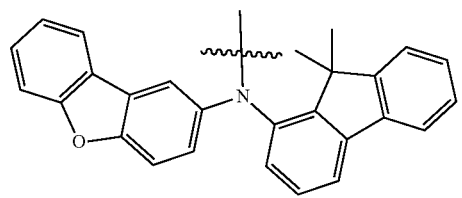 [SMILES: *N(c1ccc2oc3ccccc3c2c1)c1cccc2c1C(C)(C)c1ccccc1-2] |
| 3-14 |  |  | 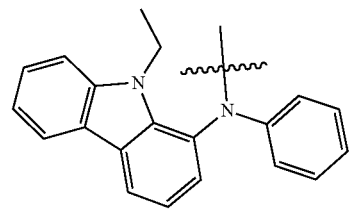 [SMILES: *N(c1ccccc1)c1cccc2c3ccccc3n(CC)c12] |

-continued
| | | | |
|---|---|---|---|
| 3-15 |  |  | 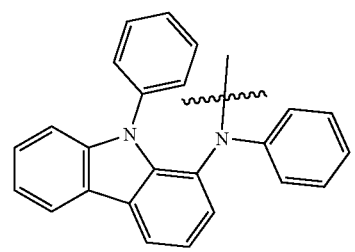 [SMILES: *N(c1ccccc1)c1cccc2c3ccccc3n(-c3ccccc3)c12] |
| 3-16 |  |  | 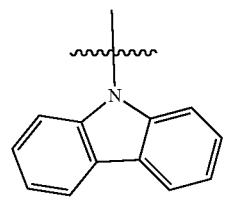 |
| 3-17 |  |  | 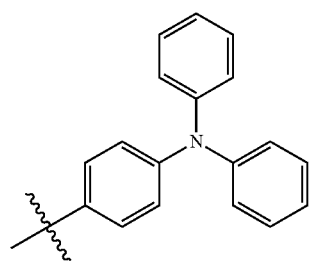 [SMILES: *c1ccc(N(c2ccccc2)c2ccccc2)cc1] |
| 3-18 |  |  | 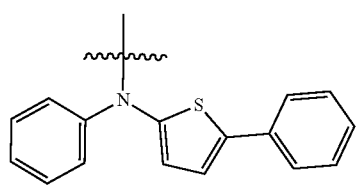 [SMILES: *N(c1ccccc1)c1ccc(-c2ccccc2)s1] |
| 3-19 |  |  | 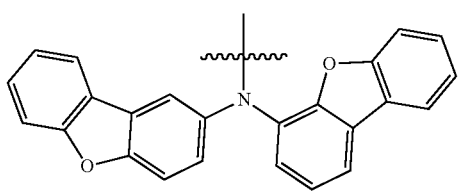 [SMILES: *N(c1ccc2oc3ccccc3c2c1)c1cccc2c1oc1ccccc12] |
| 3-20 |  |  | 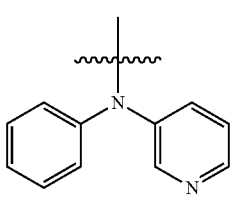 [SMILES: *N(c1ccccc1)c1cccnc1] |
| Compound | R2 | R3 to R6 |
|---|---|---|
| 3-1 | 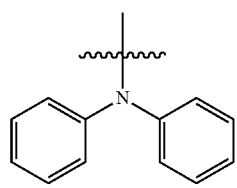 [SMILES: *N(c1ccccc1)c1ccccc1] | H |

-continued
| | | |
|---|---|---|
| 3-2 | 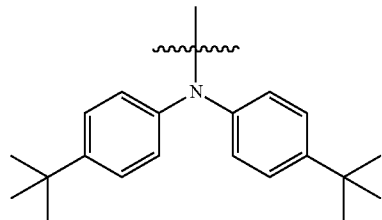 [SMILES: *N(c1ccc(C(C)(C)C)cc1)c1ccc(C(C)(C)C)cc1] | H |
| 3-3 | 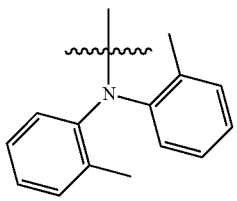 [SMILES: *N(c1ccccc1C)c1ccccc1C] | H |
| 3-4 | 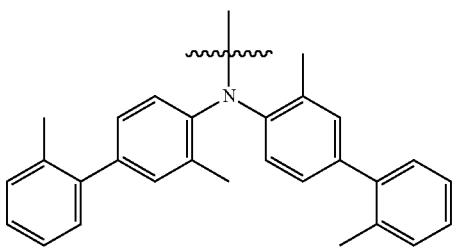 [SMILES: *N(c1ccc(-c2ccccc2C)cc1C)c1ccc(-c2ccccc2C)cc1C] | H |
| 3-5 | 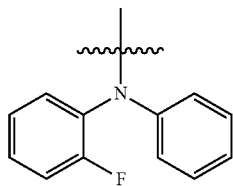 [SMILES: *N(c1ccccc1)c1ccccc1F] | H |
| 3-6 | 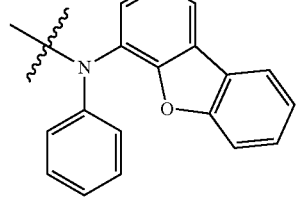 | H |
| 3-7 | 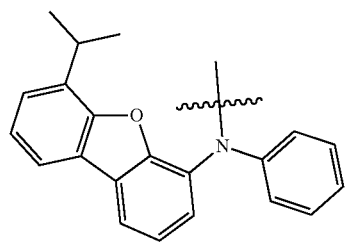 [SMILES: *N(c1ccccc1)c1cccc2c1oc1c(C(C)C)cccc12] | H |
| 3-8 | 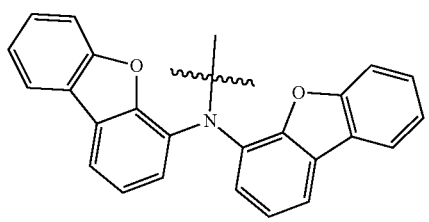 [SMILES: *N(c1cccc2c1oc1ccccc12)c1cccc2c1oc1ccccc12] | H |

-continued
| | | |
|---|---|---|
| 3-9 | 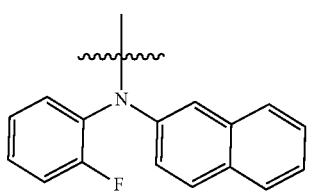 [SMILES: *N(c1ccc2ccccc2c1)c1ccccc1F] | H |
| 3-10 | 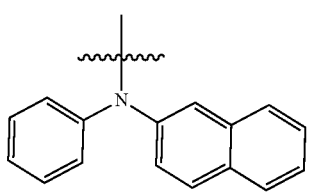 [SMILES: *N(c1ccccc1)c1ccc2ccccc2c1] | H |
| 3-11 | 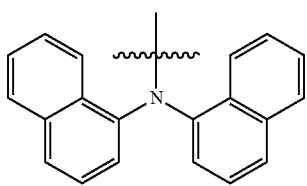 [SMILES: *N(c1cccc2ccccc12)c1cccc2ccccc12] | H |
| 3-12 | 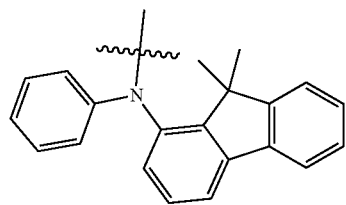 [SMILES: *N(c1ccccc1)c1cccc2c1C(C)(C)c1ccccc1-2] | H |
| 3-13 | 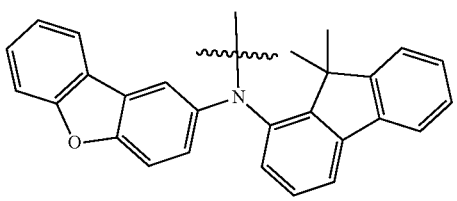 [SMILES: *N(c1ccc2oc3ccccc3c2c1)c1cccc2c1C(C)(C)c1ccccc1-2] | H |
| 3-14 | 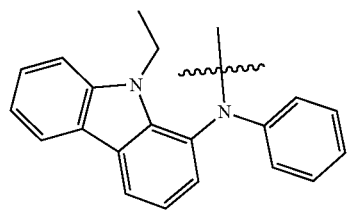 [SMILES: *N(c1ccccc1)c1cccc2c3ccccc3n(CC)c12] | H |
| 3-15 | 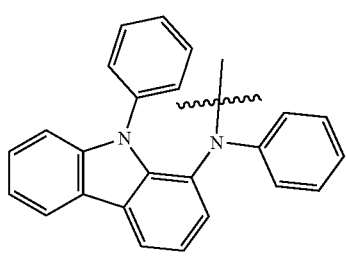 [SMILES: *N(c1ccccc1)c1cccc2c3ccccc3n(-c3ccccc3)c12] | H |

-continued
| | | |
|---|---|---|
| 3-16 | 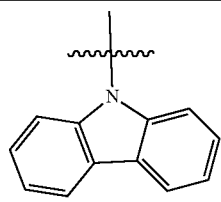 | H |
| 3-17 | 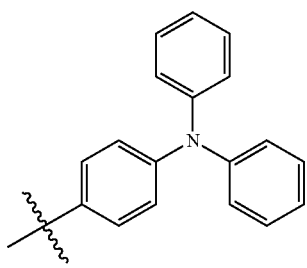 [SMILES: *c1ccc(N(c2ccccc2)c2ccccc2)cc1] | H |
| 3-18 | 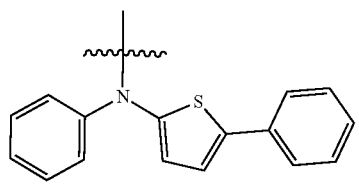 [SMILES: *N(c1ccccc1)c1ccc(-c2ccccc2)s1] | H |
| 3-19 | 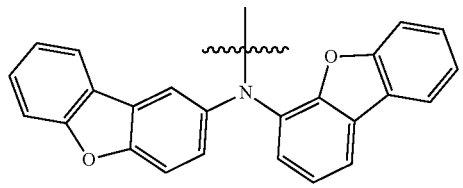 [SMILES: *N(c1ccc2oc3ccccc3c2c1)c1cccc2c1oc1ccccc12] | H |
| 3-20 | 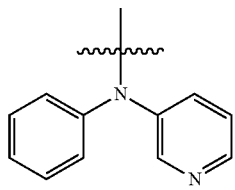 [SMILES: *N(c1ccccc1)c1cccnc1] | H |
| Compound | X1 | X2 | R1 | R2 | R3 to R6 |
|---|---|---|---|---|---|
| 4-1 | | | | | H |

-continued
| Compound | X1 | X2 | R1 | R2 | R3 to R6 |
|---|---|---|---|---|---|
| 4-2 | 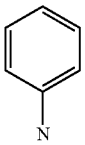 | 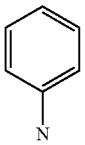 | 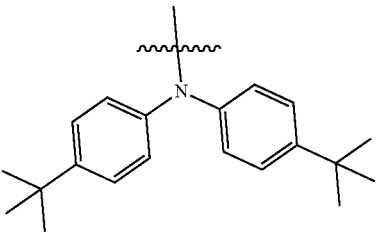 [SMILES: *N(c1ccc(C(C)(C)C)cc1)c1ccc(C(C)(C)C)cc1] | 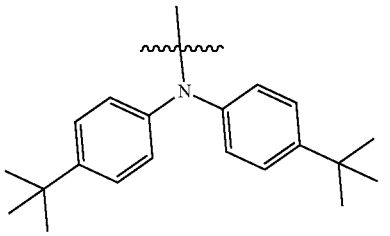 [SMILES: *N(c1ccc(C(C)(C)C)cc1)c1ccc(C(C)(C)C)cc1] | H |
| 4-3 | 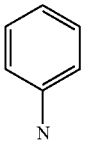 | 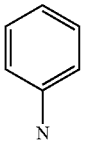 | 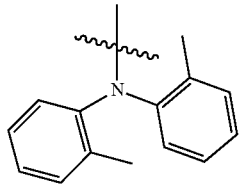 [SMILES: *N(c1ccccc1C)c1ccccc1C] | 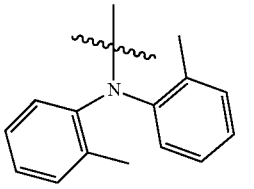 [SMILES: *N(c1ccccc1C)c1ccccc1C] | H |
| 4-4 | 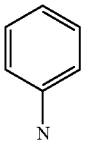 | 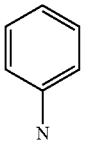 | 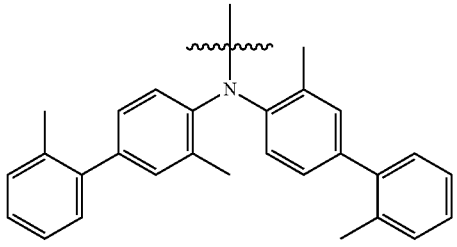 [SMILES: *N(c1ccc(-c2ccccc2C)cc1C)c1ccc(-c2ccccc2C)cc1C] | 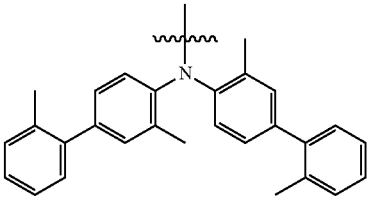 [SMILES: *N(c1ccc(-c2ccccc2C)cc1C)c1ccc(-c2ccccc2C)cc1C] | H |
| 4-5 | 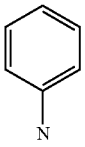 | 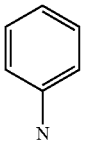 | 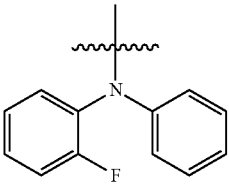 [SMILES: *N(c1ccccc1)c1ccccc1F] | 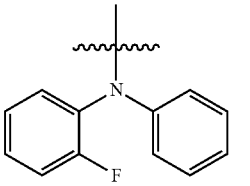 [SMILES: *N(c1ccccc1)c1ccccc1F] | H |
| 4-6 | 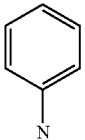 | 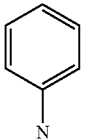 | 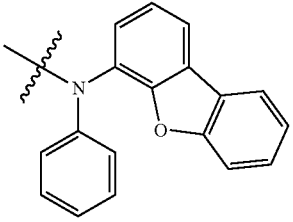 [SMILES: *N(c1ccccc1)c1cccc2c1oc1ccccc12] | 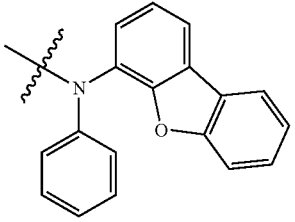 [SMILES: *N(c1ccccc1)c1cccc2c1oc1ccccc12] | H |
| 4-7 | 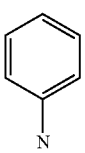 | 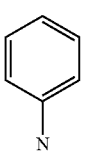 | 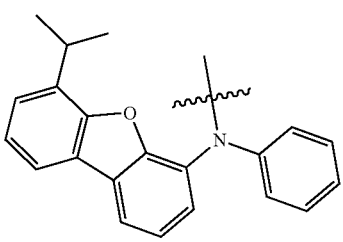 [SMILES: *N(c1ccccc1)c1cccc2c1oc1c(C(C)C)cccc12] | 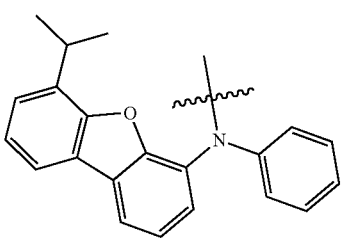 [SMILES: *N(c1ccccc1)c1cccc2c1oc1c(C(C)C)cccc12] | H |

-continued
| Compound | X1 | X2 | R1 | R2 | R3 to R6 |
|---|---|---|---|---|---|
| 4-8 | 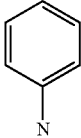 | 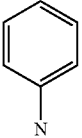 | 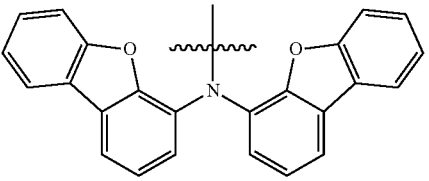 [SMILES: *N(c1cccc2c1oc1ccccc12)c1cccc2c1oc1ccccc12] | 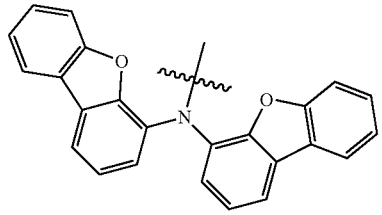 [SMILES: *N(c1cccc2c1oc1ccccc12)c1cccc2c1oc1ccccc12] | H |
| 4-9 | 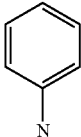 | 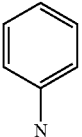 | 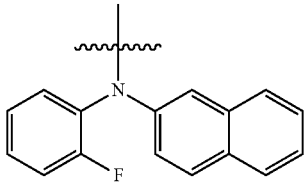 [SMILES: *N(c1ccc2ccccc2c1)c1ccccc1F] | 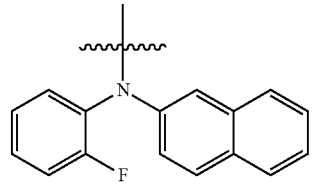 [SMILES: *N(c1ccc2ccccc2c1)c1ccccc1F] | H |
| 4-10 | 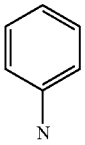 | 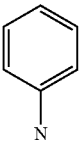 | 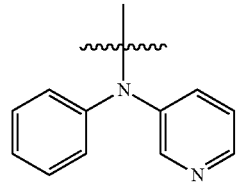 [SMILES: *N(c1ccccc1)c1cccnc1] | 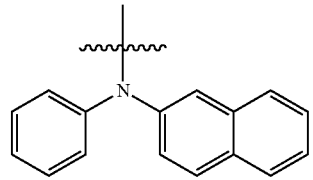 [SMILES: *N(c1ccccc1)c1ccc2ccccc2c1] | H |
| 4-11 | 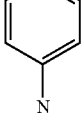 | 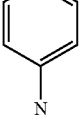 | 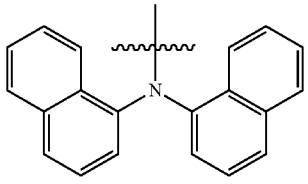 [SMILES: *N(c1cccc2ccccc12)c1cccc2ccccc12] | 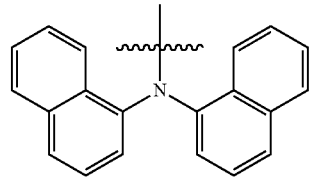 [SMILES: *N(c1cccc2ccccc12)c1cccc2ccccc12] | H |
| 4-12 | 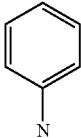 | 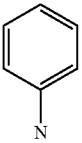 | 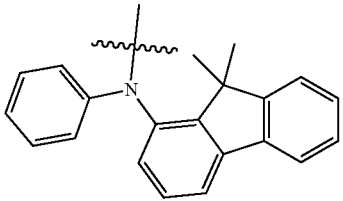 [SMILES: *N(c1ccccc1)c1cccc2c1C(C)(C)c1ccccc1-2] | 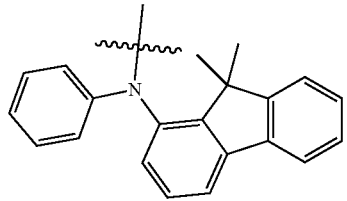 [SMILES: *N(c1ccccc1)c1cccc2c1C(C)(C)c1ccccc1-2] | H |
| 4-13 | 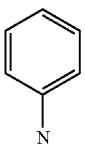 | 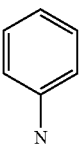 | 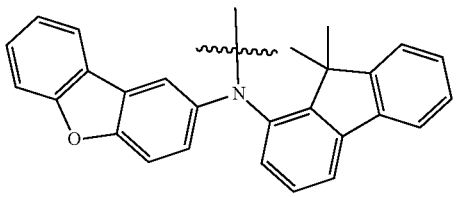 [SMILES: *N(c1ccc2oc3ccccc3c2c1)c1cccc2c1C(C)(C)c1ccccc1-2] | 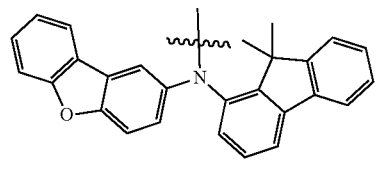 | H |
| 4-14 | 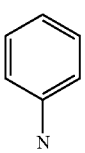 | 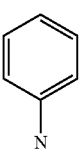 | 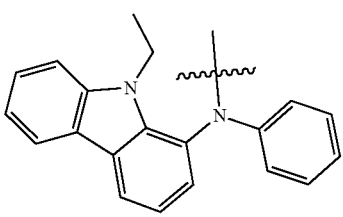 [SMILES: *N(c1ccccc1)c1cccc2c3ccccc3n(CC)c12] | 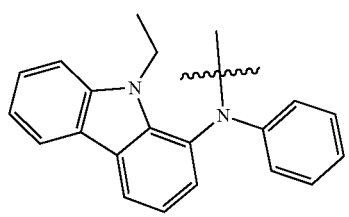 [SMILES: *N(c1ccccc1)c1cccc2c3ccccc3n(CC)c12] | H |

-continued
| Compound | X1 | X2 | R1 | R2 | R3 to R6 |
|---|---|---|---|---|---|
| 4-15 | 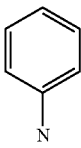 | 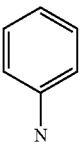 | 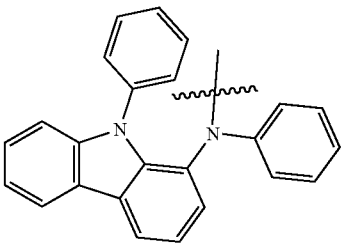 [SMILES: *N(c1ccccc1)c1cccc2c3ccccc3n(-c3ccccc3)c12] | 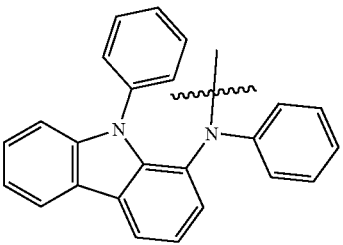 [SMILES: *N(c1ccccc1)c1cccc2c3ccccc3n(-c3ccccc3)c12] | H |
| 4-16 | 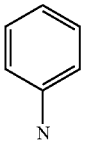 | 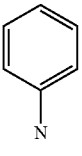 | 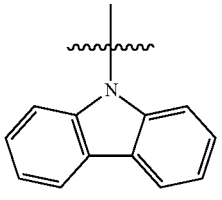 [SMILES: *n1c2ccccc2c2ccccc21] | 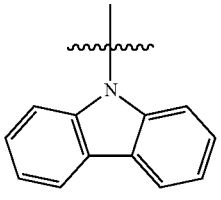 [SMILES: *n1c2ccccc2c2ccccc21] | H |
| 4-17 | 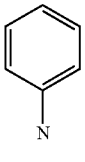 | 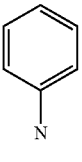 | 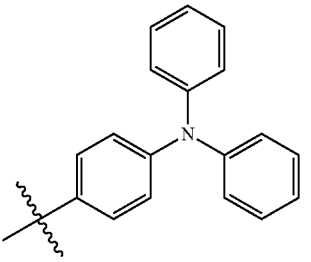 [SMILES: *c1ccc(N(c2ccccc2)c2ccccc2)cc1] | 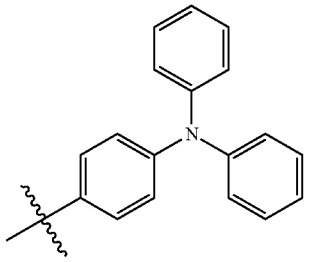 [SMILES: *c1ccc(N(c2ccccc2)c2ccccc2)cc1] | H |
| 4-18 | 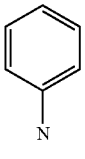 | 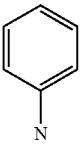 | 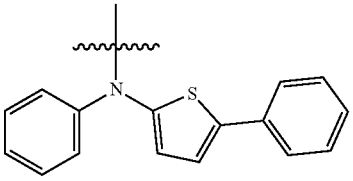 [SMILES: *N(c1ccccc1)c1ccc(-c2ccccc2)s1] | 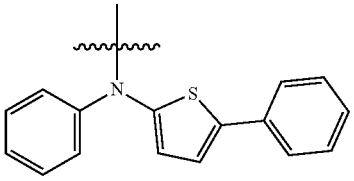 [SMILES: *N(c1ccccc1)c1ccc(-c2ccccc2)s1] | H |
| 4-19 | 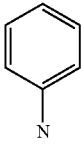 | 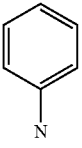 | 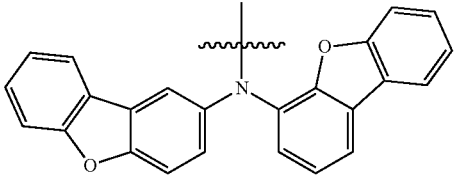 [SMILES: *N(c1ccc2oc3ccccc3c2c1)c1cccc2c1oc1ccccc12] | 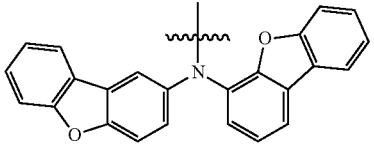 [SMILES: *N(c1ccc2oc3ccccc3c2c1)c1cccc2c1oc1ccccc12] | H |
| 4-20 | 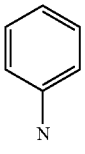 | 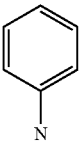 | 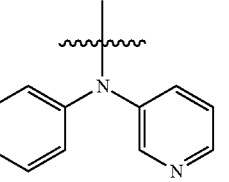 | 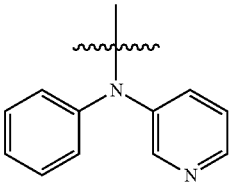 [SMILES: *N(c1ccccc1)c1cccnc1] | H |

-continued
| Compound | X1 | X2 | R1 | R2 | R3 to R6 |
|---|---|---|---|---|---|
| 4-21 | | | | | H |
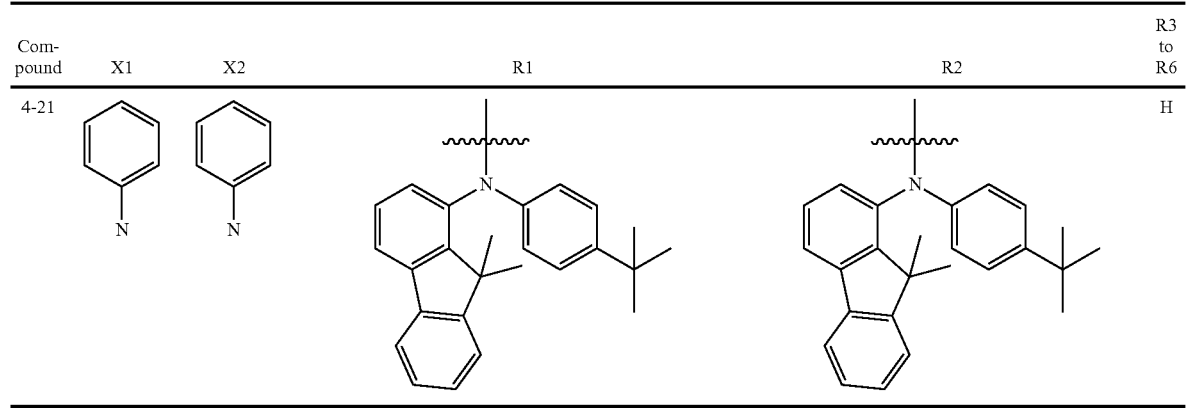
| Compound | X | Y | R1 | R2 | R3 to R6 |
|---|---|---|---|---|---|
| 5-1 | | | | | H |
| 5-2 | | | | | H |
| 5-3 | | | | | H |
| 5-4 | | | | | H |
| 5-5 | | | | | H |
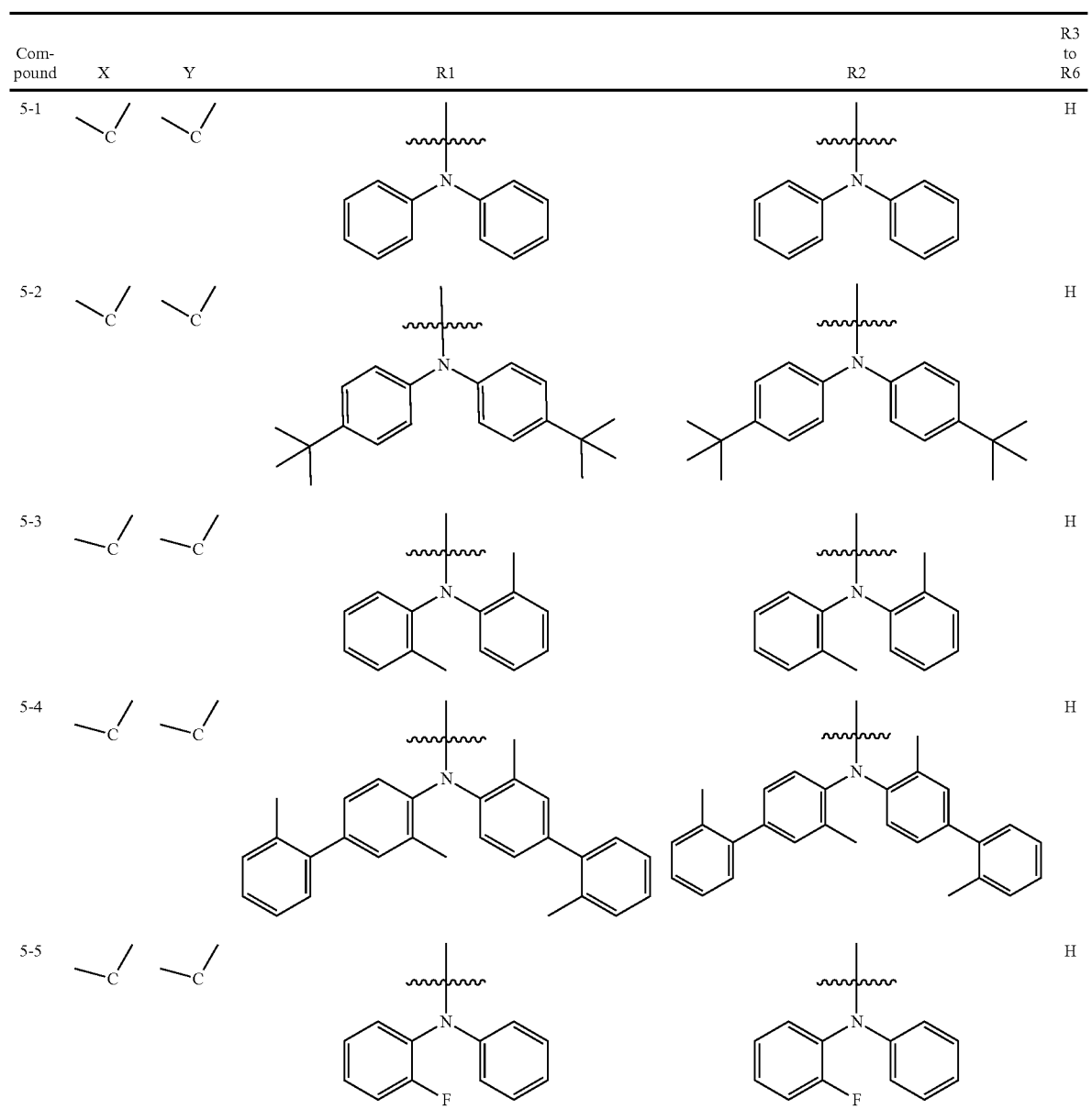

-continued

| Compound | X | Y | R1 | R2 | R3 to R6 |
|---|---|---|---|---|---|
| 5-6 | C | C | N-phenyl-N-(dibenzofuranyl) | N-phenyl-N-(dibenzofuranyl) | H |
| 5-7 | C | C | N-phenyl-N-(isopropyl-dibenzofuranyl) | N-phenyl-N-(isopropyl-dibenzofuranyl) | H |
| 5-8 | C | C | N,N-bis(dibenzofuranyl) | N,N-bis(dibenzofuranyl) | H |
| 5-9 | C | C | N-(2-fluorophenyl)-N-(2-naphthyl) | N-(2-fluorophenyl)-N-(2-naphthyl) | H |
| 5-10 | C | C | N-phenyl-N-(3-pyridyl) | N-phenyl-N-(2-naphthyl) | H |
| 5-11 | C | C | N,N-di(1-naphthyl) | N,N-di(1-naphthyl) | H |
| 5-12 | C | C | N-phenyl-N-(9,9-dimethylfluorenyl) | N-phenyl-N-(9,9-dimethylfluorenyl) | H |

-continued

| Compound | X | Y | R1 | R2 | R3 to R6 |
|---|---|---|---|---|---|
| 5-13 | C | C | (dibenzofuran-N-(9,9-dimethylfluorenyl)) | (dibenzofuran-N-(9,9-dimethylfluorenyl)) | H |
| 5-14 | C | C | (N-ethylcarbazolyl-N-phenyl) | (N-ethylcarbazolyl-N-phenyl) | H |
| 5-15 | C | C | (N-phenylcarbazolyl-N-phenyl) | (N-phenylcarbazolyl-N-phenyl) | H |
| 5-16 | C | C | (carbazol-9-yl) | (carbazol-9-yl) | H |
| 5-17 | C | C | (4-(diphenylamino)phenyl) | (4-(diphenylamino)phenyl) | H |
| 5-18 | C | C | (N-phenyl-N-(5-phenylthiophen-2-yl)) | (N-phenyl-N-(5-phenylthiophen-2-yl)) | H |
| 5-19 | C | C | (N,N-di(dibenzofuranyl)) | (N,N-di(dibenzofuranyl)) | H |

-continued
| Compound | X | Y | R1 | R2 | R3 to R6 |
|---|---|---|---|---|---|
| 5-20 | 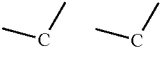 |  | 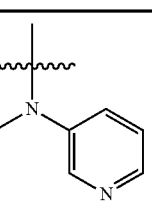 | 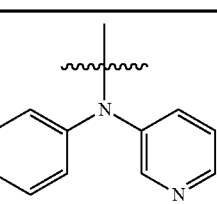 | H |
| 5-21 | 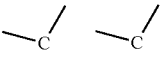 |  | 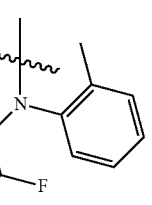 | 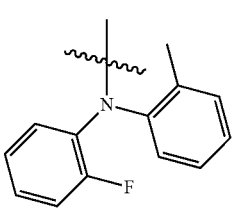 | H |

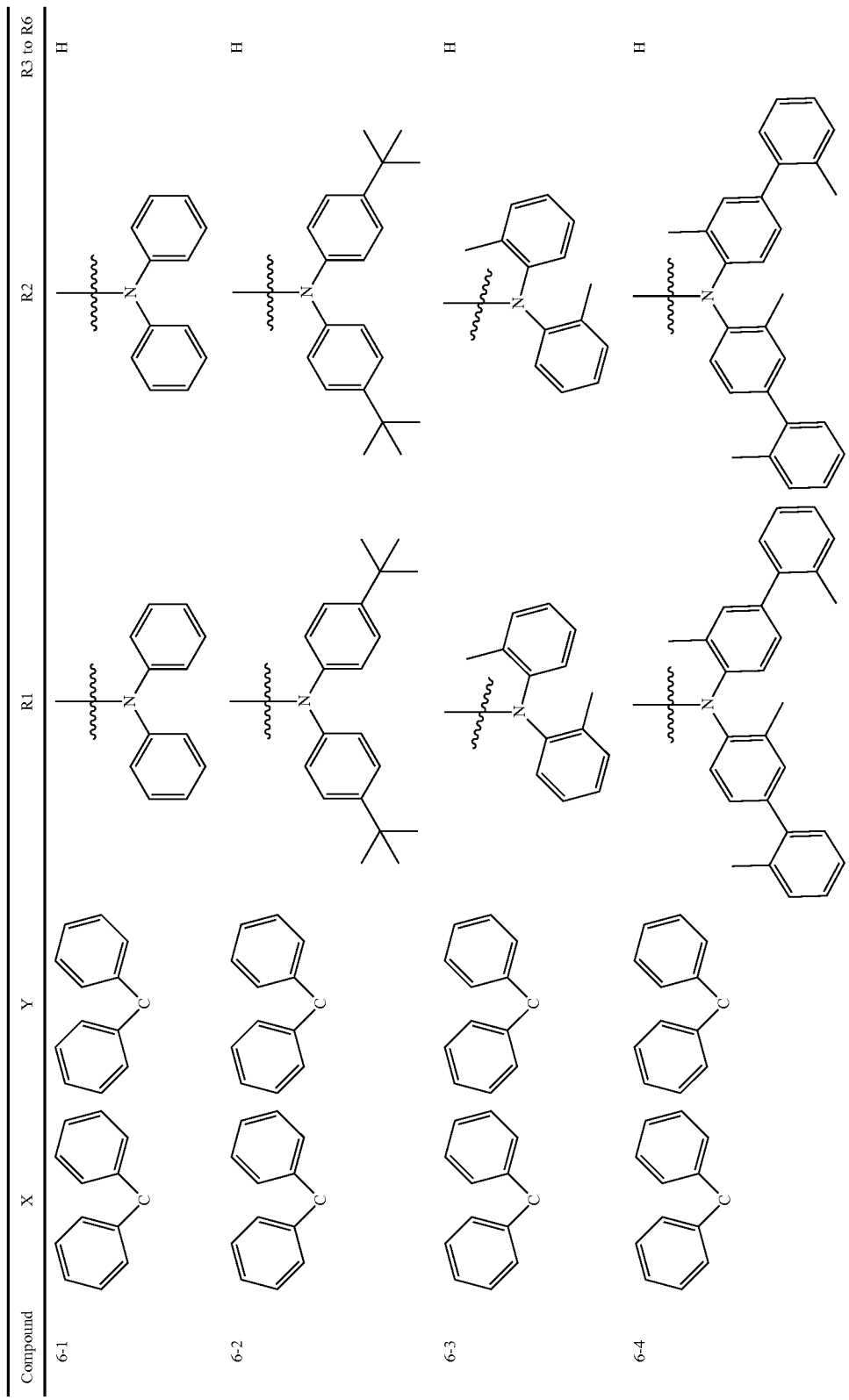

-continued
| Compound | X | Y | R1 | R2 | R3 to R6 |
|---|---|---|---|---|---|
| 6-5 | 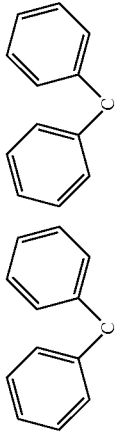 | 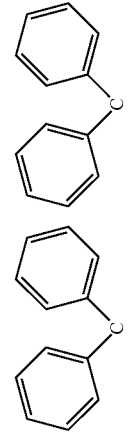 | 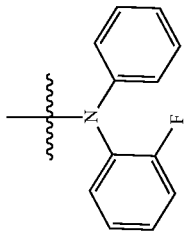 | 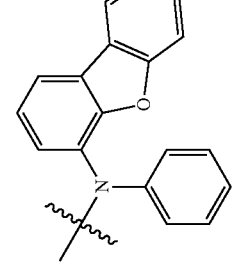 | H |
| 6-6 |  | 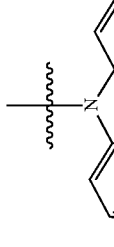 | 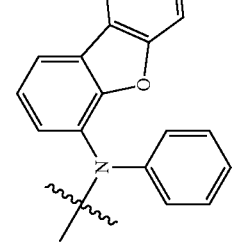 | 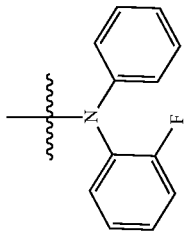 | H |
| 6-7 | 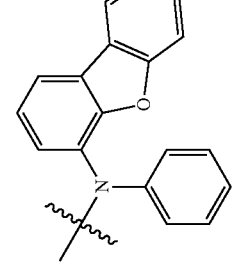 |  | 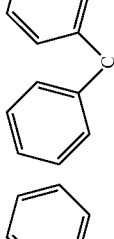 | 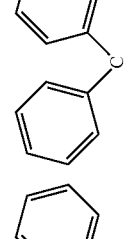 | H |
| 6-8 | 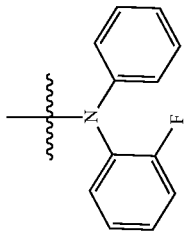 | 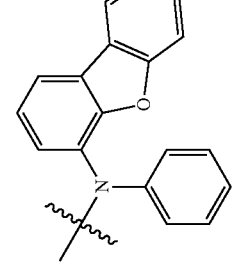 |  | 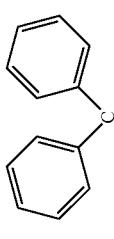 | H |

-continued

| Compound | X | Y | R1 | R2 | R3 to R6 |
|---|---|---|---|---|---|
| 6-9 | biphenyl | biphenyl | N(2-naphthyl)(2-fluorophenyl) | N(2-naphthyl)(2-fluorophenyl) | H |
| 6-10 | biphenyl | biphenyl | N(3-pyridyl)(phenyl) | N(3-pyridyl)(phenyl) | H |
| 6-11 | biphenyl | biphenyl | N(1-naphthyl)(1-naphthyl) | N(1-naphthyl)(1-naphthyl) | H |
| 6-12 | biphenyl | biphenyl | N(9,9-dimethylfluorenyl)(phenyl) | N(9,9-dimethylfluorenyl)(phenyl) | H |
| 6-13 | biphenyl | biphenyl | N(9,9-dimethylfluorenyl)(dibenzofuranyl) | N(9,9-dimethylfluorenyl)(dibenzofuranyl) | H |

| Compound | X | Y | R1 | R2 | R3 to R6 |
|---|---|---|---|---|---|
| 6-14 | 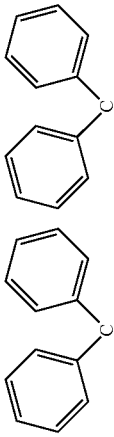 | 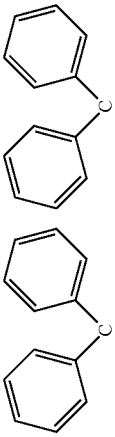 | 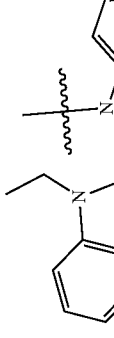 | 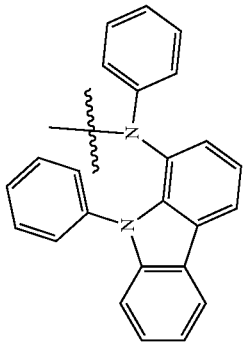 | H |
| 6-15 | 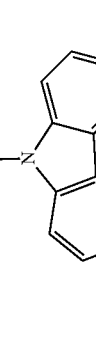 | 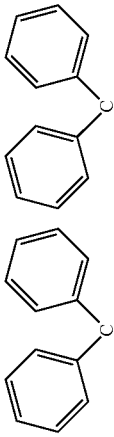 | 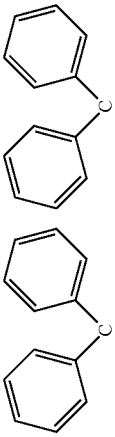 | 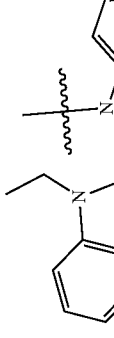 | H |
| 6-16 | 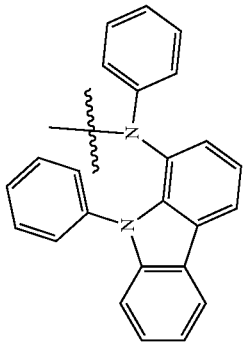 | 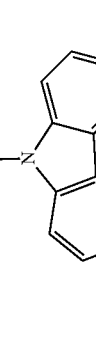 | 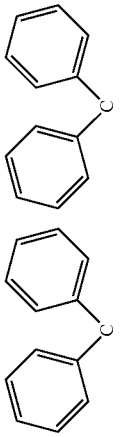 | 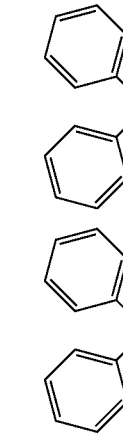 | H |
| 6-17 | 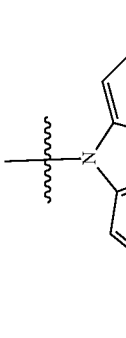 | 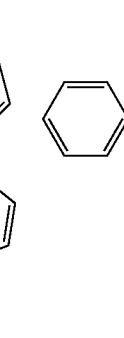 | 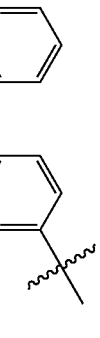 | 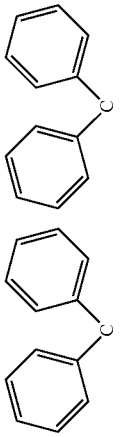 | H |

-continued

| Compound | X | Y | R1 | R2 | R3 to R6 |
|---|---|---|---|---|---|
| 6-18 | biphenyl | biphenyl | 5-phenylthiophen-2-yl(phenyl)amino | 5-phenylthiophen-2-yl(phenyl)amino | H |
| 6-19 | biphenyl | biphenyl | di(dibenzofuran-yl)amino | di(dibenzofuran-yl)amino | H |
| 6-20 | biphenyl | biphenyl | phenyl(pyridin-3-yl)amino | phenyl(pyridin-3-yl)amino | H |
| 6-21 | biphenyl | biphenyl | (4-tert-butylphenyl)(naphthalen-1-yl)amino | (4-tert-butylphenyl)(naphthalen-1-yl)amino | H |

| Compound | X1 | X2 | R1 | R2 | R3 to R6 |
|---|---|---|---|---|---|
| 7-1 | O | S | 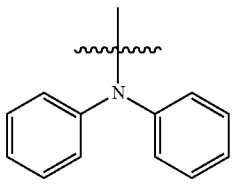 [SMILES: *N(c1ccccc1)c1ccccc1] | 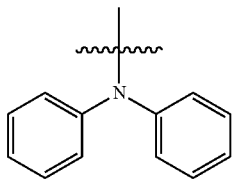 [SMILES: *N(c1ccccc1)c1ccccc1] | H |
| 7-2 | O |  |  | 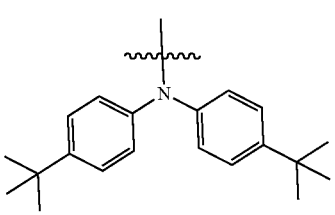 | H |
| 7-3 | O |  |  | 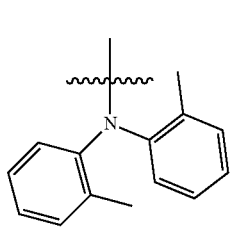 | H |
| 7-4 | O |  |  | 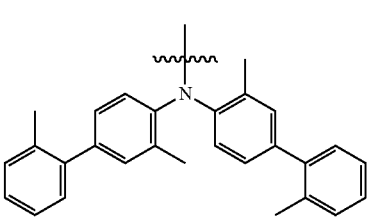 [SMILES: *N(c1ccc(-c2ccccc2C)cc1C)c1ccc(-c2ccccc2C)cc1C] | H |
| 7-5 | O |  |  | 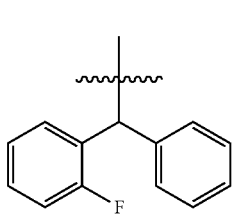 [SMILES: *N(c1ccccc1)c1ccccc1F] | H |
| 7-6 | S | 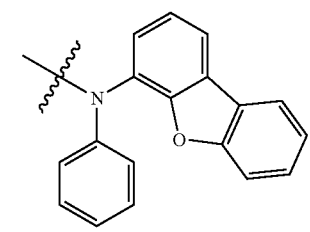 [SMILES: *N(c1ccccc1)c1cccc2c1oc1ccccc12] | 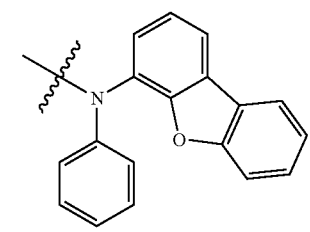 [SMILES: *N(c1ccccc1)c1cccc2c1oc1ccccc12] | 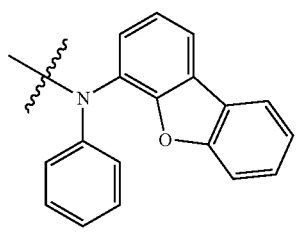 [SMILES: *N(c1ccccc1)c1cccc2c1oc1ccccc12] | H |
| 7-7 | S | 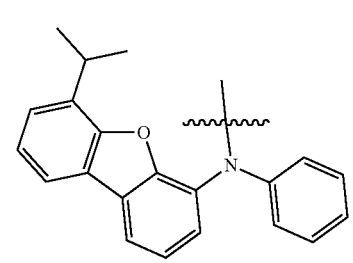 [SMILES: *N(c1ccccc1)c1cccc2c1oc1c(C(C)C)cccc12] | 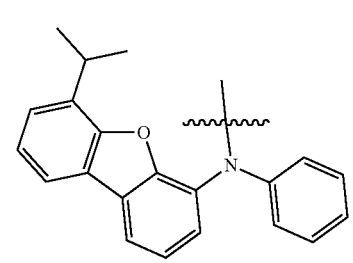 [SMILES: *N(c1ccccc1)c1cccc2c1oc1c(C(C)C)cccc12] | 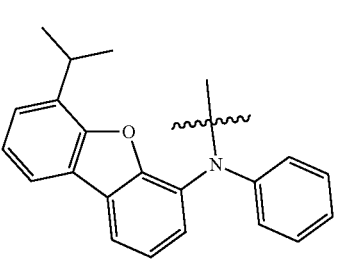 [SMILES: *N(c1ccccc1)c1cccc2c1oc1c(C(C)C)cccc12] | H |

-continued
| Compound | X1 | X2 | R1 | R2 | R3 to R6 |
|---|---|---|---|---|---|
| 7-8 | S |  | 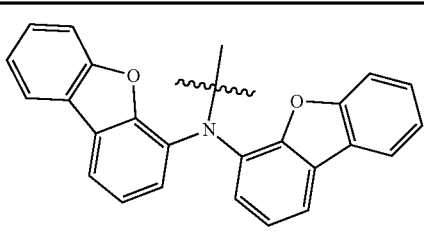 | 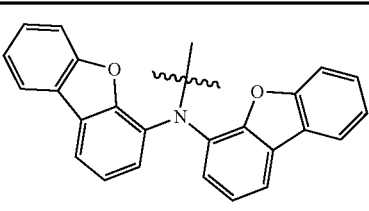 | H |
| 7-9 | S | 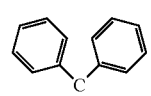 | 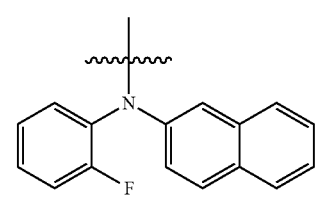 [SMILES: *N(c1ccc2ccccc2c1)c1ccccc1F] | 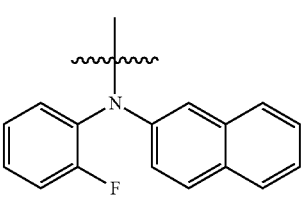 [SMILES: *N(c1ccc2ccccc2c1)c1ccccc1F] | H |
| 7-10 | 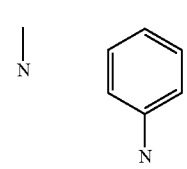 | 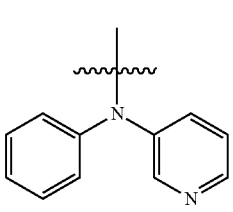 [SMILES: *N(c1ccccc1)c1cccnc1] | 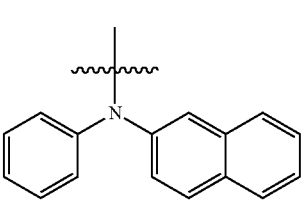 [SMILES: *N(c1ccccc1)c1ccc2ccccc2c1] | 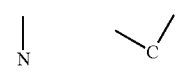 | H |
| 7-11 |  | 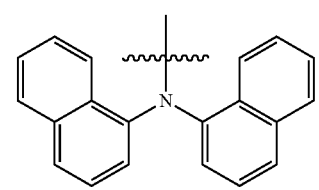 [SMILES: *N(c1cccc2ccccc12)c1cccc2ccccc12] | 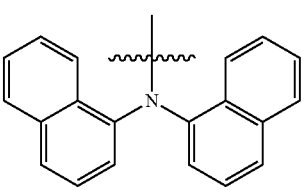 [SMILES: *N(c1cccc2ccccc12)c1cccc2ccccc12] | 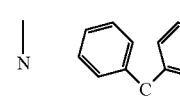 | H |
| 7-12 | 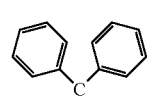 | 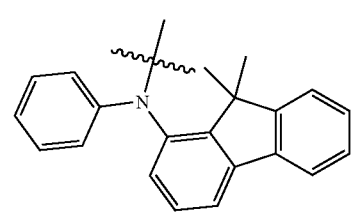 [SMILES: *N(c1ccccc1)c1cccc2c1C(C)(C)c1ccccc1-2] | 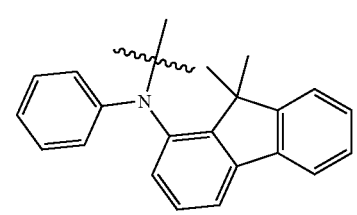 [SMILES: *N(c1ccccc1)c1cccc2c1C(C)(C)c1ccccc1-2] |  | H |
| 7-13 |  | 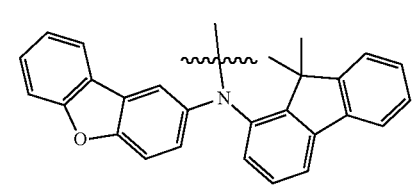 [SMILES: *N(c1ccc2oc3ccccc3c2c1)c1cccc2c1C(C)(C)c1ccccc1-2] | 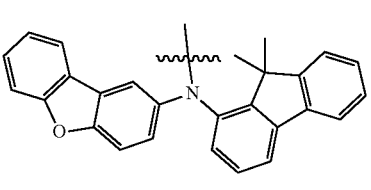 [SMILES: *N(c1ccc2oc3ccccc3c2c1)c1cccc2c1C(C)(C)c1ccccc1-2] | 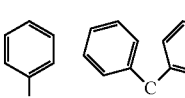 | H |
| 7-14 | 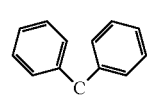 | 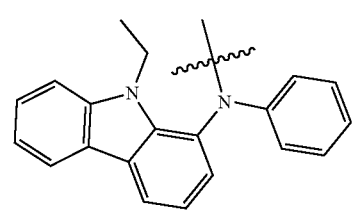 [SMILES: *N(c1ccccc1)c1cccc2c3ccccc3n(CC)c12] | 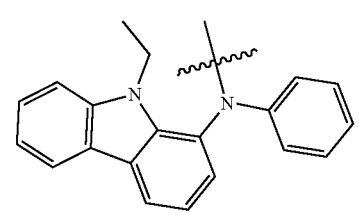 [SMILES: *N(c1ccccc1)c1cccc2c3ccccc3n(CC)c12] | | H |

-continued
| Compound | X1 | X2 | R1 | R2 | R3 to R6 |
|---|---|---|---|---|---|
| 7-15 |  | 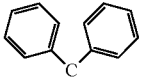 | 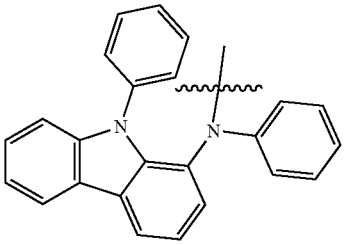 [SMILES: *N(c1ccccc1)c1cccc2c3ccccc3n(-c3ccccc3)c12] | 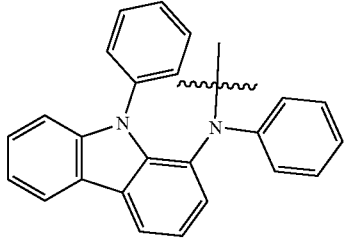 [SMILES: *N(c1ccccc1)c1cccc2c3ccccc3n(-c3ccccc3)c12] | H |
| 7-16 | O | S | 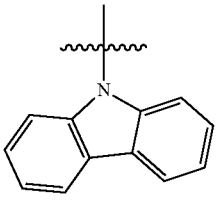 [SMILES: *n1c2ccccc2c2ccccc21] | 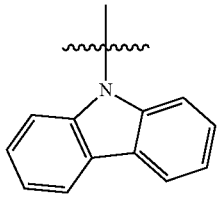 [SMILES: *n1c2ccccc2c2ccccc21] | H |
| 7-17 | O | 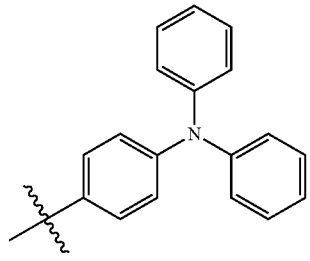 [SMILES: *c1ccc(N(c2ccccc2)c2ccccc2)cc1] | 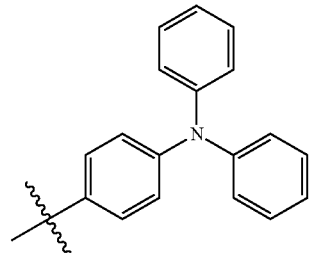 [SMILES: *c1ccc(N(c2ccccc2)c2ccccc2)cc1] | 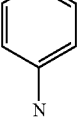 | H |
| 7-18 | O | 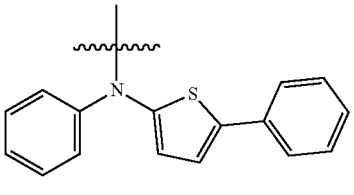 [SMILES: *N(c1ccccc1)c1ccc(-c2ccccc2)s1] | 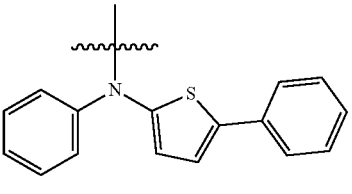 [SMILES: *N(c1ccccc1)c1ccc(-c2ccccc2)s1] |  | H |
| 7-19 | O | 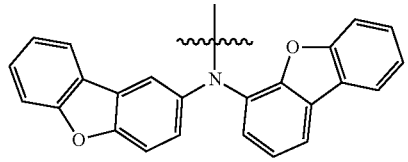 [SMILES: *N(c1ccc2oc3ccccc3c2c1)c1cccc2c1oc1ccccc12] | 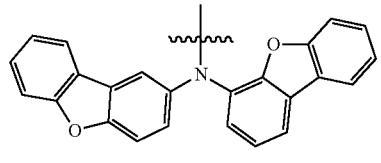 [SMILES: *N(c1ccc2oc3ccccc3c2c1)c1cccc2c1oc1ccccc12] | 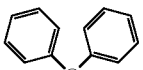 | H |
| 7-20 | O | 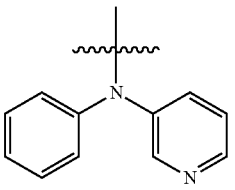 [SMILES: *N(c1ccccc1)c1cccnc1] | 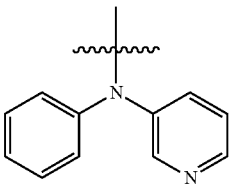 [SMILES: *N(c1ccccc1)c1cccnc1] | | H |

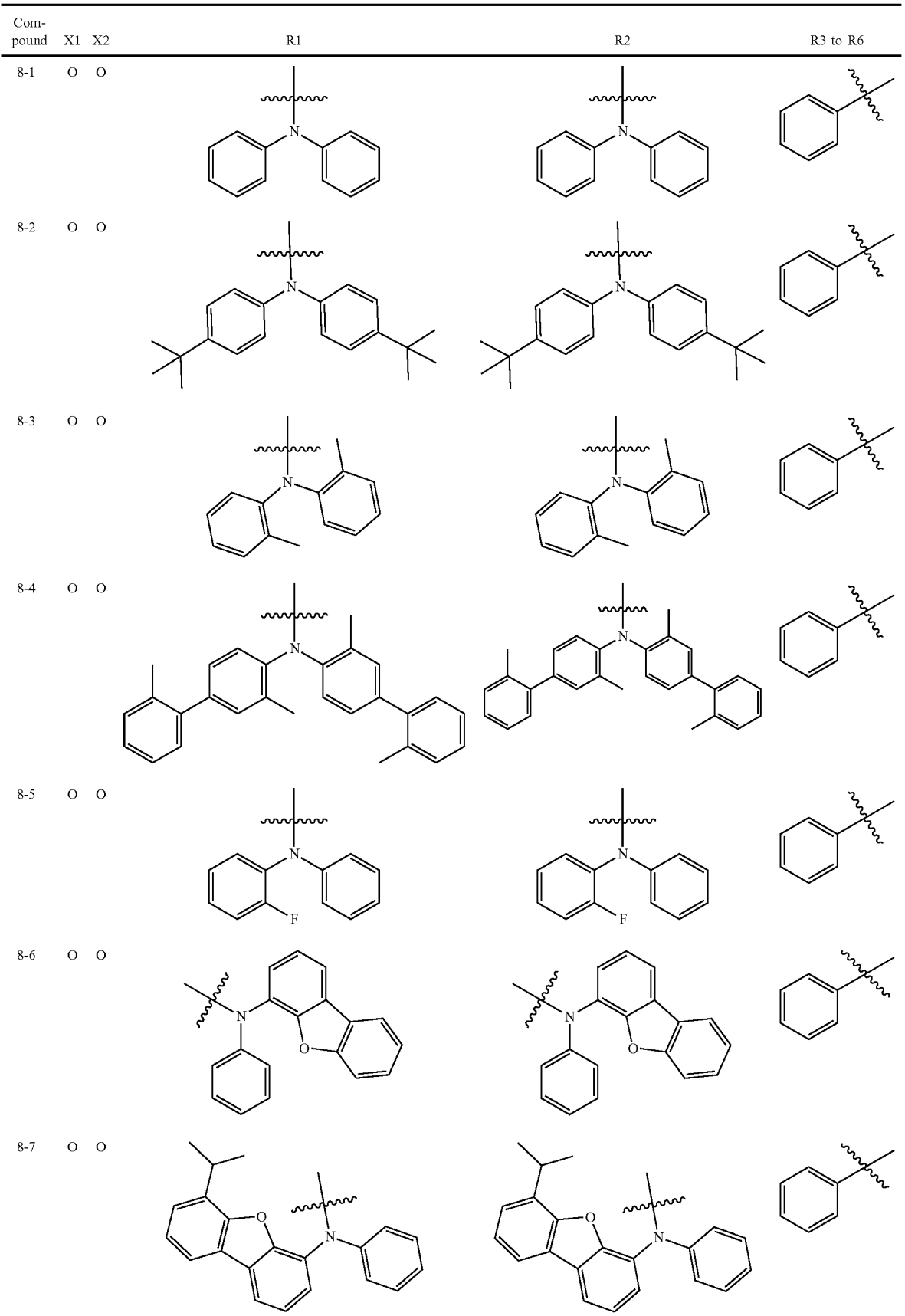

-continued

| Compound | X1 | X2 | R1 | R2 | R3 to R6 |
|---|---|---|---|---|---|
| 8-8 | O | O | | | |
| 8-9 | O | O | | | |
| 8-10 | O | O | | | |
| 8-11 | O | O | | | |
| 8-12 | O | O | | | |
| 8-13 | O | O | | | |
| 8-14 | O | O | | | |

-continued

| Compound | X1 | X2 | R1 | R2 | R3 to R6 |
|---|---|---|---|---|---|
| 8-15 | O | O | N-phenylcarbazol-1-yl-N-phenylamino | N-phenylcarbazol-1-yl-N-phenylamino | phenyl |
| 8-16 | O | O | carbazol-9-yl | carbazol-9-yl | phenyl |
| 8-17 | O | O | 4-(diphenylamino)phenyl | 4-(diphenylamino)phenyl | phenyl |
| 8-18 | O | O | N-phenyl-N-(5-phenylthiophen-2-yl)amino | N-phenyl-N-(5-phenylthiophen-2-yl)amino | phenyl |
| 8-19 | O | O | N-(dibenzofuran-2-yl)-N-(dibenzofuran-4-yl)amino | N-(dibenzofuran-2-yl)-N-(dibenzofuran-4-yl)amino | phenyl |
| 8-20 | O | O | N-phenyl-N-(pyridin-3-yl)amino | N-phenyl-N-(pyridin-3-yl)amino | phenyl |

| Compound | X1 | X2 | R1 | R2 | R3 to R6 |
|---|---|---|---|---|---|
| 9-1 | S | S | 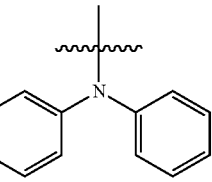 | 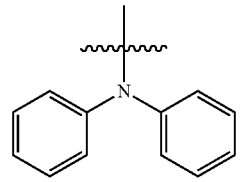 [SMILES: *N(c1ccccc1)c1ccccc1] | —CH₃ |
| 9-2 | S | S | 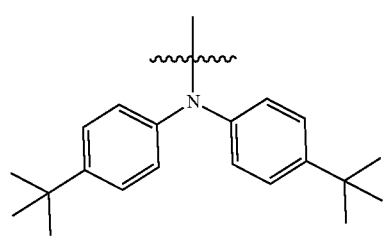 [SMILES: *N(c1ccc(C(C)(C)C)cc1)c1ccc(C(C)(C)C)cc1] | 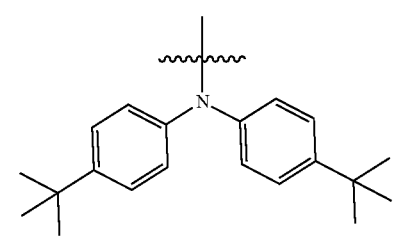 [SMILES: *N(c1ccc(C(C)(C)C)cc1)c1ccc(C(C)(C)C)cc1] | —CH₃ |
| 9-3 | S | S |  | 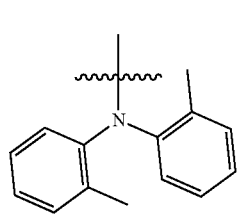 | —CH₃ |
| 9-4 | S | S | 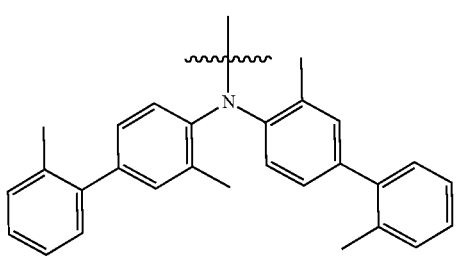 [SMILES: *N(c1ccc(-c2ccccc2C)cc1C)c1ccc(-c2ccccc2C)cc1C] | 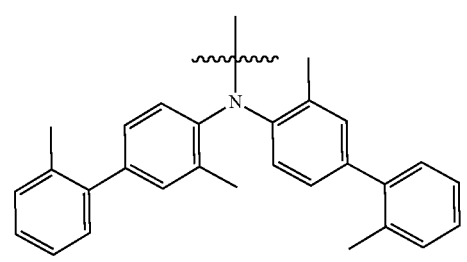 [SMILES: *N(c1ccc(-c2ccccc2C)cc1C)c1ccc(-c2ccccc2C)cc1C] | —CH₃ |
| 9-5 | S | S | 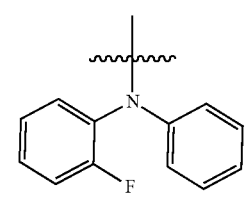 [SMILES: *N(c1ccccc1)c1ccccc1F] | 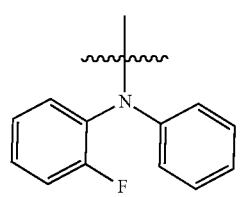 | —CH₃ |
| 9-6 | S | S | 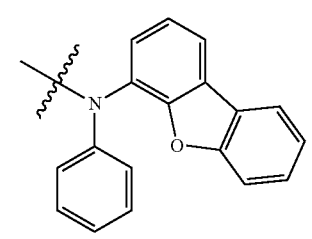 [SMILES: *N(c1ccccc1)c1cccc2c1oc1ccccc12] | 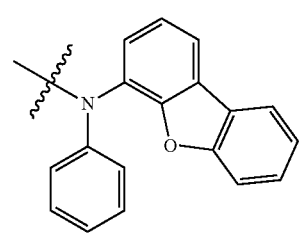 [SMILES: *N(c1ccccc1)c1cccc2c1oc1ccccc12] | —CH₃ |
| 9-7 | S | S | 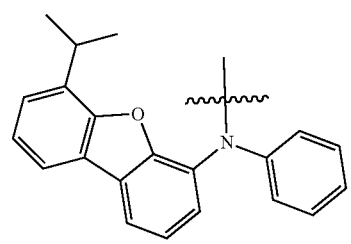 [SMILES: *N(c1ccccc1)c1cccc2c1oc1c(C(C)C)cccc12] | 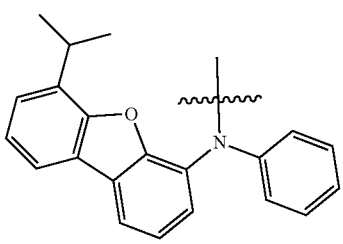 [SMILES: *N(c1ccccc1)c1cccc2c1oc1c(C(C)C)cccc12] | —CH₃ |

-continued
| Compound | X1 | X2 | R1 | R2 | R3 to R6 |
|---|---|---|---|---|---|
| 9-8 | S | S | 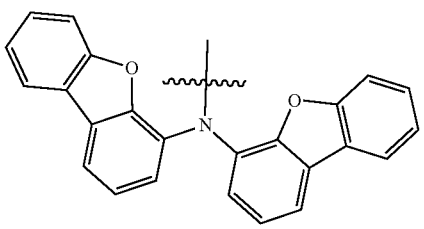 [SMILES: *N(c1cccc2c1oc1ccccc12)c1cccc2c1oc1ccccc12] | 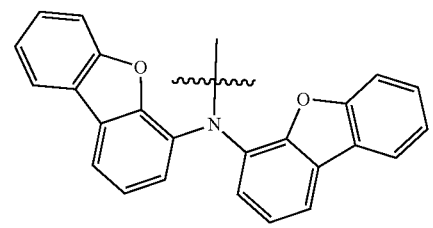 [SMILES: *N(c1cccc2c1oc1ccccc12)c1cccc2c1oc1ccccc12] | —CH₃ |
| 9-9 | S | S | 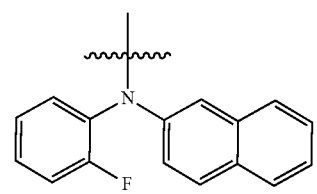 [SMILES: *N(c1ccc2ccccc2c1)c1ccccc1F] | 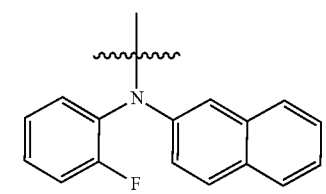 | —CH₃ |
| 9-10 | S | S | 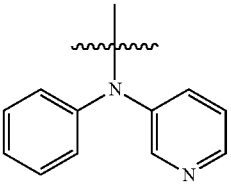 [SMILES: *N(c1ccccc1)c1cccnc1] | 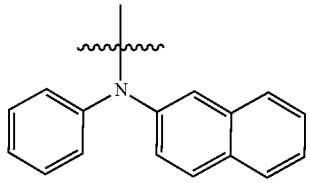 [SMILES: *N(c1ccccc1)c1ccc2ccccc2c1] | —CH₃ |
| 9-11 | S | S | 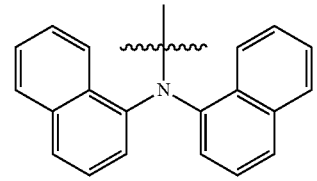 | 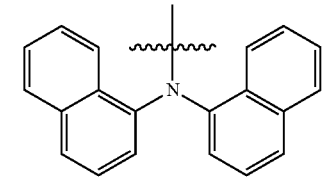 [SMILES: *N(c1cccc2ccccc12)c1cccc2ccccc12] | —CH₃ |
| 9-12 | S | S | 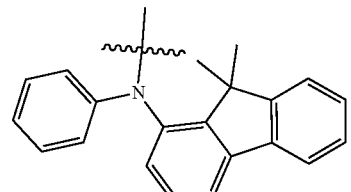 | 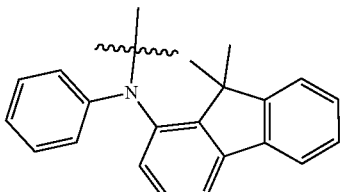 | —CH₃ |
| 9-13 | S | S | 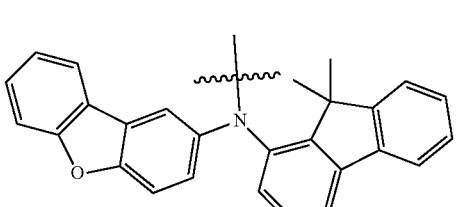 | 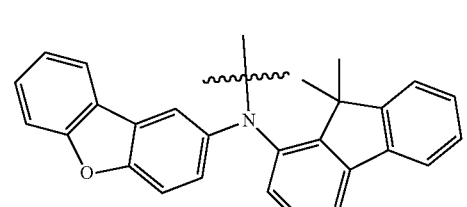 | —CH₃ |
| 9-14 | S | S | 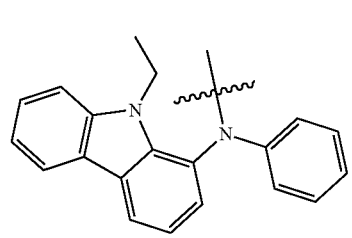 [SMILES: *N(c1ccccc1)c1cccc2c3ccccc3n(CC)c12] | 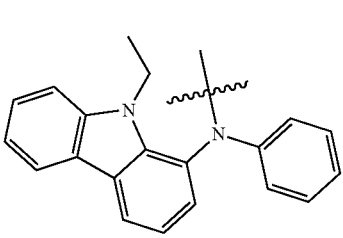 [SMILES: *N(c1ccccc1)c1cccc2c3ccccc3n(CC)c12] | —CH₃ |

-continued
| Compound | X1 | X2 | R1 | R2 | R3 to R6 |
|---|---|---|---|---|---|
| 9-15 | S | S | 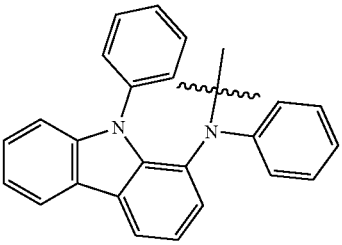 [SMILES: *N(c1ccccc1)c1cccc2c3ccccc3n(-c3ccccc3)c12] | 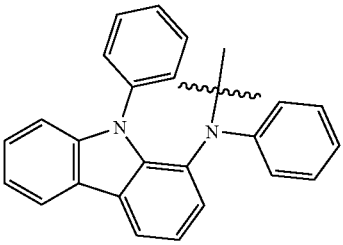 [SMILES: *N(c1ccccc1)c1cccc2c3ccccc3n(-c3ccccc3)c12] | —CH$_3$ |
| 9-16 | S | S | 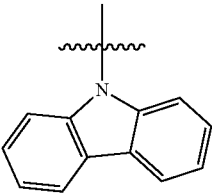 [SMILES: *n1c2ccccc2c2ccccc21] | 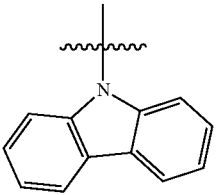 [SMILES: *n1c2ccccc2c2ccccc21] | —CH$_3$ |
| 9-17 | S | S | 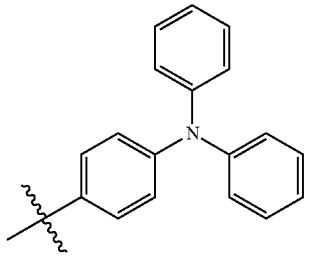 [SMILES: *c1ccc(N(c2ccccc2)c2ccccc2)cc1] | 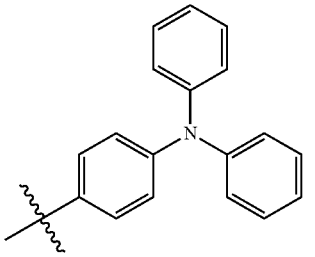 [SMILES: *c1ccc(N(c2ccccc2)c2ccccc2)cc1] | —CH$_3$ |
| 9-18 | S | S | 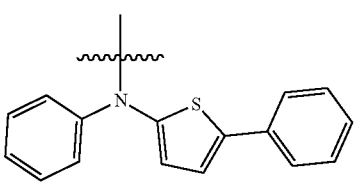 [SMILES: *N(c1ccccc1)c1ccc(-c2ccccc2)s1] | 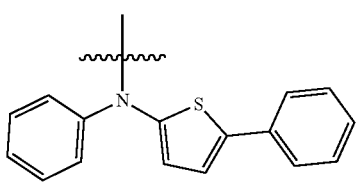 [SMILES: *N(c1ccccc1)c1ccc(-c2ccccc2)s1] | —CH$_3$ |
| 9-19 | S | S | 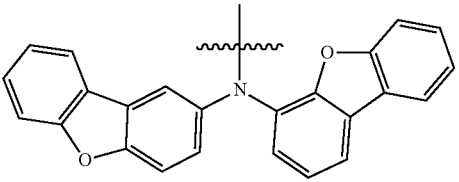 [SMILES: *N(c1ccc2oc3ccccc3c2c1)c1cccc2c1oc1ccccc12] | 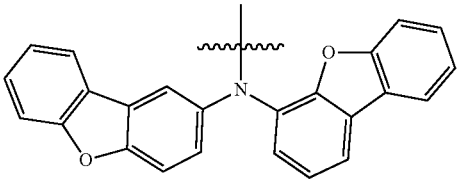 [SMILES: *N(c1ccc2oc3ccccc3c2c1)c1cccc2c1oc1ccccc12] | —CH$_3$ |
| 9-20 | S | S | 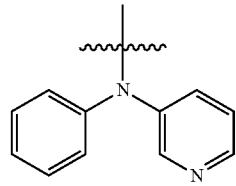 [SMILES: *N(c1ccccc1)c1cccnc1] | 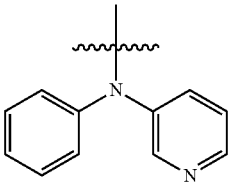 [SMILES: *N(c1ccccc1)c1cccnc1] | —CH$_3$ |

| Compound | X1 | X2 | R1 | R2 | R3 to R6 |
|---|---|---|---|---|---|
| 10-1 | N | N | N(Ph)(Ph)– | N(Ph)(Ph)– | t-Bu |
| 10-2 | N | N | N(4-t-Bu-C6H4)2– | N(4-t-Bu-C6H4)2– | t-Bu |
| 10-3 | N | N | N(2-Me-C6H4)2– | N(2-Me-C6H4)2– | t-Bu |
| 10-4 | N | N | N(3-Me-2'-Me-biphenyl-4-yl)2– | N(3-Me-2'-Me-biphenyl-4-yl)2– | t-Bu |
| 10-5 | N | N | N(Ph)(2-F-C6H4)– | N(Ph)(2-F-C6H4)– | t-Bu |
| 10-6 | N | N | N(Ph)(dibenzofuran-4-yl)– | N(Ph)(dibenzofuran-4-yl)– | t-Bu |
| 10-7 | N | N | N(Ph)(6-iPr-dibenzofuran-4-yl)– | N(Ph)(6-iPr-dibenzofuran-4-yl)– | t-Bu |

-continued
| Compound | X1 | X2 | R1 | R2 | R3 to R6 |
|---|---|---|---|---|---|
| 10-8 |  |  | 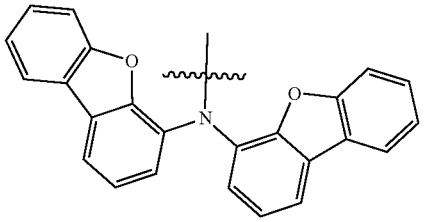 [SMILES: *N(c1cccc2c1oc1ccccc12)c1cccc2c1oc1ccccc12] | 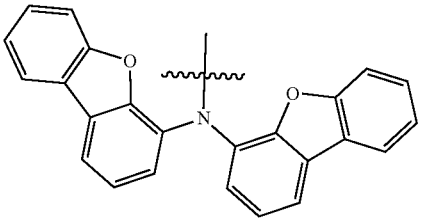 [SMILES: *N(c1cccc2c1oc1ccccc12)c1cccc2c1oc1ccccc12] | 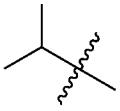 [SMILES: *C(C)C] |
| 10-9 |  |  | 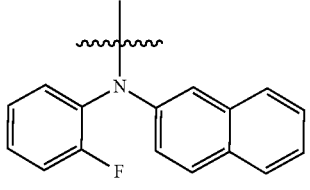 [SMILES: *N(c1ccc2ccccc2c1)c1ccccc1F] | 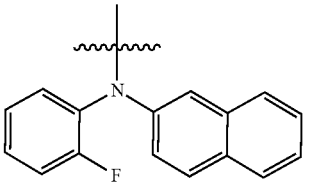 [SMILES: *N(c1ccc2ccccc2c1)c1ccccc1F] | 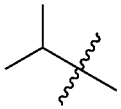 [SMILES: *C(C)C] |
| 10-10 |  |  | 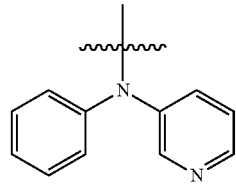 [SMILES: *N(c1ccccc1)c1cccnc1] | 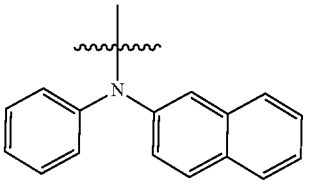 [SMILES: *N(c1ccccc1)c1ccc2ccccc2c1] | 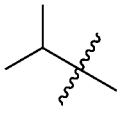 [SMILES: *C(C)C] |
| 10-11 |  |  | 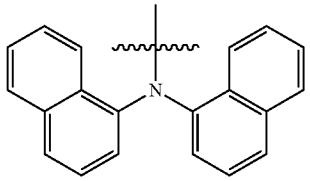 | 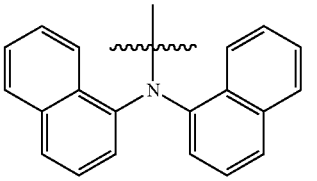 [SMILES: *N(c1cccc2ccccc12)c1cccc2ccccc12] | 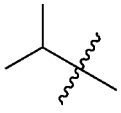 [SMILES: *C(C)C] |
| 10-12 |  |  | 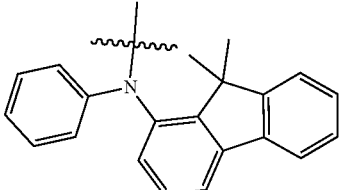 | 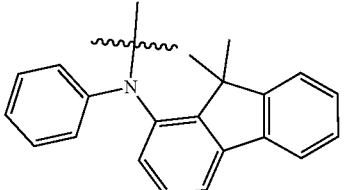 | 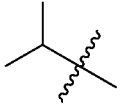 [SMILES: *C(C)C] |
| 10-13 |  |  | 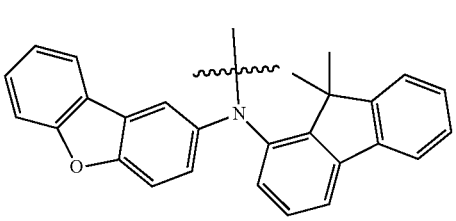 [SMILES: *N(c1ccc2oc3ccccc3c2c1)c1cccc2c1C(C)(C)c1ccccc1-2] | 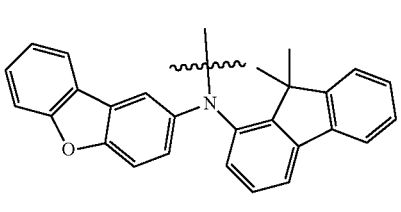 [SMILES: *N(c1ccc2oc3ccccc3c2c1)c1cccc2c1C(C)(C)c1ccccc1-2] | 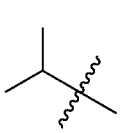 [SMILES: *C(C)C] |
| 10-14 |  |  | 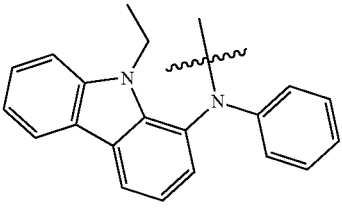 [SMILES: *N(c1ccccc1)c1cccc2c3ccccc3n(CC)c12] | 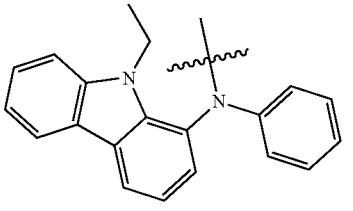 [SMILES: *N(c1ccccc1)c1cccc2c3ccccc3n(CC)c12] | 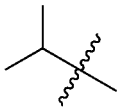 [SMILES: *C(C)C] |

-continued
| Compound | X1 | X2 | R1 | R2 | R3 to R6 |
|---|---|---|---|---|---|
| 10-15 | N | N |  | 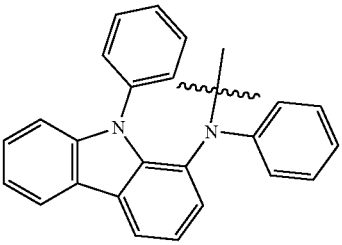 [SMILES: *N(c1ccccc1)c1cccc2c3ccccc3n(-c3ccccc3)c12] | 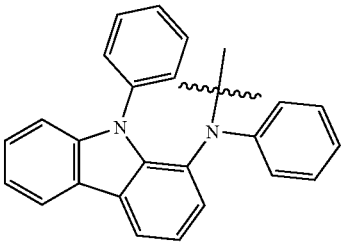 [SMILES: *N(c1ccccc1)c1cccc2c3ccccc3n(-c3ccccc3)c12] |
| 10-16 | N | N |  | 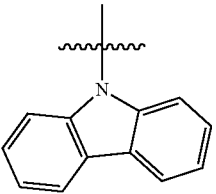 [SMILES: *n1c2ccccc2c2ccccc21] | 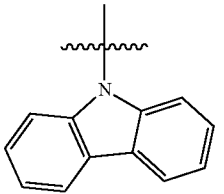 [SMILES: *n1c2ccccc2c2ccccc21] |
| 10-17 | N | N |  | 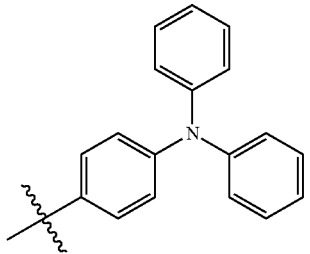 [SMILES: *c1ccc(N(c2ccccc2)c2ccccc2)cc1] | 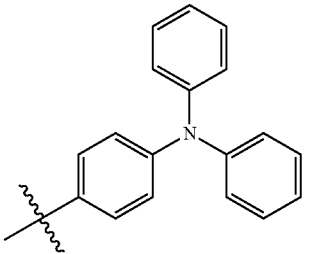 [SMILES: *c1ccc(N(c2ccccc2)c2ccccc2)cc1] |
| 10-18 | N | N |  | 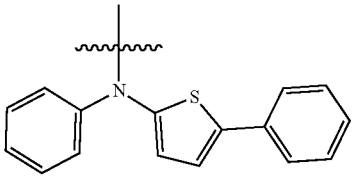 [SMILES: *N(c1ccccc1)c1ccc(-c2ccccc2)s1] | 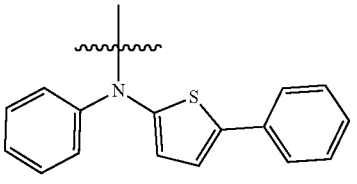 [SMILES: *N(c1ccccc1)c1ccc(-c2ccccc2)s1] |
| 10-19 | N | N |  | 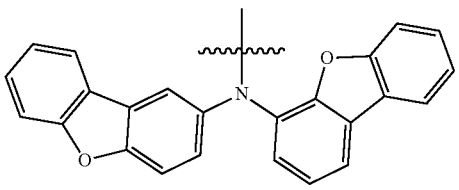 [SMILES: *N(c1ccc2oc3ccccc3c2c1)c1cccc2c1oc1ccccc12] | 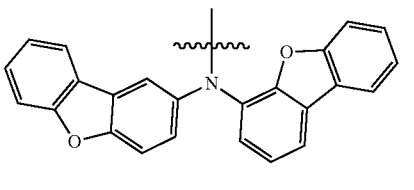 [SMILES: *N(c1ccc2oc3ccccc3c2c1)c1cccc2c1oc1ccccc12] |
| 10-20 | N | N |  | 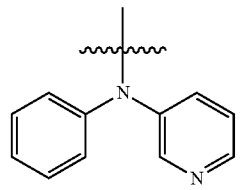 [SMILES: *N(c1ccccc1)c1cccnc1] | 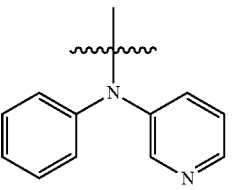 [SMILES: *N(c1ccccc1)c1cccnc1] |

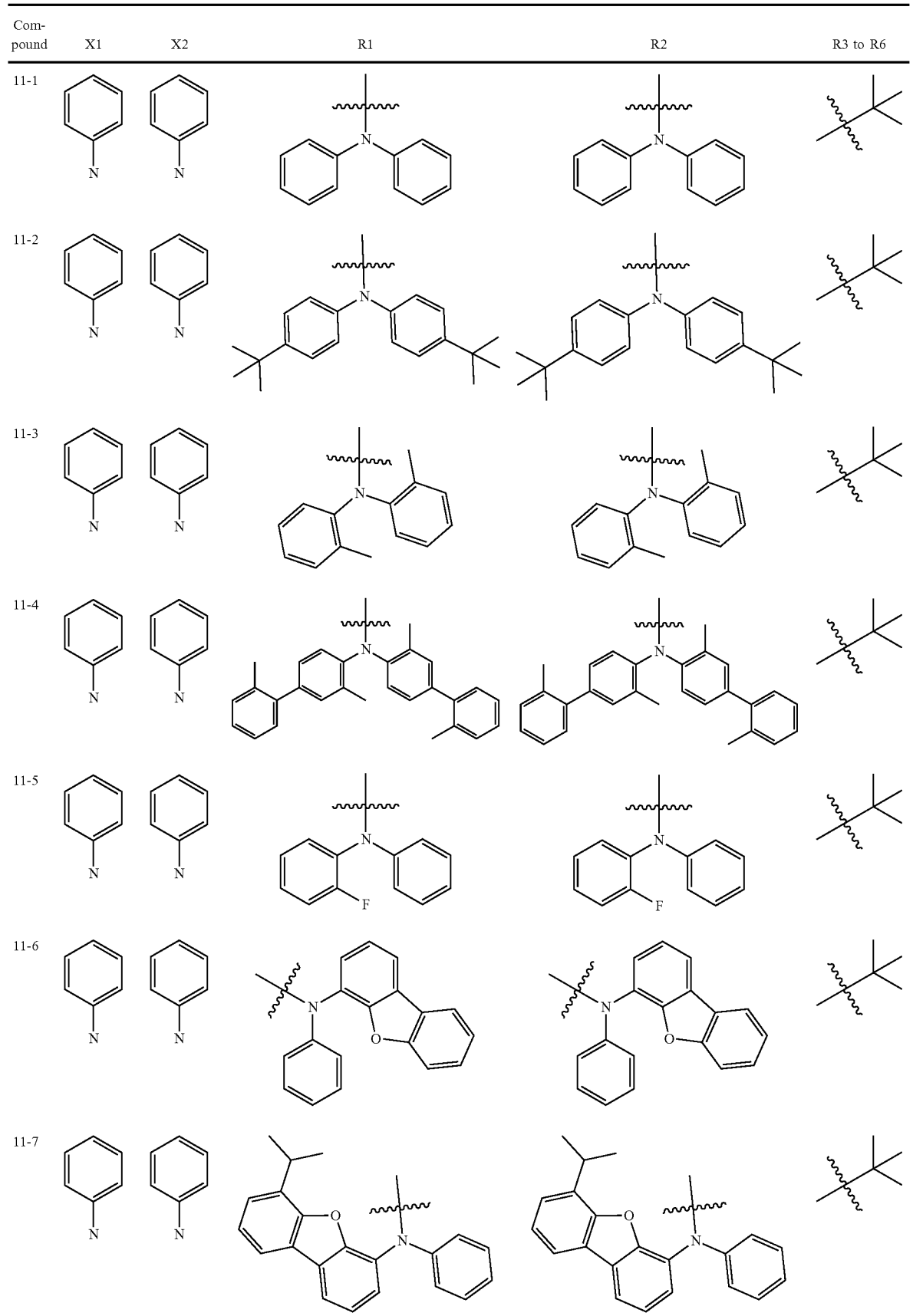

-continued

| Compound | X1 | X2 | R1 | R2 | R3 to R6 |
|---|---|---|---|---|---|
| 11-8 | | | | | |
| 11-9 | | | | | |
| 11-10 | | | | | |
| 11-11 | | | | | |
| 11-12 | | | | | |
| 11-13 | | | | | |
| 11-14 | | | | | |

| Compound | X1 | X2 | R1 | R2 | R3 to R6 |
|---|---|---|---|---|---|
| 11-15 | pyridine | pyridine | N-phenyl-carbazol-1-yl-N-phenylamino | N-phenyl-carbazol-1-yl-N-phenylamino | tert-butyl |
| 11-16 | pyridine | pyridine | carbazol-9-yl | carbazol-9-yl | tert-butyl |
| 11-17 | pyridine | pyridine | 4-(diphenylamino)phenyl | 4-(diphenylamino)phenyl | tert-butyl |
| 11-18 | pyridine | pyridine | N-phenyl-N-(5-phenylthiophen-2-yl)amino | N-phenyl-N-(5-phenylthiophen-2-yl)amino | tert-butyl |
| 11-19 | pyridine | pyridine | N,N-di(dibenzofuranyl)amino | N,N-di(dibenzofuranyl)amino | tert-butyl |
| 11-20 | pyridine | pyridine | N-phenyl-N-(pyridin-3-yl)amino | N-phenyl-N-(pyridin-3-yl)amino | tert-butyl |

| Compound | X | X | R1 |
|---|---|---|---|
| 12-1 | C | C | diphenylamino |

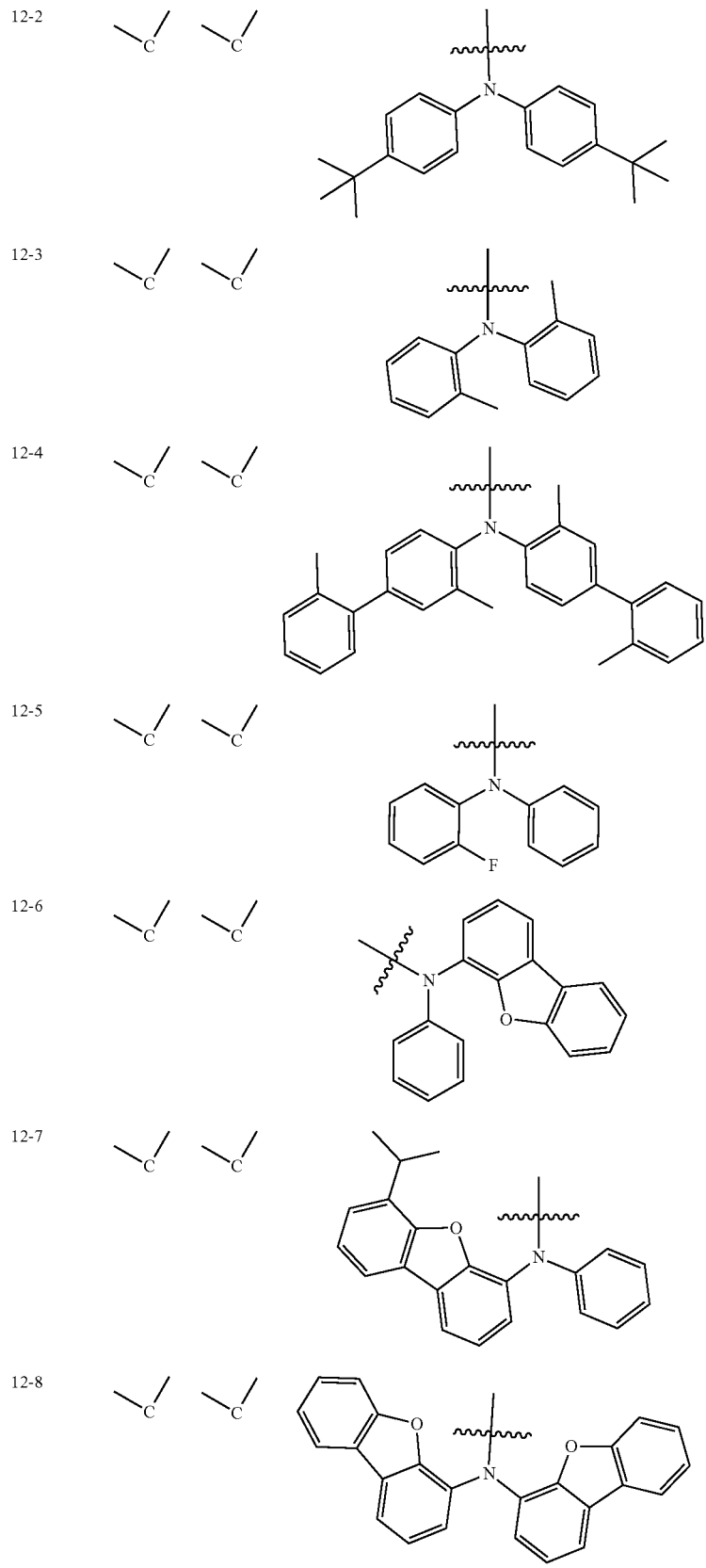

-continued
| | | |
|---|---|---|
| 12-9 | 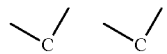 | 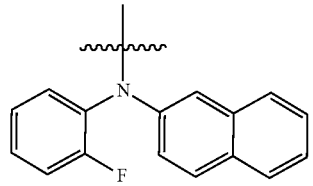 [SMILES: *N(c1ccc2ccccc2c1)c1ccccc1F] |
| 12-10 | 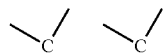 | 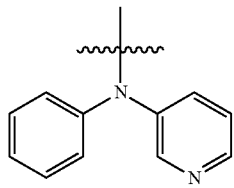 [SMILES: *N(c1ccccc1)c1cccnc1] |
| 12-11 | 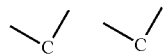 | 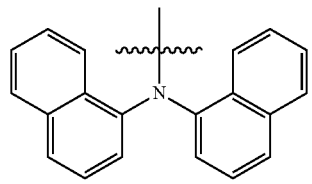 [SMILES: *N(c1cccc2ccccc12)c1cccc2ccccc12] |
| 12-12 | 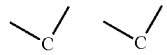 | 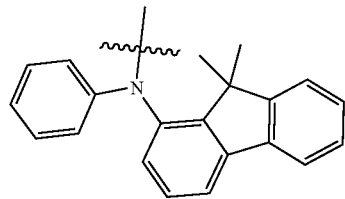 [SMILES: *N(c1ccccc1)c1cccc2c1C(C)(C)c1ccccc1-2] |
| 12-13 | 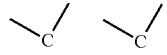 | 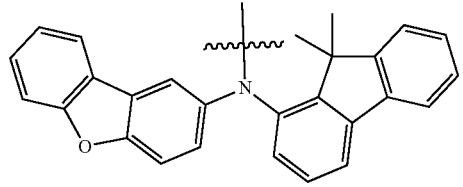 [SMILES: *N(c1ccc2oc3ccccc3c2c1)c1cccc2c1C(C)(C)c1ccccc1-2] |
| 12-14 | 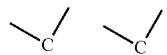 | 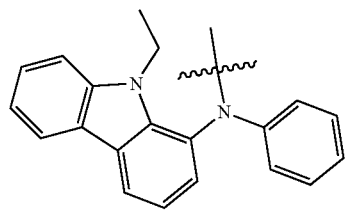 [SMILES: *N(c1ccccc1)c1cccc2c3ccccc3n(CC)c12] |
| 12-15 | 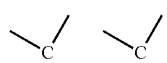 | 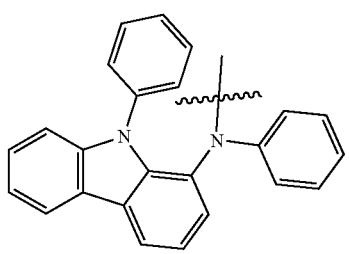 [SMILES: *N(c1ccccc1)c1cccc2c3ccccc3n(-c3ccccc3)c12] |

-continued
| | | |
|---|---|---|
| 12-16 | 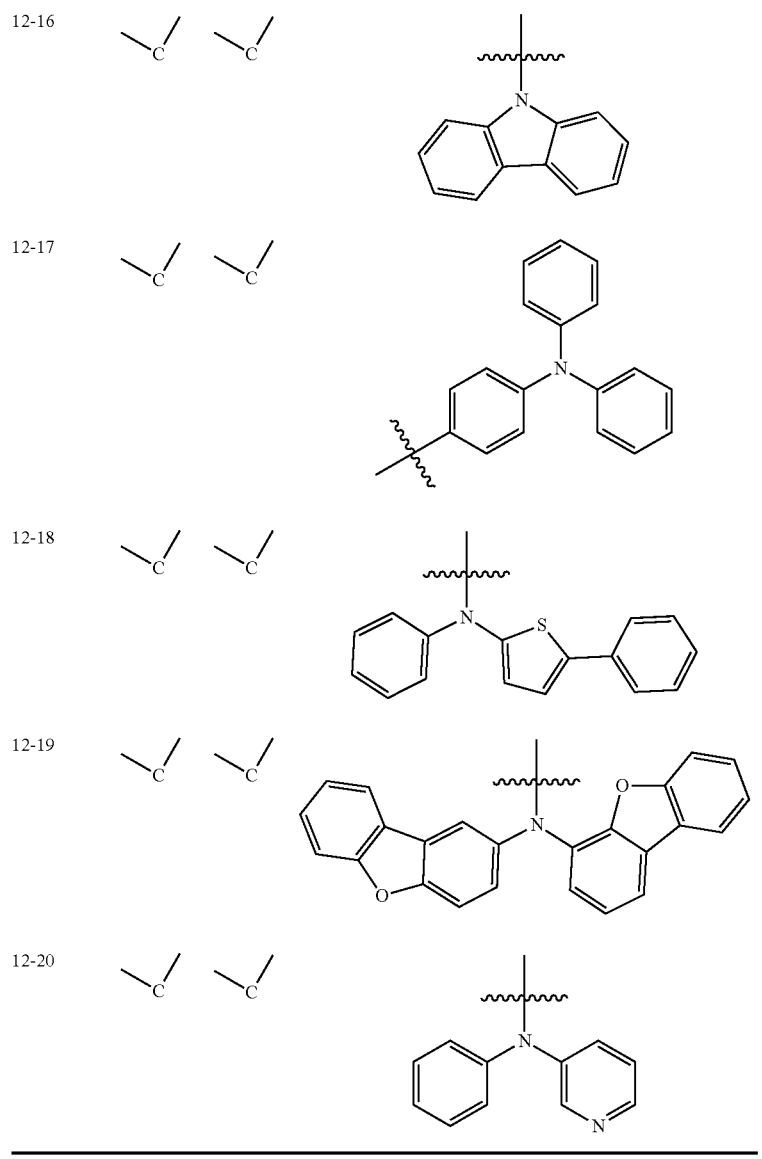 | |
| 12-17 | | |
| 12-18 | | |
| 12-19 | | |
| 12-20 | | |
| Compound | R2 | R3 to R6 |
|---|---|---|
| 12-1 | 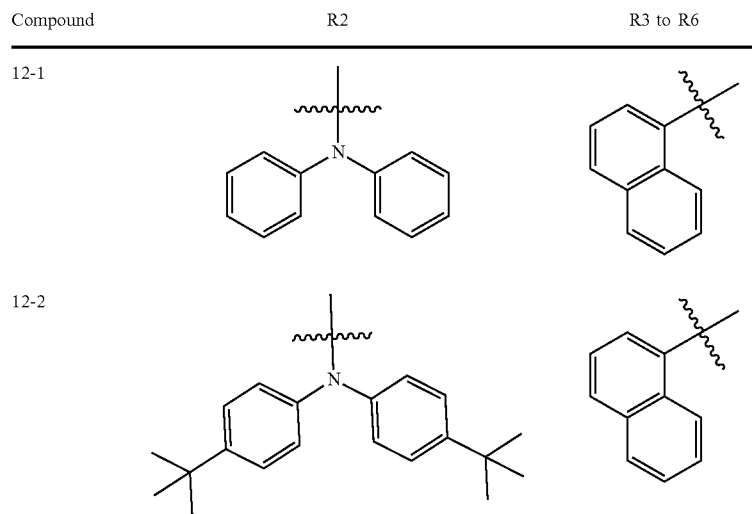 | |
| 12-2 | | |

| | | |
|---|---|---|
| 12-3 | 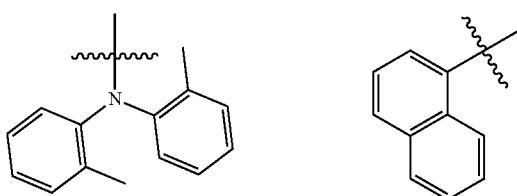 | |
| 12-4 | 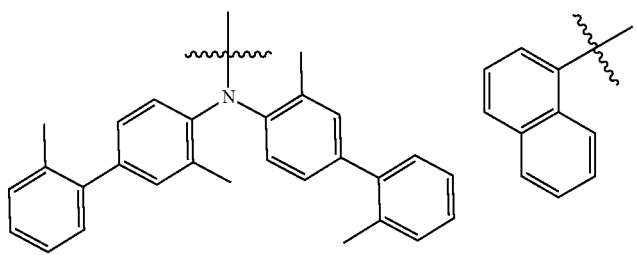 | |
| 12-5 | 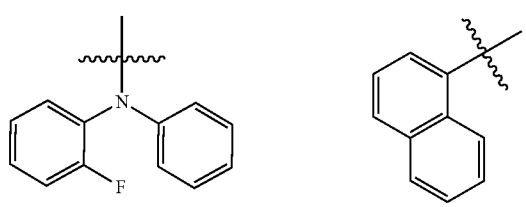 | |
| 12-6 | 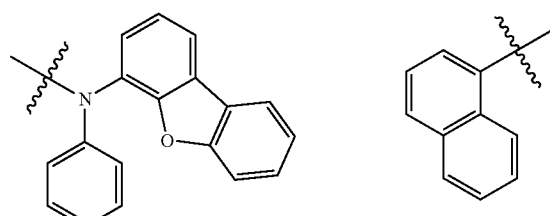 | |
| 12-7 | 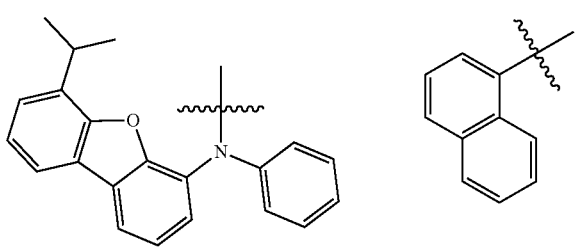 | |
| 12-8 | 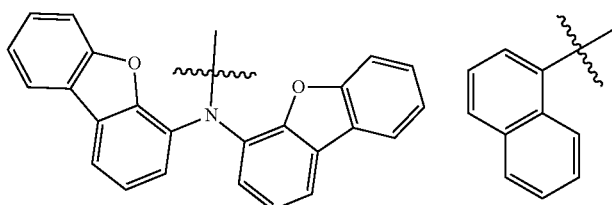 | |
| 12-9 | 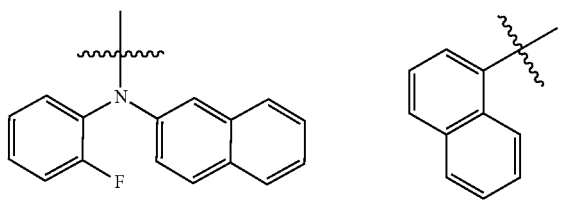 | |

-continued
| | | |
|---|---|---|
| 12-10 | 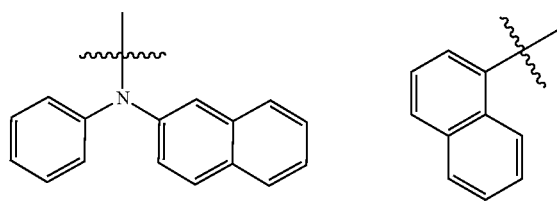 | 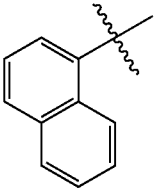 [SMILES: *c1cccc2ccccc12] |
| 12-11 | 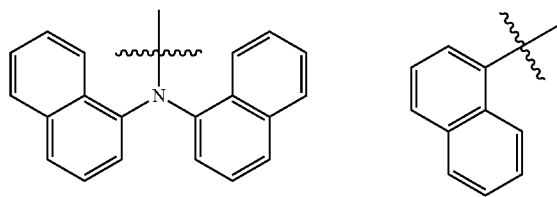 | 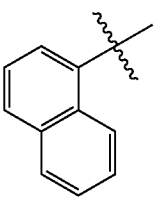 [SMILES: *c1cccc2ccccc12] |
| 12-12 | 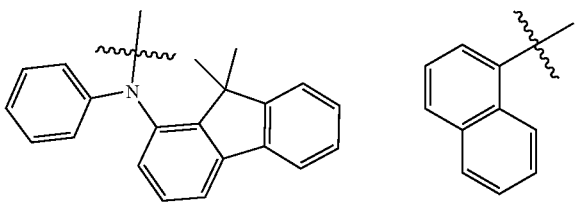 | 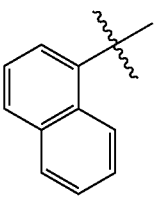 [SMILES: *c1cccc2ccccc12] |
| 12-13 | 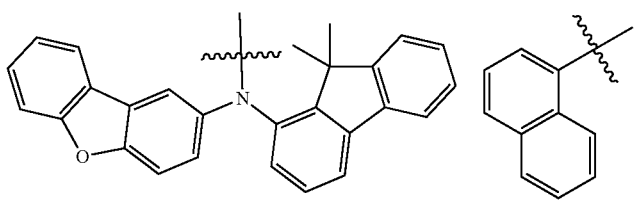 | 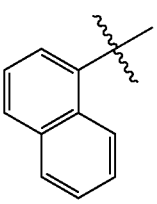 [SMILES: *c1cccc2ccccc12] |
| 12-14 | 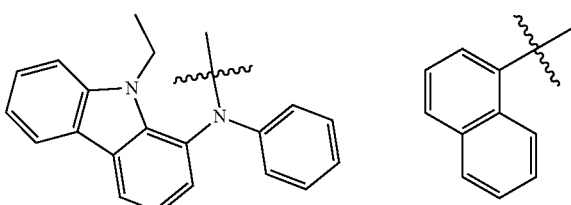 | 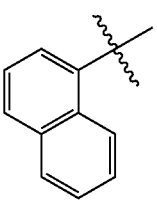 [SMILES: *c1cccc2ccccc12] |
| 12-15 | 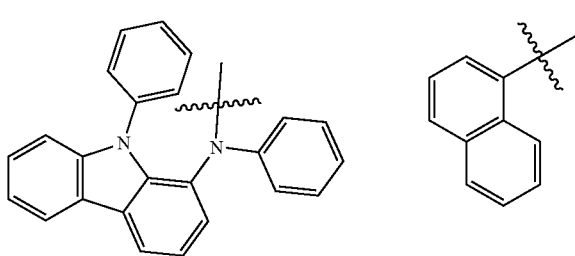 | 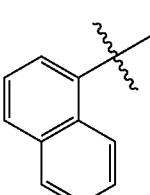 |
| 12-16 | 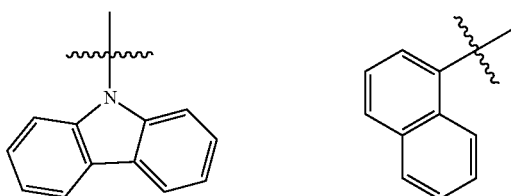 | 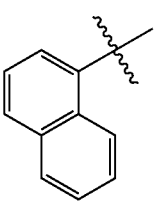 [SMILES: *c1cccc2ccccc12] |

-continued
| | | |
|---|---|---|
| 12-17 | 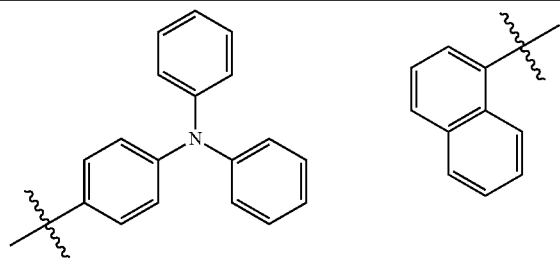 | |
| 12-18 | 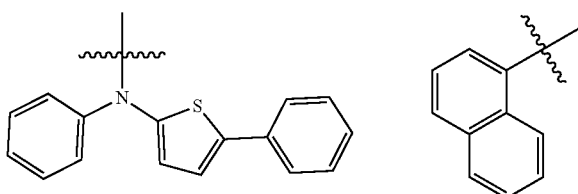 | |
| 12-19 | 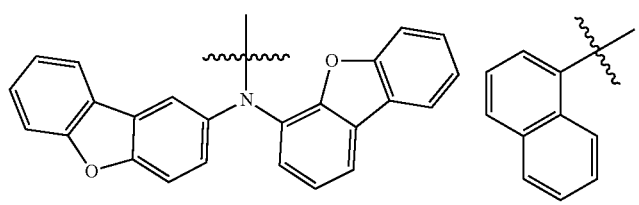 | |
| 12-20 | 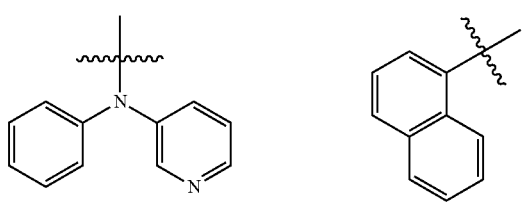 | |
| Compound | X | X | R1 |
|---|---|---|---|
| 13-1 | 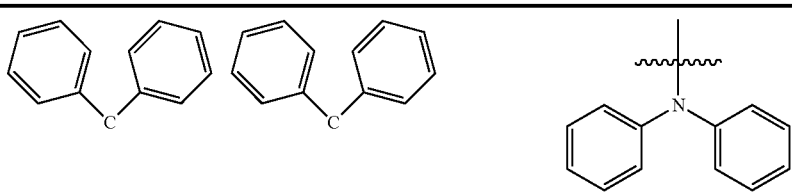 | | |
| 13-2 | 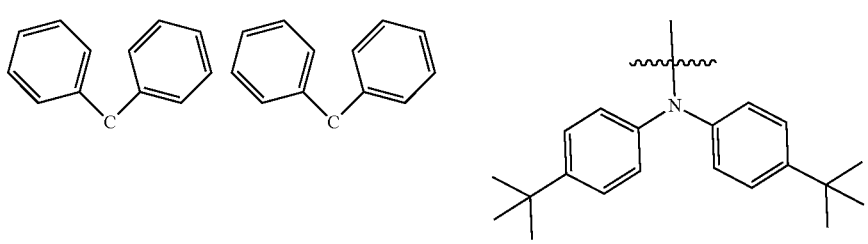 | | |
| 13-3 | 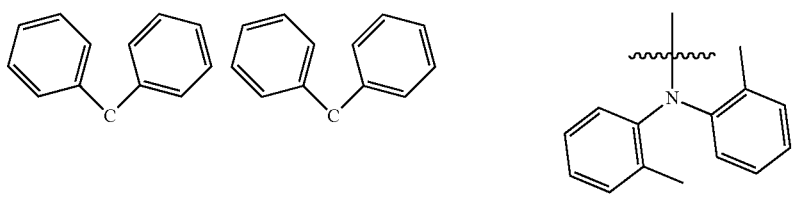 | | |

| | | |
|---|---|---|
| 13-4 | 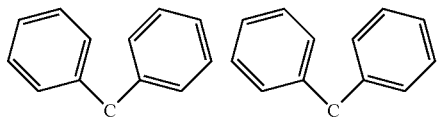 | 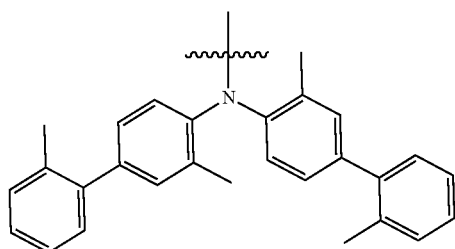 |
| 13-5 | 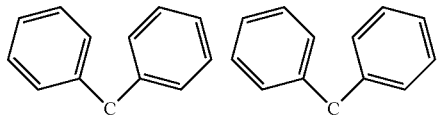 | 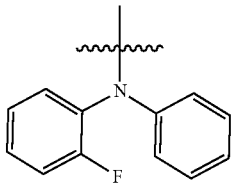 [SMILES: *N(c1ccccc1)c1ccccc1F] |
| 13-6 | 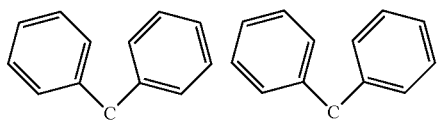 | 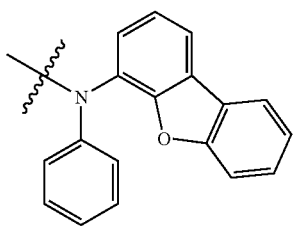 [SMILES: *N(c1ccccc1)c1cccc2c1oc1ccccc12] |
| 13-7 | 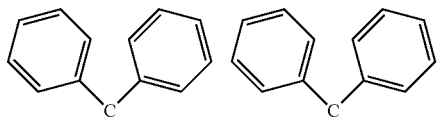 | 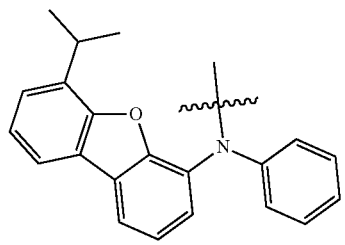 [SMILES: *N(c1ccccc1)c1cccc2c1oc1c(C(C)C)cccc12] |
| 13-8 | 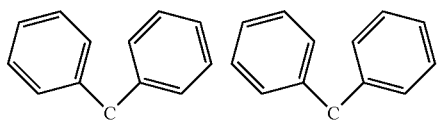 | 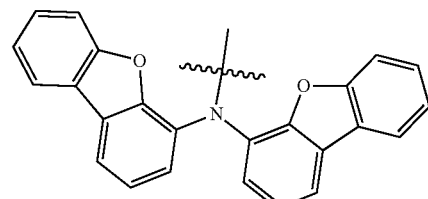 |
| 13-9 | 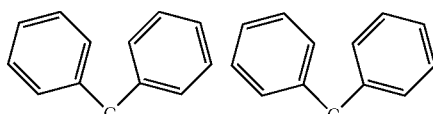 | 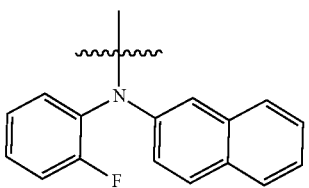 [SMILES: *N(c1ccc2ccccc2c1)c1ccccc1F] |
| 13-10 | 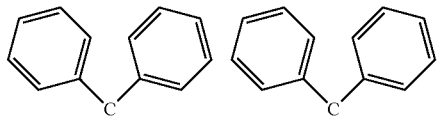 | 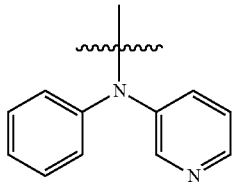 [SMILES: *N(c1ccccc1)c1cccnc1] |

| | | |
|---|---|---|
| 13-11 | 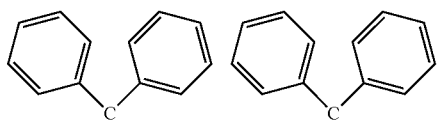 | 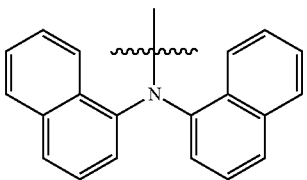 [SMILES: *N(c1cccc2ccccc12)c1cccc2ccccc12] |
| 13-12 | 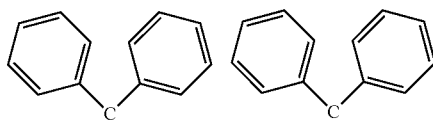 | 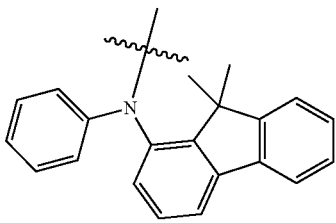 [SMILES: *N(c1ccccc1)c1cccc2c1C(C)(C)c1ccccc1-2] |
| 13-13 | 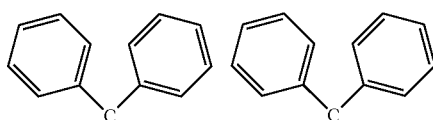 | 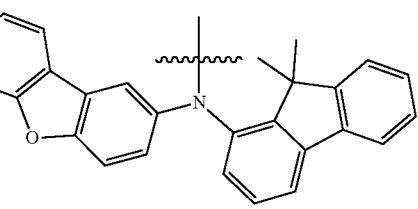 |
| 13-14 | 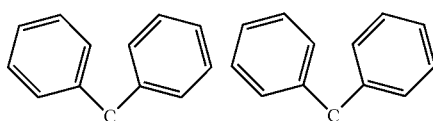 | 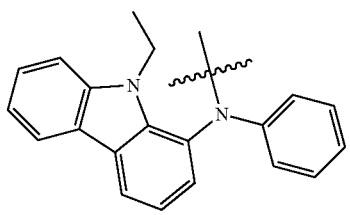 [SMILES: *N(c1ccccc1)c1cccc2c3ccccc3n(CC)c12] |
| 13-15 | 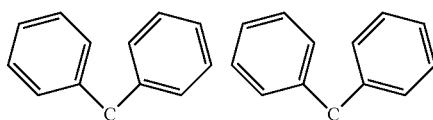 | 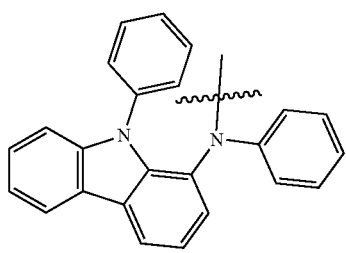 [SMILES: *N(c1ccccc1)c1cccc2c3ccccc3n(-c3ccccc3)c12] |
| 13-16 | 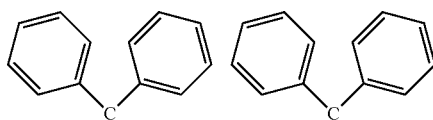 | 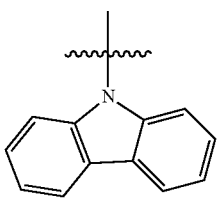 [SMILES: *n1c2ccccc2c2ccccc21] |
| 13-17 | 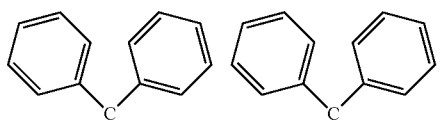 | 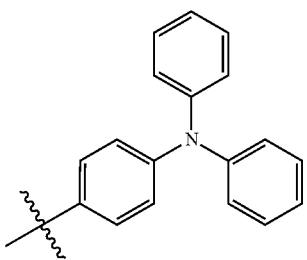 [SMILES: *c1ccc(N(c2ccccc2)c2ccccc2)cc1] |

-continued
| | | |
|---|---|---|
| 13-18 | 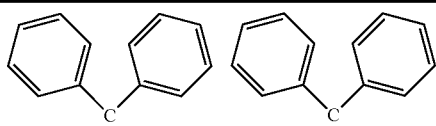 | 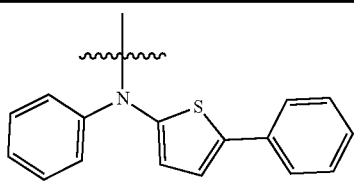 |
| 13-19 | 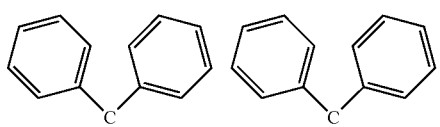 | 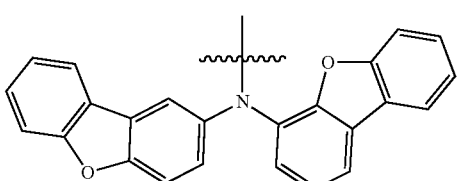 |
| 13-20 | 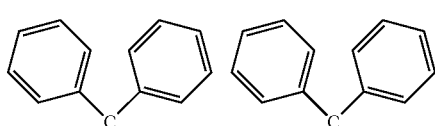 | 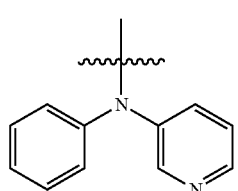 |
| Compound | R2 | R3 to R6 |
|---|---|---|
| 13-1 | 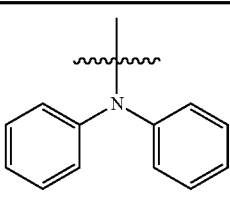 | 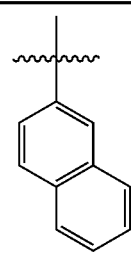 |
| 13-2 | 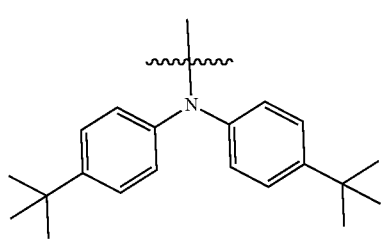 [SMILES: *N(c1ccc(C(C)(C)C)cc1)c1ccc(C(C)(C)C)cc1] | 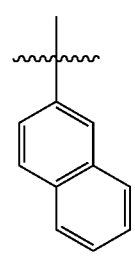 |
| 13-3 | 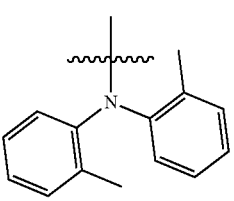 [SMILES: *N(c1ccccc1C)c1ccccc1C] | 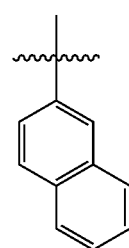 |
| 13-4 | 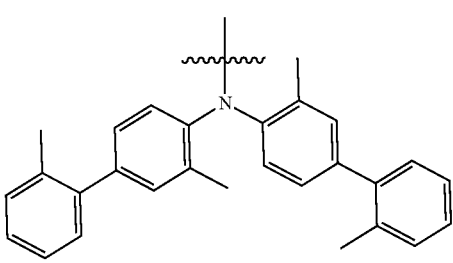 [SMILES: *N(c1ccc(-c2ccccc2C)cc1C)c1ccc(-c2ccccc2C)cc1C] | 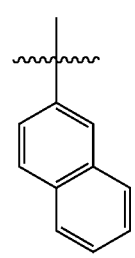 [SMILES: *c1ccc2ccccc2c1] |

| | | |
|---|---|---|
| 13-5 | 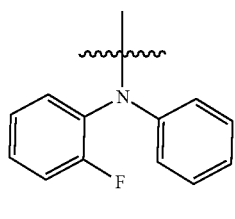 [SMILES: *N(c1ccccc1)c1ccccc1F] | 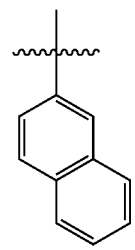 |
| 13-6 | 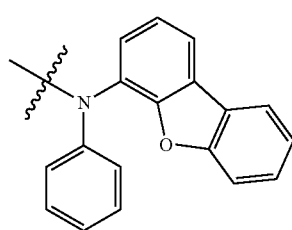 | 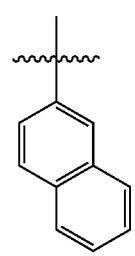 [SMILES: *c1ccc2ccccc2c1] |
| 13-7 | 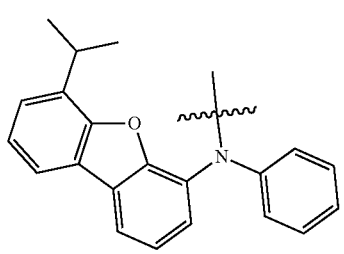 [SMILES: *N(c1ccccc1)c1cccc2c1oc1c(C(C)C)cccc12] | 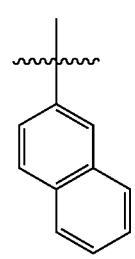 |
| 13-8 | 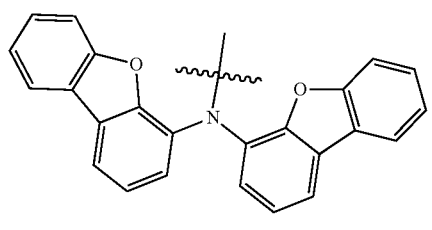 [SMILES: *N(c1cccc2c1oc1ccccc12)c1cccc2c1oc1ccccc12] | 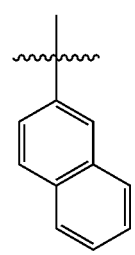 |
| 13-9 | 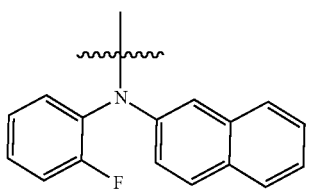 [SMILES: *N(c1ccc2ccccc2c1)c1ccccc1F] | 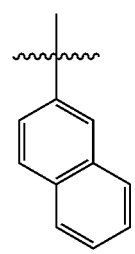 |
| 13-10 | 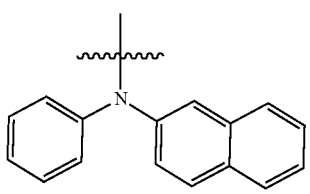 [SMILES: *N(c1ccccc1)c1ccc2ccccc2c1] | 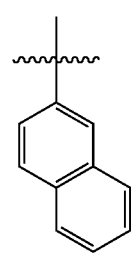 |

| | | |
|---|---|---|
| 13-11 | 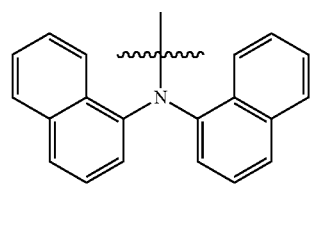 | 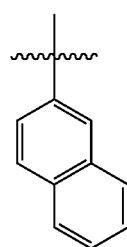 |
| 13-12 | 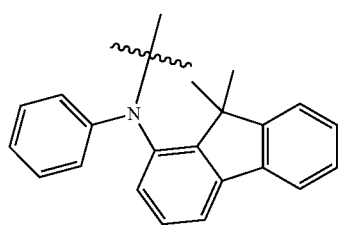 [SMILES: *N(c1ccccc1)c1cccc2c1C(C)(C)c1ccccc1-2] | 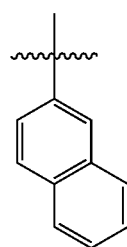 |
| 13-13 | 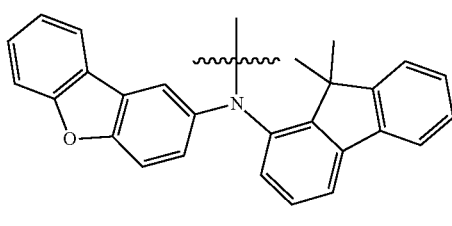 | 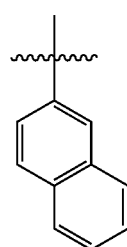 |
| 13-14 | 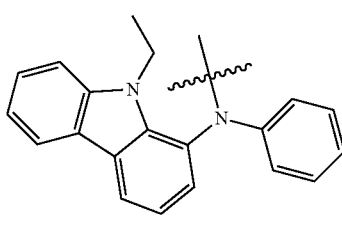 | 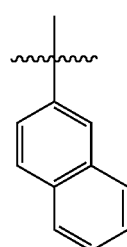 |
| 13-15 | 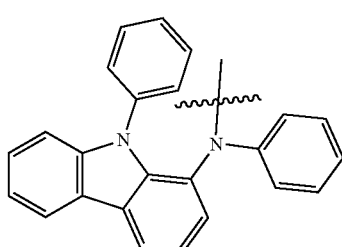 | 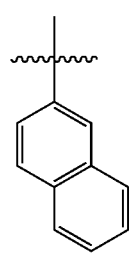 |
| 13-16 | 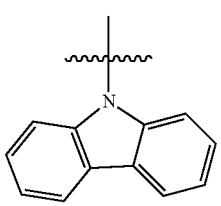 [SMILES: *n1c2ccccc2c2ccccc21] | 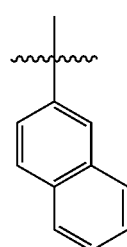 |

-continued
| | | |
|---|---|---|
| 13-17 | 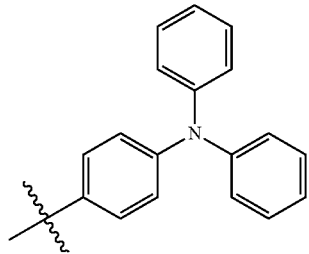 [SMILES: *c1ccc(N(c2ccccc2)c2ccccc2)cc1] | 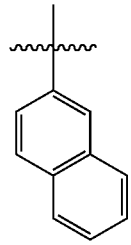 |
| 13-18 | 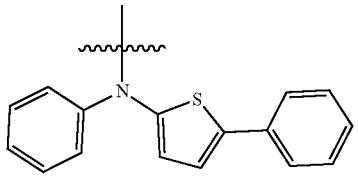 [SMILES: *N(c1ccccc1)c1ccc(-c2ccccc2)s1] | 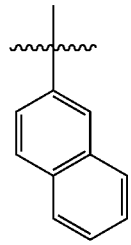 |
| 13-19 | 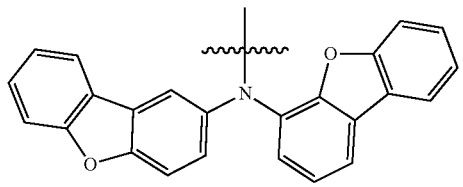 [SMILES: *N(c1ccc2oc3ccccc3c2c1)c1cccc2c1oc1ccccc12] | 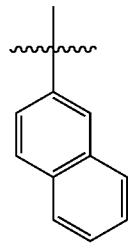 |
| 13-20 | 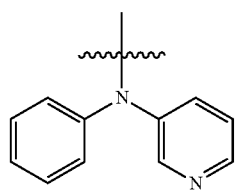 [SMILES: *N(c1ccccc1)c1cccnc1] | 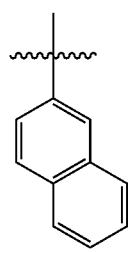 [SMILES: *c1ccc2ccccc2c1] |

| Compound | X1 | X2 | R1 | R2 | R3 to R6 |
|---|---|---|---|---|---|
| 14-1 | O | S | N(Ph)₂ | N(Ph)₂ | biphenyl |
| 14-2 | O | N | N(4-tBu-C₆H₄)₂ | N(4-tBu-C₆H₄)₂ | biphenyl |
| 14-3 | O | N-Ph | N(2-tolyl)₂ | N(2-tolyl)₂ | biphenyl |
| 14-4 | O | C | N(3-methyl-2'-methylbiphenyl-4-yl)₂ | N(3-methyl-2'-methylbiphenyl-4-yl)₂ | biphenyl |

-continued
| Compound | X1 | X2 | R1 | R2 | R3 to R6 |
|---|---|---|---|---|---|
| 14-5 | O | 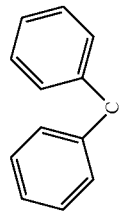 | 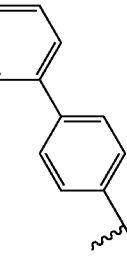 | 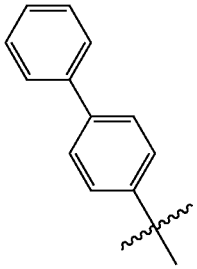 | 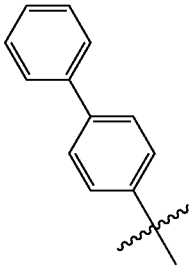 |
| 14-6 | S | —N | 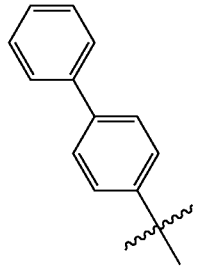 |  | 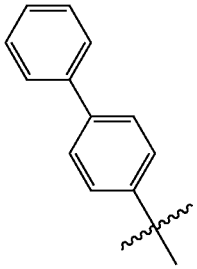 |
| 14-7 | S | 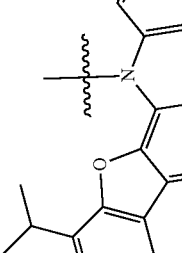 | 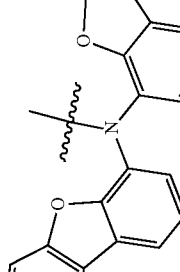 |  | 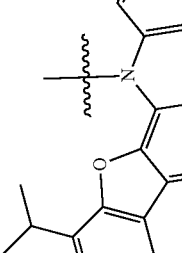 |
| 14-8 | S | 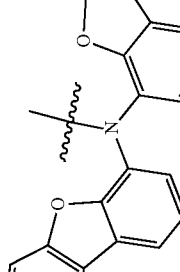 | 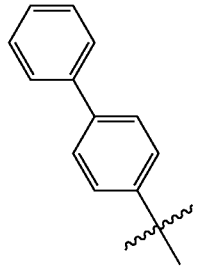 |  | 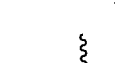 |

-continued
| Compound | X1 | X2 | R1 | R2 | R3 to R6 |
|---|---|---|---|---|---|
| 14-9 | S | 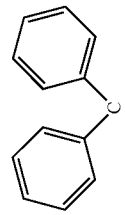 | 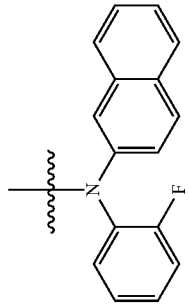 | 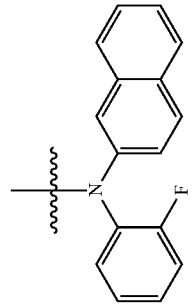 | 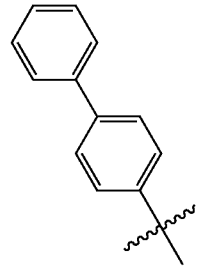 |
| 14-10 | —N | 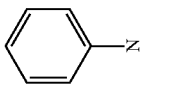 | 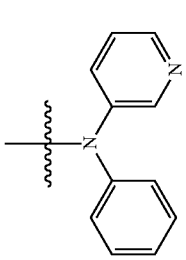 | 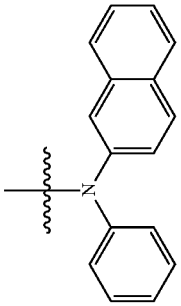 | 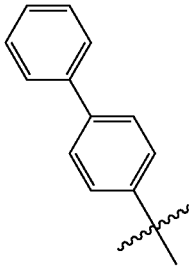 |
| 14-11 | —N | C | 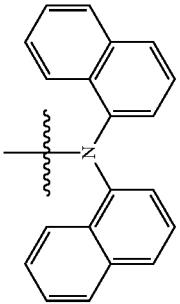 | 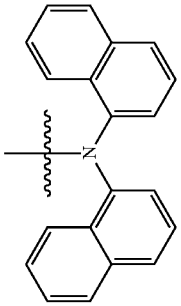 | 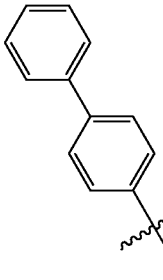 |
| 14-12 | —N | 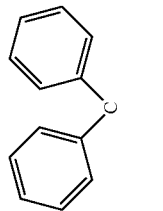 | 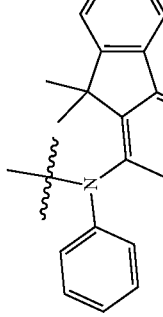 | 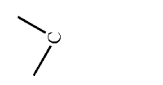 | 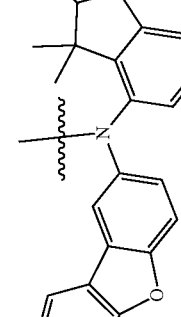 |
| 14-13 | N | C | | | |

-continued

| Compound | X1 | X2 | R1 | R2 | R3 to R6 |
|---|---|---|---|---|---|
| 14-14 | N-Ph | CPh₂ | N(Ph)(9-ethylcarbazol-1-yl) | N(Ph)(9-ethylcarbazol-1-yl) | biphenyl |
| 14-15 | C | CPh₂ | N(Ph)(9-phenylcarbazol-1-yl) | N(Ph)(9-phenylcarbazol-1-yl) | biphenyl |
| 14-16 | O | S | carbazol-9-yl | carbazol-9-yl | biphenyl |
| 14-17 | O | N | N(Ph)(4-biphenylyl)... triphenylamine | triphenylamine | biphenyl |

-continued

| Compound | X1 | X2 | R1 | R2 | R3 to R6 |
|---|---|---|---|---|---|
| 14-18 | O | phenyl-N | N-phenyl-(5-phenylthiophen-2-yl) | N-phenyl-(5-phenylthiophen-2-yl) | biphenyl |
| 14-19 | O | CH | N,N-bis(dibenzofuranyl) | N,N-bis(dibenzofuranyl) | biphenyl |
| 14-20 | O | C(phenyl)₂ | N-phenyl-(pyridin-3-yl) | N-phenyl-(pyridin-3-yl) | biphenyl |

In Compounds 1-1 to 1-23, 2-1 to 2-22, 3-1 to 3-20, 4-1 to 4-21, 5-1 to 5-21, 6-1 to 6-21, 7-1 to 7-20, 8-1 to 8-20, 9-1 to 9-20, 10-1 to 10-20, 11-1 to 11-20, 12-1 to 12-20, 13-1 to 13-20, and 14-1 to 14-20, when R5 and R6 are the substituents, a and b of Formula 1 are each an integer from 1 to 4.

In Compounds 1-1 to 1-23, 2-1 to 2-22, 3-1 to 3-20, 4-1 to 4-21, 5-1 to 5-21, 6-1 to 6-21, 7-1 to 7-20, 8-1 to 8-20, 9-1 to 9-20, 10-1 to 10-20, 11-1 to 11-20, 12-1 to 12-20, 13-1 to 13-20, and 14-1 to 14-20, when R5 and R6 are the substituents, a and b of Formula 1 are each 1.

In Compounds 1-1 to 1-23, 2-1 to 2-22, 3-1 to 3-20, 4-1 to 4-21, 5-1 to 5-21, 6-1 to 6-21, 7-1 to 7-20, 8-1 to 8-20, 9-1 to 9-20, 10-1 to 10-20, 11-1 to 11-20, 12-1 to 12-20, 13-1 to 13-20, and 14-1 to 14-20, when R5 and R6 are the substituents, a and b of Formula 1 are each 2.

In Compounds 1-1 to 1-23, 2-1 to 2-22, 3-1 to 3-20, 4-1 to 4-21, 5-1 to 5-21, 6-1 to 6-21, 7-1 to 7-20, 8-1 to 8-20, 9-1 to 9-20, 10-1 to 10-20, 11-1 to 11-20, 12-1 to 12-20, 13-1 to 13-20, and 14-1 to 14-20, when R5 and R6 are the substituents a and b of Formula 1 are each 3.

In Compounds 1-1 to 1-23, 2-1 to 2-22, 3-1 to 3-20, 4-1 to 4-21, 5-1 to 5-21, 6-1 to 6-21, 7-1 to 7-20, 8-1 to 8-20, 9-1 to 9-20, 10-1 to 10-20, 11-1 to 11-20, 12-1 to 12-20, 13-1 to 13-20, and 14-1 to 14-20, when R5 and R6 are the substituents, a and b of Formula 1 are each 4.

An exemplary embodiment of the present specification provides an organic light emitting device including: a first electrode; a second electrode provided to face the first electrode; and an organic material layer having one or more layers provided between the first electrode and the second electrode, in which one or more layers of the organic material layer include the above-described compound.

According to an exemplary embodiment of the present specification, the organic material layer of the organic light emitting device of the present specification can be composed of a mono-layer structure, but can be composed of a multi-layer structure in which organic material layers having two or more layers are stacked. For example, the organic light emitting device of the present invention can have a structure including a hole injection layer, a hole transport layer, an electron blocking layer, a light emitting layer, a hole blocking layer, an electron transport layer, an electron injection layer, and the like as organic material layers. However, the structure of the organic light emitting device is not limited thereto, and can include fewer or more organic layers.

For example, the structure of the organic light emitting device of the present specification can have structures illustrated in FIGS. 1 and 2, but is not limited thereto.

FIG. 1 exemplifies a structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and can further include other organic material layers.

FIG. 2 exemplifies a structure of an organic light emitting device in which the first electrode 30, a hole injection layer 60, a hole transport layer 70, the light emitting layer 40, an electron transport layer 80, an electron injection layer 90, and the second electrode 50 are sequentially stacked on the substrate 20. FIG. 2 is an exemplified structure according to an exemplary embodiment of the present specification, and can further include other organic material layers.

According to an exemplary embodiment of the present specification, the organic material layer includes a light emitting layer, and the light emitting layer includes the compound of Formula 1.

According to an exemplary embodiment of the present specification, the organic material layer includes a light emitting layer, and the light emitting layer includes the compound of Formula 1 as a dopant of the light emitting layer.

According to an exemplary embodiment of the present specification, the organic material layer includes a light emitting layer, and the light emitting layer includes a compound of the following Formula 1A:

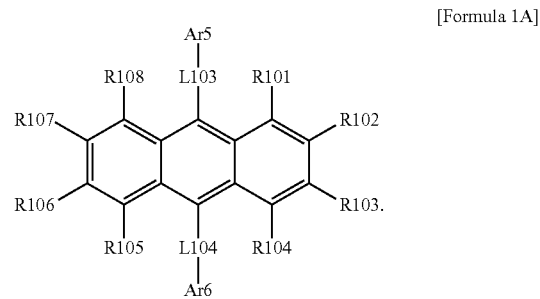

[Formula 1A]

In Formula 1A:

L103 and L104 are the same as or different from each other, and are each independently a direct bond, a substituted or unsubstituted arylene group, or a substituted or unsubstituted heteroarylene group;

Ar5 and Ar6 are the same as or different from each other, and are each independently a substituted or unsubstituted aryl group, or a substituted or unsubstituted heteroaryl group; and R101 to R108 are the same as or different from each other, and are each independently hydrogen, deuterium, a halogen group, a nitrile group, a nitro group, a substituted or unsubstituted alkyl group, a substituted or unsubstituted cycloalkyl group, a substituted or unsubstituted silyl group, a substituted or unsubstituted phosphine oxide group, a substituted or unsubstituted aryl group, or a substituted or unsubstituted heteroaryl group.

According to an exemplary embodiment of the present specification, L103 and L104 are a direct bond.

According to an exemplary embodiment of the present specification, L103 and L104 are the same as or different from each other, and are each independently a substituted or unsubstituted arylene group having 6 to 30 carbon atoms.

According to an exemplary embodiment of the present specification, L103 and L104 are the same as or different from each other, and are each independently a substituted or unsubstituted phenylene group, a substituted or unsubstituted biphenylylene group, or a substituted or unsubstituted naphthylene group.

According to an exemplary embodiment of the present specification, L103 and L104 are the same as or different from each other, and are each independently a phenylene group, a biphenylylene group, or a naphthylene group.

According to an exemplary embodiment of the present specification, L103 and L104 are the same as or different from each other, and are each independently selected from the substituents in the following Table 1.

TABLE 1
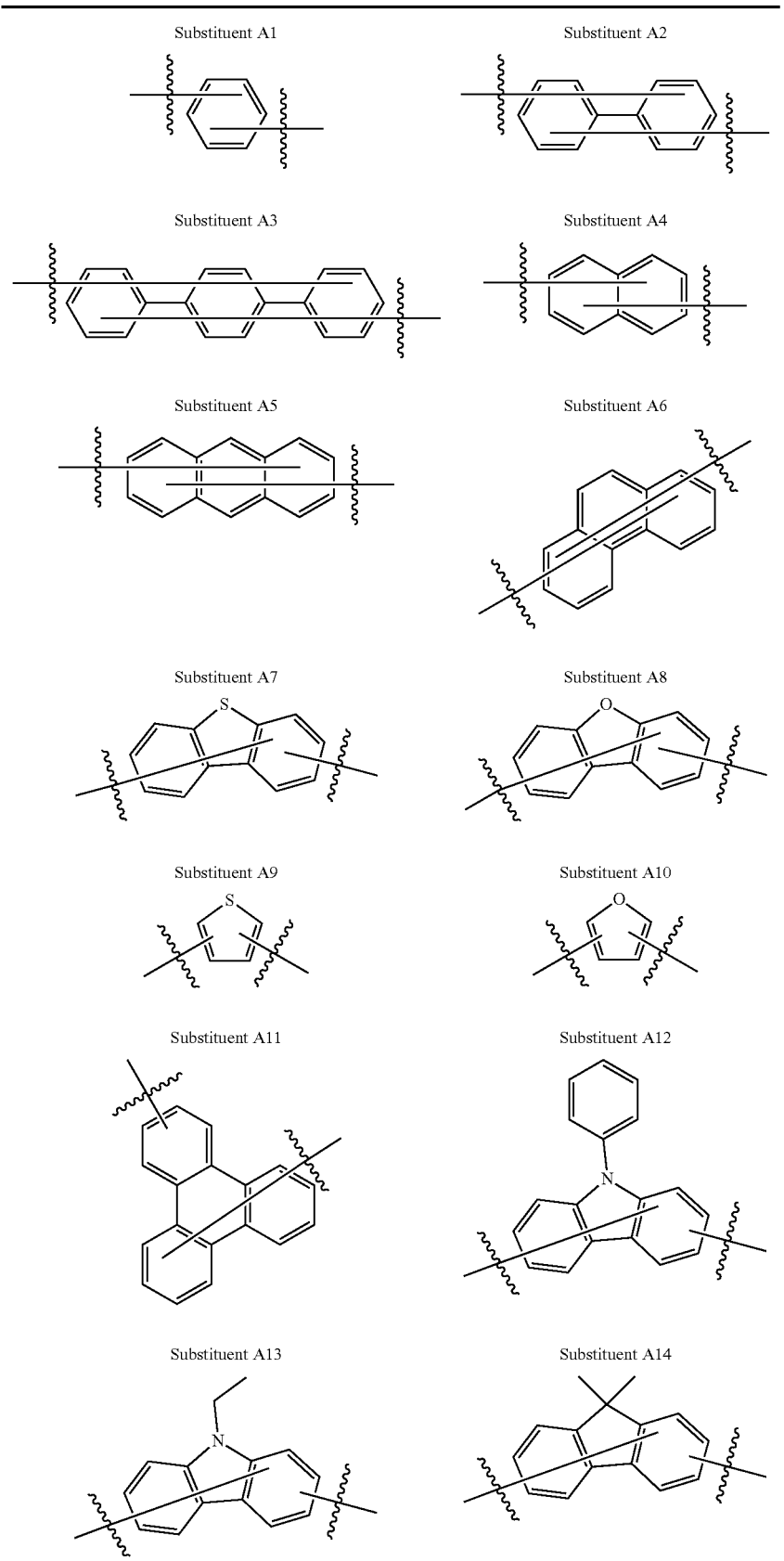

TABLE 1-continued

Substituent A15

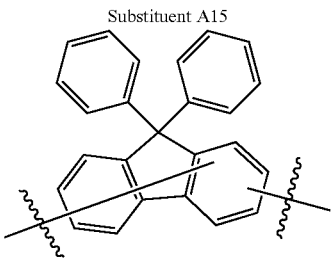

According to an exemplary embodiment of the present specification, Ar5 and Ar6 are the same as or different from each other, and are each independently a substituted or unsubstituted aryl group having 6 to 30 carbon atoms.

According to an exemplary embodiment of the present specification, Ar5 and Ar6 are the same as or different from each other, and are each independently a substituted or unsubstituted phenyl group, a substituted or unsubstituted biphenyl group, or a substituted or unsubstituted naphthyl group.

According to an exemplary embodiment of the present specification, Ar5 and Ar6 are the same as or different from each other, and are each independently a phenyl group, a biphenyl group, or a naphthyl group.

According to an exemplary embodiment of the present specification, Ar5 and Ar6 are the same as or different from each other, and are each independently a substituted or unsubstituted heteroaryl group having 6 to 50 carbon atoms.

According to an exemplary embodiment of the present specification, Ar5 and Ar6 are the same as or different from each other, and are each independently a dibenzothiophene group in which a fused ring is formed.

According to an exemplary embodiment of the present specification, Ar5 and Ar6 are the same as or different from each other, and are each independently

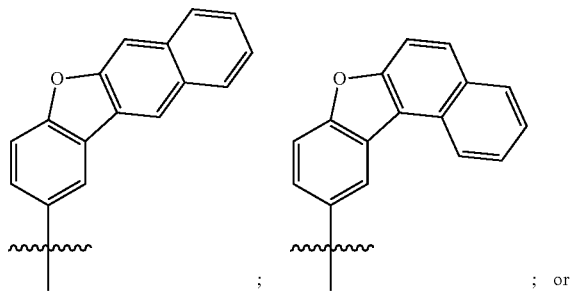

According to an exemplary embodiment of the present specification, Ar5 and Ar6 are the same as or different from each other, and are each independently a carbazolyl group in which a fused ring is formed.

According to an exemplary embodiment of the present specification, Ar5 and Ar6 are the same as or different from each other, and are each independently

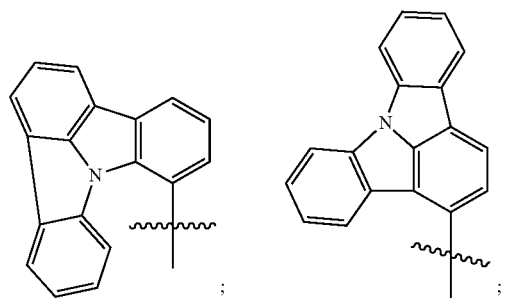

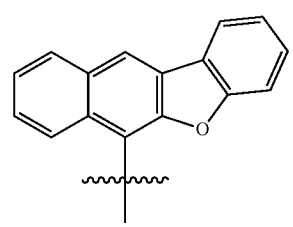

According to an exemplary embodiment of the present specification, Ar5 and Ar6 are the same as or different from each other, and are each independently a thiophene group which is unsubstituted or substituted with an aryl group.

According to an exemplary embodiment of the present specification, Ar5 and Ar6 are the same as or different from each other, and are each independently a thiophene group which is unsubstituted or substituted with a phenyl group.

According to an exemplary embodiment of the present specification, Ar5 and Ar6 are the same as or different from each other, and are each independently selected from the substituents in the following Table 2.

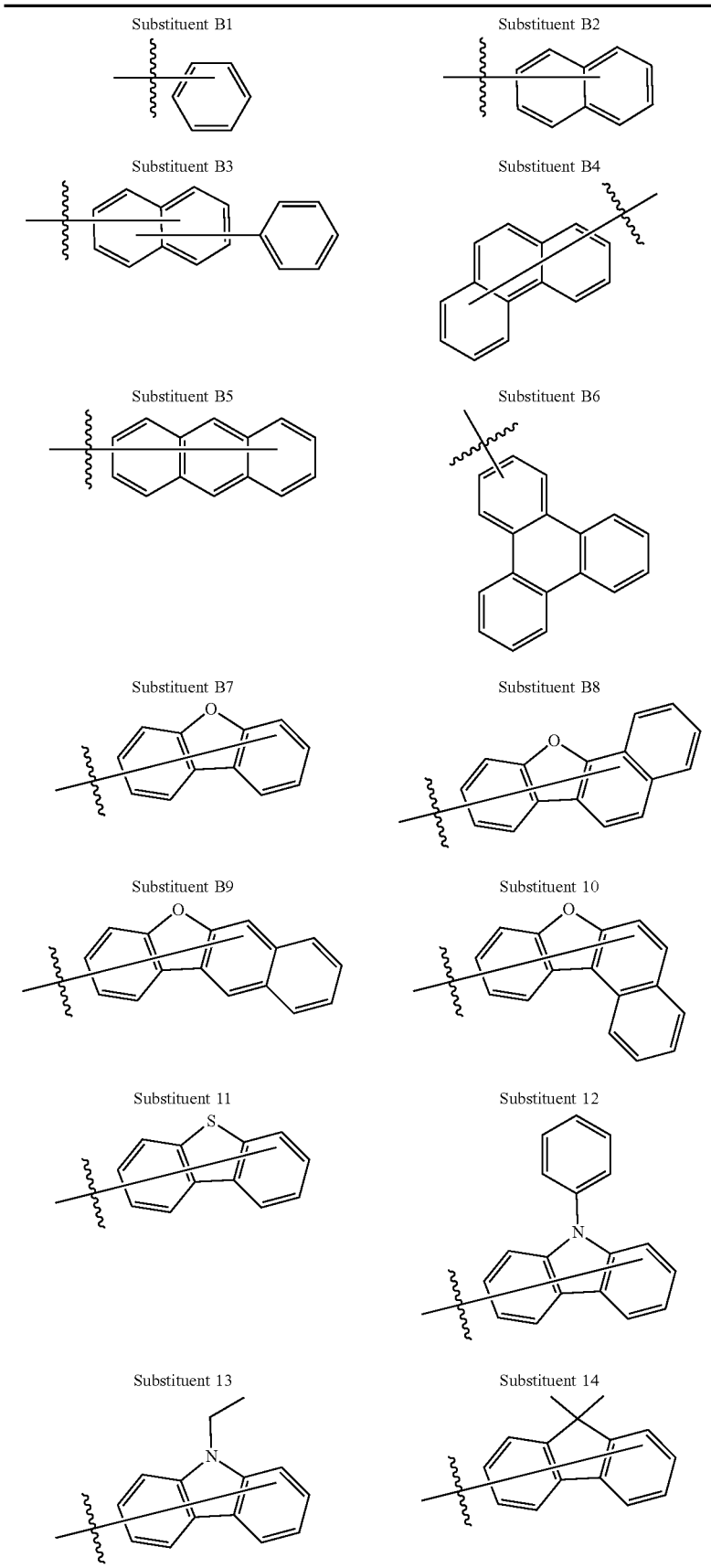

-continued
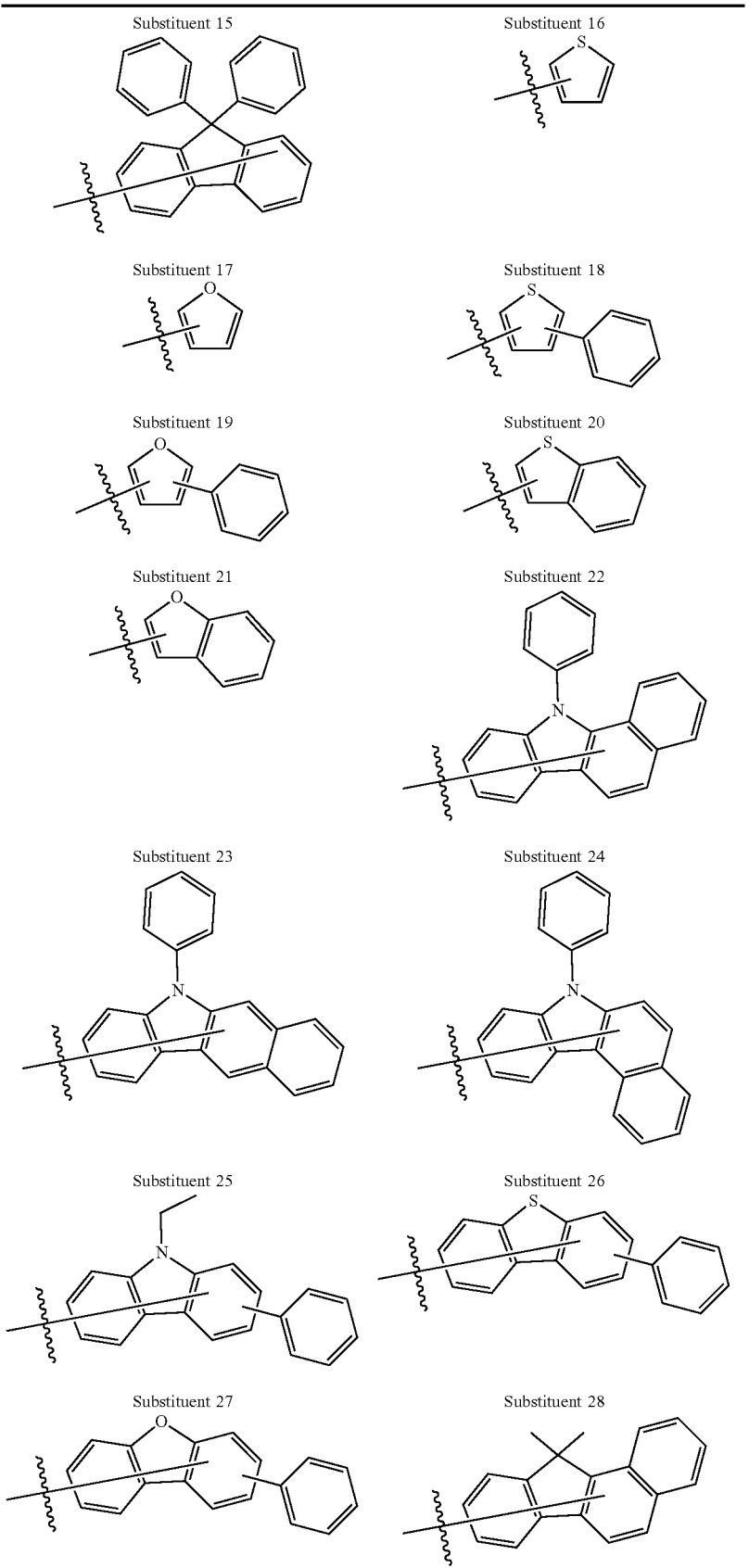

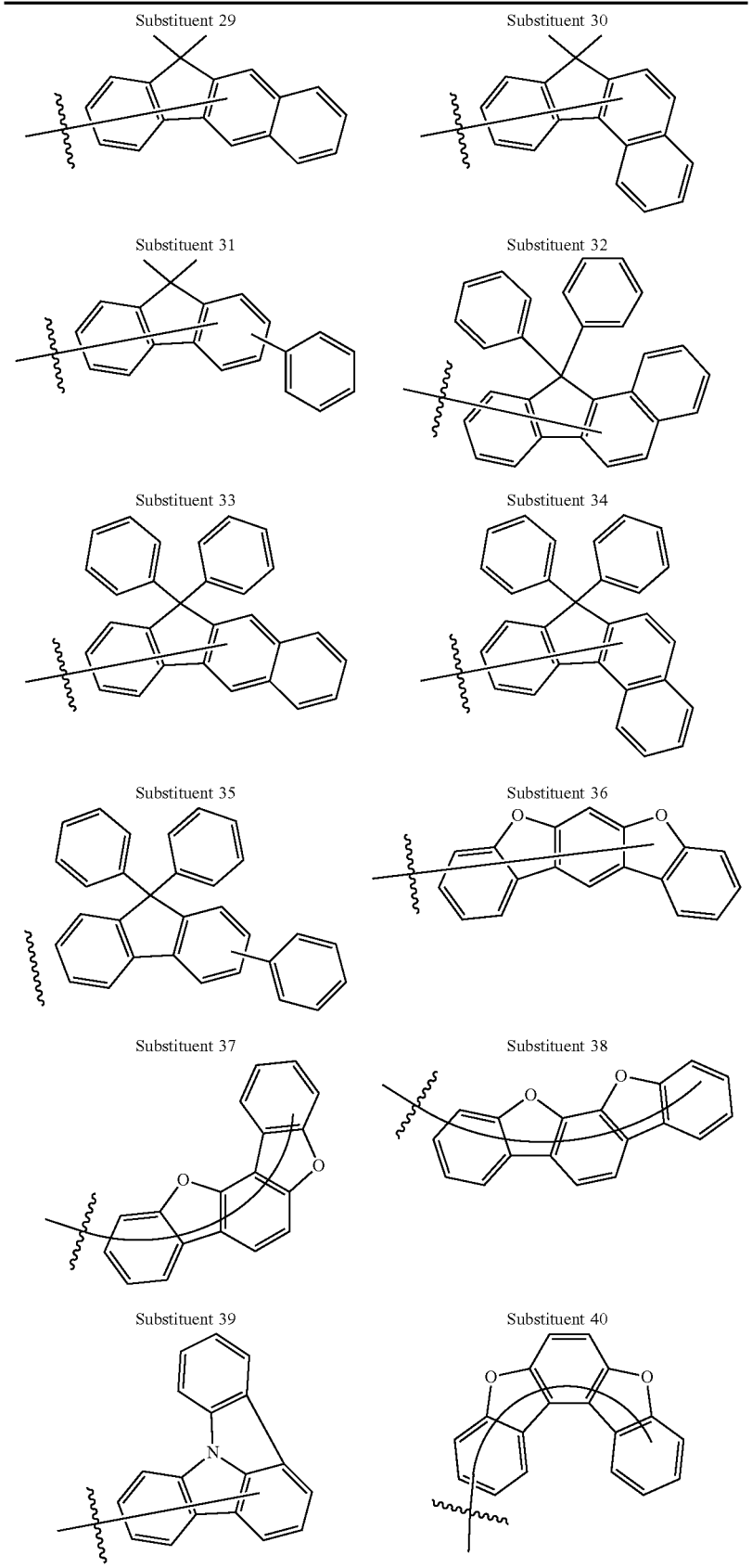

-continued
Substituent 41
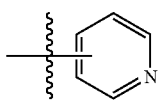
Substituent 42
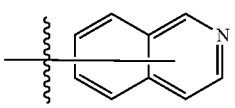
Substituent 43
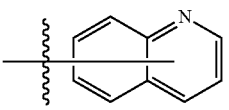
Substituent 44
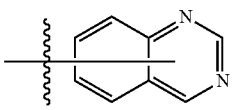
Substituent 45
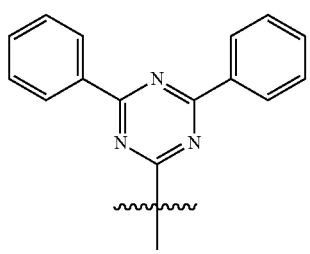 [SMILES: *c1nc(-c2ccccc2)nc(-c2ccccc2)n1]
Substituent 46
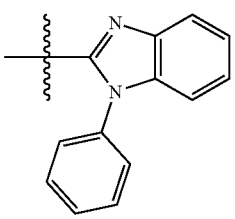 [SMILES: *c1nc2ccccc2n1-c1ccccc1]
Substituent 47
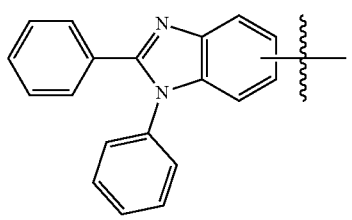
Substituent 48
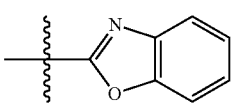 [SMILES: *c1nc2ccccc2o1]
Substituent 49
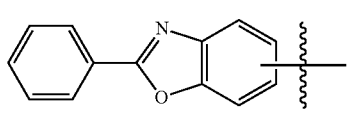
Substituent 50
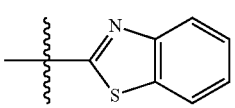
Substituent 51
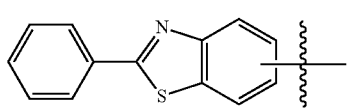
Substituent 52
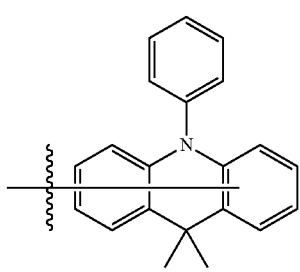
Substituent 53
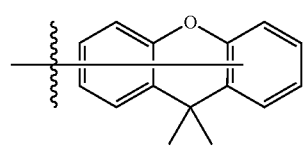
Substituent 54
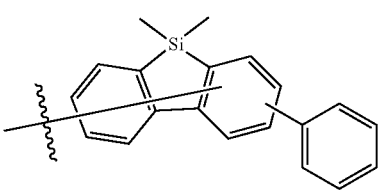

| Substituent 55 | Substituent 56 |
|---|---|
| 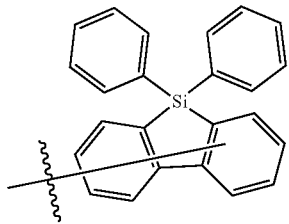 | 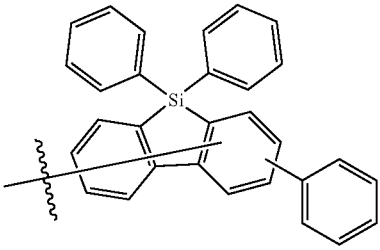 |
According to an exemplary embodiment of the present specification, Formula 1A is selected from the following compounds:
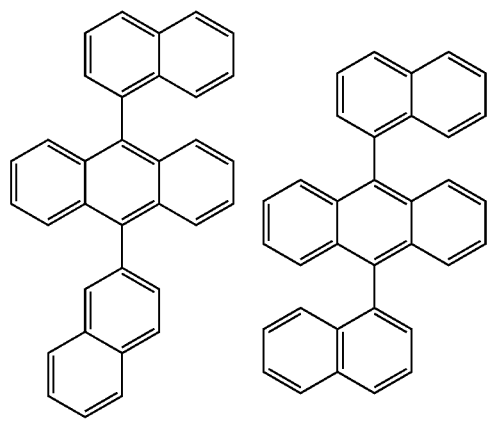
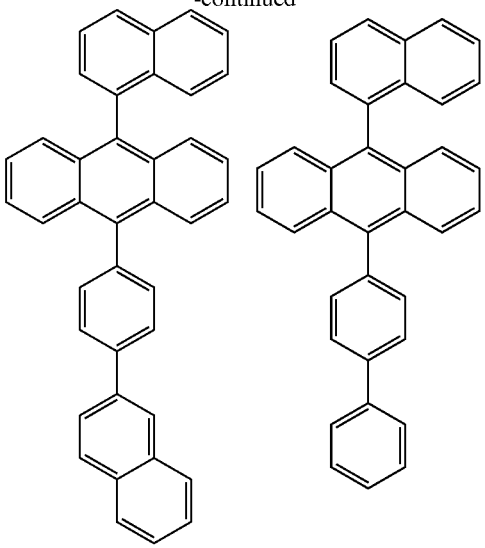
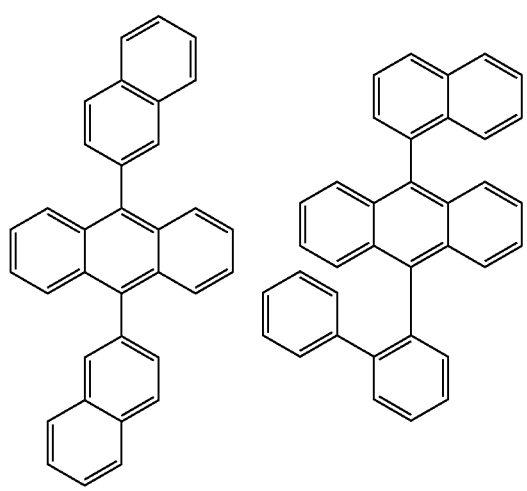
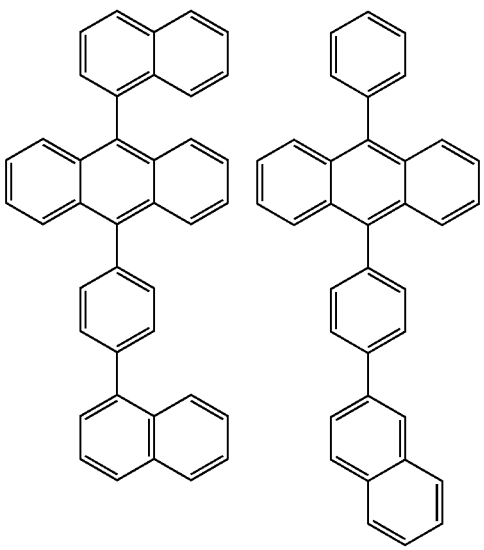

149
-continued
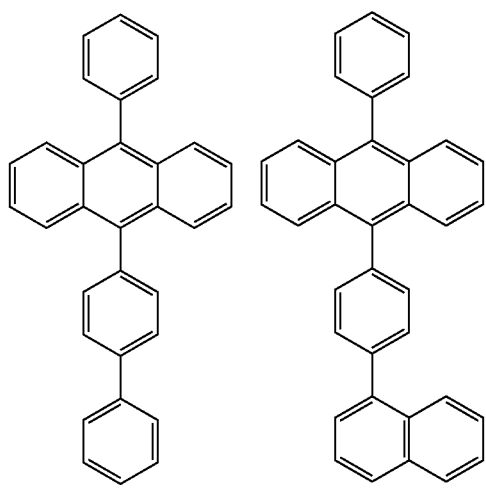
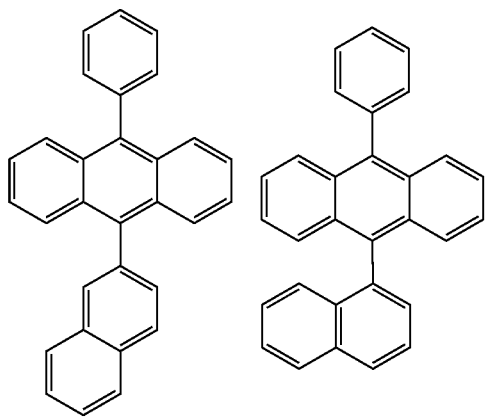
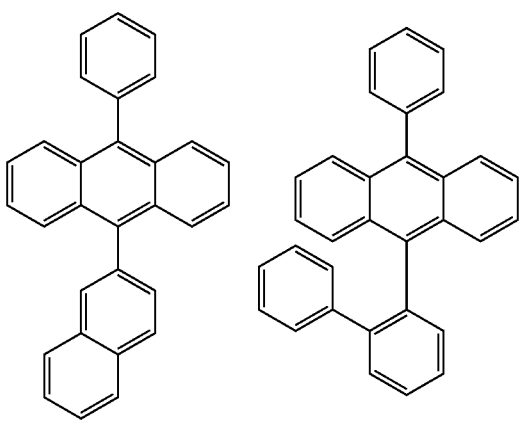
150
-continued
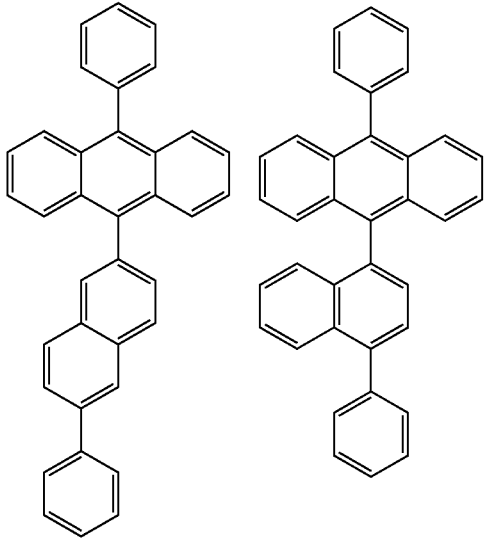
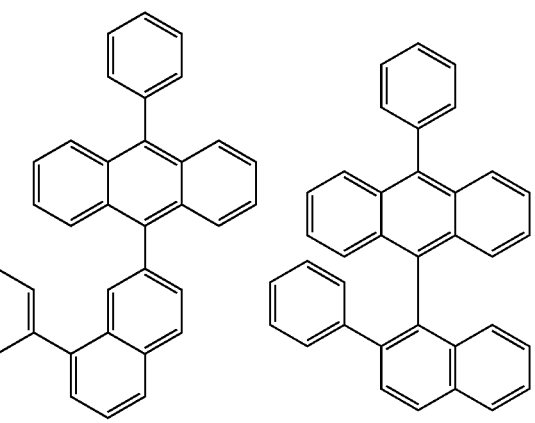
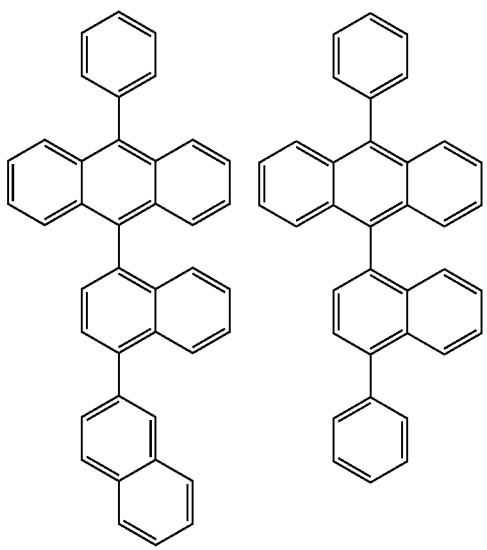

151
-continued
152
-continued
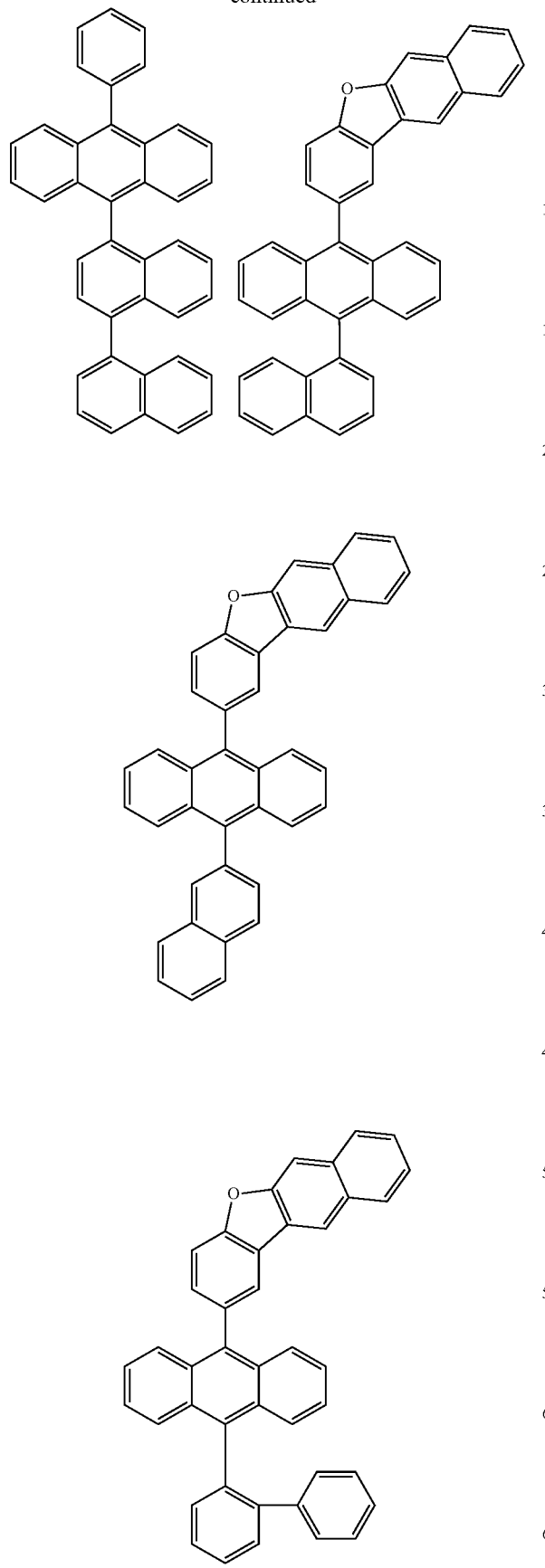
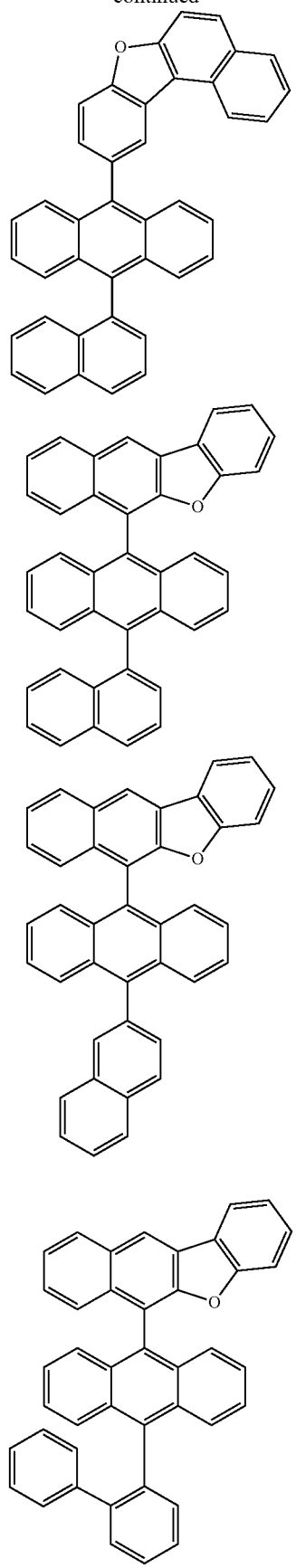

153
-continued
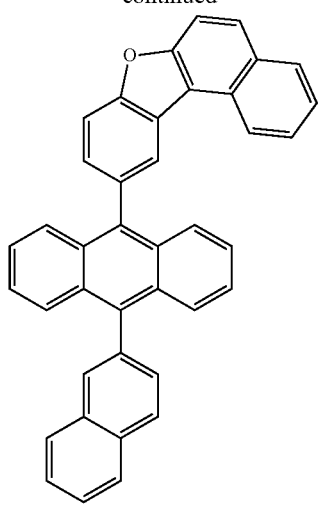
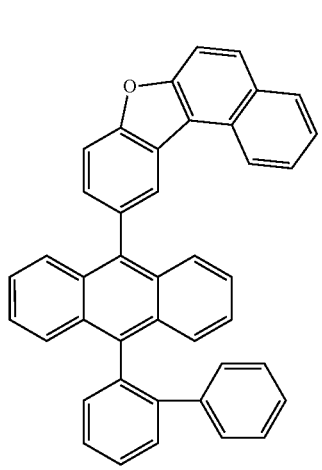
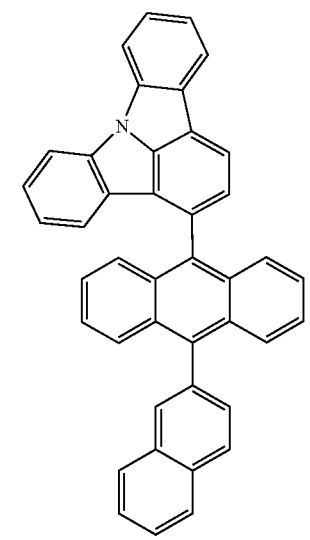
154
-continued
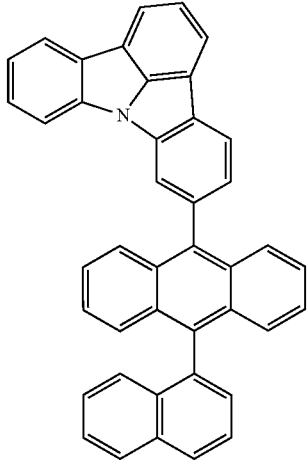
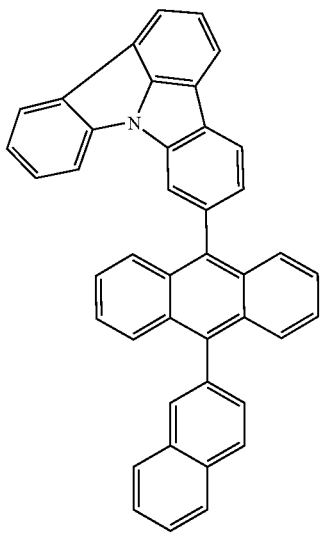
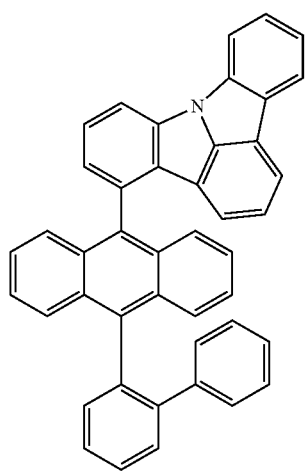

155
-continued
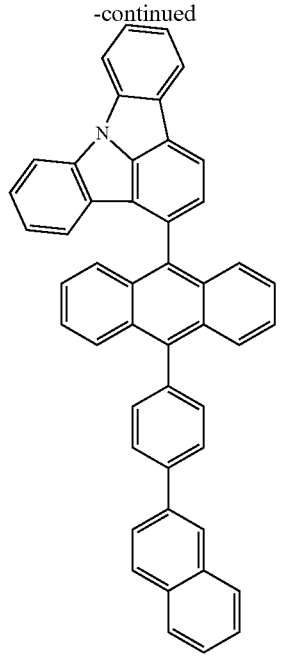
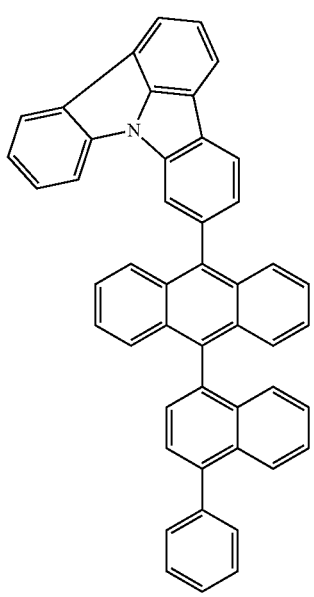
156
-continued
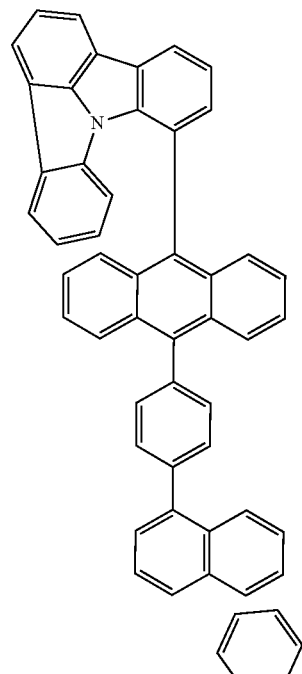
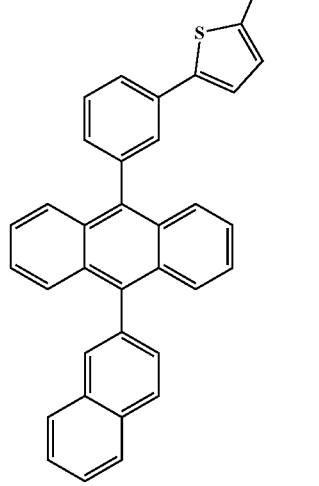
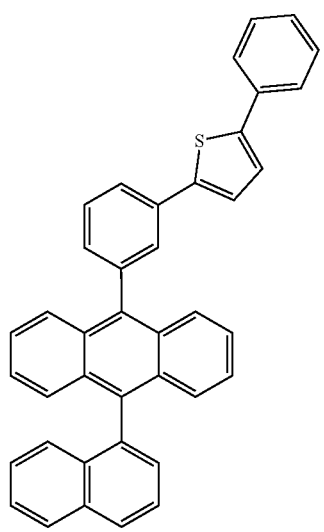

157
-continued
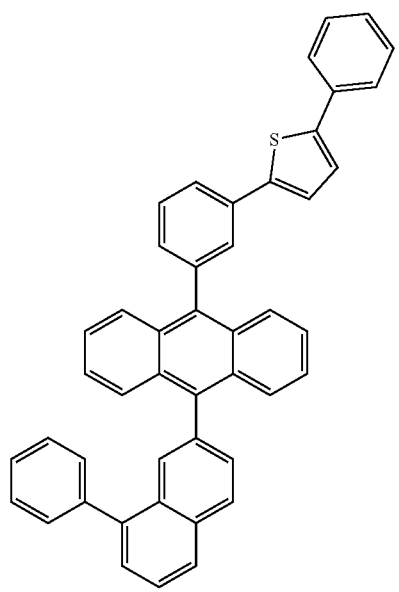
158
-continued
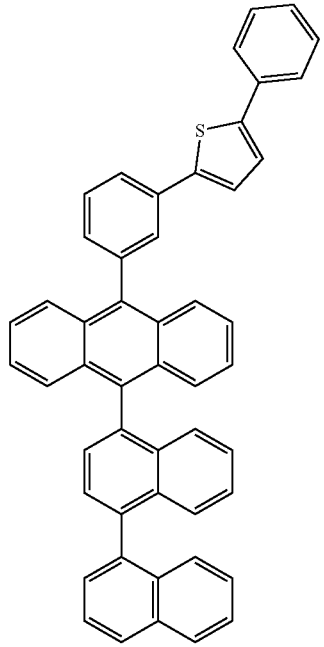
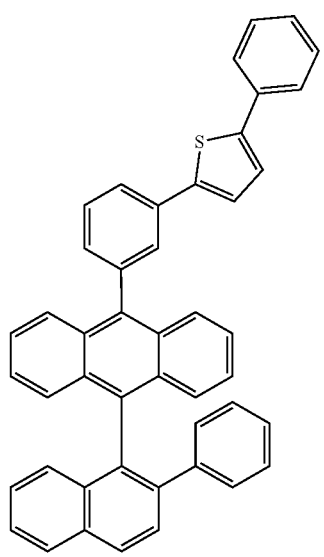

-continued

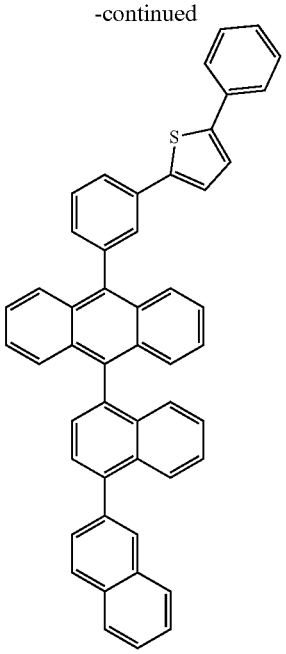

According to an exemplary embodiment of the present specification, the organic material layer includes a light emitting layer, and the light emitting layer includes the compound of Formula 1 as a dopant of the light emitting layer, and includes the compound of Formula 1A as a host of the light emitting layer.

According to an exemplary embodiment of the present specification, the light emitting layer includes the compound of Formula 1 and the compound of Formula 1A at a weight ratio of 1:99 to 10:90.

According to an exemplary embodiment of the present specification, the organic material layer includes a light emitting layer, and the light emitting layer includes a compound of the following Formula 1B:

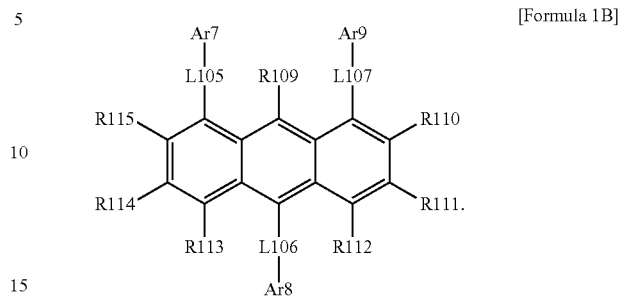

[Formula 1B]

In Formula 1B:

L105 to L107 are the same as or different from each other, and are each independently a direct bond, a substituted or unsubstituted arylene group, or a substituted or unsubstituted heteroarylene group;

Ar7 to Ar9 are the same as or different from each other, and are each independently a substituted or unsubstituted aryl group, or a substituted or unsubstituted heteroaryl group; and R109 to R115 are the same as or different from each other, and are each independently hydrogen, deuterium, a halogen group, a nitrile group, a nitro group, a substituted or unsubstituted alkyl group, a substituted or unsubstituted cycloalkyl group, a substituted or unsubstituted silyl group, a substituted or unsubstituted phosphine oxide group, a substituted or unsubstituted aryl group, or a substituted or unsubstituted heteroaryl group.

According to an exemplary embodiment of the present specification, L105 to L107 are a direct bond.

According to an exemplary embodiment of the present specification, L105 to L107 are the same as or different from each other, and are each independently selected from the substituents in the following Table 3.

TABLE 3

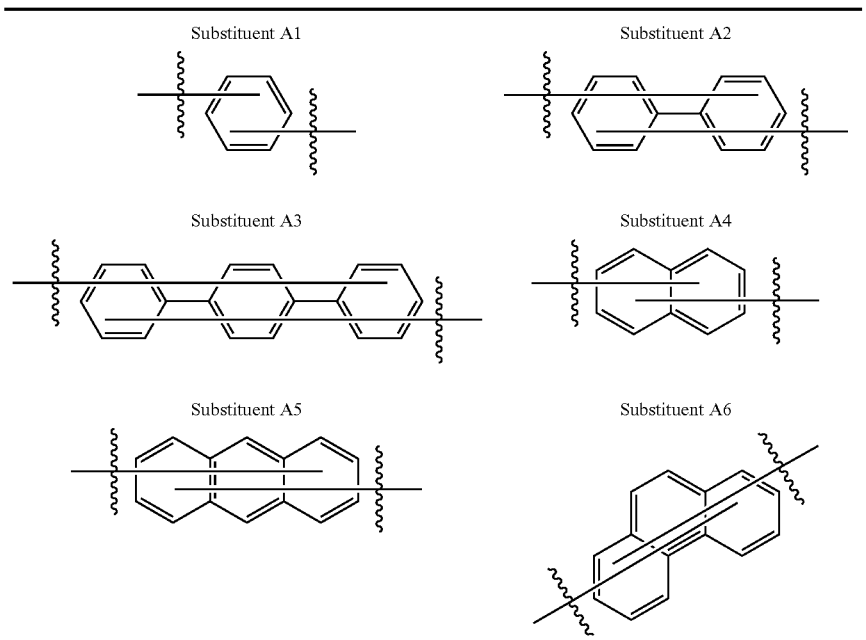

TABLE 3-continued

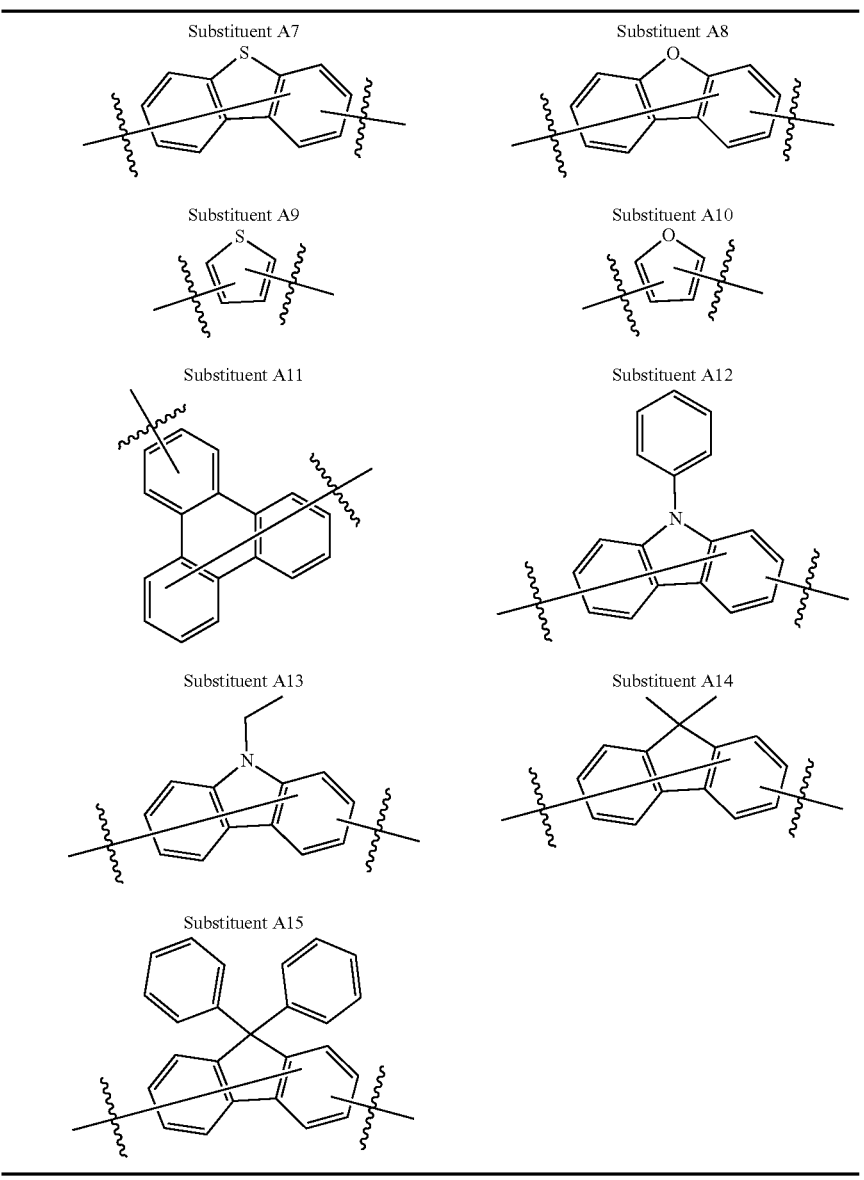

According to an exemplary embodiment of the present specification, Ar7 to Ar9 are the same as or different from each other, and are each independently a substituted or unsubstituted aryl group having 6 to 30 carbon atoms.

According to an exemplary embodiment of the present specification, Ar7 to Ar9 are the same as or different from each other, and are each independently a substituted or unsubstituted phenyl group, a substituted or unsubstituted biphenyl group, a substituted or unsubstituted naphthyl group, or a substituted or unsubstituted fluorenyl group.

According to an exemplary embodiment of the present specification, Ar7 to Ar9 are the same as or different from each other, and are each independently a phenyl group, a biphenyl group, a naphthyl group, or a fluorenyl group.

According to an exemplary embodiment of the present specification, Ar7 to Ar9 are the same as or different from each other, and are each independently a substituted or unsubstituted heteroaryl group having 6 to 50 carbon atoms.

According to an exemplary embodiment of the present specification, Ar7 to Ar9 are the same as or different from each other, and are each independently a substituted or unsubstituted carbazolyl group.

According to an exemplary embodiment of the present specification, Ar7 to Ar9 are the same as or different from each other, and are each independently a carbazole group which is unsubstituted or substituted with an alkyl group or an aryl group.

According to an exemplary embodiment of the present specification, Ar7 to Ar9 are the same as or different from each other, and are each independently a carbazole group which is unsubstituted or substituted with a methyl group or a phenyl group.

According to an exemplary embodiment of the present specification, Ar7 to Ar9 are the same as or different from each other, and are each independently a carbazolyl group in which a fused ring is formed.

According to an exemplary embodiment of the present specification, Ar7 to Ar9 are a carbazolyl group.

According to an exemplary embodiment of the present specification, Ar7 to Ar9 are the same as or different from each other, and are each independently a substituted or unsubstituted dibenzothiophene group.

According to an exemplary embodiment of the present specification, Ar7 to Ar9 are the same as or different from each other, and are each independently a dibenzothiophene group in which a fused ring is formed.

According to an exemplary embodiment of the present application, Ar7 to Ar9 are a dibenzothiophene group.

According to an exemplary embodiment of the present specification, Ar7 to Ar9 are the same as or different from each other, and are each independently a substituted or unsubstituted dibenzofuran group.

According to an exemplary embodiment of the present specification, Ar7 to Ar9 are the same as or different from each other, and are each independently a dibenzofuran group in which a fused ring is formed.

According to an exemplary embodiment of the present application, Ar7 to Ar9 are a dibenzofuran group.

According to an exemplary embodiment of the present specification, Ar7 to Ar9 are the same as or different from each other, and are each independently

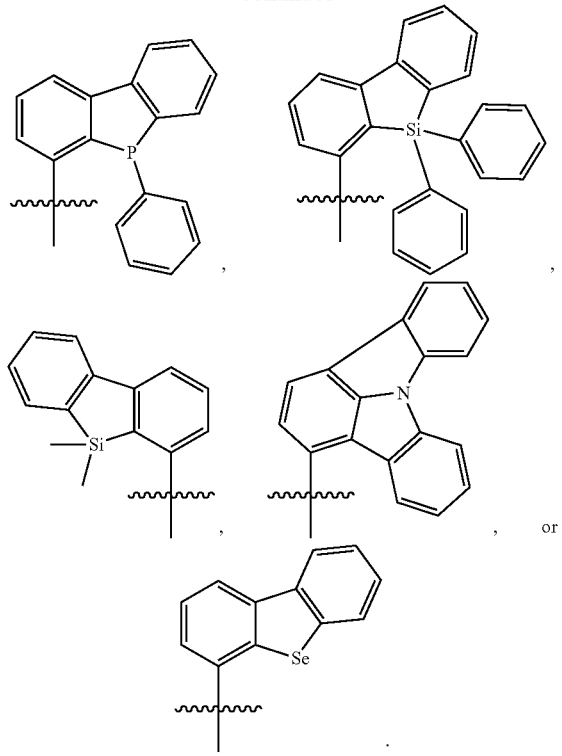

According to an exemplary embodiment of the present specification, Ar7 to Arg are the same as or different from each other, and are each independently selected from the substituents in the following Table 4.

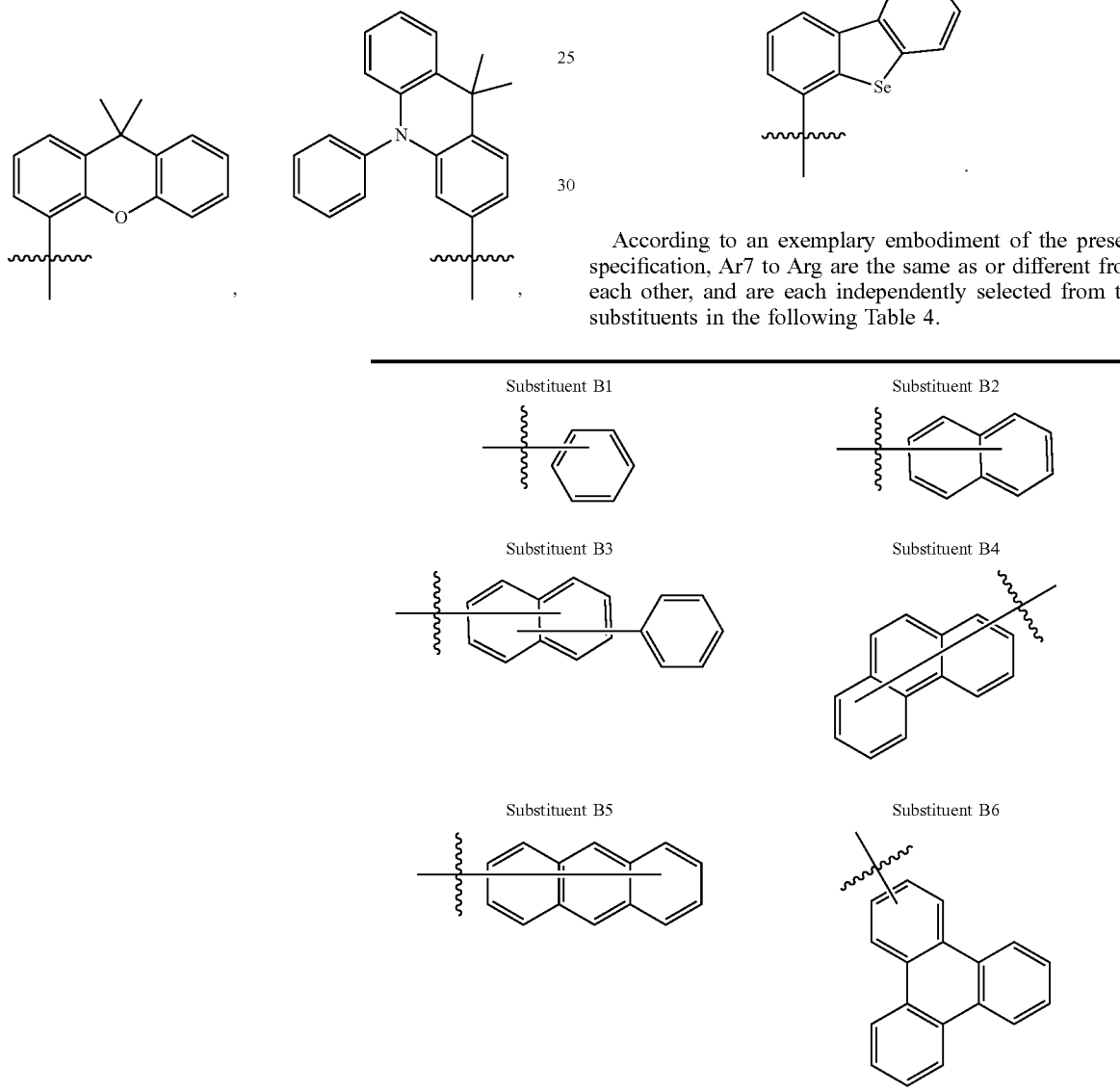

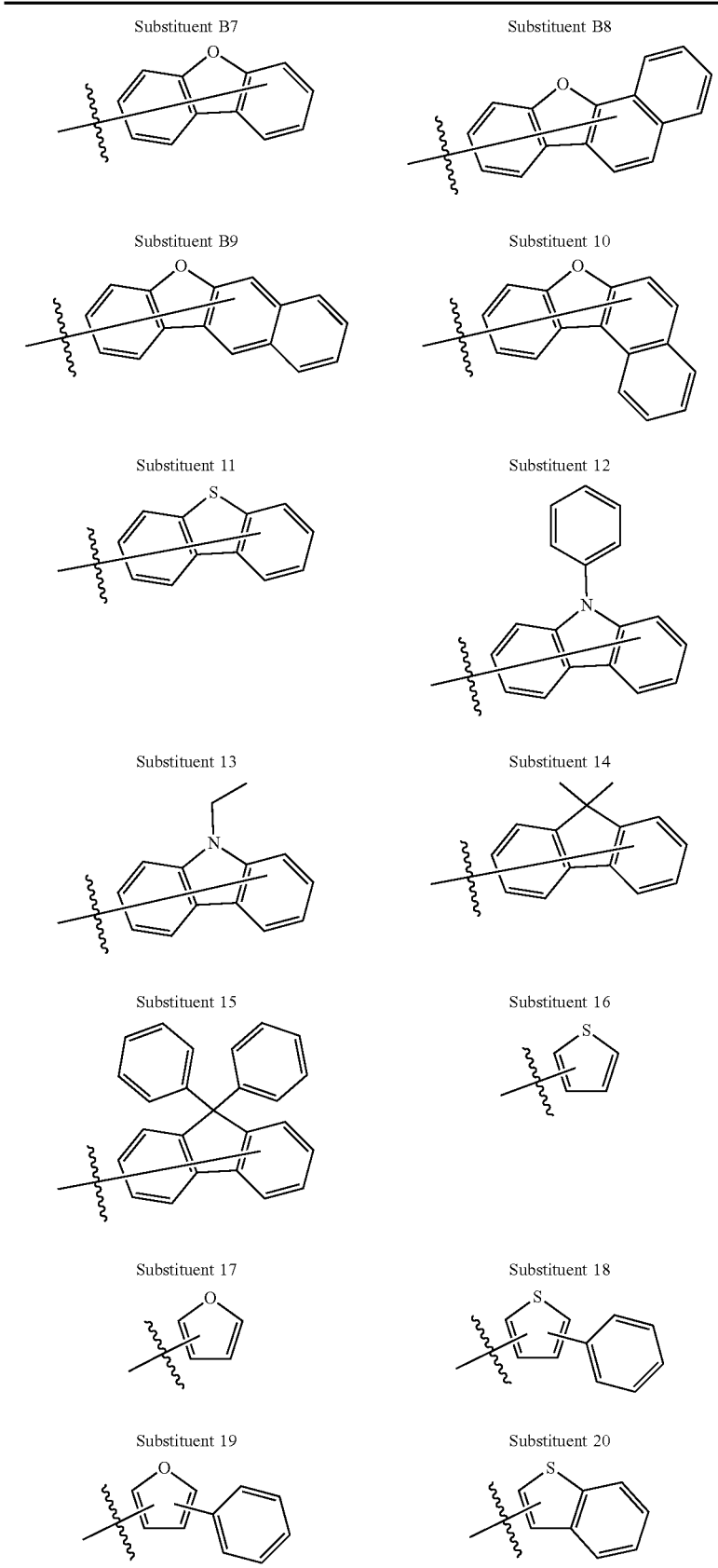

-continued
Substituent 21
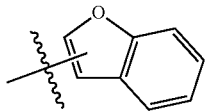
Substituent 22
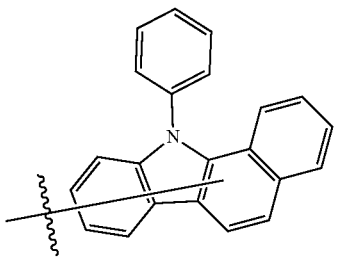
Substituent 23
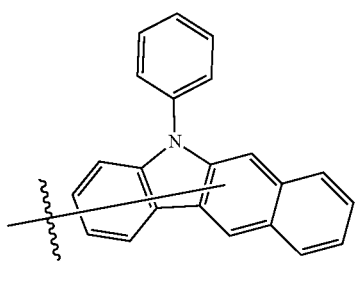
Substituent 24
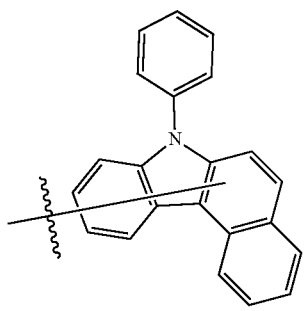
Substituent 25
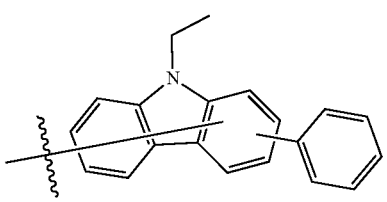
Substituent 26
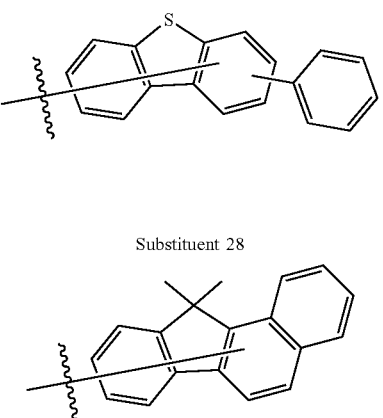
Substituent 27
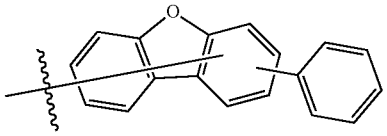
Substituent 28
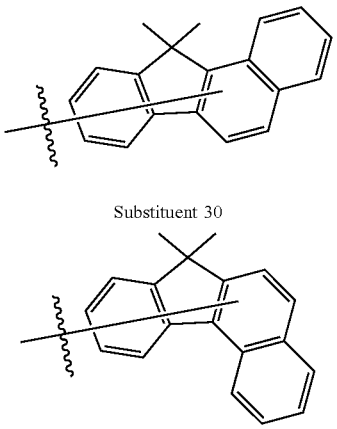
Substituent 29
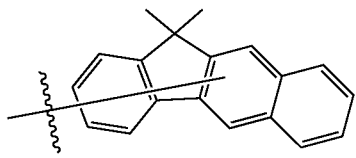
Substituent 30
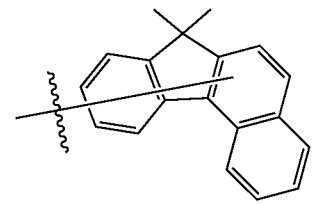
Substituent 31
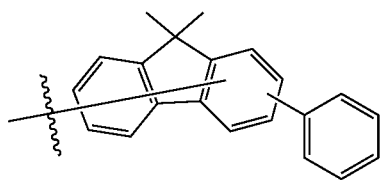
Substituent 32
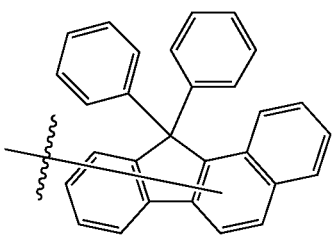

-continued
Substituent 33
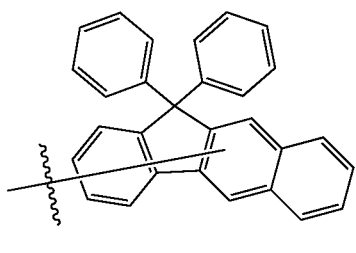
Substituent 34
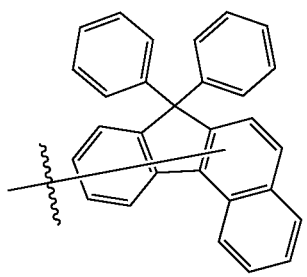
Substituent 35
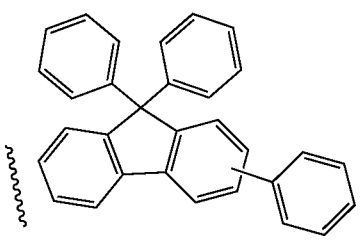
Substituent 36
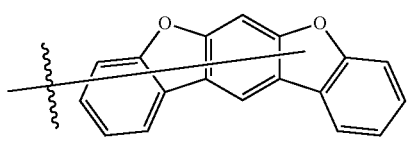
Substituent 37
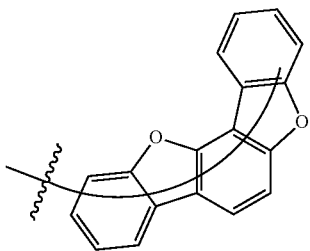
Substituent 38
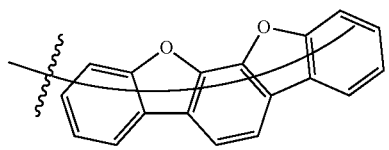
Substituent 39
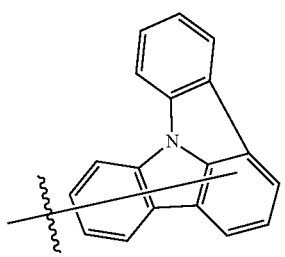
Substituent 40
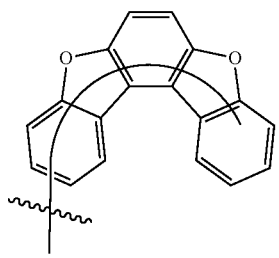
Substituent 41
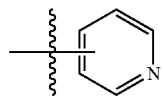
Substituent 42
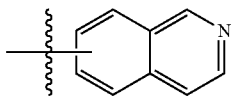
Substituent 43
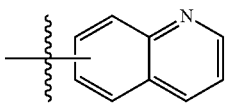
Substituent 44
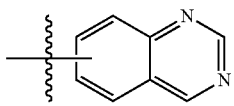

-continued
Substituent 45
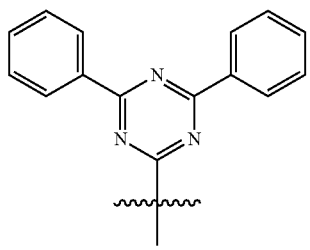 [SMILES: *c1nc(-c2ccccc2)nc(-c2ccccc2)n1]
Substituent 46
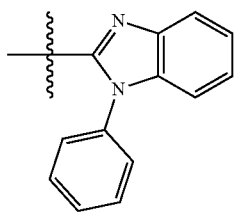 [SMILES: *c1nc2ccccc2n1-c1ccccc1]
Substituent 47
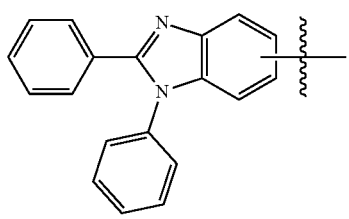
Substituent 48
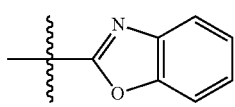 [SMILES: *c1nc2ccccc2o1]
Substituent 49
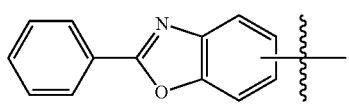
Substituent 50
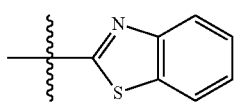 [SMILES: *c1nc2ccccc2s1]
Substituent 51
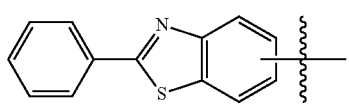
Substituent 52
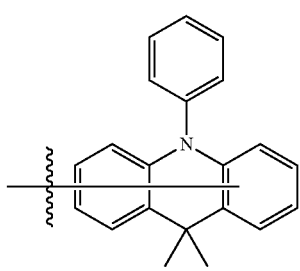
Substituent 53
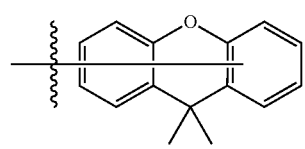
Substituent 54
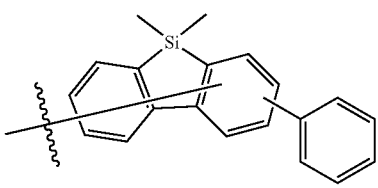
Substituent 55
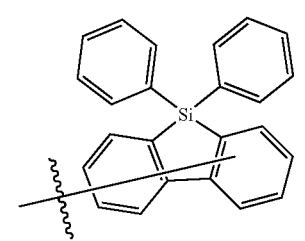
Substituent 56
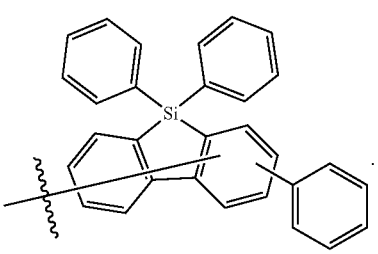

According to an exemplary embodiment of the present specification, Formula 1B is selected from the following compounds:
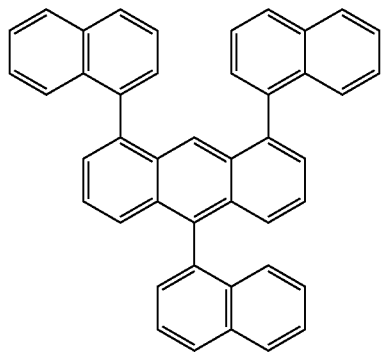
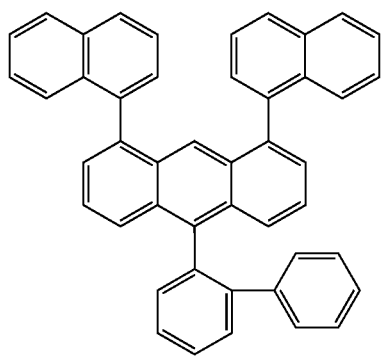
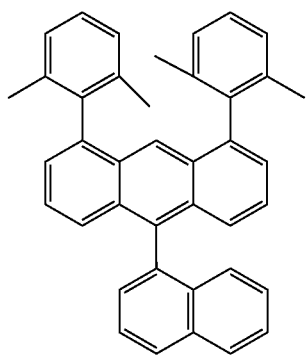
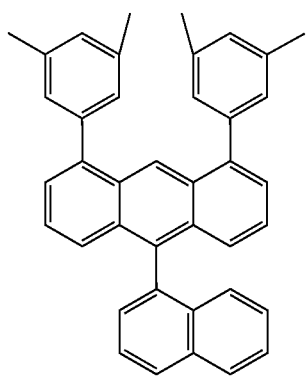
-continued
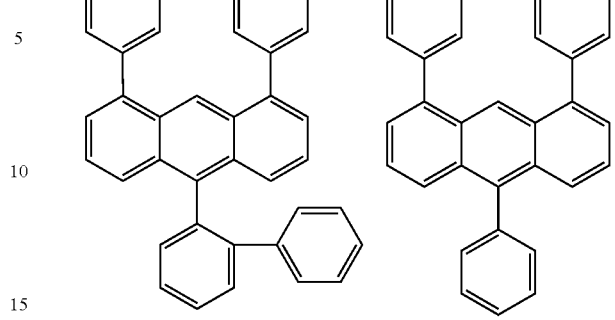
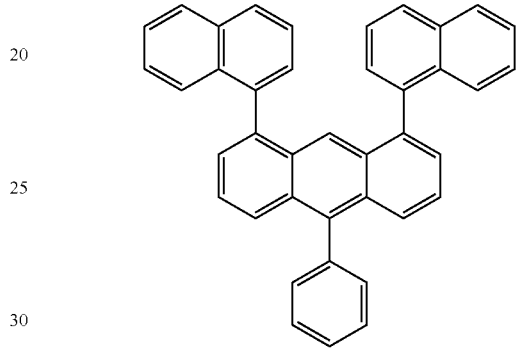
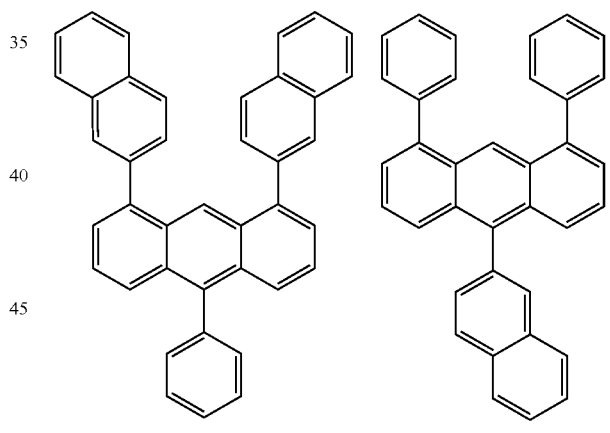
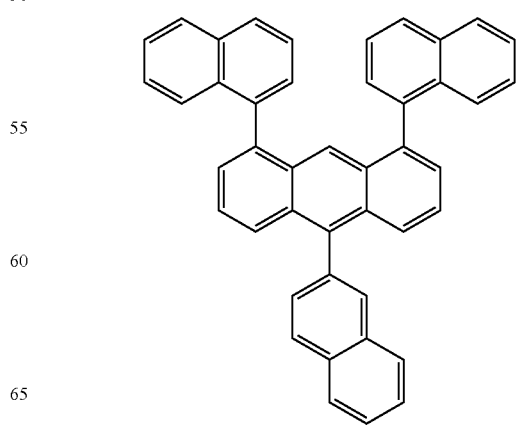

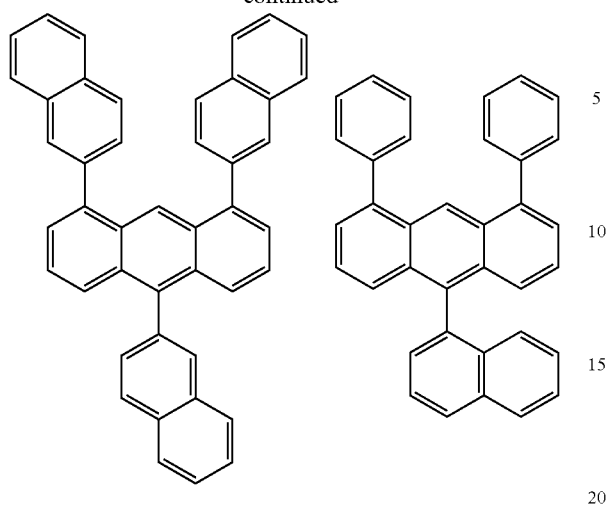
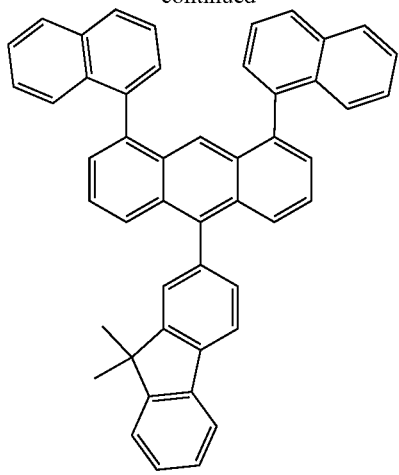
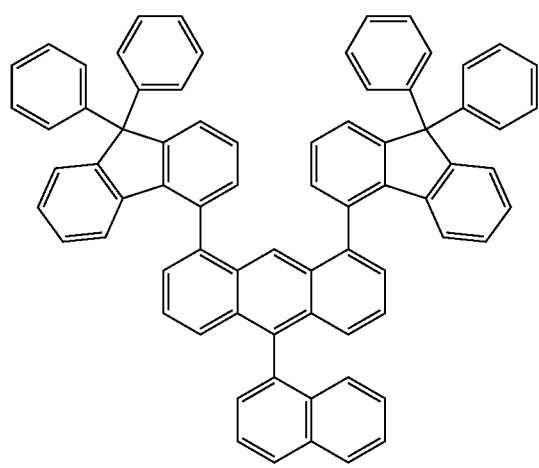
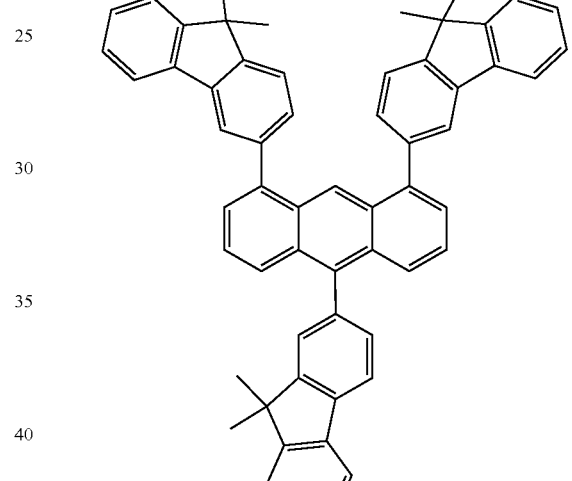
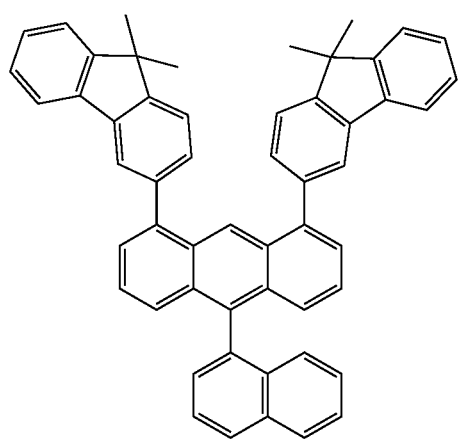
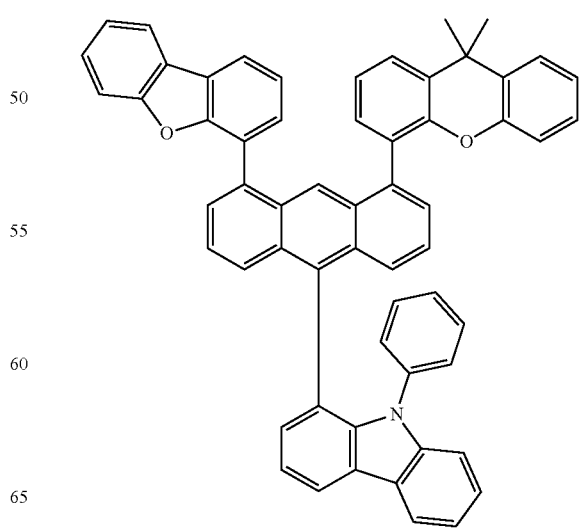

177
-continued
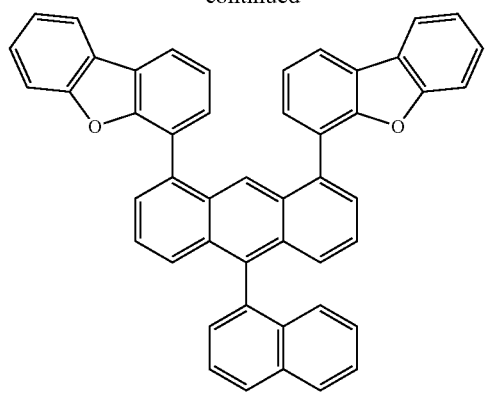
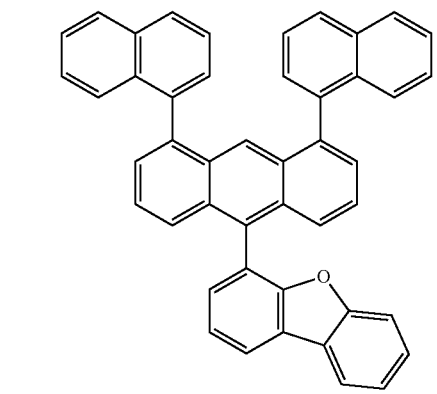
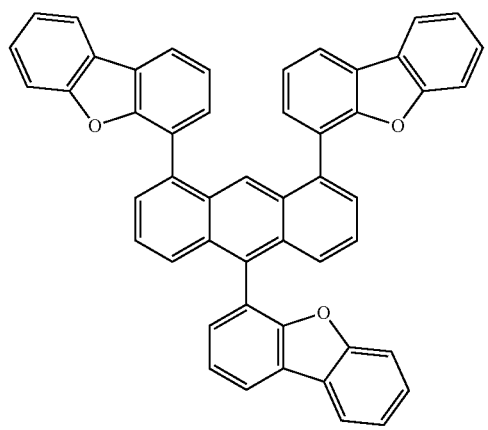
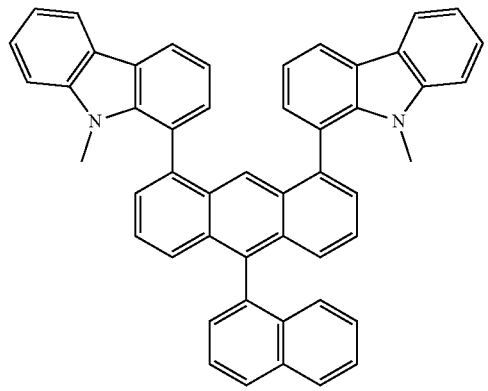
178
-continued
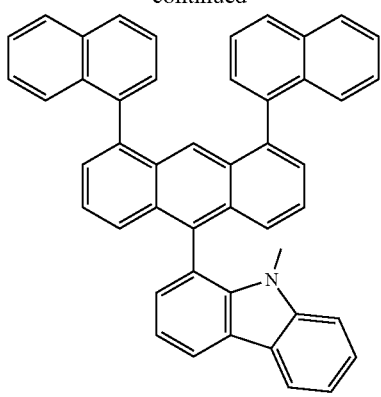
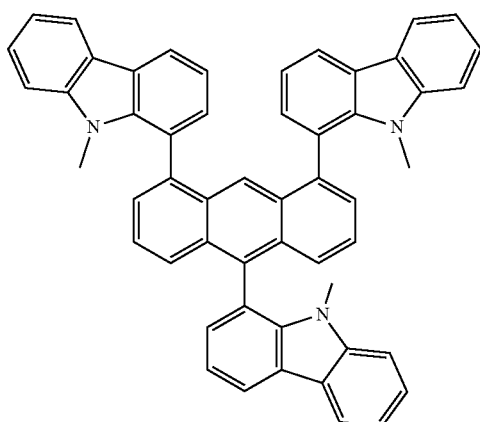
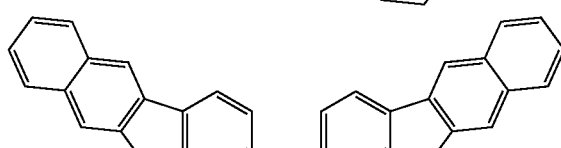
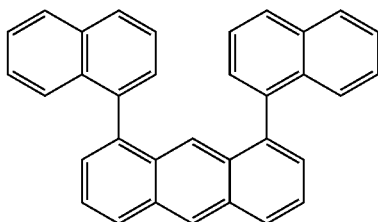
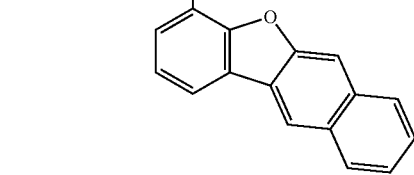

179
-continued
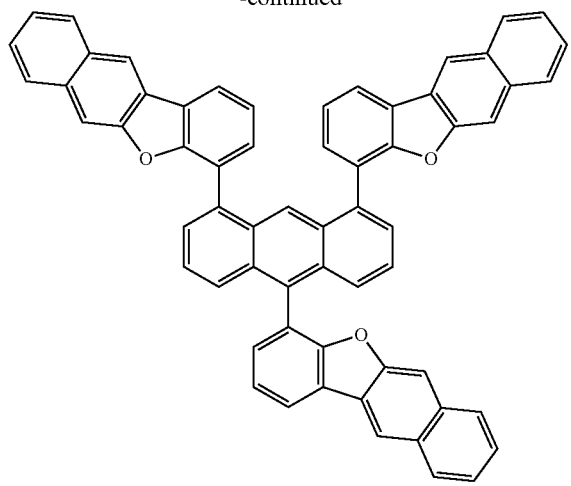
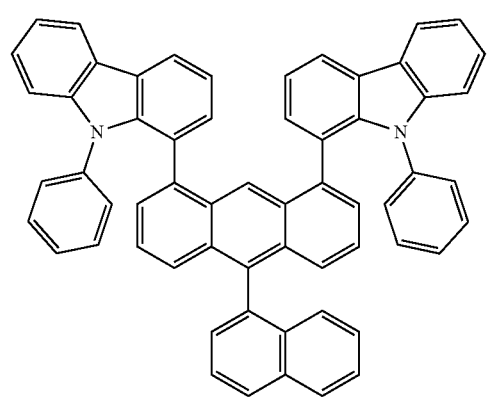
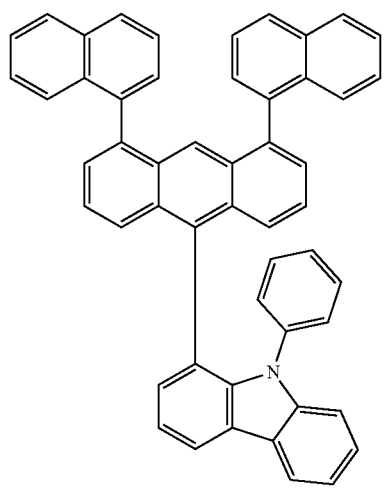
180
-continued
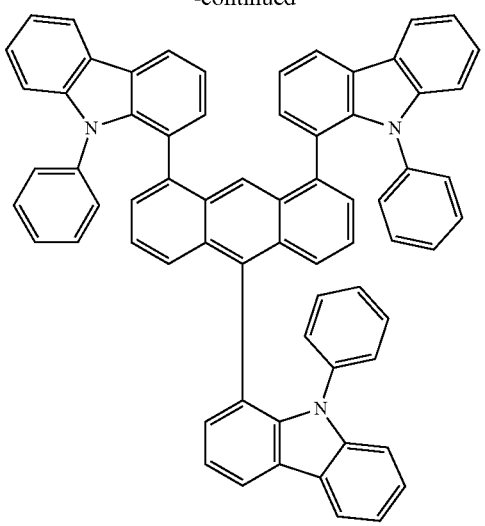
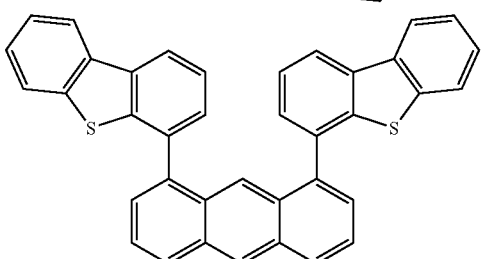
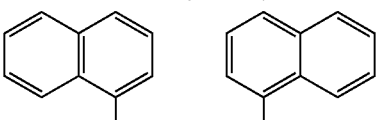
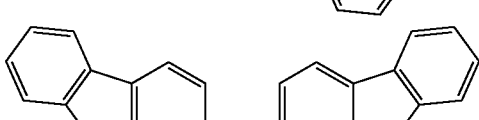
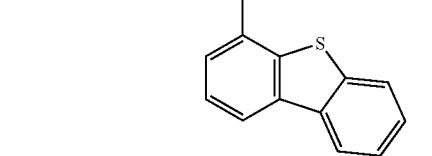

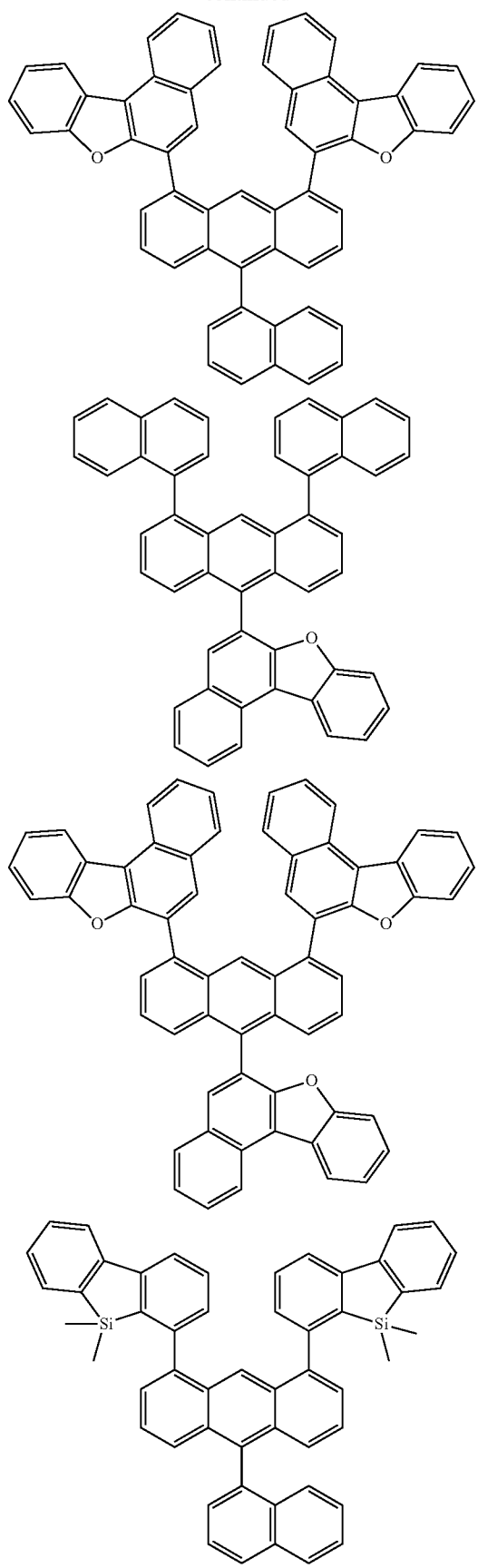

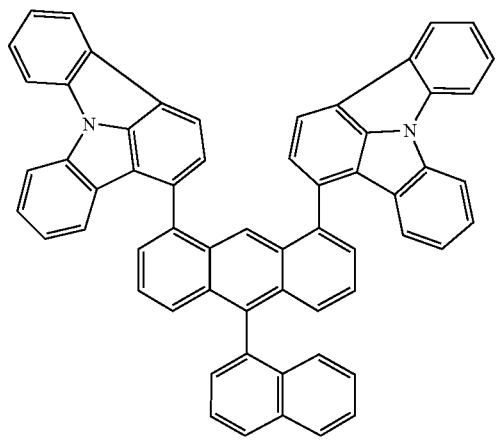
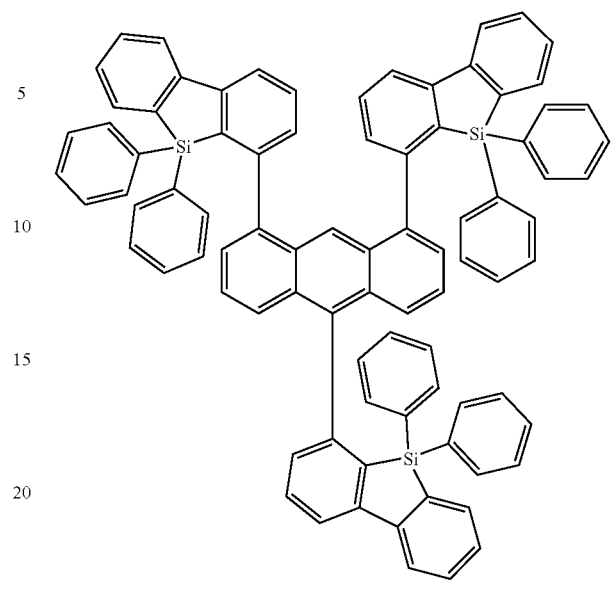
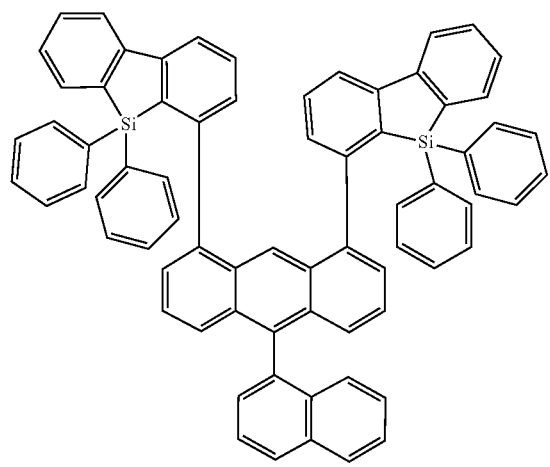
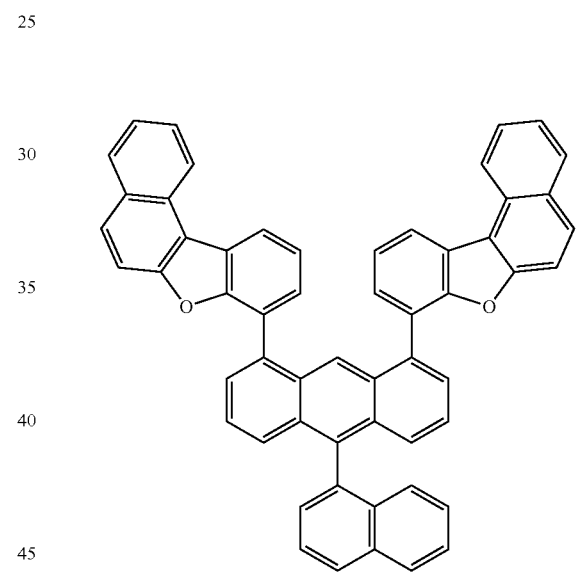
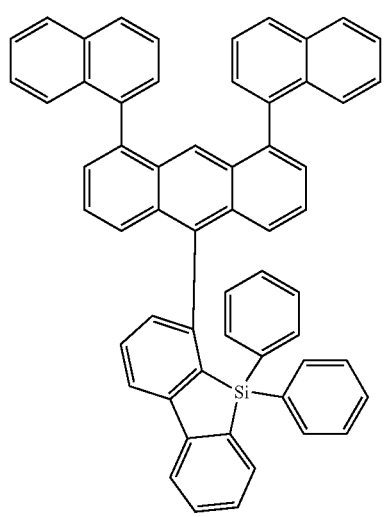
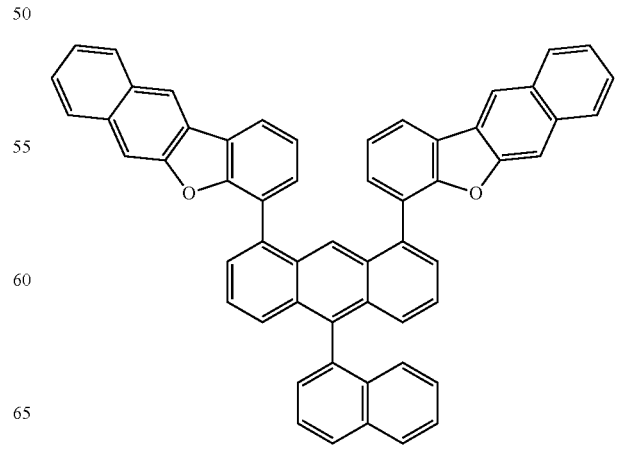

185
-continued
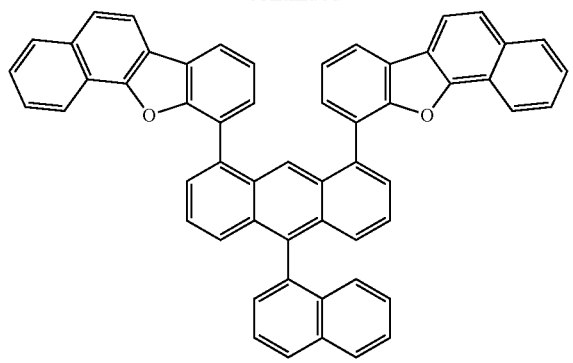
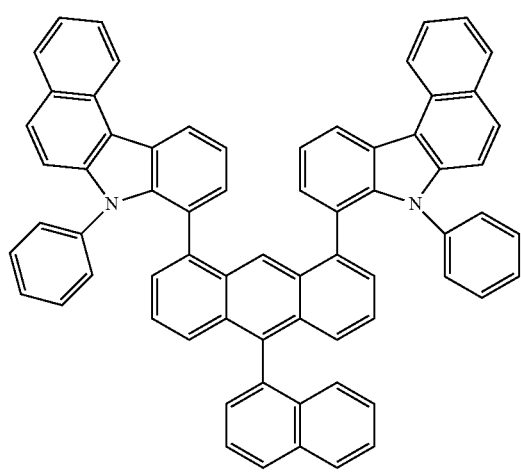
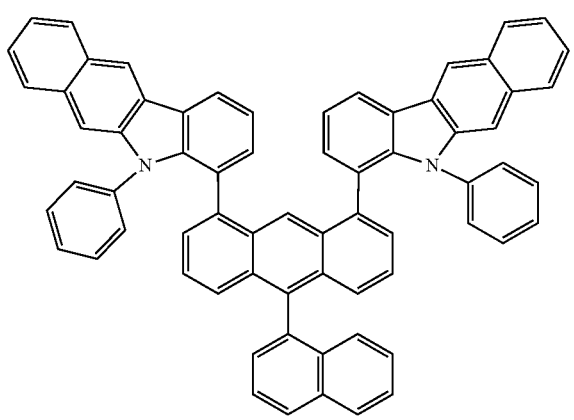
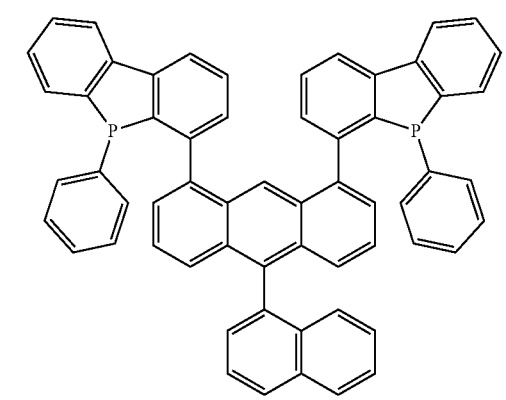
186
-continued
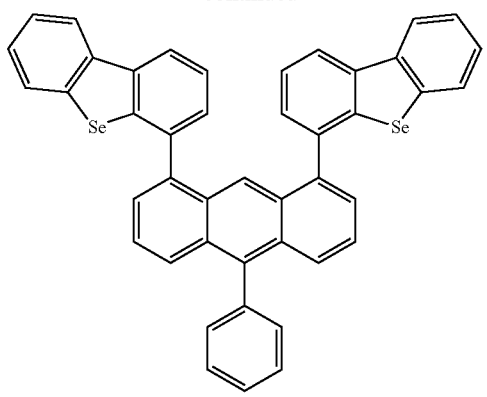
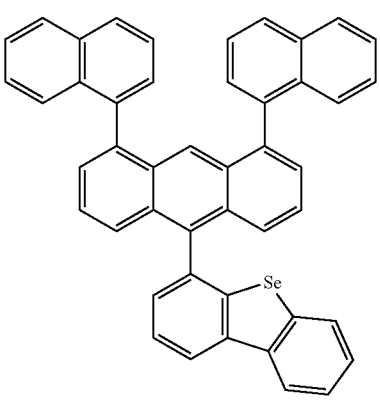
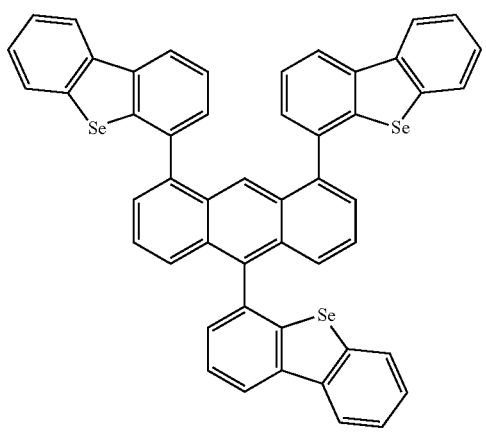
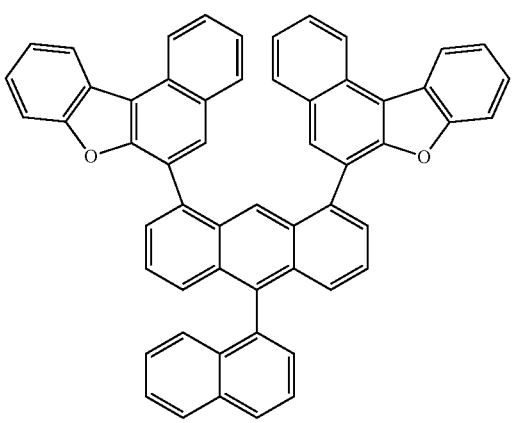

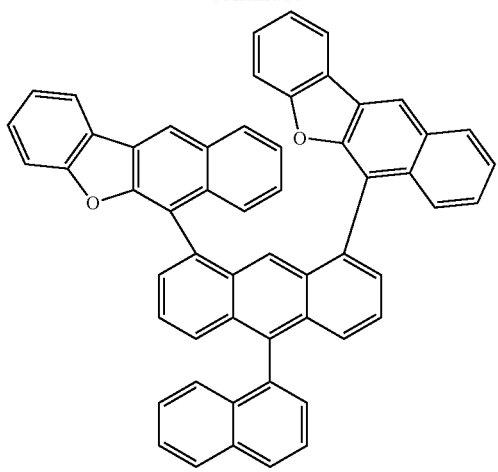

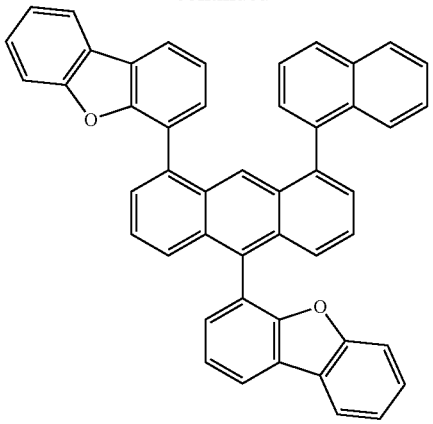

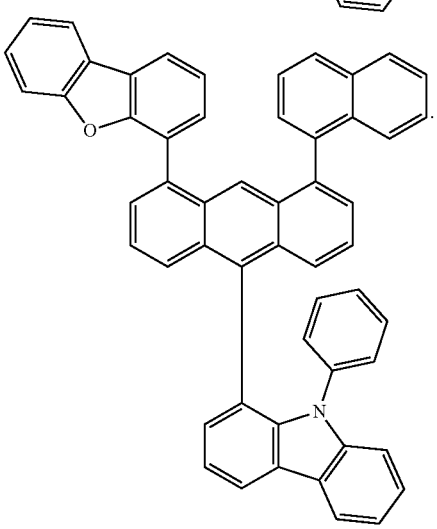

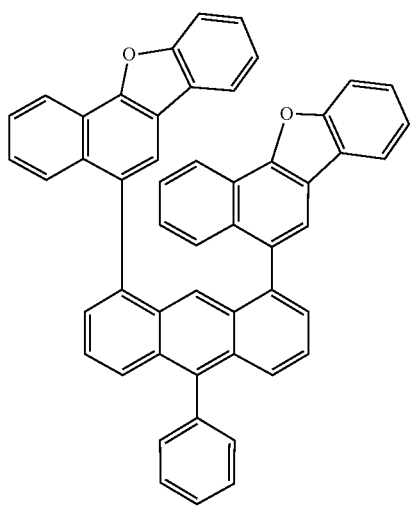

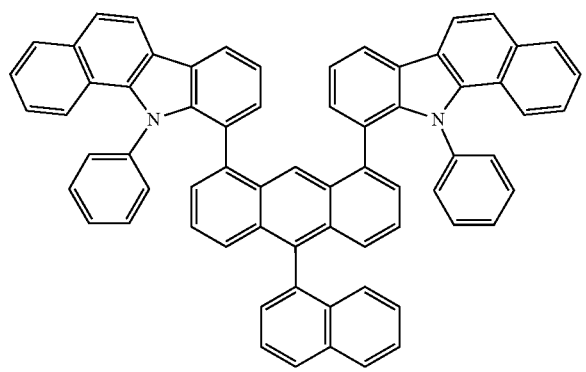

According to an exemplary embodiment of the present specification, the organic material layer includes a light emitting layer, and the light emitting layer includes the compound of Formula 1 as a dopant of the light emitting layer, and includes the compound of Formula 1B as a host of the light emitting layer.

According to an exemplary embodiment of the present specification, the light emitting layer includes the compound of Formula 1 and the compound of Formula 1B at a weight ratio of 1:99 to 10:90.

According to an exemplary embodiment of the present specification, the organic material layer includes a light emitting layer, and the light emitting layer includes the compound of Formula 1 as a dopant of the light emitting layer, and includes one or more of the compounds of Formulae 1A and 1B as a host of the light emitting layer.

According to an exemplary embodiment of the present specification, the light emitting layer includes the compound of Formula 1 and one or more of the compounds of Formulae 1A and 1B at a weight ratio of 1:99 to 10:90.

According to an exemplary embodiment of the present specification, the organic material layer includes a light emitting layer, the light emitting layer includes the compound of Formula 1 as a dopant of the light emitting layer, and the dopant is a blue dopant.

According to an exemplary embodiment of the present specification, the organic light emitting device is a blue organic light emitting device.

According to an exemplary embodiment of the present specification, the organic material layer includes a hole injection layer or a hole transport layer, and the hole injection layer or the hole transport layer includes the compound of Formula 1.

According to an exemplary embodiment of the present specification, the organic material layer includes an electron transport layer or an electron injection layer, and the electron transport layer or the electron injection layer includes the compound of Formula 1.

According to an exemplary embodiment of the present specification, the organic material layer includes an electron blocking layer or a hole blocking layer, and the electron blocking layer or the hole blocking layer includes the compound of Formula 1.

According to an exemplary embodiment of the present specification, the organic material layer can further include one or more layers selected from the group consisting of a light emitting layer, a hole injection layer, a hole transport layer, an electron injection layer, an electron transport layer, an electron blocking layer, and a hole blocking layer.

The organic light emitting device of the present specification can be manufactured by the materials and methods known in the art, except that one or more layers of the organic material layer include the compound of the present specification, that is, the compound of Formula 1.

When the organic light emitting device includes a plurality of organic material layers, the organic material layers can be formed of the same material or different materials.

For example, the organic light emitting device of the present specification can be manufactured by sequentially stacking a first electrode, an organic material layer, and a second electrode on a substrate. In this case, the organic light emitting device can be manufactured by depositing a metal or a metal oxide having conductivity, or an alloy thereof on a substrate to form a first electrode, forming an organic material layer including a hole injection layer, a hole transport layer, a light emitting layer, and an electron transport layer thereon, and then depositing a material, which can be used as a second electrode, thereon, by using a physical vapor deposition (PVD) method such as sputtering or e-beam evaporation. In addition to the method described above, an organic light emitting device can be made by sequentially depositing a second electrode material, an organic material layer, and a first electrode material on a substrate. Further, the compound of Formula 1 can be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode.

As the positive electrode material, materials having a high work function are usually preferred so as to facilitate the injection of holes into an organic material layer. Specific examples of the positive electrode material which can be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or SnO$_2$:Sb; a conductive polymer such as poly(3-methy-lthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material such as LiF/Al or LiO$_2$/Al and Mg/Ag; and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transport layer is a layer which accepts holes from a hole injection layer and transports the holes to a light emitting layer, and a hole transporting material is suitably a material having high hole mobility which can accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The electron blocking layer is a layer which can improve the service life and efficiency of the device by preventing electrons injected from an electron injection layer from passing through a light emitting layer and entering a hole injection layer, and can be formed at an appropriate portion between the light emitting layer and the hole injection layer by using publicly-known materials, if necessary.

When the light emitting layer includes an additional light emitting layer in addition to the light emitting layer including the compound of Formula 1, a light emitting material for the light emitting layer is preferably a material having good quantum efficiency for fluorescence or phosphorescence as a material which can emit light in a visible ray region by accepting holes and electrons from the hole transport layer and the electron transport layer, respectively, and combining the holes and the electrons. Specific examples thereof include: an 8-hydroxy-quinoline aluminum complex (Alq$_3$), carbazole-based compounds, dimerized styryl compounds, BAlq, 10-hydroxybenzoquinoline-metal compounds, benzoxazole-based, benzothiazole-based and benzimidazole-based compounds, poly(p-phenylenevinylene) (PPV)-based polymers, spiro compounds, polyfluorene, rubrene, and the like, but are not limited thereto.

When the light emitting layer includes an additional light emitting layer in addition to the light emitting layer including the compound of Formula 1, the light emitting layer can include a host material and a dopant material. Examples of the host material include fused aromatic ring derivatives, or hetero ring-containing compounds, and the like. Specific examples of the fused aromatic ring derivatives include anthracene derivatives, pyrene derivatives, naphthalene derivatives, pentacene derivatives, phenanthrene compounds, fluoranthene compounds, and the like, and examples of the hetero ring-containing compounds include carbazole derivatives, dibenzofuran derivatives, ladder-type furan compounds, pyrimidine derivatives, and the like, but the examples thereof are not limited thereto.

When the light emitting layer includes an additional light emitting layer in addition to the light emitting layer including the compound of Formula 1, examples of the dopant material include aromatic amine derivatives, styrylamine compounds, boron complexes, fluoranthene compounds, metal complexes, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The hole blocking layer is a layer which can improve the service life and efficiency of the device by preventing holes injected from a hole injection layer from passing through a light emitting layer and entering an electron injection layer, and can be formed at an appropriate portion between the light emitting layer and the electron injection layer by using publicly-known materials, if necessary.

The electron transport layer is a layer which accepts electrons from an electron injection layer and transports the electrons to a light emitting layer, and an electron transporting material is suitably a material having high electron mobility which can proficiently accept electrons from a negative electrode and transfer the electrons to a light emitting layer. Specific examples thereof include: an Al complex of 8-hydroxyquinoline; complexes including $Alq_3$; organic radical compounds; hydroxyflavone-metal complexes, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a negative electrode, and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxy-quinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification can be a top emission type, a bottom emission type, or a dual emission type according to the materials to be used.

MODE FOR INVENTION

Hereinafter, the present specification will be described in detail with reference to Examples for specifically describing the present specification. However, the Examples according to the present specification can be modified in various forms, and it is not interpreted that the scope of the present specification is limited to the Examples described below in detail. The Examples of the present specification are provided to more completely explain the present specification to a person with ordinary skill in the art.

SYNTHESIS EXAMPLES

[Compound 1-2]

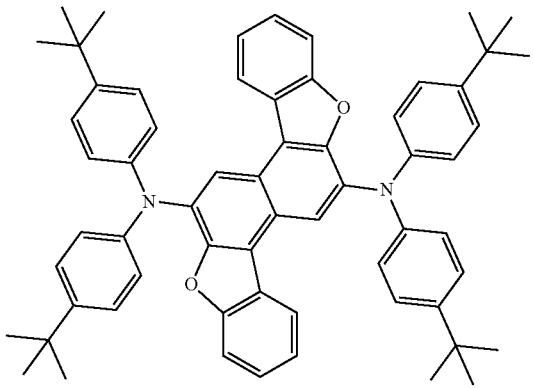

[Compound 1-21]
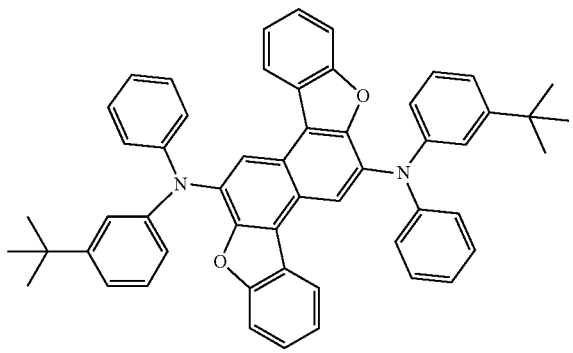
[Compound 1-22]
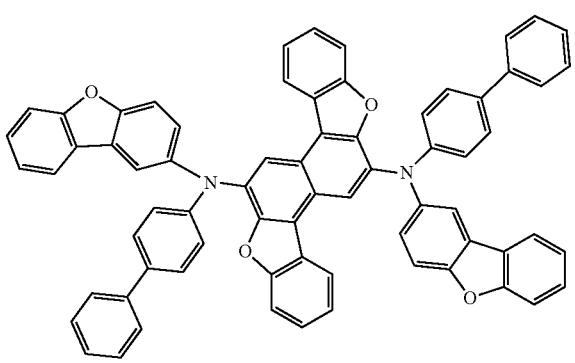
[Compound 1-23]
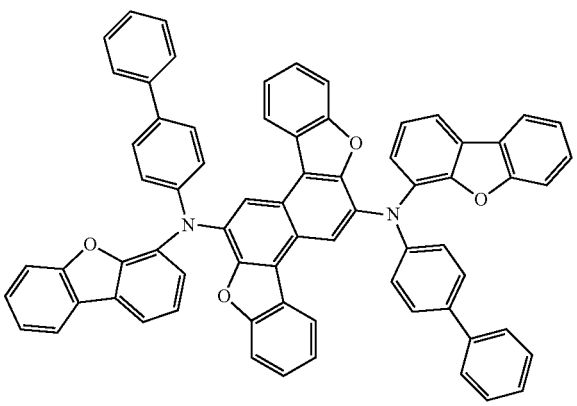
[Compound 4-3]
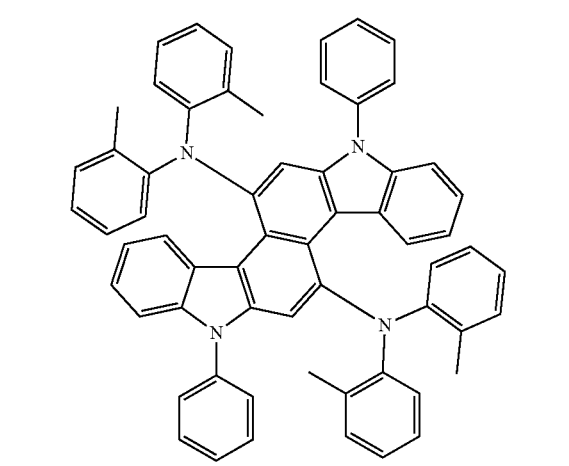
[Compound 4-21]
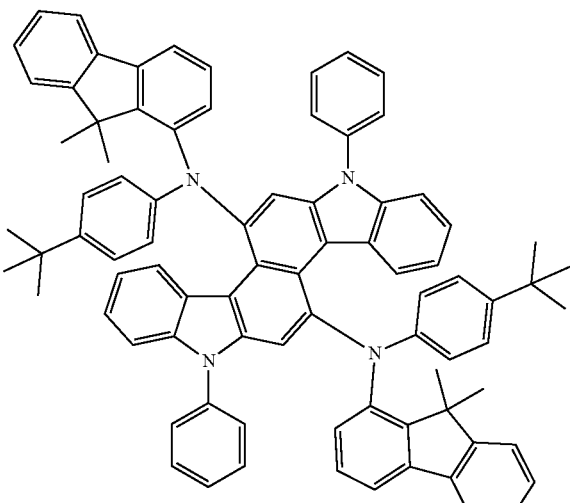
[Compound 2-21]
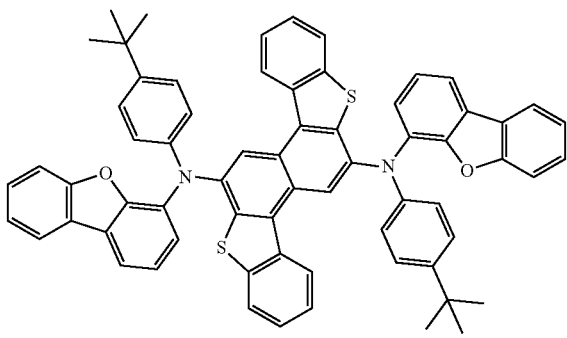
[Compound 2-22]
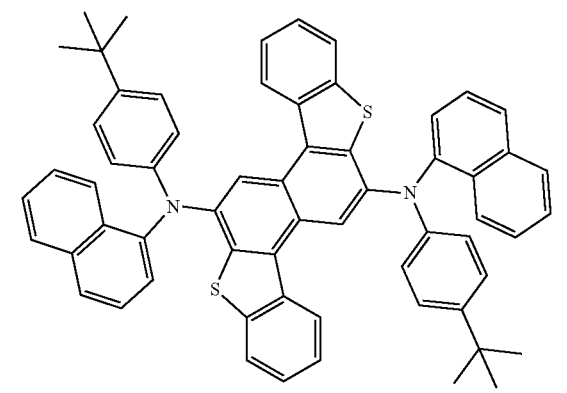

[Compound 5-2]

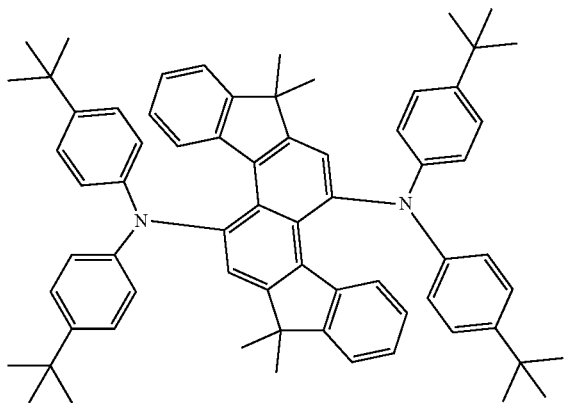

[Compound 5-21]

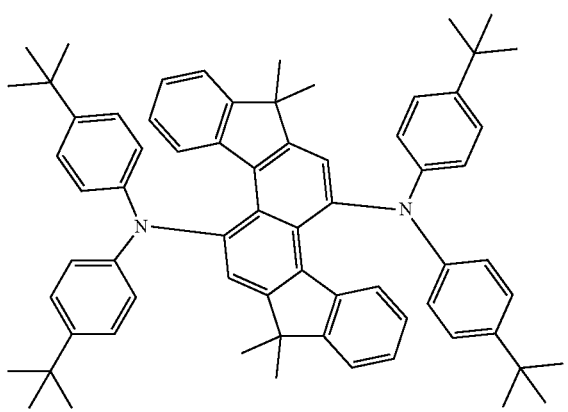

[Compound 6-21]

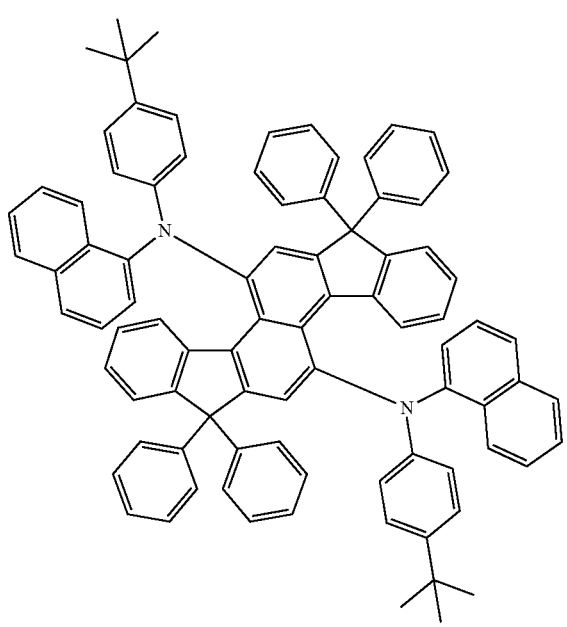

[Compound 6-1]

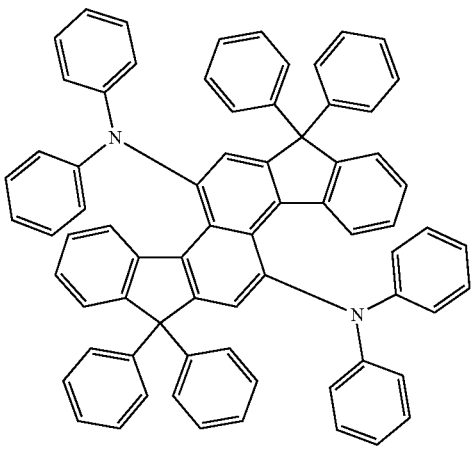

Synthesis Example 1: Synthesis of Compound 1-2

1) Synthesis of Intermediate 1-a

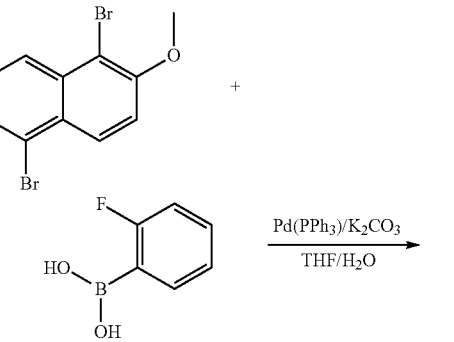

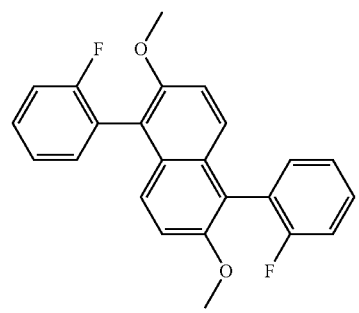

Intermediate 1-a

After 1,5-bromo-2,6-dihydroxynaphthalene (20.0 g, 58 mmol) and 2-fluorophenylboronic acid (20 g, 145 mmol) were completely dissolved in 300 mL of tetrahydrofuran, 100 mL of an aqueous solution of potassium carbonate (24.0 g, 174 mmol) was added thereto, tetrakis-(triphenylphosphine) palladium (3.4 g, 2.9 mmol) was added thereto, and then the resulting mixture was refluxed and stirred for 24 hours. After completion of the reaction, the temperature was lowered to room temperature, and then the organic layer was separated by extraction with water and ethyl acetate. The organic layer was treated with anhydrous magnesium sulfate, and then filtered and concentrated under reduced pressure. The solid was recrystallized with ethyl acetate to obtain Intermediate 1-a (19.2 g, 88%). MS [M+]=376.1

2) Synthesis of Intermediate 1-b

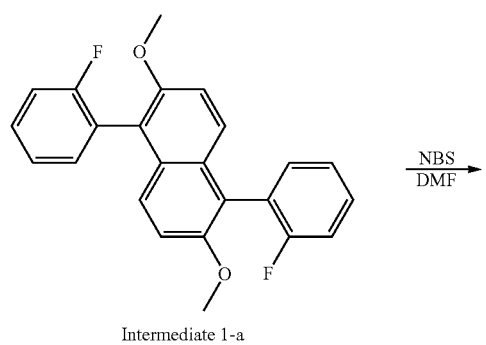

Intermediate 1-a (19.2 g, 51 mmol) was dissolved in 300 mL of dimethylformamide, and then N-bromosuccinimide (19.1 g, 107 mmol) was added thereto, and the resulting mixture was stirred for 2 hours. After completion of the reaction, the organic layer was separated by extraction with water and ethyl acetate. The organic layer was treated with anhydrous magnesium sulfate, and then filtered and concentrated under reduced pressure. The solid was recrystallized with ethyl acetate and hexane to obtain Intermediate 1-b (25 g, 90%). MS [M+]=534.1

3) Synthesis of Intermediate 1-c

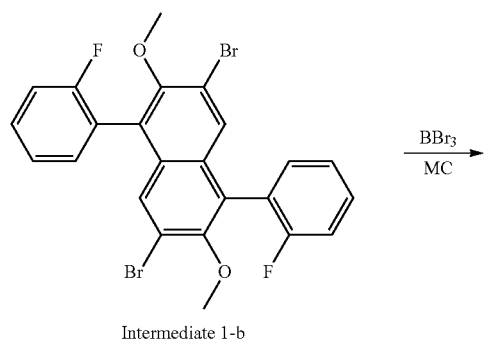

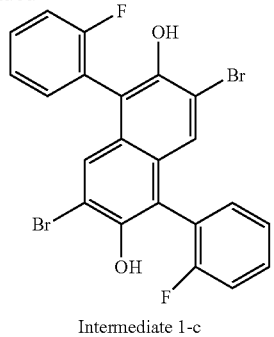

Intermediate 1-b (25 g, 46 mmol) and 300 mL of dichloromethane were put into a container, 1 M BBr$_3$ in CH$_2$Cl$_2$ (115 ml, 115 mmol) was slowly added dropwise thereto at 0° C., and then the resulting mixture was stirred for 8 hours. After completion of the reaction, the product was neutralized with NaHCO$_3$, and then the organic layer was separated by extraction with water and CH$_2$Cl$_2$. The organic layer was treated with anhydrous magnesium sulfate, and then filtered and concentrated under reduced pressure to obtain Intermediate 1-c (19 g, 83%). MS [M+]=506.1

4) Synthesis of Intermediate 1-d

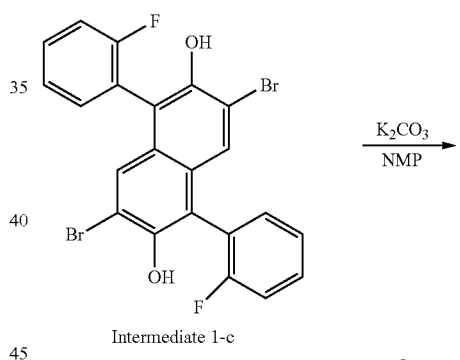

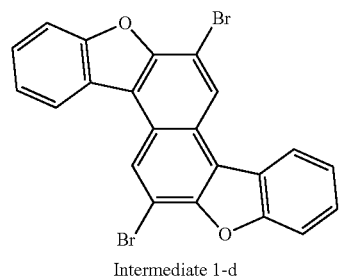

Intermediate 1-c (19 g, 38.2 mmol) and K$_2$CO$_3$ (26.2 g, 191 mmol) were put into 150 mL of N-methylpyrrolidone (NMP), and the resulting mixture was stirred at 150° C. for 8 hours. After completion of the reaction, 500 mL of water was put thereinto, and the organic layer was separated by extraction with ethyl acetate. The organic layer was treated with anhydrous magnesium sulfate, and then filtered and concentrated under reduced pressure. The solid was recrystallized with toluene and hexane to obtain Intermediate 1-d (15.1 g, 83%). MS [M+]=466.1

5) Synthesis of Compound 1-2

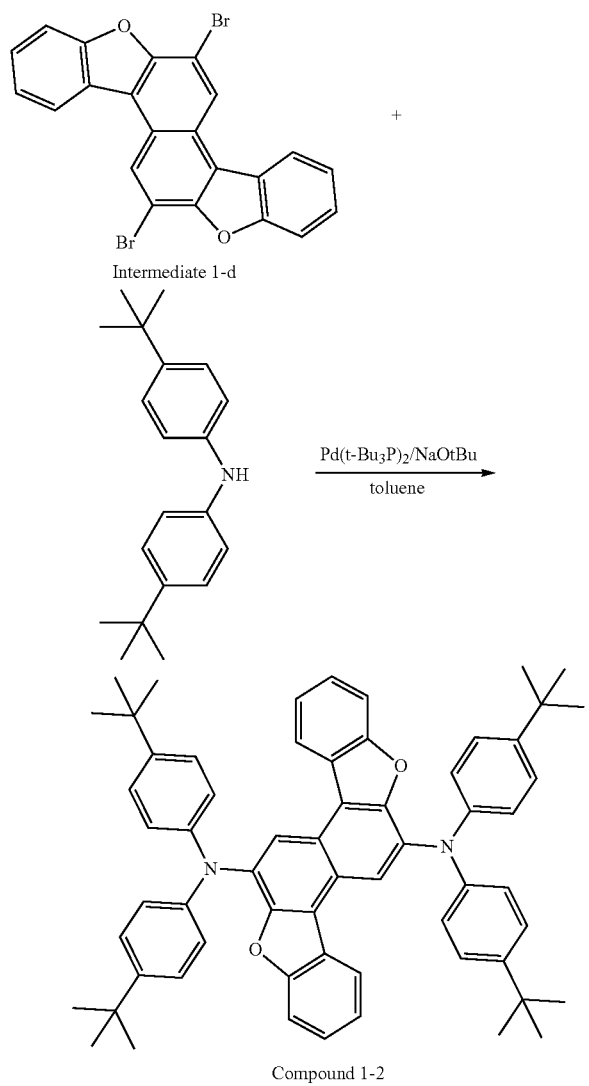

Intermediate 1-d

Compound 1-2

Intermediate 1-d (6.0 g, 12.9 mmol), bis(4-tertbutylphenyl)amine (10.9 g, 38.6 mmol), sodium tert-butoxide (6.2 g, 64.5 mmol), and bis(tri-tert-butylphosphine)palladium (0) (0.33 g, 0.6 mmol) were put into 150 mL of toluene in a round bottom flask under a nitrogen atmosphere, and the resulting mixture was refluxed and stirred. When the reaction was terminated, the product was cooled to room temperature, and then extraction with toluene and water was performed, and the aqueous layer was removed. The remaining product was treated with anhydrous magnesium sulfate, and then filtered and concentrated under reduced pressure. The product was separated and purified with column chromatography, and then recrystallized with toluene and hexane to obtain Compound 1-2 (7.3 g, 65%). MS [M+]=867.1

Synthesis Example 2. Synthesis of Compound 1-21

Compound 1-21 was obtained in the same manner as in Synthesis Example 1, except that N-4-(tert-butyl)phenyl phenylamine was used instead of bis(4-tertbutylphenyl)amine in 5) of Synthesis Example 1. MS [M+]=754.9

Synthesis Example 3. Synthesis of Compound 1-22

Compound 1-22 was obtained in the same manner as in Synthesis Example 1, except that N-biphenyl-4-yl-2-dibenzofuranylamine was used instead of bis(4-tertbutyl-phenyl)amine in 5) of Synthesis Example 1. MS[M+]=975.1

Synthesis Example 4. Synthesis of Compound 1-23

Compound 1-23 was obtained in the same manner as in Synthesis Example 1, except that N-biphenyl-4-yl-4-dibenzofuranylamine was used instead of bis(4-tertbutyl-phenyl)amine in 5) of Synthesis Example 1. MS[M+]=975.1

Synthesis Example 5. Synthesis of Compound 4-3

1) Synthesis of Intermediate 4-a

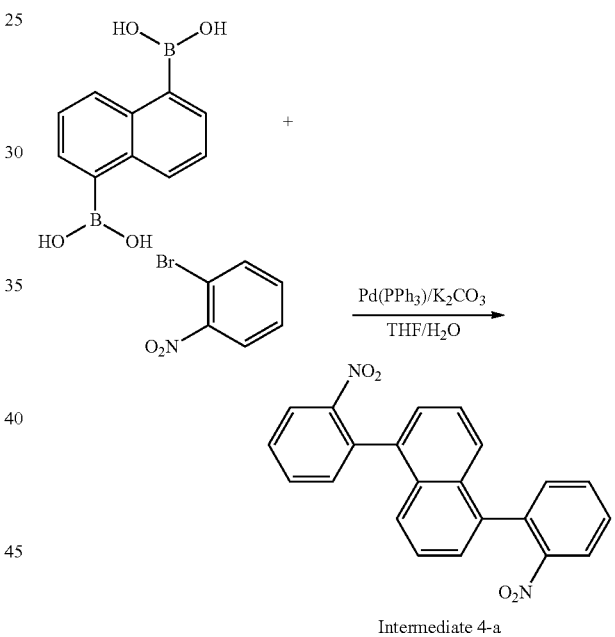

Intermediate 4-a

After naphthanlene-1,5-diboronic acid (20.0 g, 93 mmol) and 1-bromo-2-nitrobenzene (56.2 g, 278 mmol) were completely dissolved in 300 mL of tetrahydrofuran, 100 mL of an aqueous solution of potassium carbonate (38.6 g, 279 mmol) was added thereto, tetrakis-(triphenylphosphine) palladium (5.4 g, 4.7 mmol) was added thereto, and then the resulting mixture was refluxed and stirred for 24 hours. After completion of the reaction, the temperature was lowered to room temperature, and then the organic layer was separated by extraction with water and ethyl acetate. The organic layer was treated with anhydrous magnesium sulfate, and then filtered and concentrated under reduced pressure. The solid was recrystallized with ethyl acetate to obtain Intermediate 4-a (28.9 g, 84%). MS [M+]=370.3

2) Synthesis of Intermediate 4-b

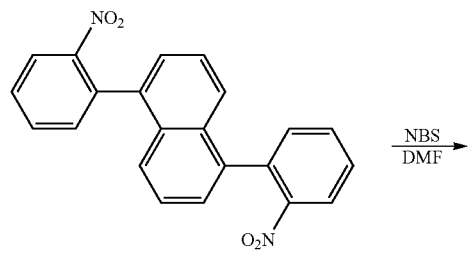

Intermediate 4-a

Intermediate 4-b

Intermediate 4-a (28.9 g, 78 mmol) was dissolved in 300 mL of dimethylformamide, and then N-bromosuccinimide (29.1 g, 164 mmol) was added thereto, and the resulting mixture was stirred for 2 hours. After completion of the reaction, the organic layer was separated by extraction with water and ethyl acetate. The organic layer was treated with anhydrous magnesium sulfate, and then filtered and concentrated under reduced pressure. The solid was recrystallized with ethyl acetate and hexane to obtain Intermediate 4-b (25 g, 60%). MS [M+]=528.1

3) Synthesis of Intermediate 4-c

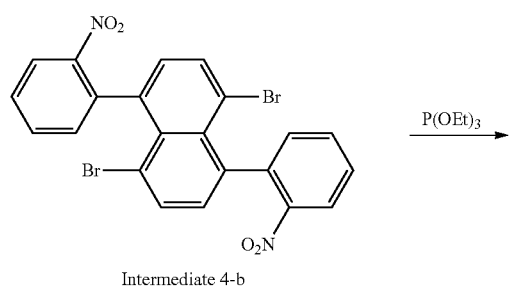

Intermediate 4-b

Intermediate 4-c

After Intermediate 4-b (25.0 g, 37 mmol) was dissolved in 300 mL of triethyl phosphite, the resulting solution was stirred while being heated at 180° C. for 5 hours. After completion of the reaction, the product was precipitated by adding water to the reaction solution, and then the precipitate was filtered. The thus obtained solid was separated and purified with flash column chromatography to obtain Intermediate 4-c (12.2 g, 71%). MS [M+]=464.1

4) Synthesis of Intermediate 4-d

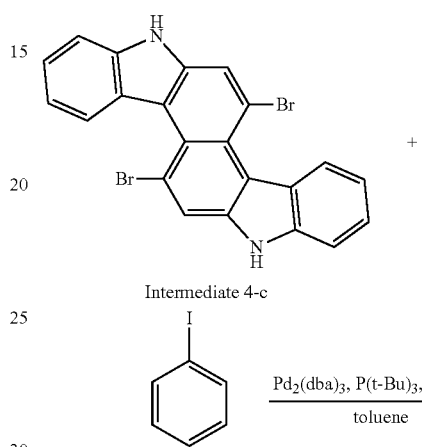

Intermediate 4-c

Intermediate 4-d

After Intermediate 4-c (12 g, 26 mmol) was dissolved in 300 mL of toluene, iodobenzene (16 g, 78 mmol), tris (diphenylideneacetone)dipalladium (o) (0.24 g, 0.26 mmol), tris-tert butylphosphine (0.26 g, 1.3 mmol), and sodium tert-butoxide (2.5 g, 26 mmol) were sequentially added thereto, and the resulting mixture was stirred while being heated at 100° C. for 24 hours. After completion of the reaction, the organic layer was separated by extraction with water and ethyl acetate. The organic layer was treated with anhydrous magnesium sulfate, and then filtered and concentrated under reduced pressure. The solid was recrystallized with ethyl acetate and hexane to obtain Intermediate 4-d (10.4 g, 65%). MS [M+]=606.3

5) Synthesis of Compound 4-3

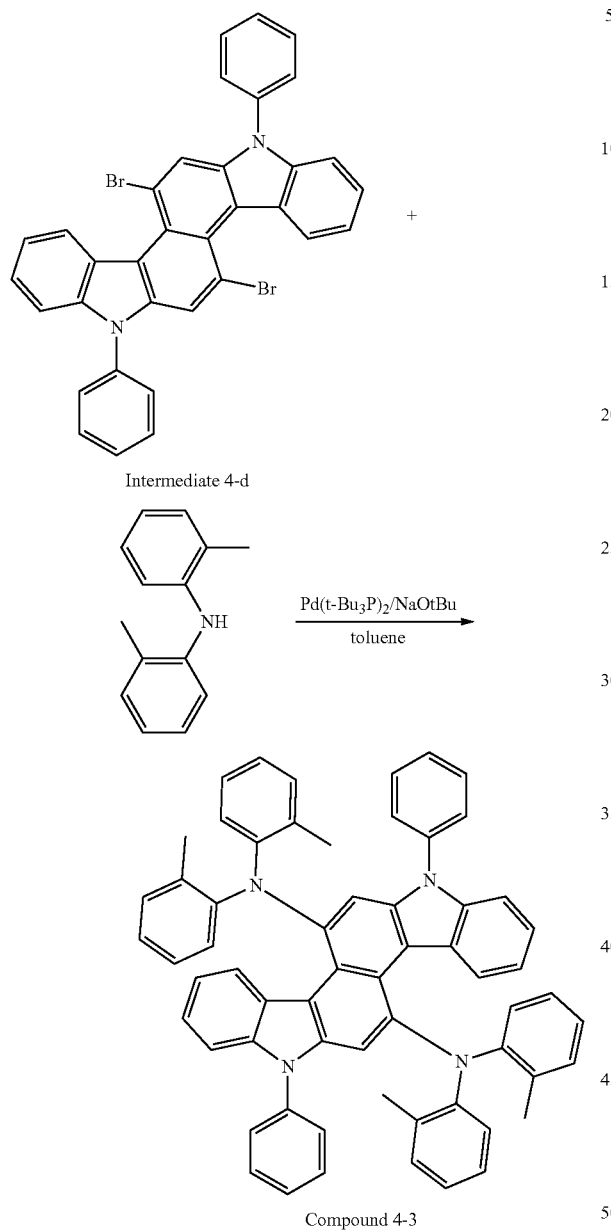

Intermediate 4-d

Compound 4-3 then recrystallized with toluene and hexane to obtain Compound 4-3 (4.1 g, 60%). MS [M+]=849.0

Synthesis Example 6. Synthesis of Compound 4-21

Compound 4-21 was obtained in the same manner as in Synthesis Example 5, except that N-4-(tert-butyl)phenyl-9,9-dimethyl-1-fluorenylamine was used instead of di (ortho-tolyl) amine in 5) of Synthesis Example 5. MS [M+]=1137.5

Synthesis Example 7. Synthesis of Compound 2-21

1) Synthesis of Intermediate 2-a

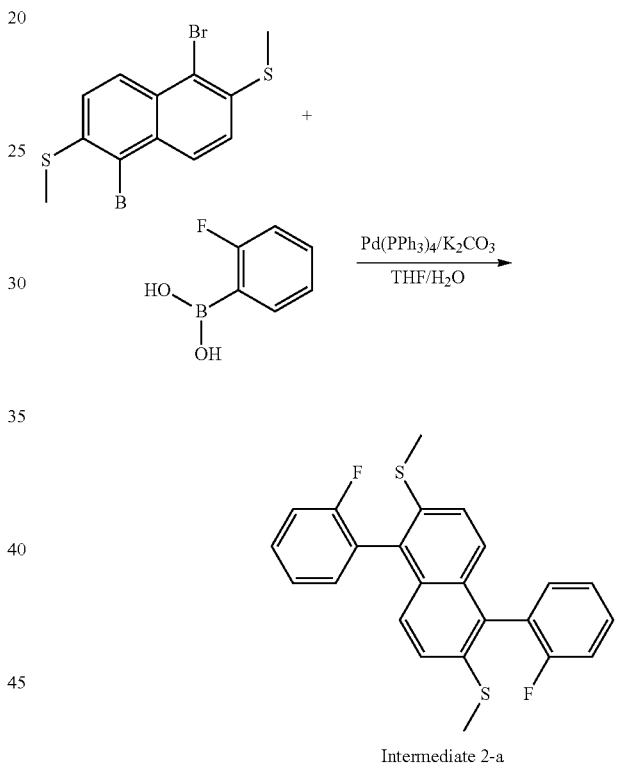

Intermediate 2-a

Intermediate 4-d (5.0 g, 8.1 mmol), di (ortho-tolyl) amine (4.8 g, 24.3 mmol), sodium tert-butoxide (3.9 g, 40.5 mmol), and bis(tri-tert-butylphosphine)palladium (0) (0.21 g, 0.4 mmol) were put into 100 mL of toluene in a round bottom flask under a nitrogen atmosphere, and the resulting mixture was refluxed and stirred. When the reaction was terminated, the product was cooled to room temperature, and then extraction with toluene and water was performed, and the aqueous layer was removed. The remaining product was treated with anhydrous magnesium sulfate, and then filtered and concentrated under reduced pressure. The product was separated and purified with column chromatography, and After 1,5-bromo-2,6-dimethylsulfone (20.0 g, 53 mmol) and 2-fluorophenylboronic acid (18.5 g, 132.5 mmol) were completely dissolved in 300 mL of tetrahydrofuran, 100 mL of an aqueous solution of potassium carbonate (22 g, 159 mmol) was added thereto, tetrakis-(triphenylphosphine)palladium (3.1 g, 2.7 mmol) was added thereto, and then the resulting mixture was refluxed and stirred for 24 hours. After completion of the reaction, the temperature was lowered to room temperature, and then the organic layer was separated by extraction with water and ethyl acetate. The organic layer was treated with anhydrous magnesium sulfate, and then filtered and concentrated under reduced pressure. The solid was recrystallized with ethyl acetate to obtain Intermediate 2-a (18.4 g, 85%). MS [M+]=408.5

2) Synthesis of Intermediate 2-b

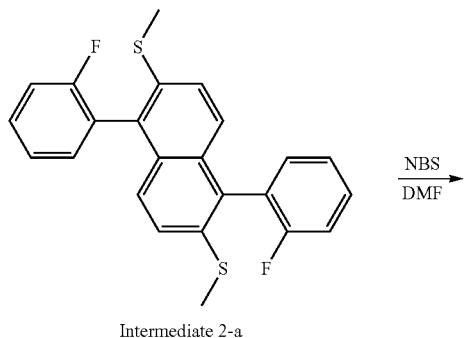

Intermediate 2-a

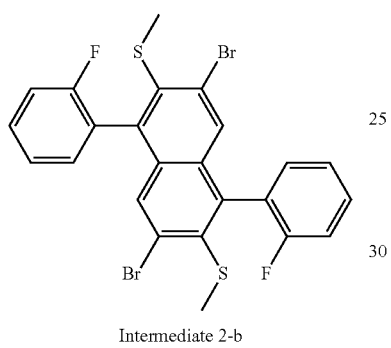

Intermediate 2-b

Intermediate 2-a (18 g, 44 mmol) was dissolved in 300 mL of dimethylformamide, and then N-bromosuccinimide (16.5 g, 93 mmol) was added thereto, and the resulting mixture was stirred for 2 hours. After completion of the reaction, the organic layer was separated by extraction with water and ethyl acetate. The organic layer was treated with anhydrous magnesium sulfate, and then filtered and concentrated under reduced pressure. The solid was recrystallized with ethyl acetate and hexane to obtain Intermediate 2-b (20 g, 80%). MS [M+]=566.3

3) Synthesis of Intermediate 2-c

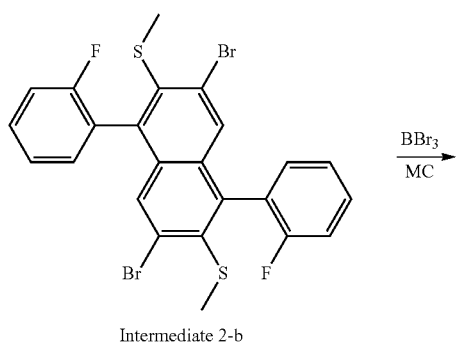

Intermediate 2-b

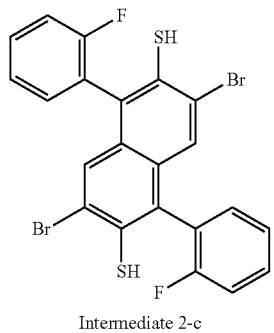

Intermediate 2-c

Intermediate 2-b (20 g, 35 mmol) and 300 mL of dichloromethane were put into a container, 1 M BBr$_3$ in CH$_2$Cl$_2$ (140 ml, 140 mmol) was slowly added dropwise thereto at 0° C., and then the resulting mixture was stirred for 8 hours. After completion of the reaction, the product was neutralized with NaHCO$_3$, and then the organic layer was separated by extraction with water and CH$_2$Cl$_2$. The organic layer was treated with anhydrous magnesium sulfate, and then filtered and concentrated under reduced pressure to obtain Intermediate 2-c (14 g, 75%). MS [M+]=538.2

4) Synthesis of Intermediate 2-d

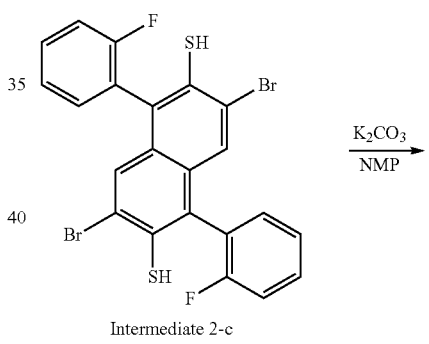

Intermediate 2-c

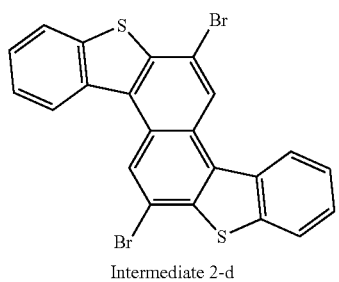

Intermediate 2-d

Intermediate 2-c (14 g, 26.3 mmol) and K$_2$CO$_3$ (14.5 g, 105 mmol) were put into 150 mL of NMP and the resulting mixture was stirred at 150° C. for 8 hours. After completion of the reaction, 500 mL of water was put thereinto, and the organic layer was separated by extraction with ethyl acetate. The organic layer was treated with anhydrous magnesium sulfate, and then filtered and concentrated under reduced pressure. The solid was recrystallized with toluene and hexane to obtain Intermediate 2-d (10.9 g, 83%). MS [M+]= 498.2

5) Synthesis of Compound 2-21

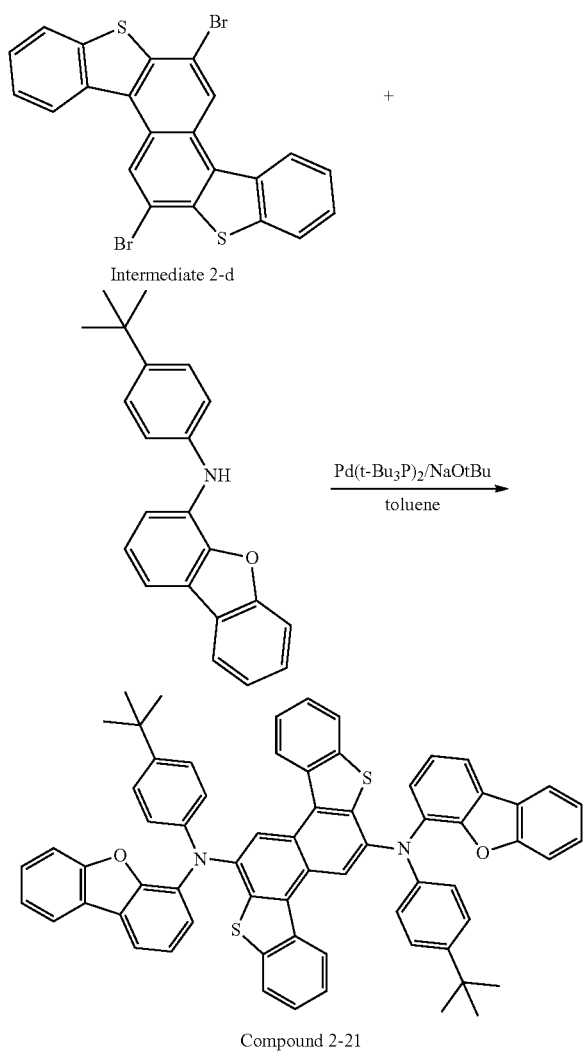

Intermediate 2-d (5.0 g, 10 mmol), 4-tertbutylphenyl-4-dibenzofuranylamine (7 g, 22 mmol), sodium tert-butoxide (4.8 g, 50 mmol), and bis(tri-tert-butylphosphine)palladium (0) (0.102 g, 0.2 mmol) were put into 150 mL of toluene in a round bottom flask under a nitrogen atmosphere, and the resulting mixture was refluxed and stirred. When the reaction was terminated, the product was cooled to room temperature, and then extraction with toluene and water was performed, and the aqueous layer was removed. The remaining product was treated with anhydrous magnesium sulfate, and then filtered and concentrated under reduced pressure. The product was separated and purified with column chromatography, and then recrystallized with toluene and hexane to obtain Compound 2-21 (6.8 g, 70%). MS [M+]=967.2

Synthesis Example 8. Synthesis of Compound 2-22

Compound 2-22 was obtained in the same manner as in Synthesis Example 7, except that N-4-(tert-butyl)phenyl-1-naphthylamine was used instead of 4-tertbutylphenyl-4-dibenzofuranylamine in 5) of Synthesis Example 7. MS[M+]=887.2

Synthesis Example 9. Synthesis of Compound 5-2

1) Synthesis of Intermediate 5-a

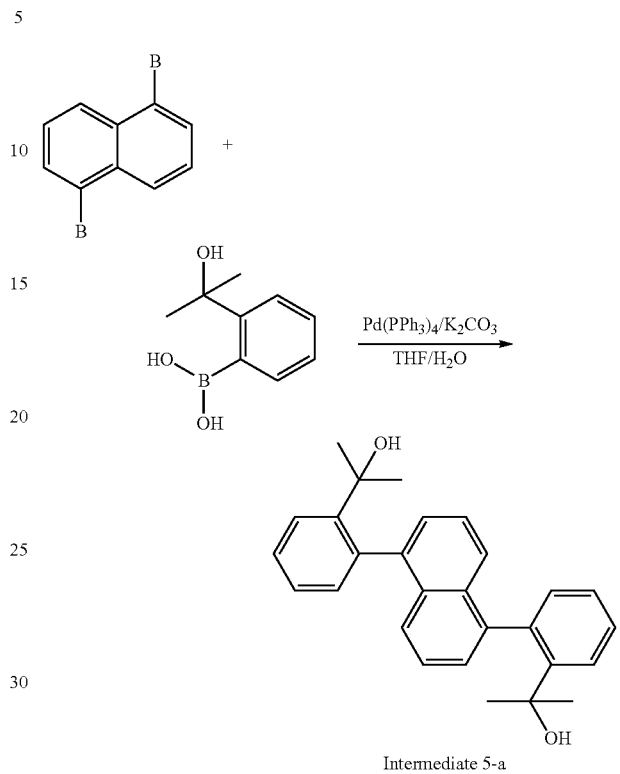

After 1,5-dibromonaphthalene (20.0 g, 70 mmol) and 2-hydroxypropanephenylboronic acid (27.7 g, 154 mmol) were completely dissolved in 400 mL of tetrahydrofuran, 150 mL of an aqueous solution of potassium carbonate (29 g, 210 mmol) was added thereto, tetrakis-(triphenylphosphine) palladium (4 g, 3.5 mmol) was added thereto, and then the resulting mixture was refluxed and stirred for 12 hours. After completion of the reaction, the temperature was lowered to room temperature, and then the organic layer was separated by extraction with water and ethyl acetate. The organic layer was treated with anhydrous magnesium sulfate, and then filtered and concentrated under reduced pressure. The solid was recrystallized with ethyl acetate to obtain Intermediate 5-a (24.4 g, 88%). MS [M+]=396.5

2) Synthesis of Intermediate 5-b

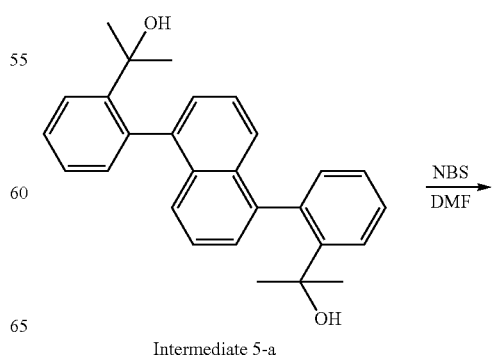

Intermediate 5-a

-continued

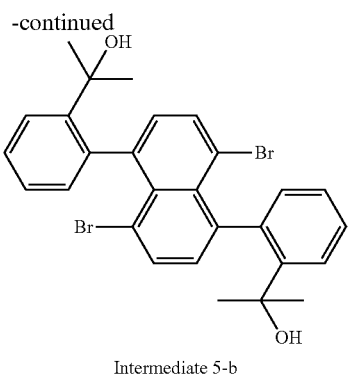

Intermediate 5-b

Intermediate 5-a (20 g, 50 mmol) was dissolved in 300 mL of dimethylformamide, and then N-bromosuccinimide (18.7 g, 105 mmol) was added thereto, and the resulting mixture was stirred for 2 hours. After completion of the reaction, the organic layer was separated by extraction with water and ethyl acetate. The organic layer was treated with anhydrous magnesium sulfate, and then filtered and concentrated under reduced pressure. The solid was recrystallized with ethyl acetate and hexane to obtain Intermediate 5-b (25 g, 90%). MS [M+]=554.3

3) Synthesis of Intermediate 5-c

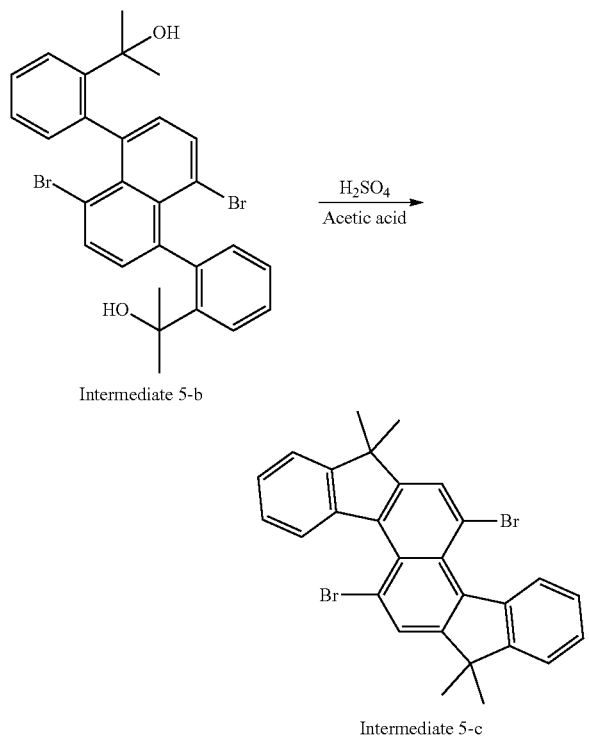

Intermediate 5-b (25 g, 45.1 mmol) was put into 150 mL of acetic acid, one or two drops of sulfuric acid was or were added thereto, and then the resulting mixture was stirred at room temperature for 8 hours. After completion of the reaction, 500 mL of water was put thereinto, and the organic layer was separated by extraction with ethyl acetate. The organic layer was treated with anhydrous magnesium sulfate, and then filtered and concentrated under reduced pressure. The solid was recrystallized with toluene to obtain Intermediate 5-c (21.7 g, 93%). MS [M+]=518.2

4) Synthesis of Compound 5-2

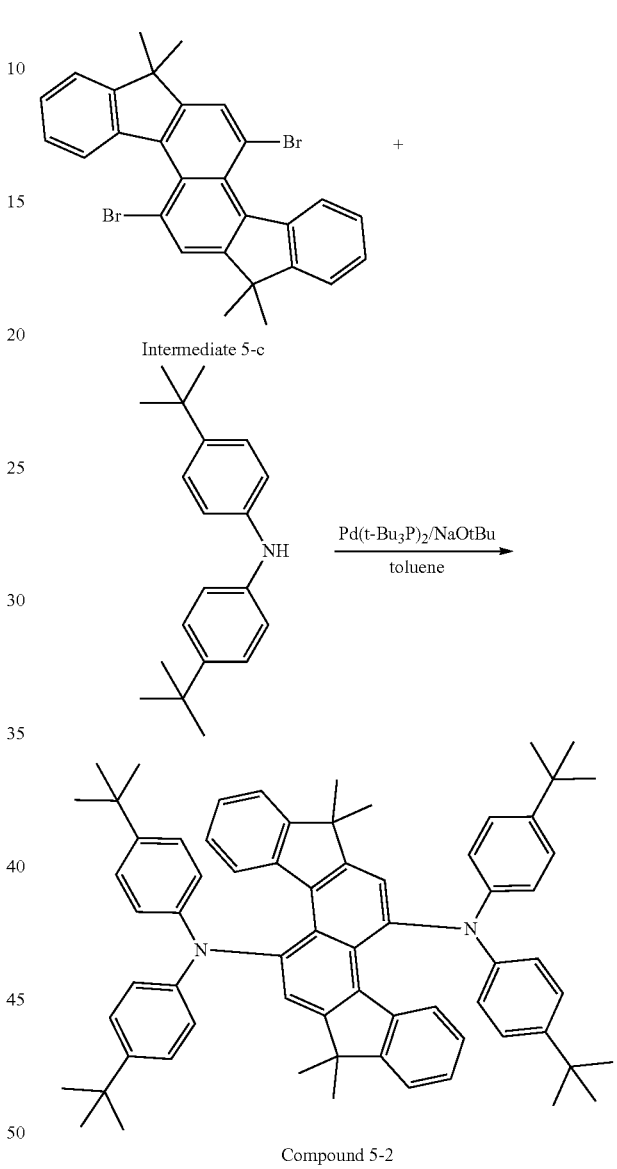

Intermediate 5-c (10 g, 19 mmol), 4-bis-tertbutyl-phenylamine (13.3 g, 47.5 mmol), sodium tert-butoxide (7.3 g, 76 mmol), and bis(tri-tert-butylphosphine)palladium (0) (0.485 g, 0.95 mmol) were put into 150 mL of toluene in a round bottom flask under a nitrogen atmosphere, and the resulting mixture was refluxed and stirred. When the reaction was terminated, the product was cooled to room temperature, and then extraction with toluene and water was performed, and the aqueous layer was removed. The remaining product was treated with anhydrous magnesium sulfate, and then filtered and concentrated under reduced pressure. The product was separated and purified with column chromatography, and then recrystallized with toluene and hexane to obtain Compound 5-2 (11.3 g, 65%). MS [M+]=919.3

Synthesis Example 10. Synthesis of Compound 5-21

Compound 5-21 was obtained in the same manner as in Synthesis Example 9, except that 2-fluoro-o-toluylamine was used instead of 4-bistertbutylphenylamine in 4) of Synthesis Example 9. MS[M+]=758.9

Synthesis Example 11. Synthesis of Compound 6-21

1) Synthesis of Intermediate 6-a

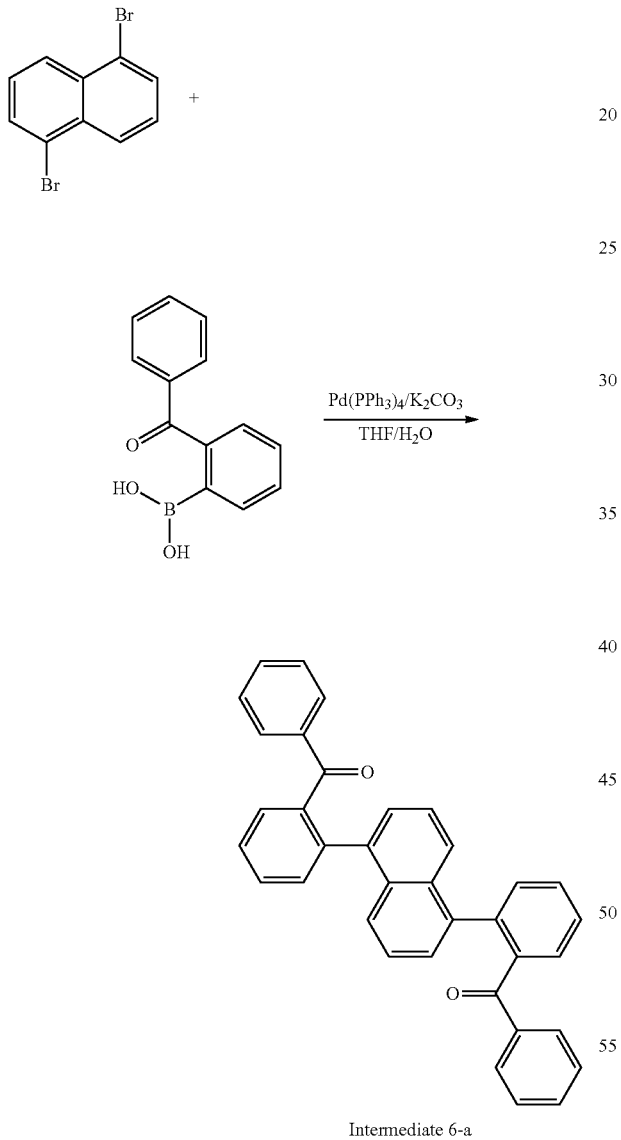

Intermediate 6-a

After 1,5-dibromonaphthalene (20.0 g, 70 mmol) and 2-benzophenylboronic acid (35 g, 154 mmol) were completely dissolved in 400 mL of tetrahydrofuran, 150 mL of an aqueous solution of potassium carbonate (29 g, 210 mmol) was added thereto, tetrakis-(triphenylphosphine) palladium (4 g, 3.5 mmol) was added thereto, and then the resulting mixture was refluxed and stirred for 12 hours. After completion of the reaction, the temperature was lowered to room temperature, and then the organic layer was separated by extraction with water and ethyl acetate. The organic layer was treated with anhydrous magnesium sulfate, and then filtered and concentrated under reduced pressure. The solid was recrystallized with ethyl acetate to obtain Intermediate 6-a (28.7 g, 84%). MS [M+]=488.5

2) Synthesis of Intermediate 6-b

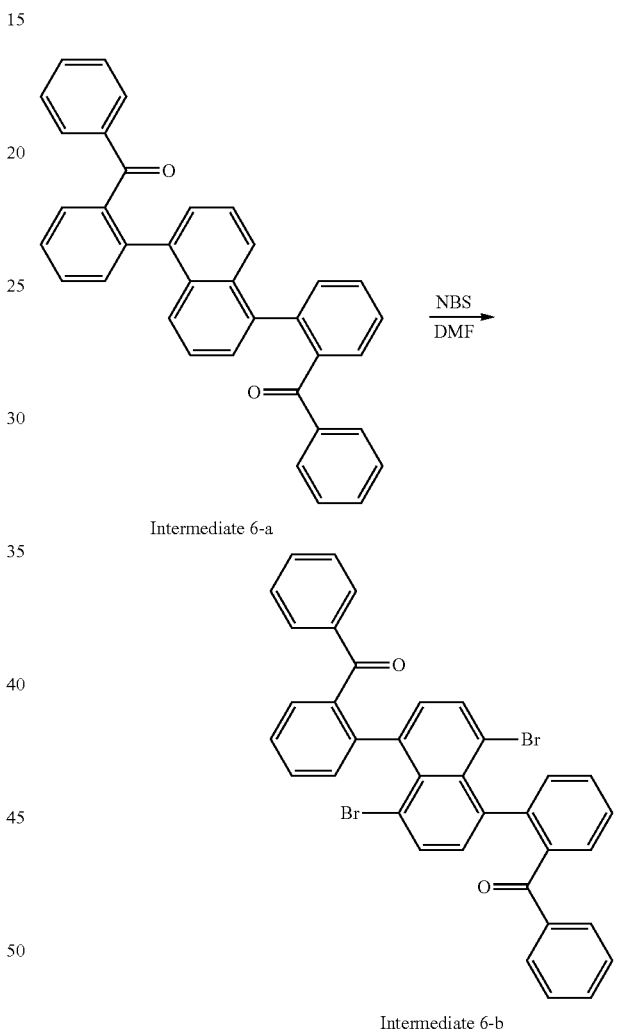

Intermediate 6-b

Intermediate 6-a (24.4 g, 50 mmol) was dissolved in 300 mL of dimethylformamide, and then N-bromosuccinimide (18.7 g, 105 mmol) was added thereto, and the resulting mixture was stirred for 2 hours. After completion of the reaction, the organic layer was separated by extraction with water and ethyl acetate. The organic layer was treated with anhydrous magnesium sulfate, and then filtered and concentrated under reduced pressure. The solid was recrystallized with ethyl acetate and hexane to obtain Intermediate 6-b (27.5 g, 85%). MS [M+]=646.3

3) Synthesis of Intermediate 6-c

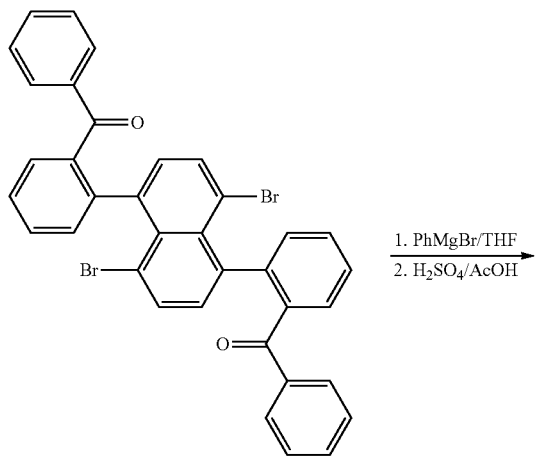

Intermediate 6-b

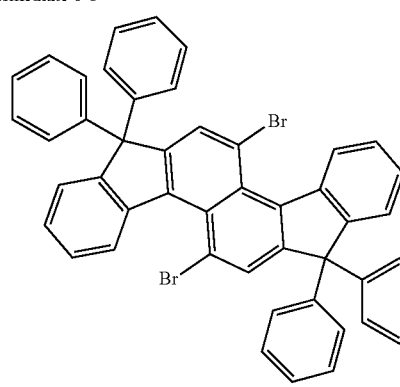

Intermediate 6-c

Intermediate 6-b (20 g, 38 mmol) was dissolved in 300 mL of anhydrous THF under a nitrogen atmosphere, and then phenylmagnesium bromide (41 ml, 41.8 mmol) was added thereto at 0° C., and the resulting mixture was stirred at room temperature for 2 hours. Next, the temperature was lowered to 0° C., and then phenylmagnesium bromide (41 ml, 41.8 mmol) was added thereto, and the resulting mixture was stirred at room temperature for 2 hours. After completion of the reaction, the organic layer was separated by extraction with water and ethyl acetate. The organic layer was treated with anhydrous magnesium sulfate, and then filtered and concentrated under reduced pressure. Without any separate purification, the product was put into 150 mL of acetic acid, one or two drops of sulfuric acid was or were added thereto, and then the resulting mixture was stirred at room temperature for 8 hours. After completion of the reaction, 500 mL of water was put thereinto, and the organic layer was separated by extraction with ethyl acetate. The organic layer was treated with anhydrous magnesium sulfate, and then filtered and concentrated under reduced pressure. The solid was recrystallized with toluene to obtain Intermediate 6-c (21.7 g, 75%). MS [M+]=766.5

4) Synthesis of Compound 6-21

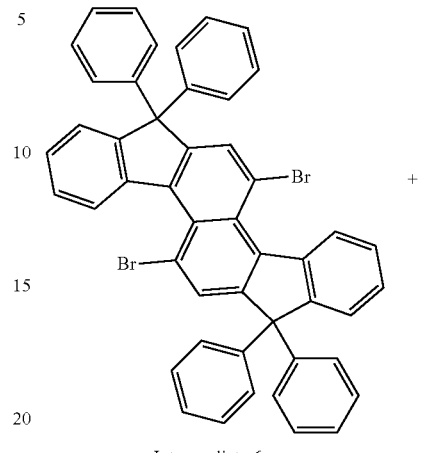

Intermediate 6-c

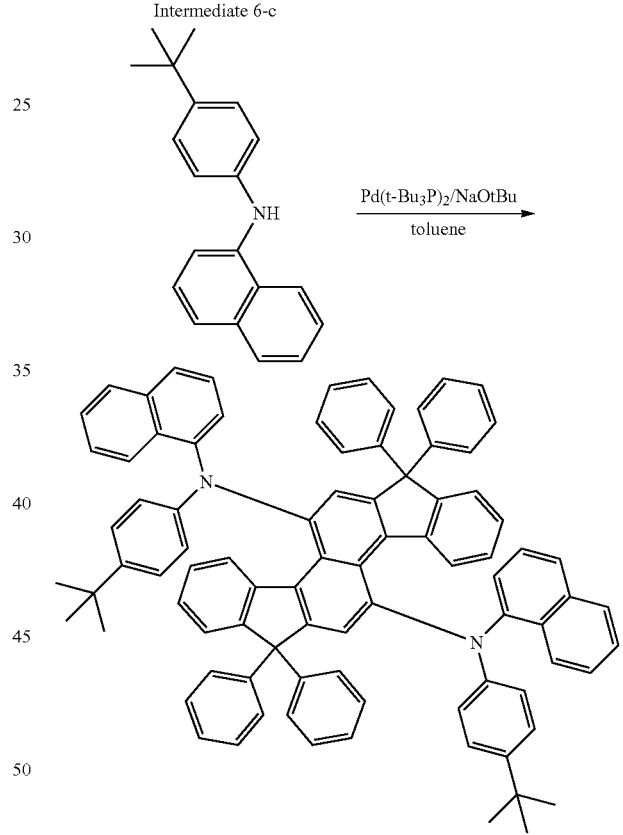

Compound 6-21

Intermediate 6-c (14.5 g, 19 mmol), 4-tertbutyl-1-naphthylamine (13.1 g, 47.5 mmol), sodium tert-butoxide (7.3 g, 76 mmol), and bis(tri-tert-butylphosphine)palladium (0) (0.485 g, 0.95 mmol) were put into 150 mL of toluene in a round bottom flask under a nitrogen atmosphere, and the resulting mixture was refluxed and stirred. When the reaction was terminated, the product was cooled to room temperature, and then extraction with toluene and water was performed, and the aqueous layer was removed. The remaining product was treated with anhydrous magnesium sulfate, and then filtered and concentrated under reduced pressure. The product was separated and purified with column chromatography, and then recrystallized with toluene and hexane to obtain Compound 6-21 (13.2 g, 60%). MS [M+]=1155.5

Synthesis Example 12. Synthesis of Compound 6-1

Compound 6-1 was obtained in the same manner as in Synthesis Example 11, except that diphenylamine was used instead of 4-tertbutyl-1-naphthylamine in 4) of Synthesis Example 11. MS[M+]=943.2

Manufacture of Organic Light Emitting Device

Example 1

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

The following HAT was thermally vacuum-deposited to have a thickness of 50 Å on the ITO transparent electrode thus prepared, thereby forming a hole injection layer. The following HT-A was vacuum-deposited as a hole transport layer to have a thickness of 1,000 Å thereon, and the following HT-B was deposited to have a thickness of 100 Å. The following H-A as a host of a light emitting layer was doped with 4% of Compound 1-2 in Synthesis Example 1 as a dopant of the light emitting layer, thereby vacuum-depositing the light emitting layer to have a thickness of 200 Å. Next, the following ET-A and the following Liq were deposited at a ratio of 1:1 to have a thickness of 300 Å, and magnesium (Mg) doped with 10 wt % of silver (Ag) and having a thickness of 150 Å and aluminum having a thickness of 1,000 Å were sequentially deposited thereon to form a negative electrode, thereby manufacturing an organic light emitting device.

In the aforementioned procedure, the deposition rates of the organic material, LiF, and aluminum were maintained at 1 Å/sec, 0.2 Å/sec, and 3 to 7 Å/sec, respectively.

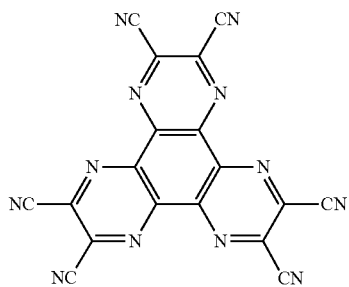

HAT

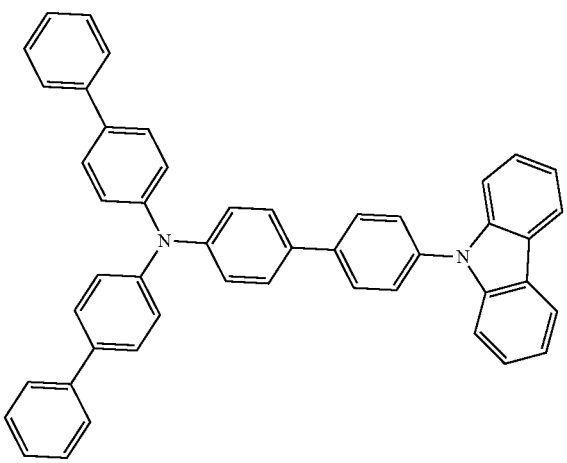

HT-B

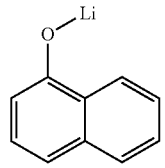

Liq

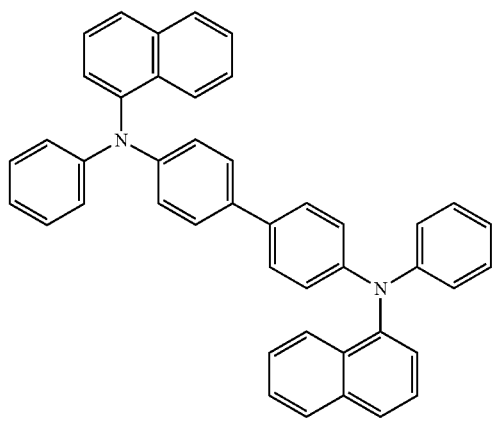

HT-A

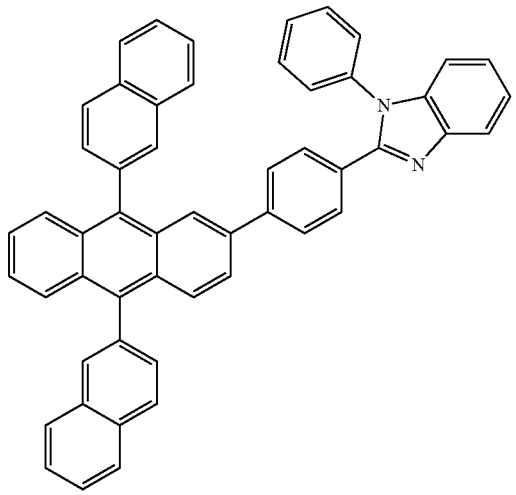

ET-A

H-A
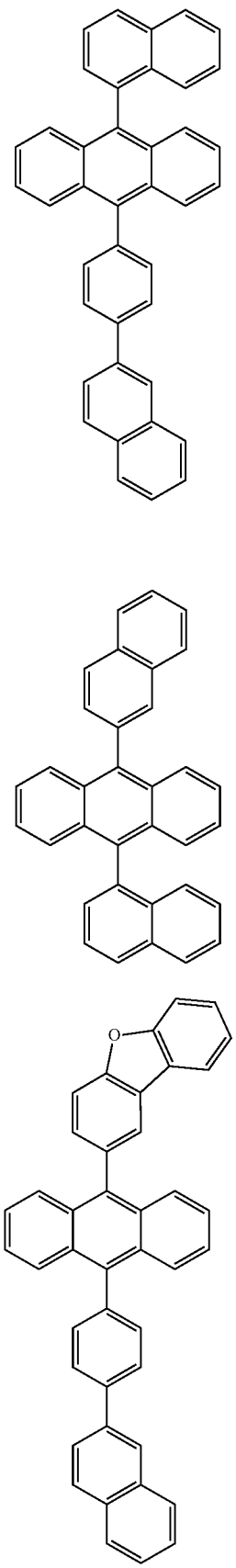
H-B
H-C
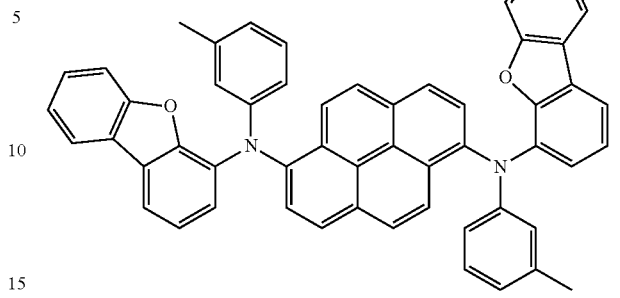
D-1
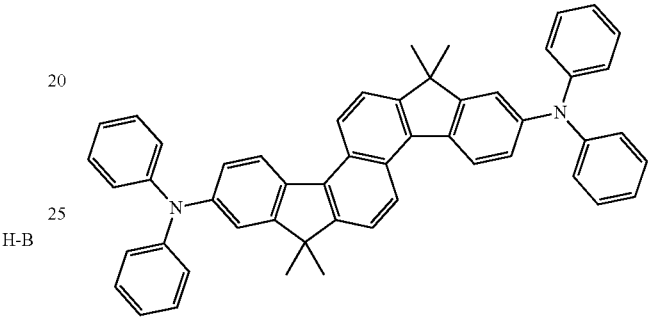
D-2
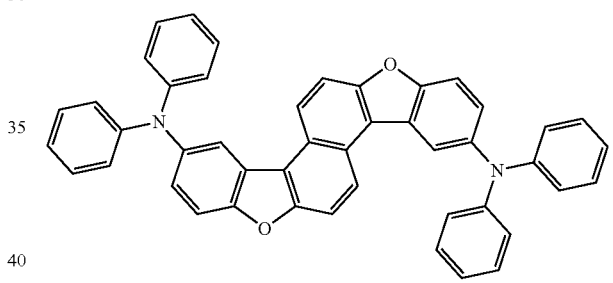
D-3
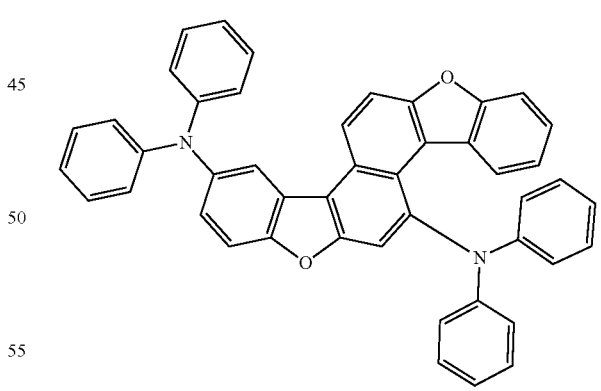
D-4
Examples 2 to 36 and Comparative Examples 1 to 12
Organic light emitting devices were manufactured in the same manner as in Example 1, except that in Example 1, hosts in the following Tables 5 to 7 were used instead of H-A as a host of the light emitting layer, and dopants in the following Tables 5 to 7 were used instead of Compound 1-2 as a dopant of the light emitting layer.

For the organic light emitting devices of Examples 1 to 36 and Comparative Examples 1 to 12, the driving voltage and the light emitting efficiency were measured at a current density of 10 mA/cm$^2$, and a time (LT95) for reaching a 95% value compared to the initial luminance was measured at a current density of 20 mA/cm$^2$. The results are shown in the following Tables 5 to 7.

TABLE 5

| | Host | Dopant | @ 10 mA/cm$^2$ Voltage (V) | @ 10 mA/cm$^2$ Efficiency (cd/A) | color | T 95 Service life (hr) |
|---|---|---|---|---|---|---|
| Example 1 | H-A | Compound 1-2 | 4.22 | 7.28 | blue | 100 |
| Example 2 | H-A | Compound 1-21 | 4.21 | 6.84 | blue | 130 |
| Example 3 | H-A | Compound 1-22 | 4.32 | 6.96 | blue | 125 |
| Example 4 | H-A | Compound 1-23 | 4.32 | 6.61 | blue | 125 |
| Example 5 | H-A | Compound 4-3 | 4.30 | 6.51 | blue | 110 |
| Example 6 | H-A | Compound 4-21 | 4.20 | 6.66 | blue | 115 |
| Example 7 | H-A | Compound 2-21 | 4.18 | 6.89 | blue | 110 |
| Example 8 | H-A | Compound 2-22 | 4.26 | 6.82 | blue | 120 |
| Example 9 | H-A | Compound 5-2 | 4.14 | 6.91 | blue | 105 |
| Example 10 | H-A | Compound 5-21 | 4.08 | 6.72 | blue | 105 |
| Example 11 | H-A | Compound 6-21 | 4.14 | 6.87 | blue | 115 |
| Example 12 | H-A | Compound 6-1 | 4.16 | 6.42 | blue | 120 |
| Comparative Example 1 | H-A | D-1 | 4.39 | 5.13 | blue | 75 |
| Comparative Example 2 | H-A | D-2 | 4.42 | 3.50 | blue | 50 |
| Comparative Example 3 | H-A | D-3 | 4.40 | 5.12 | blue | 85 |
| Comparative Example 4 | H-A | D-4 | 4.54 | 4.88 | blue | 55 |

TABLE 6

| | Host | Dopant | @ 10 mA/cm$^2$ Voltage (V) | @ 10 mA/cm$^2$ Efficiency (cd/A) | color | T 95 Service life (hr) |
|---|---|---|---|---|---|---|
| Example 13 | H-B | Compound 1-2 | 4.35 | 7.21 | blue | 120 |
| Example 14 | H-B | Compound 1-21 | 4.34 | 6.77 | blue | 140 |
| Example 15 | H-B | Compound 1-22 | 4.45 | 6.89 | blue | 135 |
| Example 16 | H-B | Compound 1-23 | 4.45 | 6.54 | blue | 125 |
| Example 17 | H-B | Compound 4-3 | 4.43 | 6.44 | blue | 115 |
| Example 18 | H-B | Compound 4-21 | 4.33 | 6.79 | blue | 115 |
| Example 19 | H-B | Compound 2-21 | 4.31 | 6.82 | blue | 135 |
| Example 20 | H-B | Compound 2-22 | 4.39 | 6.75 | blue | 130 |
| Example 21 | H-B | Compound 5-2 | 4.26 | 6.84 | blue | 120 |
| Example 22 | H-B | Compound 5-21 | 4.20 | 6.35 | blue | 120 |
| Example 23 | H-B | Compound 6-21 | 4.26 | 6.80 | blue | 120 |
| Example 24 | H-B | Compound 6-1 | 4.28 | 6.56 | blue | 125 |
| Comparative Example 5 | H-B | D-1 | 4.56 | 5.18 | blue | 80 |
| Comparative Example 6 | H-B | D-2 | 4.54 | 4.50 | blue | 60 |
| Comparative Example 7 | H-B | D-3 | 4.55 | 5.32 | blue | 95 |
| Comparative Example 8 | H-B | D-4 | 4.60 | 5.58 | blue | 70 |

TABLE 7

| | Host | Dopant | @ 10 mA/cm$^2$ Voltage (V) | @ 10 mA/cm$^2$ Efficiency (cd/A) | color | T 95 Service life (hr) |
|---|---|---|---|---|---|---|
| Example 25 | H-C | Compound 1-2 | 4.14 | 6.28 | blue | 120 |
| Example 26 | H-C | Compound 1-21 | 4.13 | 6.54 | blue | 120 |
| Example 27 | H-C | Compound 1-22 | 4.23 | 6.66 | blue | 115 |
| Example 28 | H-C | Compound 1-23 | 4.23 | 6.30 | blue | 125 |
| Example 29 | H-C | Compound 4-3 | 4.21 | 6.10 | blue | 120 |
| Example 30 | H-C | Compound 4-21 | 4.12 | 6.06 | blue | 115 |
| Example 31 | H-C | Compound 2-21 | 4.10 | 6.09 | blue | 120 |
| Example 32 | H-C | Compound 2-22 | 4.17 | 6.42 | blue | 130 |
| Example 33 | H-C | Compound 5-2 | 4.06 | 6.42 | blue | 115 |
| Example 34 | H-C | Compound 5-21 | 4.00 | 6.22 | blue | 125 |
| Example 35 | H-C | Compound 6-21 | 4.06 | 6.16 | blue | 115 |
| Example 36 | H-C | Compound 6-1 | 4.08 | 6.22 | blue | 125 |
| Comparative Example 9 | H-C | D-1 | 4.32 | 4.86 | blue | 70 |
| Comparative Example 10 | H-C | D-2 | 4.33 | 4.50 | blue | 60 |
| Comparative Example 11 | H-C | D-3 | 4.40 | 4.88 | blue | 75 |
| Comparative Example 12 | H-C | D-4 | 4.40 | 4.24 | blue | 50 |

According to Tables 5 to 7, Formula 1 according to an exemplary embodiment of the present specification includes an amine group (Formula A) at least two of the R1 to R4 positions, and the organic light emitting devices of Examples 1 to 36, which include the same as a dopant of the light emitting layer, have a low driving voltage, excellent efficiency, and long service life characteristics as compared to the organic light emitting devices of Comparative Examples 1, 5, and 9 whose cores are different from Formula 1 of the present specification, the organic light emitting devices of Comparative Examples 2, 3, 6, 7, 10, and 11 which include an amine group at the R5 and R6 positions, and the organic light emitting devices of Comparative Examples 4, 8, and 12 which include an amine group at the R4 and R6 (or R2 and R6) positions. In particular, in terms of service life, it can be seen that the organic light emitting devices of Examples 1 to 36 are better by 110% to 270% than the organic light emitting devices in Comparative Examples 1 to 12.

14-19 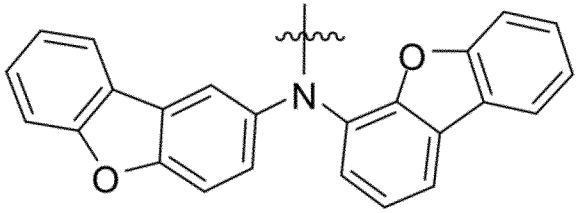 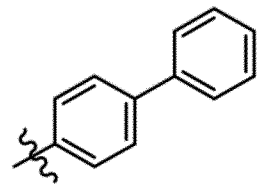

The invention claimed is:
1. A compound of Formula 1:

[Formula 1]

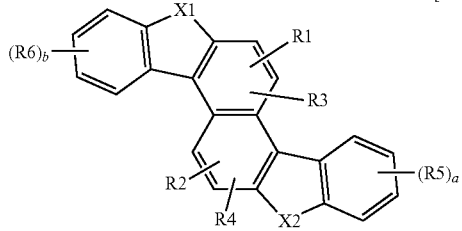

wherein in Formula 1:
X1 and X2 are the same as or different from each other, and are each independently —O—, —S—, —C(R7R8)-, or —N(R9);
at least two of R1 to R4 are the same as or different from each other, and are each independently a group of the following Formula A;
groups which are not the following Formula A among R1 to R4 are the same as or different from each other, and are each independently hydrogen, deuterium, a substituted or unsubstituted alkyl group, a substituted or unsubstituted aryl group, or a substituted or unsubstituted heteroaryl group;
R5 and R6 are the same as or different from each other, and are each independently hydrogen, deuterium, a substituted or unsubstituted alkyl group, a substituted or unsubstituted aryl group, or a substituted or unsubstituted heteroaryl group, or adjacent groups are bonded to each other to form a substituted or unsubstituted ring;
R7 to R9 are the same as or different from each other, and are each independently a substituted or unsubstituted alkyl group, a substituted or unsubstituted aryl group, or a substituted or unsubstituted heteroaryl group;
a and b are each an integer from 1 to 4;
when a and b are each 2 or more, two or more structures in the parenthesis are the same as or different from each other:

[Formula A]

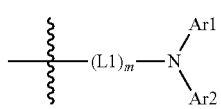

wherein in Formula A:
L1 is a direct bond, a substituted or unsubstituted arylene group, or a substituted or unsubstituted heteroarylene group;
Ar1 and Ar2 are the same as or different from each other, and are each independently a substituted or unsubstituted aryl group, or a substituted or unsubstituted heteroaryl group, or are optionally bonded to each other to form a substituted or unsubstituted ring;
m is an integer from 1 to 5;
when m is 2 or more, two or more L1's are the same as or different from each other; and

is a moiety bonded to Formula 1.

2. The compound of claim 1, wherein Formula 1 is any one of the following Formulae 1-1 to 1-3:

[Formula 1-1]

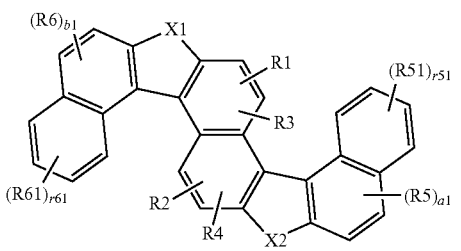

[Formula 1-2]

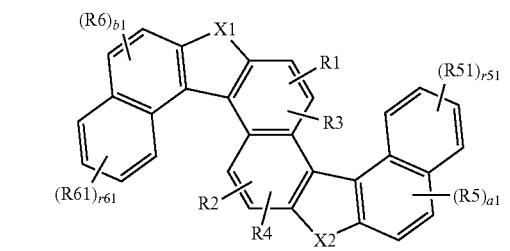

[Formula 1-3]

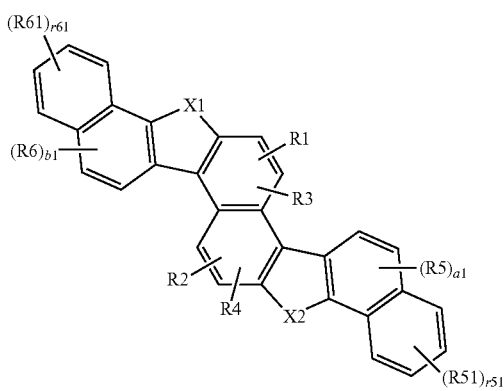

wherein in Formulae 1-1 to 1-3:
the definitions of X1, X2, and R1 to R4 are the same as those defined in Formula 1;
R5, R6, R51, and R61 are the same as or different from each other, and are each independently hydrogen, deuterium, a substituted or unsubstituted alkyl group, a substituted or unsubstituted aryl group, or a substituted or unsubstituted heteroaryl group;
a1 and b1 are each 1 or 2;
r51 and r61 are each an integer from 1 to 4;
when a1 and b1 are each 2, the structures in the parenthesis are the same as or different from each other; and
when r51 and r61 are each 2 or more, two or more structures in the parenthesis are the same as or different from each other.

3. The compound of claim 1, wherein Formula 1 is any one of the following Formulae 1-4 to 1-7:

[Formula 1-4]
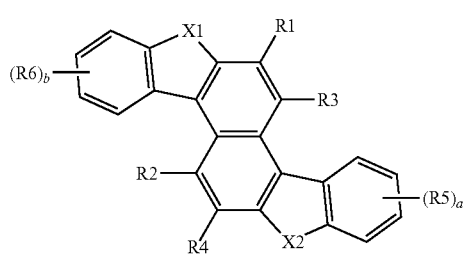

[Formula 1-5]
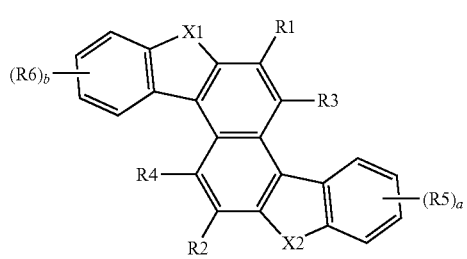

[Formula 1-6]
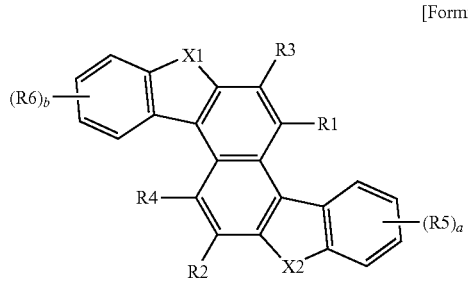

[Formula 1-7]
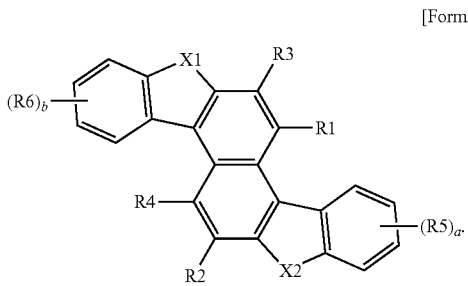

wherein in Formulae 1-4 to 1-7:
the definitions of X1, X2, R5, R6, a, and b are the same as those defined in Formula 1;
R1 and R2 are the same as or different from each other, and are each independently a group of Formula A; and
R3 and R4 are the same as or different from each other, and are each independently hydrogen, deuterium, a substituted or unsubstituted alkyl group, a substituted or unsubstituted aryl group, or a substituted or unsubstituted heteroaryl group.

4. The compound of claim 1, wherein Formula 1 is any one of the following Formulae 1-9 to 1-12:

[Formula 1-9]
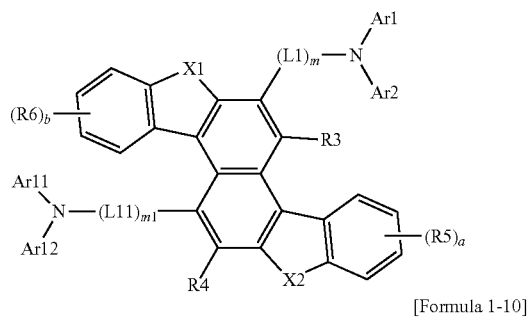

[Formula 1-10]
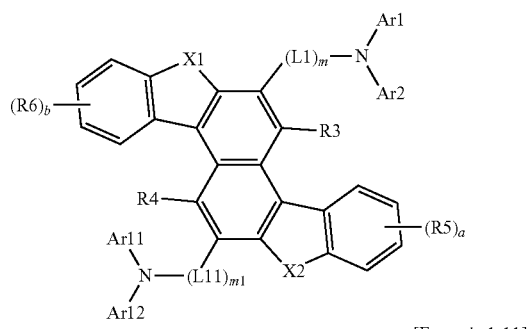

[Formula 1-11]
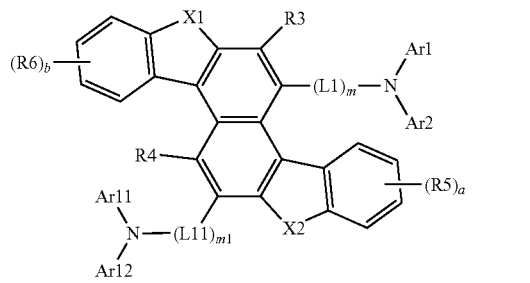

[Formula 1-12]
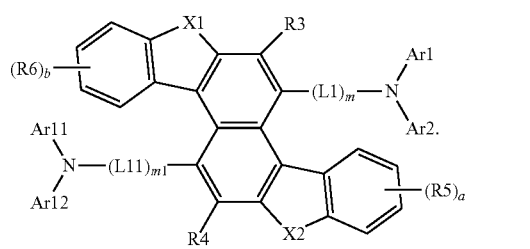

wherein in Formulae 1-9 to 1-12:
the definitions of X1, X2, R5, R6, a, and b are the same as those defined in Formula
the definitions of L1, m, Ar1, and Ar2 are the same as those defined in Formula A;
R3 and R4 are the same as or different from each other, and are each independently hydrogen, deuterium, a substituted or unsubstituted alkyl group, a substituted or unsubstituted aryl group, or a substituted or unsubstituted heteroaryl group;
L11 is a direct bond, a substituted or unsubstituted arylene group, or a substituted or unsubstituted heteroarylene group;
Ar11 and Ar12 are the same as or different from each other, and are each independently a substituted or unsubstituted aryl group, or a substituted or unsubstituted heteroaryl group, or are optionally bonded to each other to form a substituted or unsubstituted ring;

m1 is an integer from 1 to 5; and when m1 is 2 or more, two or more L11's are the same as or different from each other.

5. The compound of claim 1, wherein L1 is a direct bond or an arylene group.

6. The compound of claim 1, wherein Ar1 and Ar2 are the same as or different from each other, and are each independently an aryl group which is unsubstituted or substituted with a halogen group, an alkyl group, or an aryl group; or a heteroaryl group which is unsubstituted or substituted with an alkyl group or an aryl group.

7. The compound of claim 1, wherein the compound of Formula 1 is selected from among the following compounds:

| Compound | X1 | X2 | R1 | R2 | R3 to R6 |
|---|---|---|---|---|---|
| 1-1 | O | O | 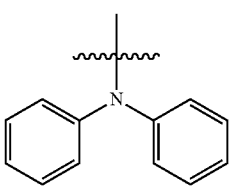 [SMILES: *N(c1ccccc1)c1ccccc1] | 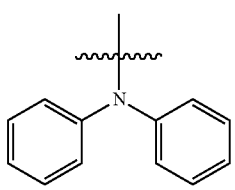 [SMILES: *N(c1ccccc1)c1ccccc1] | H |
| 1-2 | O | O | 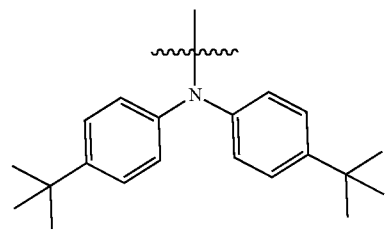 [SMILES: *N(c1ccc(C(C)(C)C)cc1)c1ccc(C(C)(C)C)cc1] | 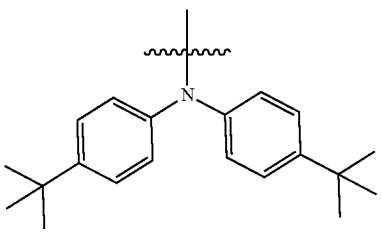 [SMILES: *N(c1ccc(C(C)(C)C)cc1)c1ccc(C(C)(C)C)cc1] | H |
| 1-3 | O | O | 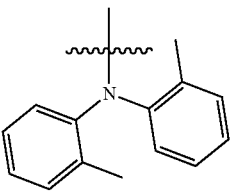 [SMILES: *N(c1ccccc1C)c1ccccc1C] | 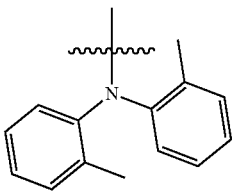 [SMILES: *N(c1ccccc1C)c1ccccc1C] | H |
| 1-4 | O | O | 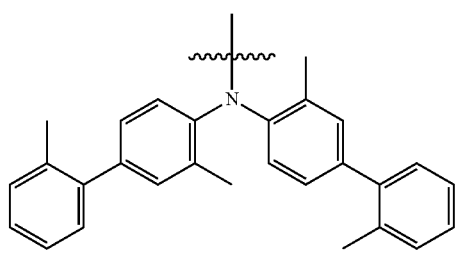 [SMILES: *N(c1ccc(-c2ccccc2C)cc1C)c1ccc(-c2ccccc2C)cc1C] | 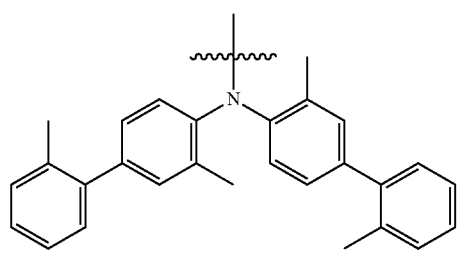 [SMILES: *N(c1ccc(-c2ccccc2C)cc1C)c1ccc(-c2ccccc2C)cc1C] | H |
| 1-5 | O | O | 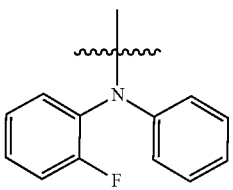 [SMILES: *N(c1ccccc1)c1ccccc1F] | 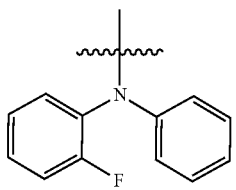 [SMILES: *N(c1ccccc1)c1ccccc1F] | H |
| 1-6 | O | O | 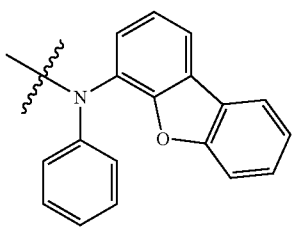 [SMILES: *N(c1ccccc1)c1cccc2c1oc1ccccc12] | 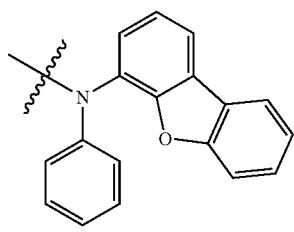 [SMILES: *N(c1ccccc1)c1cccc2c1oc1ccccc12] | H |

-continued

| Compound | X1 | X2 | R1 | R2 | R3 to R6 |
|---|---|---|---|---|---|
| 1-7 | O | O | 7-isopropyl-N-phenyl-dibenzofuran-1-amine | 7-isopropyl-N-phenyl-dibenzofuran-1-amine | H |
| 1-8 | O | O | N,N-di(dibenzofuran-4-yl)amine | N,N-di(dibenzofuran-4-yl)amine | H |
| 1-9 | O | O | N-(2-fluorophenyl)-N-(naphthalen-2-yl)amine | N-(2-fluorophenyl)-N-(naphthalen-2-yl)amine | H |
| 1-10 | O | O | N-phenyl-N-(pyridin-3-yl)amine | N-phenyl-N-(naphthalen-2-yl)amine | H |
| 1-11 | O | O | N,N-di(naphthalen-1-yl)amine | N,N-di(naphthalen-1-yl)amine | H |
| 1-12 | O | O | N-phenyl-N-(9,9-dimethyl-9H-fluoren-1-yl)amine | N-phenyl-N-(9,9-dimethyl-9H-fluoren-1-yl)amine | H |
| 1-13 | O | O | N-(dibenzofuran-2-yl)-N-(9,9-dimethyl-9H-fluoren-1-yl)amine | N-(dibenzofuran-2-yl)-N-(9,9-dimethyl-9H-fluoren-1-yl)amine | H |

-continued

| Compound | X1 | X2 | R1 | R2 | R3 to R6 |
|---|---|---|---|---|---|
| 1-14 | O | O | | | H |
| 1-15 | O | O | | | H |
| 1-16 | O | O | | | H |
| 1-17 | O | O | | | H |
| 1-18 | O | O | | | H |
| 1-19 | O | O | | | H |
| 1-20 | O | O | | | H |

-continued

| Compound | X1 | X2 | R1 | R2 | R3 to R6 |
|---|---|---|---|---|---|
| 1-21 | O | O | N(phenyl)(3-tert-butylphenyl) | N(phenyl)(3-tert-butylphenyl) | H |
| 1-22 | O | O | N(4-biphenyl)(dibenzofuran-2-yl) | N(4-biphenyl)(dibenzofuran-2-yl) | H |
| 1-23 | O | O | N(4-biphenyl)(dibenzofuran-4-yl) | N(4-biphenyl)(dibenzofuran-4-yl) | H |

| Compound | X1 | X2 | R1 | R2 | R3 to R6 |
|---|---|---|---|---|---|
| 2-1 | S | S | N(phenyl)(phenyl) | N(phenyl)(phenyl) | H |
| 2-2 | S | S | N(4-tert-butylphenyl)(4-tert-butylphenyl) | N(4-tert-butylphenyl)(4-tert-butylphenyl) | H |

-continued
| Compound | X1 | X2 | R1 | R2 | R3 to to R6 |
|---|---|---|---|---|---|
| 2-3 | S | S | 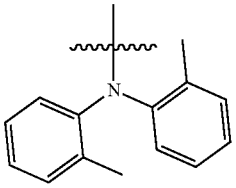 [SMILES: *N(c1ccccc1C)c1ccccc1C] | 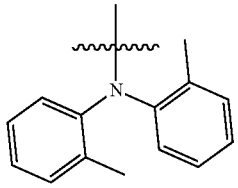 [SMILES: *N(c1ccccc1C)c1ccccc1C] | H |
| 2-4 | S | S | 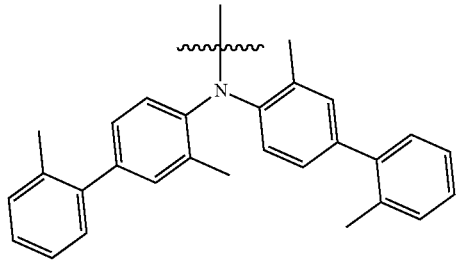 [SMILES: *N(c1ccc(-c2ccccc2C)cc1C)c1ccc(-c2ccccc2C)cc1C] | 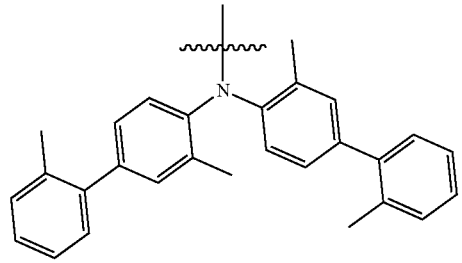 [SMILES: *N(c1ccc(-c2ccccc2C)cc1C)c1ccc(-c2ccccc2C)cc1C] | H |
| 2-5 | S | S | 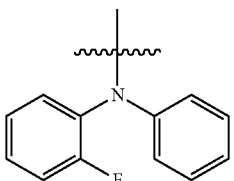 | 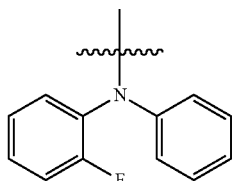 | H |
| 2-6 | S | S | 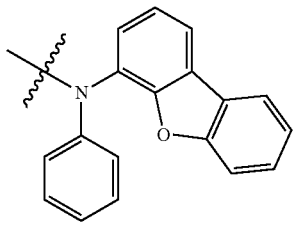 [SMILES: *N(c1ccccc1)c1cccc2c1oc1ccccc12] | 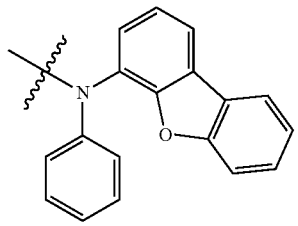 [SMILES: *N(c1ccccc1)c1cccc2c1oc1ccccc12] | H |
| 2-7 | S | S | 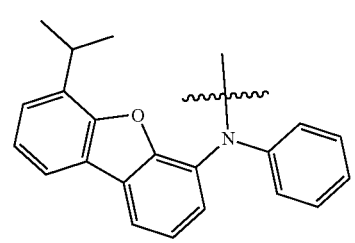 [SMILES: *N(c1ccccc1)c1cccc2c1oc1c(C(C)C)cccc12] | 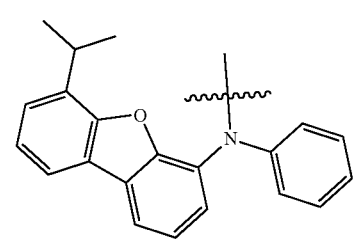 [SMILES: *N(c1ccccc1)c1cccc2c1oc1c(C(C)C)cccc12] | H |
| 2-8 | S | S | 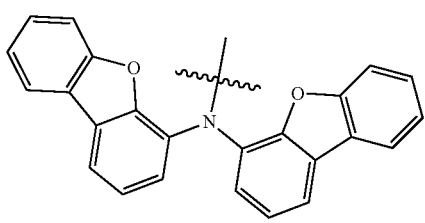 [SMILES: *N(c1cccc2c1oc1ccccc12)c1cccc2c1oc1ccccc12] | 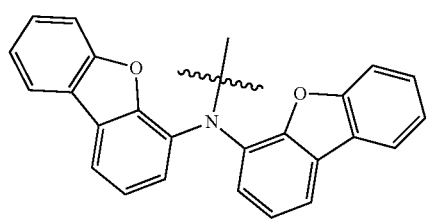 [SMILES: *N(c1cccc2c1oc1ccccc12)c1cccc2c1oc1ccccc12] | H |
| 2-9 | S | S | 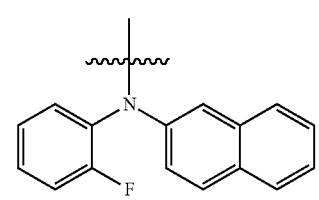 [SMILES: *N(c1ccc2ccccc2c1)c1ccccc1F] | 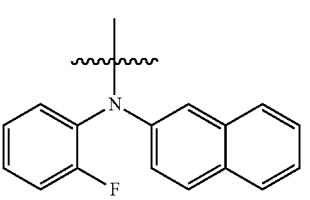 [SMILES: *N(c1ccc2ccccc2c1)c1ccccc1F] | H |

-continued
| Compound | X1 | X2 | R1 | R2 | R3 to to R6 |
|---|---|---|---|---|---|
| 2-10 | S | S | 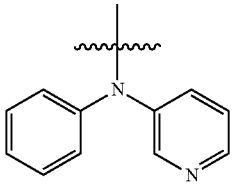 [SMILES: *N(c1ccccc1)c1cccnc1] | 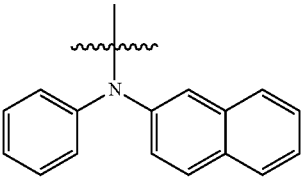 [SMILES: *N(c1ccccc1)c1ccc2ccccc2c1] | H |
| 2-11 | S | S | 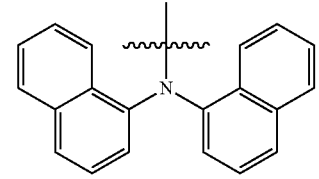 [SMILES: *N(c1cccc2ccccc12)c1cccc2ccccc12] | 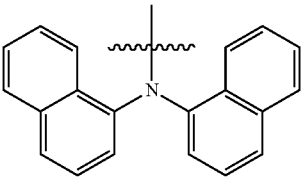 [SMILES: *N(c1cccc2ccccc12)c1cccc2ccccc12] | H |
| 2-12 | S | S | 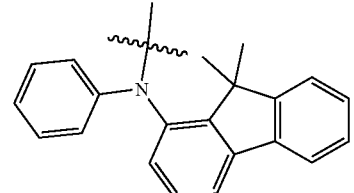 | 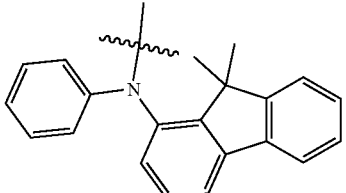 | H |
| 2-13 | S | S | 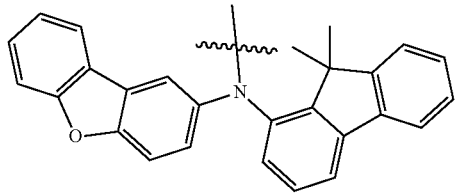 [SMILES: *N(c1ccc2oc3ccccc3c2c1)c1cccc2c1C(C)(C)c1ccccc1-2] | 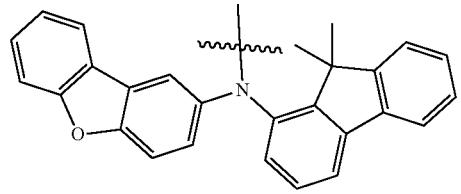 [SMILES: *N(c1ccc2oc3ccccc3c2c1)c1cccc2c1C(C)(C)c1ccccc1-2] | H |
| 2-14 | S | S | 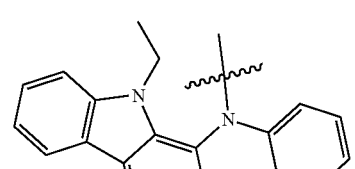 | 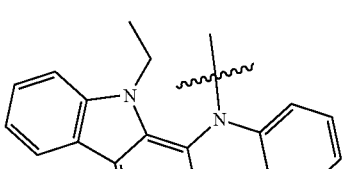 | H |
| 2-15 | S | S | 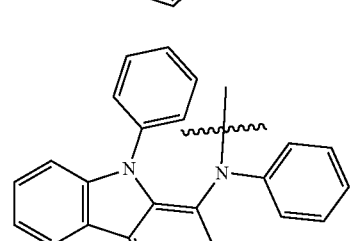 | 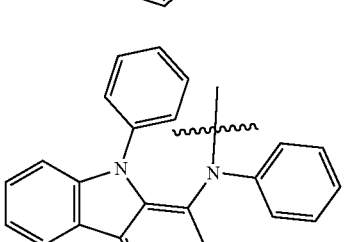 | H |
| 2-16 | S | S | 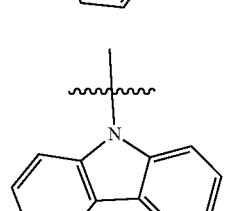 | 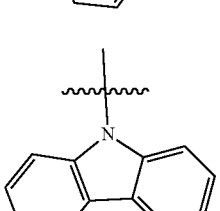 | H |

-continued

| Compound | X1 | X2 | R1 | R2 | R3 to to R6 |
|---|---|---|---|---|---|
| 2-17 | S | S | 4-(diphenylamino)phenyl | 4-(diphenylamino)phenyl | H |
| 2-18 | S | S | N-phenyl-N-(5-phenylthiophen-2-yl)amino | N-phenyl-N-(5-phenylthiophen-2-yl)amino | H |
| 2-19 | S | S | N,N-di(dibenzofuranyl)amino | N,N-di(dibenzofuranyl)amino | H |
| 2-20 | S | S | N-phenyl-N-(pyridin-3-yl)amino | N-phenyl-N-(pyridin-3-yl)amino | H |
| 2-21 | S | S | N-(dibenzofuran-1-yl)-N-(4-tert-butylphenyl)amino | N-(dibenzofuran-1-yl)-N-(4-tert-butylphenyl)amino | H |
| 2-22 | S | S | N-(4-tert-butylphenyl)-N-(naphthalen-1-yl)amino | N-(4-tert-butylphenyl)-N-(naphthalen-1-yl)amino | H |

| Compound | X1 | X2 | R1 | R2 | R3 to R6 |
|---|---|---|---|---|---|
| 3-1 | N | N | N,N-diphenylamino | N,N-diphenylamino | H |
| 3-2 | N | N | N,N-bis(4-tert-butylphenyl)amino | N,N-bis(4-tert-butylphenyl)amino | H |
| 3-3 | N | N | N,N-bis(2-methylphenyl)amino | N,N-bis(2-methylphenyl)amino | H |
| 3-4 | N | N | N,N-bis(3-methyl-2'-methylbiphenyl-4-yl)amino | N,N-bis(3-methyl-2'-methylbiphenyl-4-yl)amino | H |
| 3-5 | N | N | N-(2-fluorophenyl)-N-phenylamino | N-(2-fluorophenyl)-N-phenylamino | H |
| 3-6 | N | N | N-(dibenzofuran-4-yl)-N-phenylamino | N-(dibenzofuran-4-yl)-N-phenylamino | H |
| 3-7 | N | N | N-(6-isopropyldibenzofuran-4-yl)-N-phenylamino | N-(6-isopropyldibenzofuran-4-yl)-N-phenylamino | H |

-continued

| Compound | X1 | X2 | R1 | R2 | R3 to R6 |
|---|---|---|---|---|---|
| 3-8 | N | N | | | H |
| 3-9 | N | N | | | H |
| 3-10 | N | N | | | H |
| 3-11 | N | N | | | H |
| 3-12 | N | N | | | H |
| 3-13 | N | N | | | H |
| 3-14 | N | N | | | H |

-continued
| Compound | X1 | X2 | R1 | R2 | R3 to R6 |
|---|---|---|---|---|---|
| 3-15 | N | N |  |  | H |
| 3-16 | N | N | 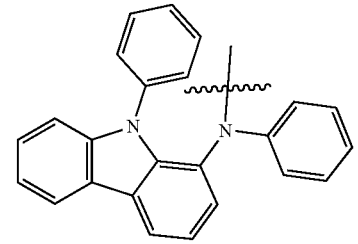 [SMILES: *N(c1ccccc1)c1cccc2c3ccccc3n(-c3ccccc3)c12] | 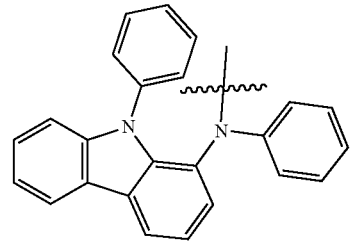 [SMILES: *N(c1ccccc1)c1cccc2c3ccccc3n(-c3ccccc3)c12] | H |
| 3-17 | N | N |  |  | H |
| 3-18 | N | N | 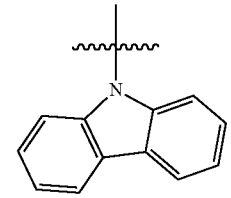 [SMILES: *n1c2ccccc2c2ccccc21] | 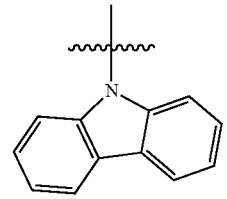 | H |
| 3-19 | N | N |  |  | H |
| 3-20 | N | N | 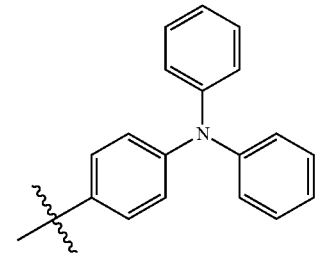 [SMILES: *c1ccc(N(c2ccccc2)c2ccccc2)cc1] | 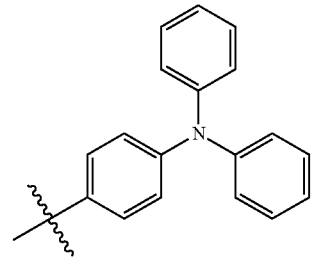 [SMILES: *c1ccc(N(c2ccccc2)c2ccccc2)cc1] | H |

| Compound | X1 | X2 | R1 |
|---|---|---|---|
| 4-1 | 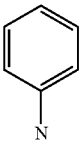 | 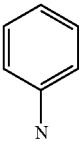 | 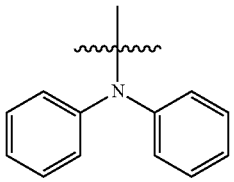 [SMILES: *N(c1ccccc1)c1ccccc1] |
| 4-2 | 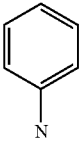 | 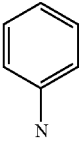 | 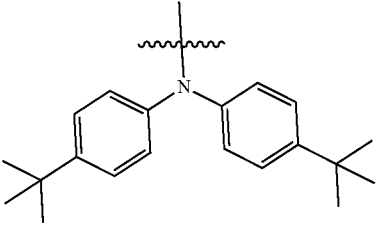 [SMILES: *N(c1ccc(C(C)(C)C)cc1)c1ccc(C(C)(C)C)cc1] |
| 4-3 | 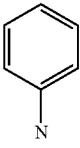 | 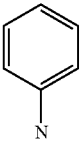 | 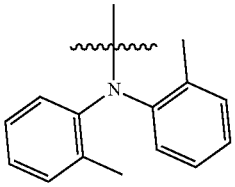 [SMILES: *N(c1ccccc1C)c1ccccc1C] |
| 4-4 | 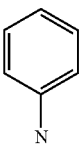 | 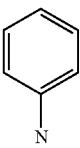 | 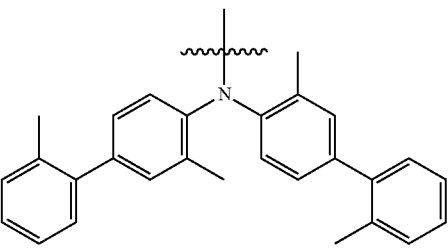 [SMILES: *N(c1ccc(-c2ccccc2C)cc1C)c1ccc(-c2ccccc2C)cc1C] |
| 4-5 | 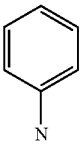 | 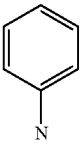 | 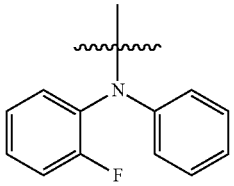 [SMILES: *N(c1ccccc1)c1ccccc1F] |
| 4-6 | 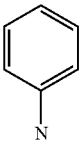 | 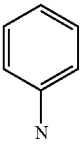 | 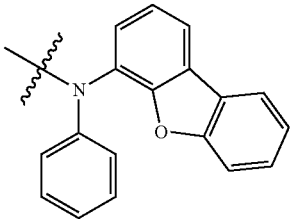 [SMILES: *N(c1ccccc1)c1cccc2c1oc1ccccc12] |
| 4-7 | 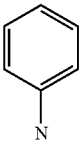 | 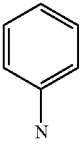 | 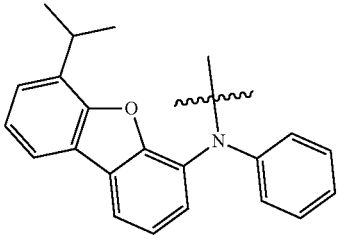 [SMILES: *N(c1ccccc1)c1cccc2c1oc1c(C(C)C)cccc12] |

-continued
| | | |
|---|---|---|
| 4-8 | 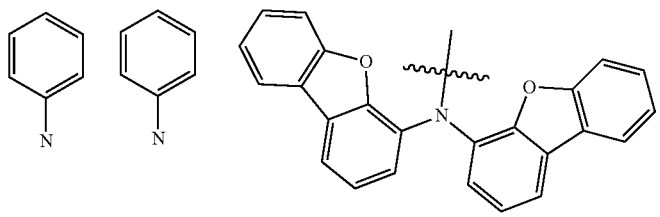 | |
| 4-9 | 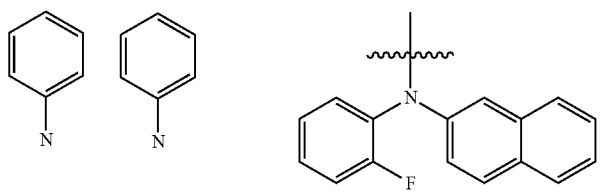 | |
| 4-10 | 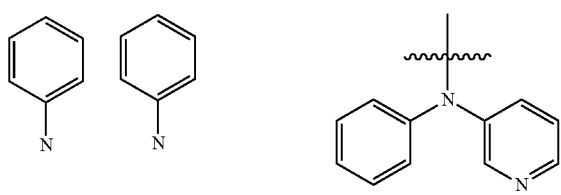 | |
| 4-11 | 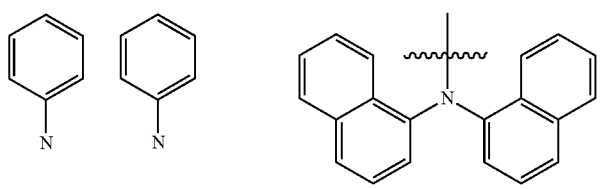 | |
| 4-12 | 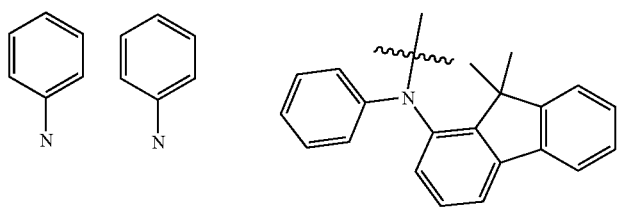 | |
| 4-13 | 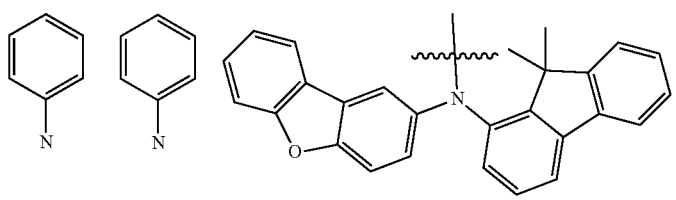 | |
| 4-14 | 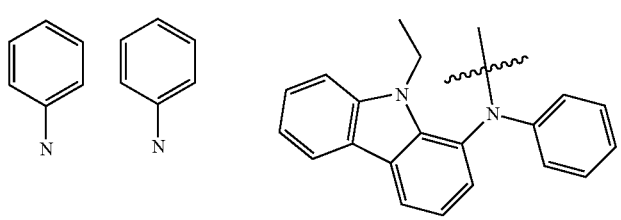 | |

-continued
| | | | |
|---|---|---|---|
| 4-15 | 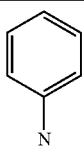 | 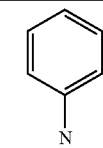 | 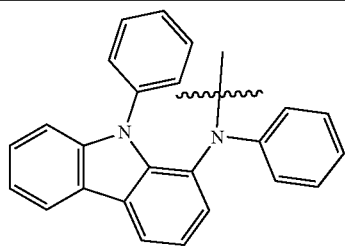 |
| 4-16 | 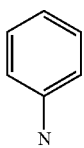 | 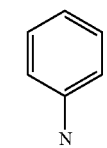 | 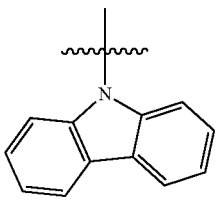 [SMILES: *n1c2ccccc2c2ccccc21] |
| 4-17 | 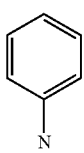 | 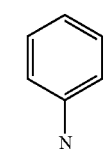 | 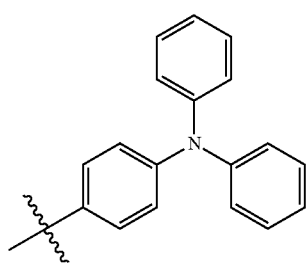 [SMILES: *c1ccc(N(c2ccccc2)c2ccccc2)cc1] |
| 4-18 | 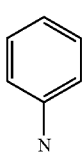 | 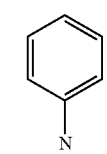 | 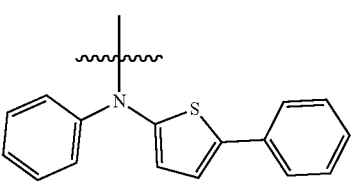 [SMILES: *N(c1ccccc1)c1ccc(-c2ccccc2)s1] |
| 4-19 | 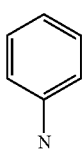 | 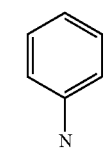 | 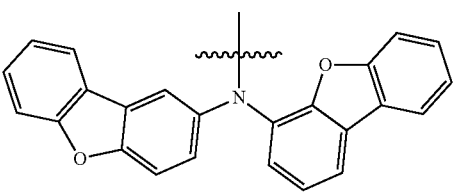 [SMILES: *N(c1ccc2oc3ccccc3c2c1)c1cccc2c1oc1ccccc12] |
| 4-20 | 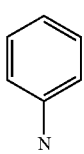 | 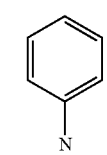 | 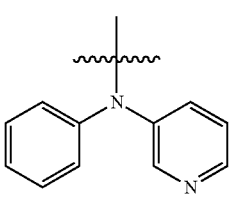 [SMILES: *N(c1ccccc1)c1cccnc1] |
| 4-21 | 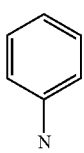 | 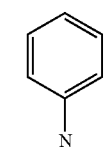 | 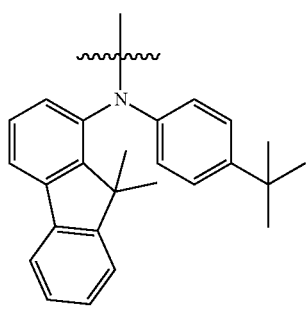 [SMILES: *N(c1ccc(C(C)(C)C)cc1)c1cccc2c1C(C)(C)c1ccccc1-2] |

-continued
| Compound | R2 | R3 to R6 |
|---|---|---|
| 4-1 | 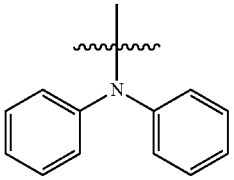 [SMILES: *N(c1ccccc1)c1ccccc1] | H |
| 4-2 | 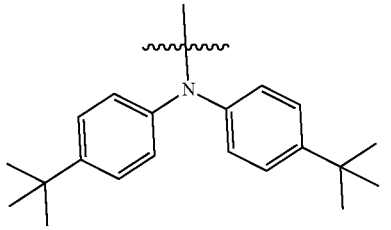 [SMILES: *N(c1ccc(C(C)(C)C)cc1)c1ccc(C(C)(C)C)cc1] | H |
| 4-3 | 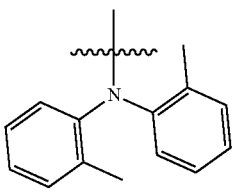 [SMILES: *N(c1ccccc1C)c1ccccc1C] | H |
| 4-4 | 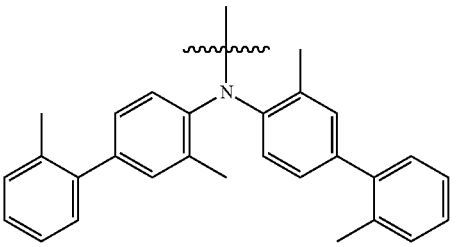 [SMILES: *N(c1ccc(-c2ccccc2C)cc1C)c1ccc(-c2ccccc2C)cc1C] | H |
| 4-5 | 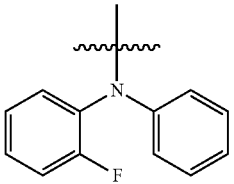 [SMILES: *N(c1ccccc1)c1ccccc1F] | H |
| 4-6 | 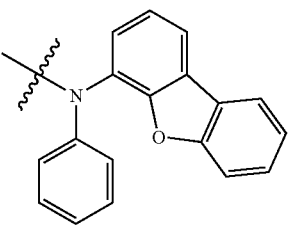 [SMILES: *N(c1ccccc1)c1cccc2c1oc1ccccc12] | H |
| 4-7 | 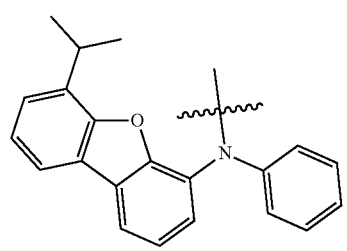 [SMILES: *N(c1ccccc1)c1cccc2c1oc1c(C(C)C)cccc12] | H |

-continued
| | | |
|---|---|---|
| 4-8 | 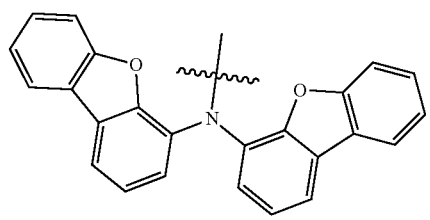 [SMILES: *N(c1cccc2c1oc1ccccc12)c1cccc2c1oc1ccccc12] | H |
| 4-9 | 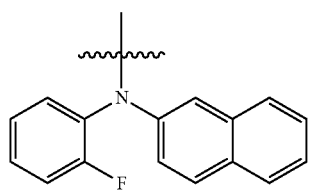 [SMILES: *N(c1ccc2ccccc2c1)c1ccccc1F] | H |
| 4-10 | 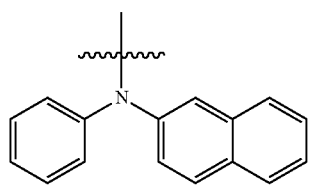 [SMILES: *N(c1ccccc1)c1ccc2ccccc2c1] | H |
| 4-11 | 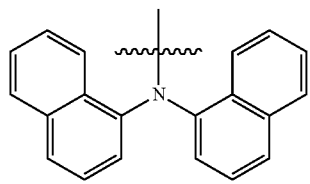 [SMILES: *N(c1cccc2ccccc12)c1cccc2ccccc12] | H |
| 4-12 | 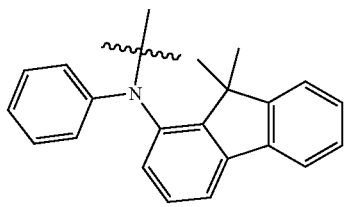 [SMILES: *N(c1ccccc1)c1cccc2c1C(C)(C)c1ccccc1-2] | H |
| 4-13 | 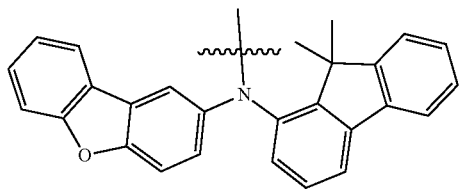 [SMILES: *N(c1ccc2oc3ccccc3c2c1)c1cccc2c1C(C)(C)c1ccccc1-2] | H |
| 4-14 | 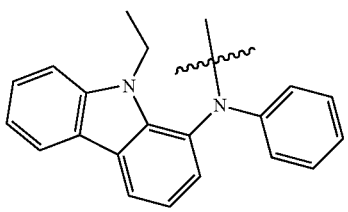 [SMILES: *N(c1ccccc1)c1cccc2c3ccccc3n(CC)c12] | H |

| | | |
|---|---|---|
| 4-15 | 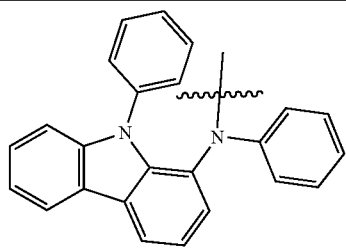 | H |
| 4-16 | 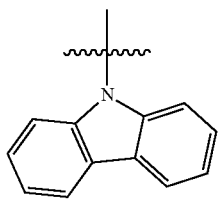 [SMILES: *n1c2ccccc2c2ccccc21] | H |
| 4-17 | 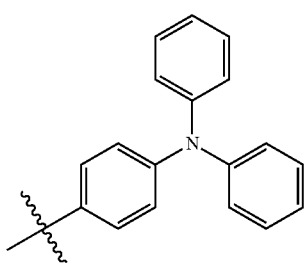 [SMILES: *c1ccc(N(c2ccccc2)c2ccccc2)cc1] | H |
| 4-18 | 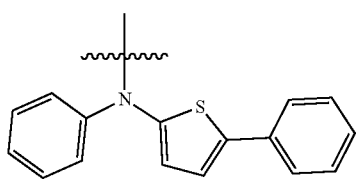 [SMILES: *N(c1ccccc1)c1ccc(-c2ccccc2)s1] | H |
| 4-19 | 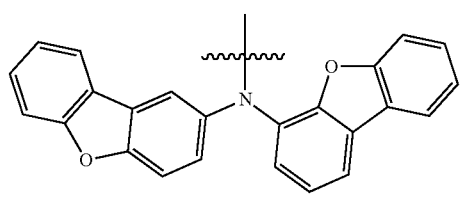 [SMILES: *N(c1ccc2oc3ccccc3c2c1)c1cccc2c1oc1ccccc12] | H |
| 4-20 | 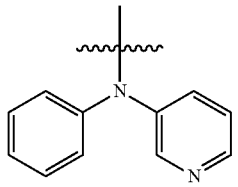 [SMILES: *N(c1ccccc1)c1cccnc1] | H |
| 4-21 | 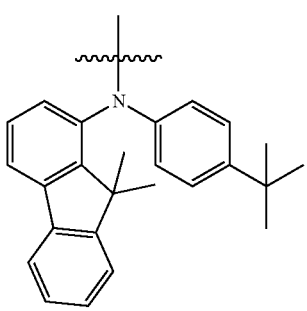 [SMILES: *N(c1ccc(C(C)(C)C)cc1)c1cccc2c1C(C)(C)c1ccccc1-2] | H |

| Compound | X | Y | R1 |
|---|---|---|---|
| 5-1 | -C/ | -C/ | N(phenyl)(phenyl) (diphenylamino) |
| 5-2 | -C/ | -C/ | N(4-tert-butylphenyl)₂ |
| 5-3 | -C/ | -C/ | N(2-methylphenyl)₂ |
| 5-4 | -C/ | -C/ | N(3-methyl-2'-methylbiphenyl-4-yl)₂ |
| 5-5 | -C/ | -C/ | N(phenyl)(2-fluorophenyl) |
| 5-6 | -C/ | -C/ | N(phenyl)(dibenzofuran-4-yl) |
| 5-7 | -C/ | -C/ | (6-isopropyldibenzofuran-4-yl)(phenyl)N- |

-continued
| 5-8 | 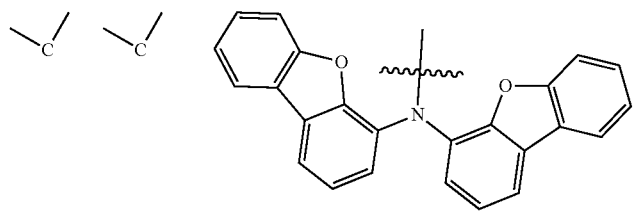 |
| 5-9 | 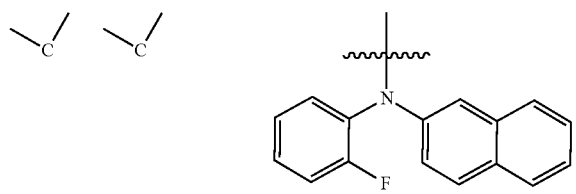 |
| 5-10 | 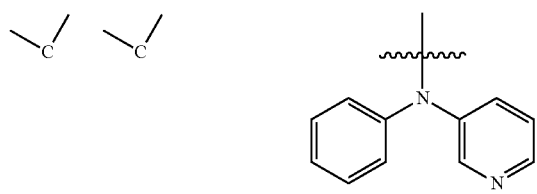 |
| 5-11 | 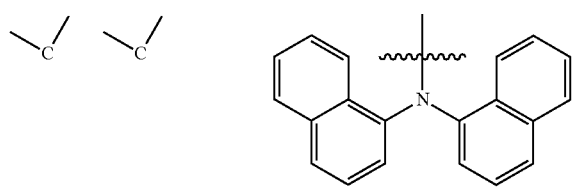 |
| 5-12 | 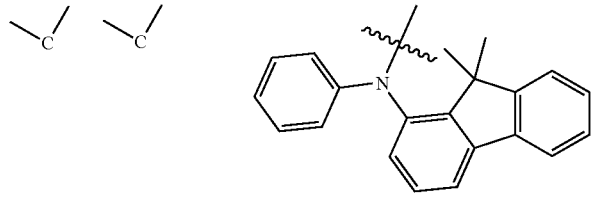 |
| 5-13 | 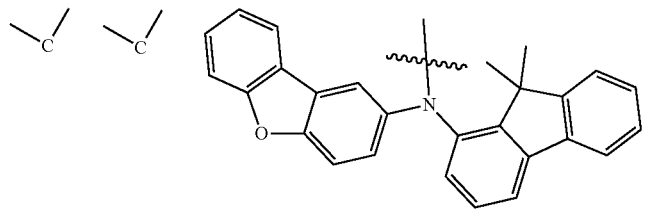 |
| 5-14 | 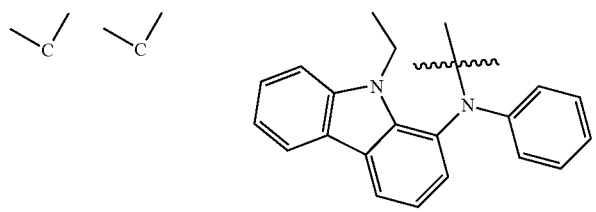 |

-continued
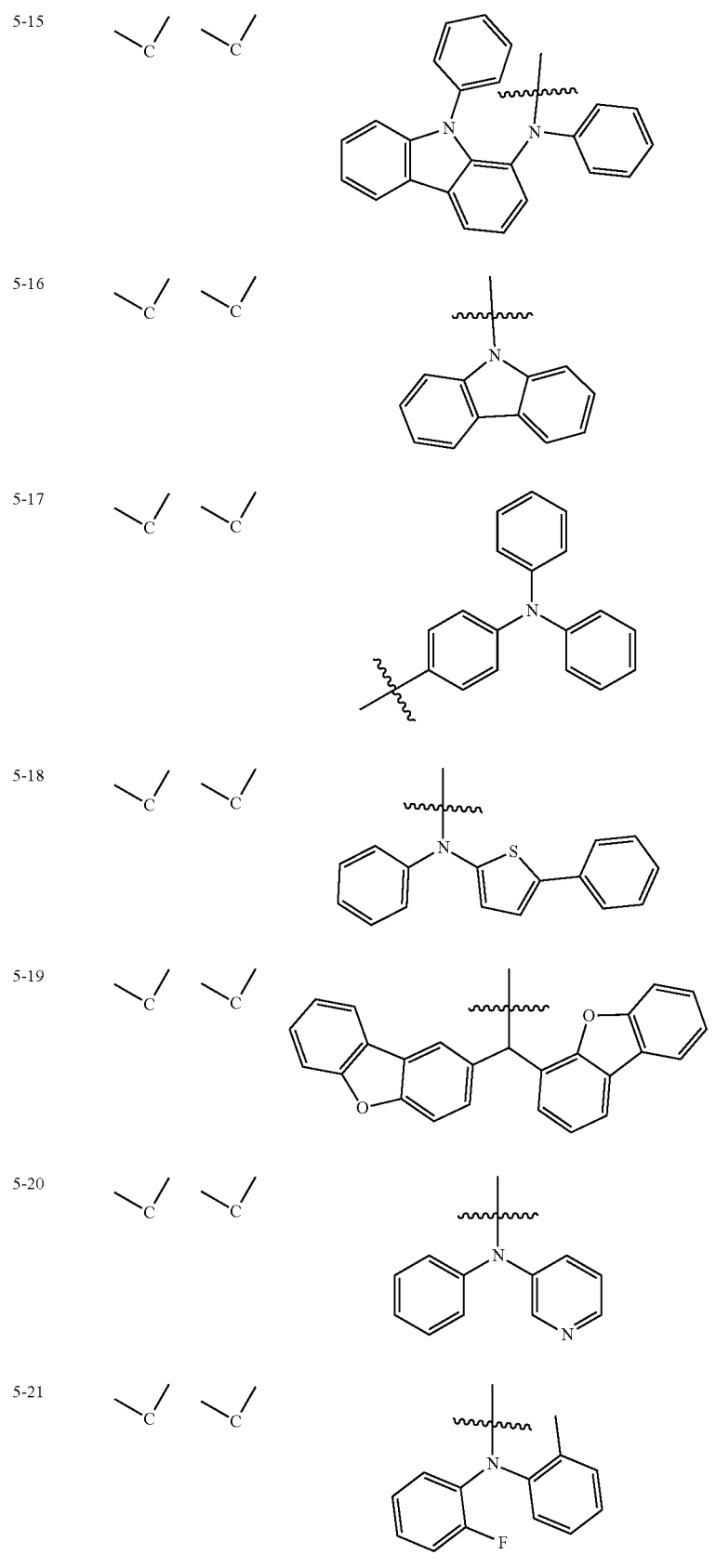

-continued
| Compound | R2 | R3 to R6 |
|---|---|---|
| 5-1 | 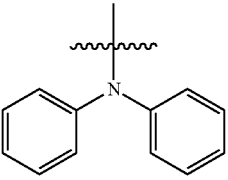 [SMILES: *N(c1ccccc1)c1ccccc1] | H |
| 5-2 | 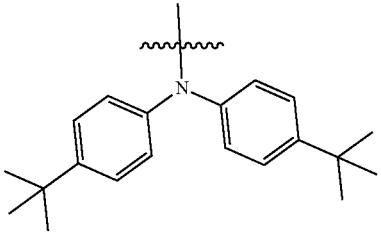 [SMILES: *N(c1ccc(C(C)(C)C)cc1)c1ccc(C(C)(C)C)cc1] | H |
| 5-3 | 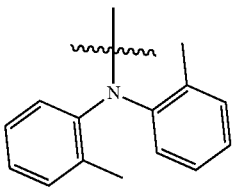 [SMILES: *N(c1ccccc1C)c1ccccc1C] | H |
| 5-4 | 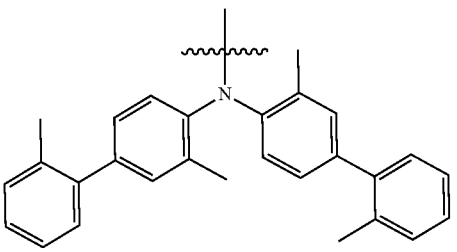 [SMILES: *N(c1ccc(-c2ccccc2C)cc1C)c1ccc(-c2ccccc2C)cc1C] | H |
| 5-5 | 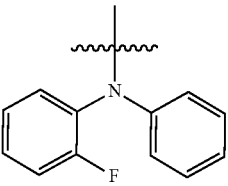 [SMILES: *N(c1ccccc1)c1ccccc1F] | H |
| 5-6 | 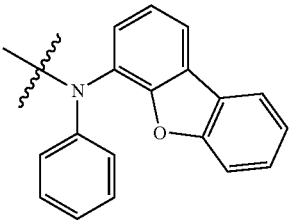 [SMILES: *N(c1ccccc1)c1cccc2c1oc1ccccc12] | H |
| 5-7 | 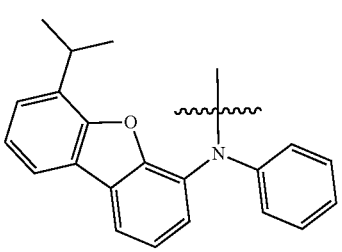 [SMILES: *N(c1ccccc1)c1cccc2c1oc1c(C(C)C)cccc12] | H |

| | | |
|---|---|---|
| 5-8 | 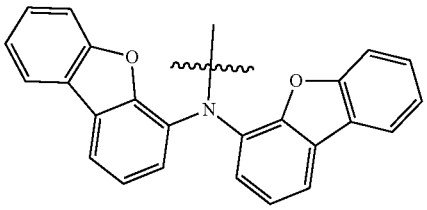 [SMILES: *N(c1cccc2c1oc1ccccc12)c1cccc2c1oc1ccccc12] | H |
| 5-9 | 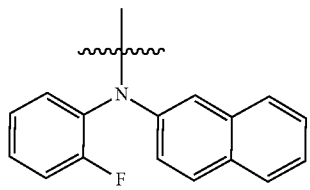 [SMILES: *N(c1ccc2ccccc2c1)c1ccccc1F] | H |
| 5-10 | 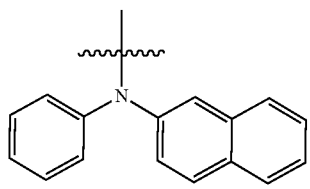 [SMILES: *N(c1ccccc1)c1ccc2ccccc2c1] | H |
| 5-11 | 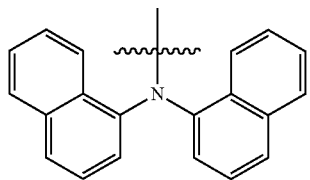 [SMILES: *N(c1cccc2ccccc12)c1cccc2ccccc12] | H |
| 5-12 | 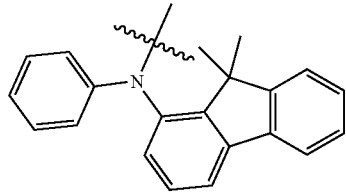 [SMILES: *N(c1ccccc1)c1cccc2c1C(C)(C)c1ccccc1-2] | H |
| 5-13 | 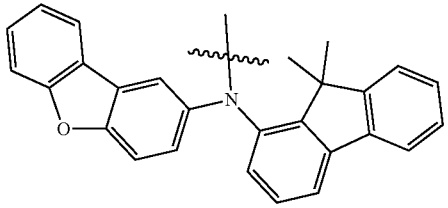 [SMILES: *N(c1ccc2oc3ccccc3c2c1)c1cccc2c1C(C)(C)c1ccccc1-2] | H |
| 5-14 | 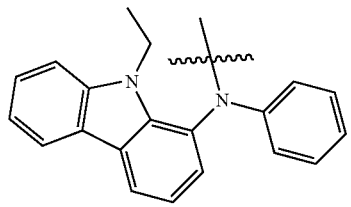 [SMILES: *N(c1ccccc1)c1cccc2c3ccccc3n(CC)c12] | H |

| | | |
|---|---|---|
| 5-15 | 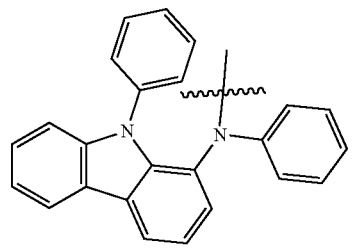 [SMILES: *N(c1ccccc1)c1cccc2c3ccccc3n(-c3ccccc3)c12] | H |
| 5-16 | 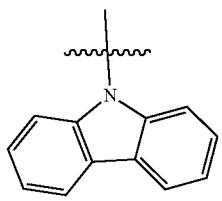 [SMILES: *n1c2ccccc2c2ccccc21] | H |
| 5-17 | 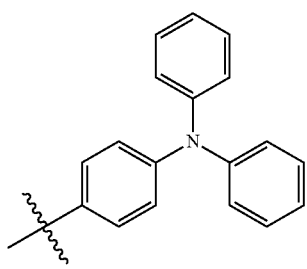 [SMILES: *c1ccc(N(c2ccccc2)c2ccccc2)cc1] | H |
| 5-18 | 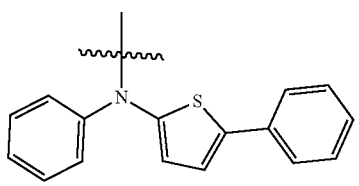 [SMILES: *N(c1ccccc1)c1ccc(-c2ccccc2)s1] | H |
| 5-19 | 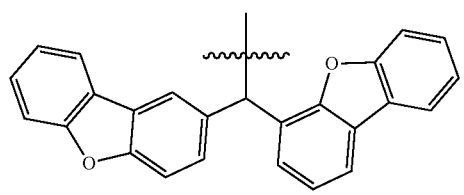 [SMILES: *C(c1ccc2oc3ccccc3c2c1)c1cccc2c1oc1ccccc12] | H |
| 5-20 | 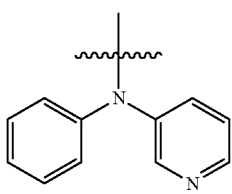 [SMILES: *N(c1ccccc1)c1cccnc1] | H |
| 5-21 | 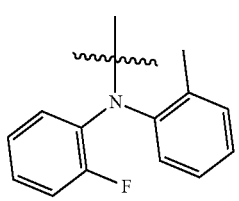 [SMILES: *N(c1ccccc1C)c1ccccc1F] | H |

| Compound | X | Y | R1 |
|---|---|---|---|
| 6-1 | 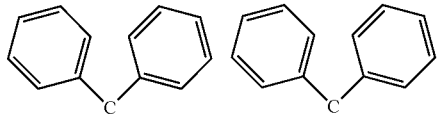 | 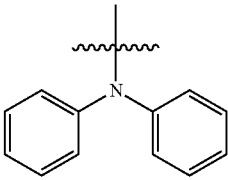 [SMILES: *N(c1ccccc1)c1ccccc1] | 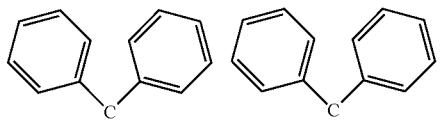 |
| 6-2 | 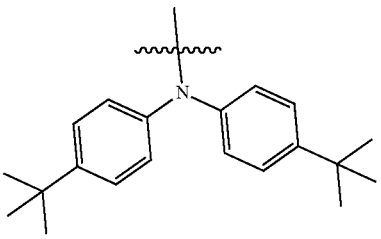 [SMILES: *N(c1ccc(C(C)(C)C)cc1)c1ccc(C(C)(C)C)cc1] | 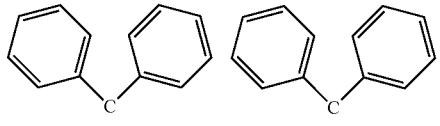 | 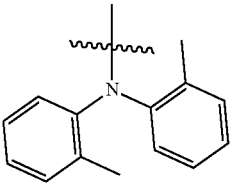 [SMILES: *N(c1ccccc1C)c1ccccc1C] |
| 6-3 | 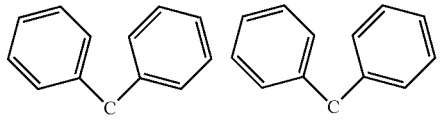 | 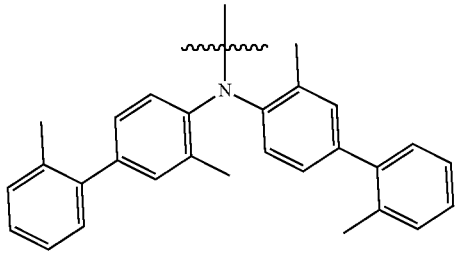 [SMILES: *N(c1ccc(-c2ccccc2C)cc1C)c1ccc(-c2ccccc2C)cc1C] | 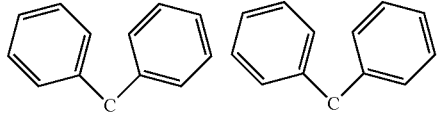 |
| 6-4 | 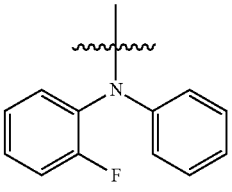 [SMILES: *N(c1ccccc1)c1ccccc1F] | 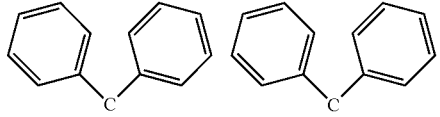 | 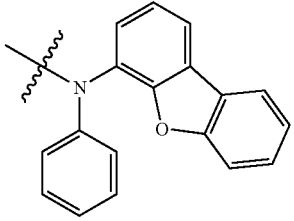 [SMILES: *N(c1ccccc1)c1cccc2c1oc1ccccc12] |
| 6-5 | 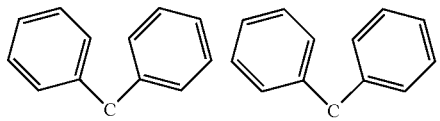 | 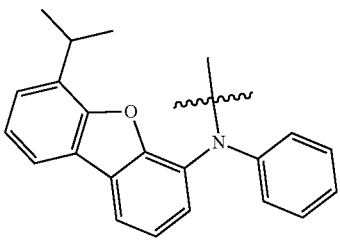 [SMILES: *N(c1ccccc1)c1cccc2c1oc1c(C(C)C)cccc12] | |
| 6-6 | | | |
| 6-7 | | | |

-continued
| 6-8 | 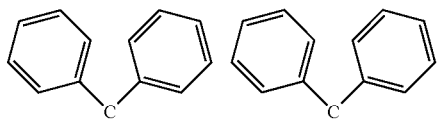 | 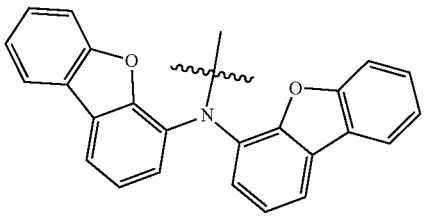 [SMILES: *N(c1cccc2c1oc1ccccc12)c1cccc2c1oc1ccccc12] |
| 6-9 | 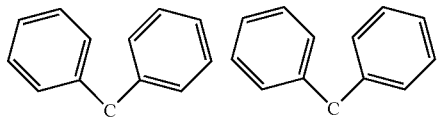 | 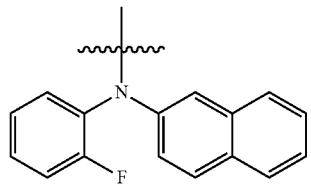 [SMILES: *N(c1ccc2ccccc2c1)c1ccccc1F] |
| 6-10 | 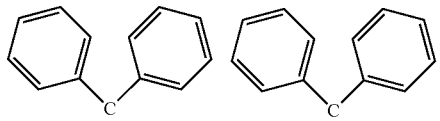 | 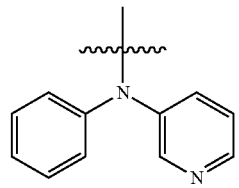 [SMILES: *N(c1ccccc1)c1cccnc1] |
| 6-11 | 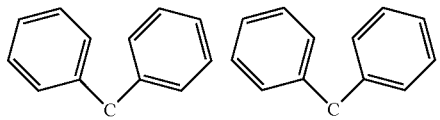 | 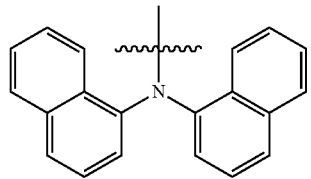 [SMILES: *N(c1cccc2ccccc12)c1cccc2ccccc12] |
| 6-12 | 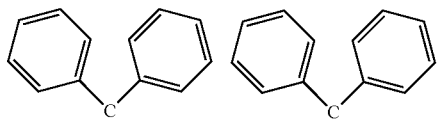 | 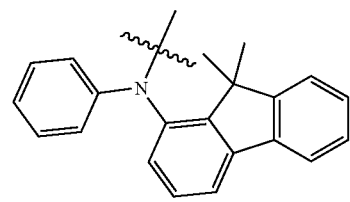 [SMILES: *N(c1ccccc1)c1cccc2c1C(C)(C)c1ccccc1-2] |
| 6-13 | 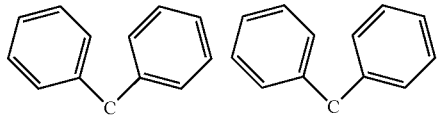 | 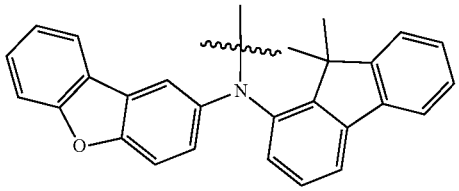 [SMILES: *N(c1ccc2oc3ccccc3c2c1)c1cccc2c1C(C)(C)c1ccccc1-2] |
| 6-14 | 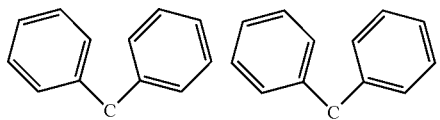 | 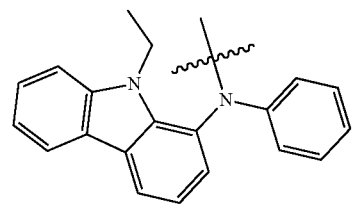 [SMILES: *N(c1ccccc1)c1cccc2c3ccccc3n(CC)c12] |

| | | |
|---|---|---|
| 6-15 | 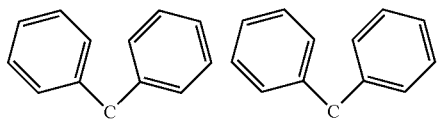 | 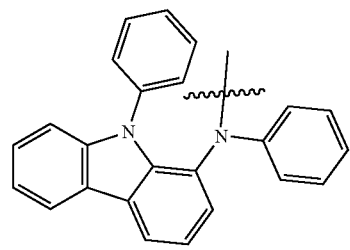 [SMILES: *N(c1ccccc1)c1cccc2c3ccccc3n(-c3ccccc3)c12] |
| 6-16 | 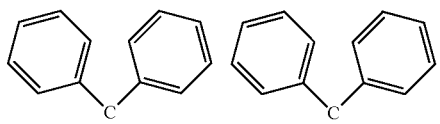 | 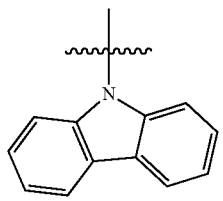 |
| 6-17 | 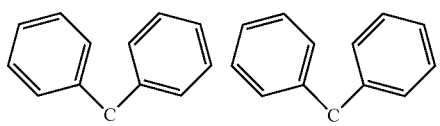 | 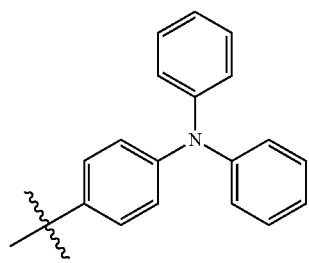 [SMILES: *c1ccc(N(c2ccccc2)c2ccccc2)cc1] |
| 6-18 | 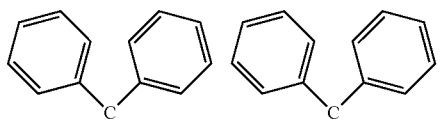 | 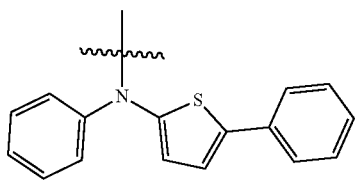 [SMILES: *N(c1ccccc1)c1ccc(-c2ccccc2)s1] |
| 6-19 | 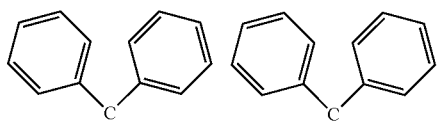 | 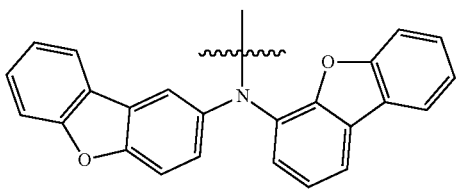 [SMILES: *N(c1ccc2oc3ccccc3c2c1)c1cccc2c1oc1ccccc12] |
| 6-20 | 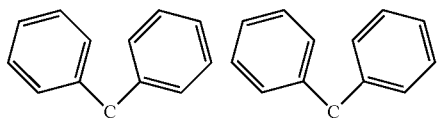 | 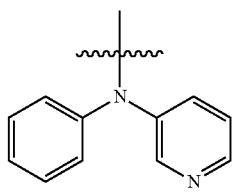 [SMILES: *N(c1ccccc1)c1cccnc1] |
| 6-21 | 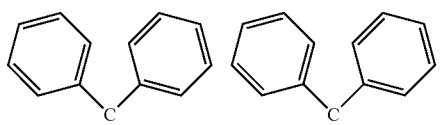 | 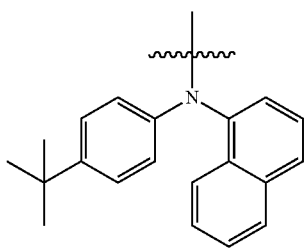 [SMILES: *N(c1ccc(C(C)(C)C)cc1)c1cccc2ccccc12] |

-continued

| Compound | R2 | R3 to R6 |
|---|---|---|
| 6-1 | N,N-diphenylamino | H |
| 6-2 | bis(4-tert-butylphenyl)amino | H |
| 6-3 | bis(2-methylphenyl)amino | H |
| 6-4 | bis(2'-methyl-3-methylbiphenyl-4-yl)amino | H |
| 6-5 | N-(2-fluorophenyl)-N-phenylamino | H |
| 6-6 | N-phenyl-N-(dibenzofuran-yl)amino | H |
| 6-7 | N-phenyl-N-(isopropyl-dibenzofuranyl)amino | H |

-continued
| | | |
|---|---|---|
| 6-8 | 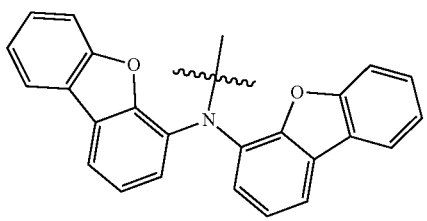 [SMILES: *N(c1cccc2c1oc1ccccc12)c1cccc2c1oc1ccccc12] | H |
| 6-9 | 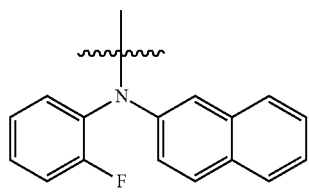 [SMILES: *N(c1ccc2ccccc2c1)c1ccccc1F] | H |
| 6-10 | 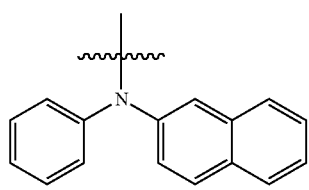 [SMILES: *N(c1ccccc1)c1ccc2ccccc2c1] | H |
| 6-11 | 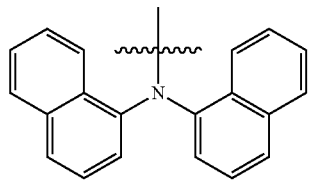 [SMILES: *N(c1cccc2ccccc12)c1cccc2ccccc12] | H |
| 6-12 | 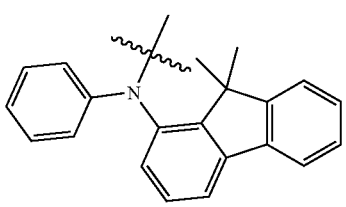 [SMILES: *N(c1ccccc1)c1cccc2c1C(C)(C)c1ccccc1-2] | H |
| 6-13 | 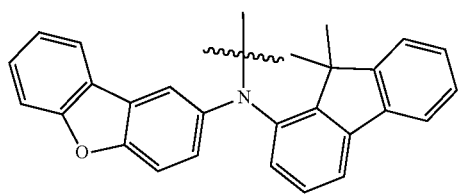 [SMILES: *N(c1ccc2oc3ccccc3c2c1)c1cccc2c1C(C)(C)c1ccccc1-2] | H |
| 6-14 | 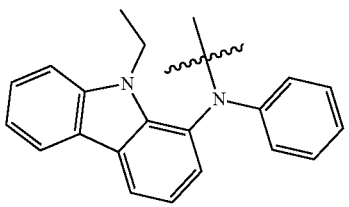 [SMILES: *N(c1ccccc1)c1cccc2c3ccccc3n(CC)c12] | H |

-continued
| | | |
|---|---|---|
| 6-15 | 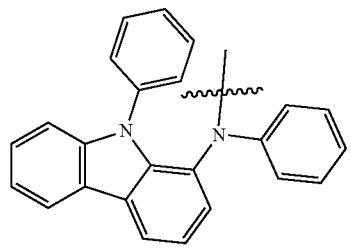 [SMILES: *N(c1ccccc1)c1cccc2c3ccccc3n(-c3ccccc3)c12] | H |
| 6-16 | 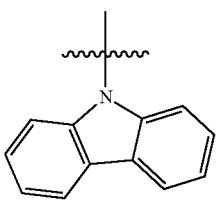 [SMILES: *n1c2ccccc2c2ccccc21] | H |
| 6-17 | 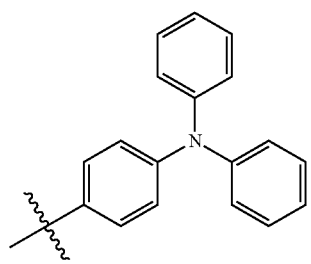 [SMILES: *c1ccc(N(c2ccccc2)c2ccccc2)cc1] | H |
| 6-18 | 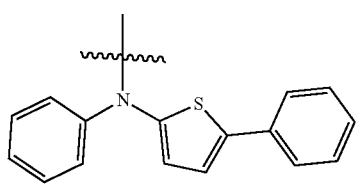 [SMILES: *N(c1ccccc1)c1ccc(-c2ccccc2)s1] | H |
| 6-19 | 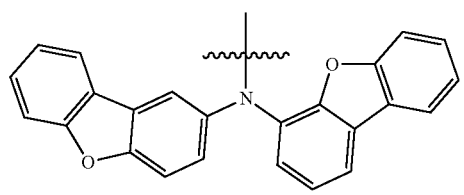 [SMILES: *N(c1ccc2oc3ccccc3c2c1)c1cccc2c1oc1ccccc12] | H |
| 6-20 | 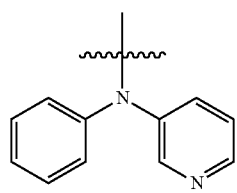 [SMILES: *N(c1ccccc1)c1cccnc1] | H |
| 6-21 | 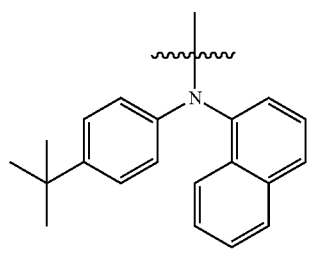 [SMILES: *N(c1ccc(C(C)(C)C)cc1)c1cccc2ccccc12] | H |

| Compound | X1 | X2 | R1 |
|---|---|---|---|
| 7-1 | O | S | 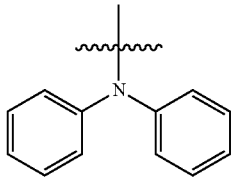 [SMILES: *N(c1ccccc1)c1ccccc1] |
| 7-2 | O | 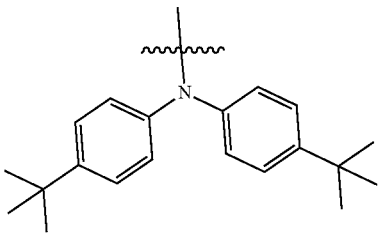 [SMILES: *N(c1ccc(C(C)(C)C)cc1)c1ccc(C(C)(C)C)cc1] | 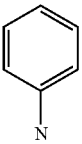 |
| 7-3 | O | 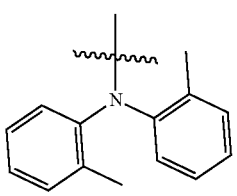 [SMILES: *N(c1ccccc1C)c1ccccc1C] |  |
| 7-4 | O | 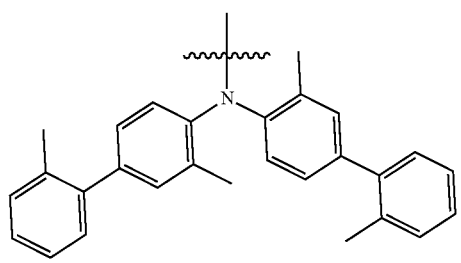 [SMILES: *N(c1ccc(-c2ccccc2C)cc1C)c1ccc(-c2ccccc2C)cc1C] | 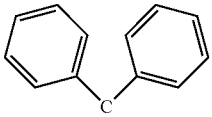 |
| 7-5 | O | 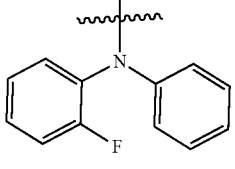 | 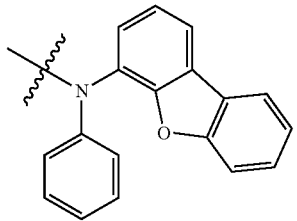 [SMILES: *N(c1ccccc1)c1cccc2c1oc1ccccc12] |
| 7-6 | S | 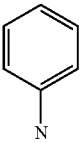 | 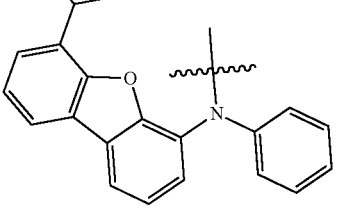 |
| 7-7 | S | | |

-continued
| 7-8 | S |  | 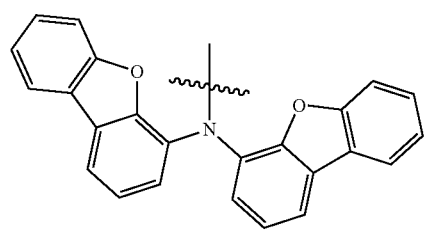 [SMILES: *N(c1cccc2c1oc1ccccc12)c1cccc2c1oc1ccccc12] |
| 7-9 | S | 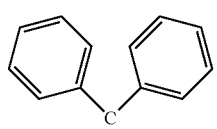 | 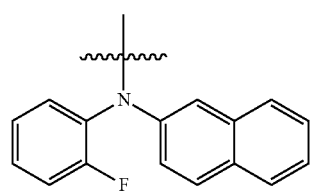 [SMILES: *N(c1ccc2ccccc2c1)c1ccccc1F] |
| 7-10 | 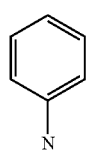 | 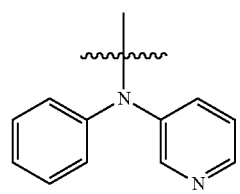 [SMILES: *N(c1ccccc1)c1cccnc1] | |
| 7-11 |  | | 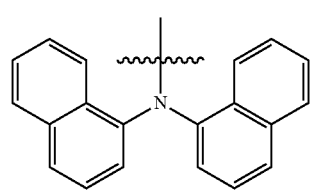 |
| 7-12 | 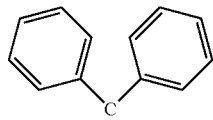 | | 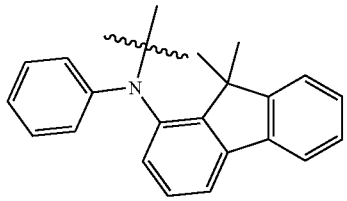 [SMILES: *N(c1ccccc1)c1cccc2c1C(C)(C)c1ccccc1-2] |
| 7-13 | 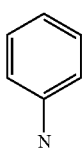 | 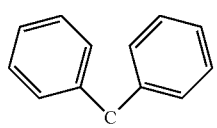 | 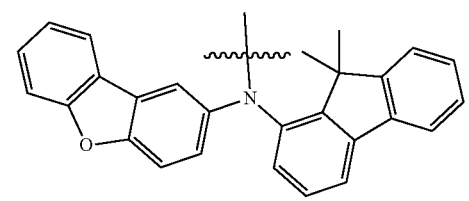 [SMILES: *N(c1ccc2oc3ccccc3c2c1)c1cccc2c1C(C)(C)c1ccccc1-2] |
| 7-14 | 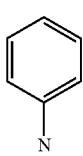 | | 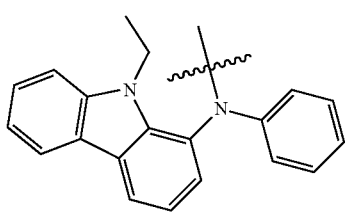 [SMILES: *N(c1ccccc1)c1cccc2c3ccccc3n(CC)c12] |

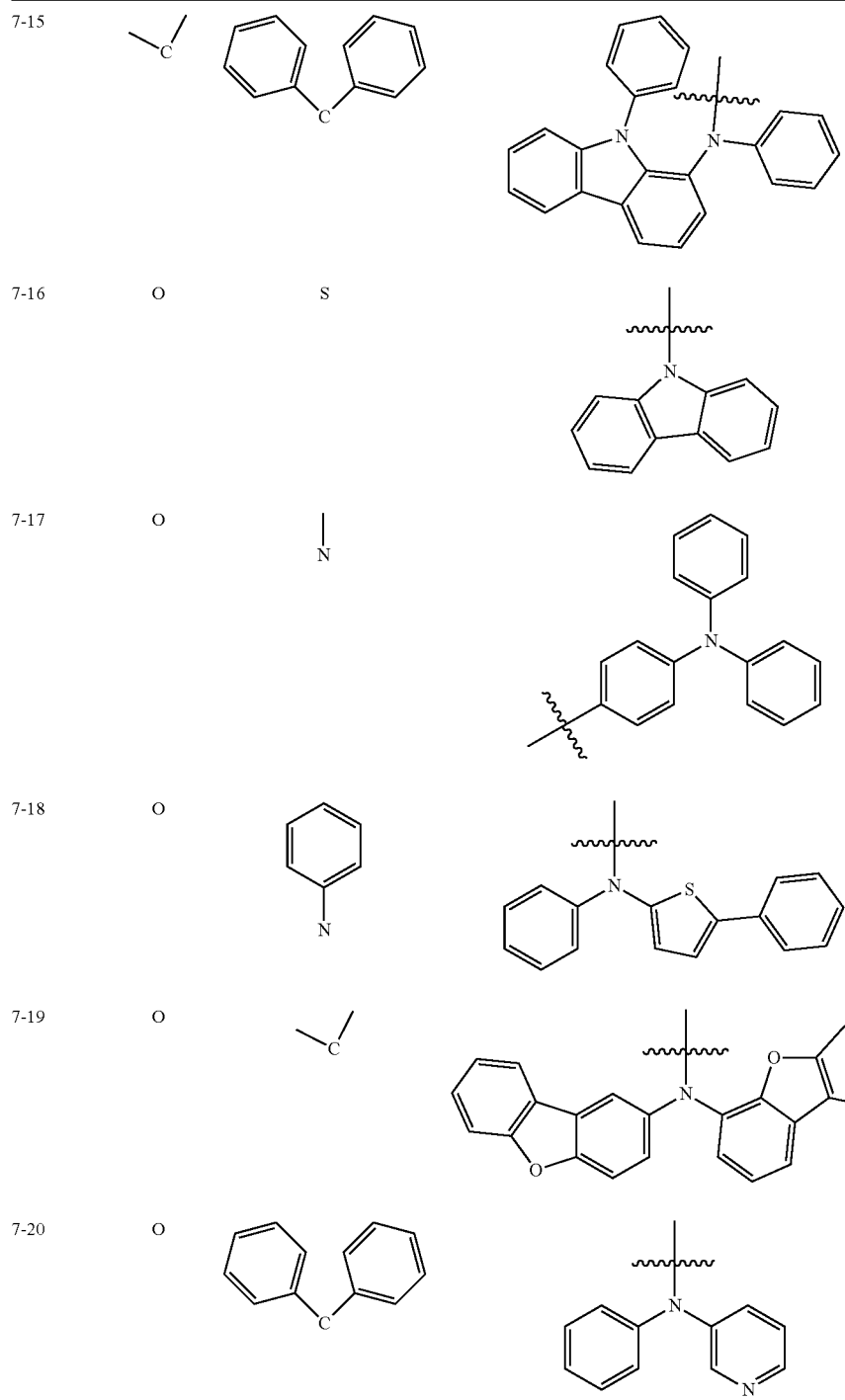# -continued
| Compound | R2 | R3 to R6 |
|---|---|---|
| 7-1 | 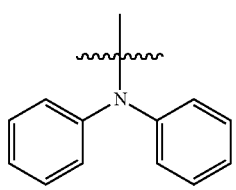 [SMILES: *N(c1ccccc1)c1ccccc1] | H |

-continued
| | | |
|---|---|---|
| 7-2 | 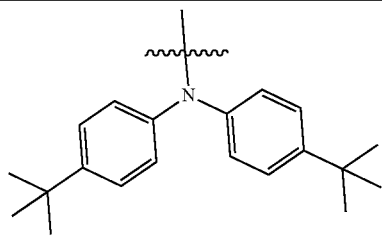 | H |
| 7-3 | 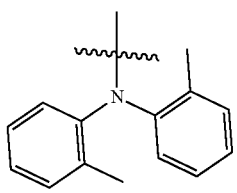 [SMILES: *N(c1ccccc1C)c1ccccc1C] | H |
| 7-4 | 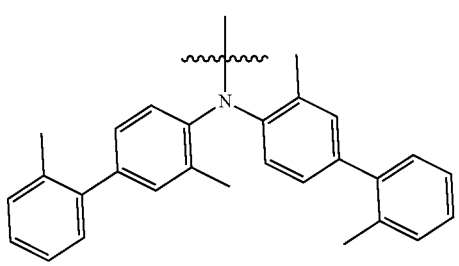 [SMILES: *N(c1ccc(-c2ccccc2C)cc1C)c1ccc(-c2ccccc2C)cc1C] | H |
| 7-5 | 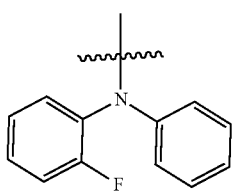 [SMILES: *N(c1ccccc1)c1ccccc1F] | H |
| 7-6 | 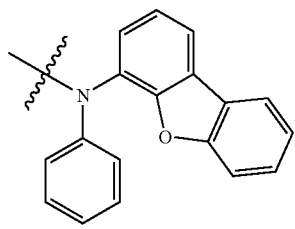 [SMILES: *N(c1ccccc1)c1cccc2c1oc1ccccc12] | H |
| 7-7 | 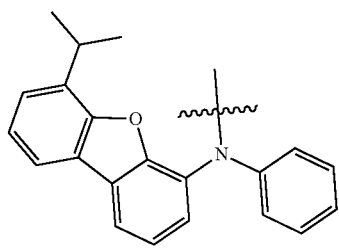 [SMILES: *N(c1ccccc1)c1cccc2c1oc1c(C(C)C)cccc12] | H |
| 7-8 | 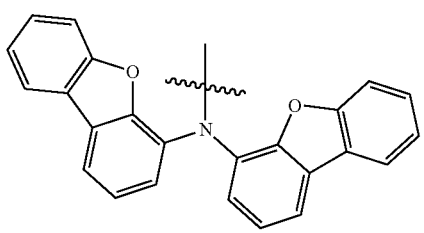 [SMILES: *N(c1cccc2c1oc1ccccc12)c1cccc2c1oc1ccccc12] | H |

| | | |
|---|---|---|
| 7-9 | 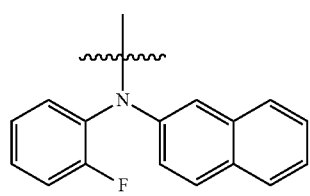 [SMILES: *N(c1ccc2ccccc2c1)c1ccccc1F] | H |
| 7-10 | 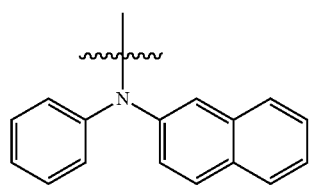 [SMILES: *N(c1ccccc1)c1ccc2ccccc2c1] | H |
| 7-11 | 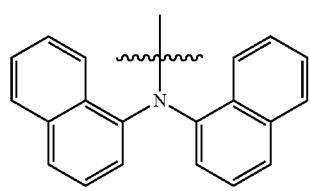 [SMILES: *N(c1cccc2ccccc12)c1cccc2ccccc12] | H |
| 7-12 | 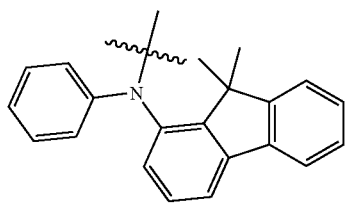 [SMILES: *N(c1ccccc1)c1cccc2c1C(C)(C)c1ccccc1-2] | H |
| 7-13 | 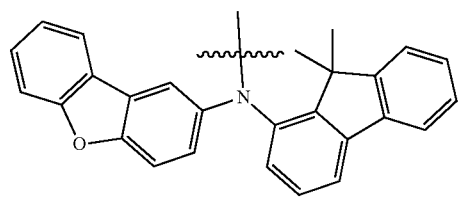 [SMILES: *N(c1ccc2oc3ccccc3c2c1)c1cccc2c1C(C)(C)c1ccccc1-2] | H |
| 7-14 | 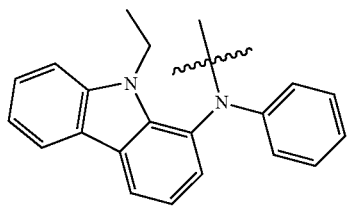 [SMILES: *N(c1ccccc1)c1cccc2c3ccccc3n(CC)c12] | H |
| 7-15 | 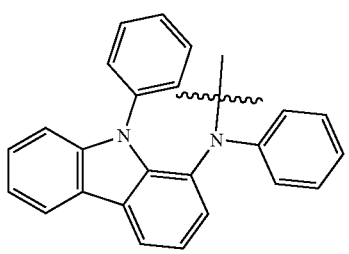 [SMILES: *N(c1ccccc1)c1cccc2c3ccccc3n(-c3ccccc3)c12] | H |

-continued
| | | |
|---|---|---|
| 7-16 | 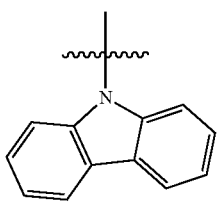 [SMILES: *n1c2ccccc2c2ccccc21] | H |
| 7-17 | 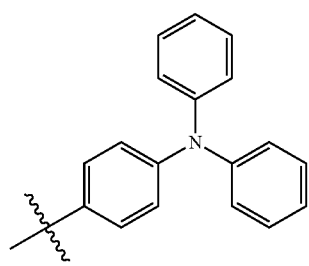 [SMILES: *c1ccc(N(c2ccccc2)c2ccccc2)cc1] | H |
| 7-18 | 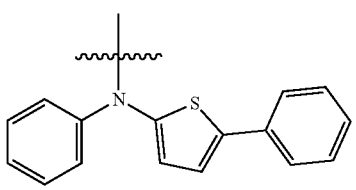 [SMILES: *N(c1ccccc1)c1ccc(-c2ccccc2)s1] | H |
| 7-19 | 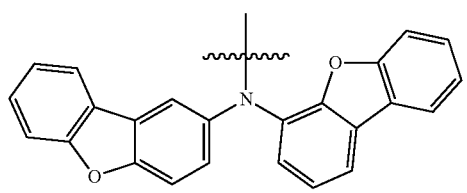 [SMILES: *N(c1ccc2oc3ccccc3c2c1)c1cccc2c1oc1ccccc12] | H |
| 7-20 | 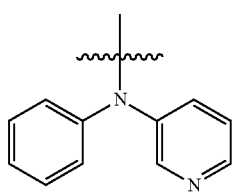 [SMILES: *N(c1ccccc1)c1cccnc1] | H |
| Compound | X1 | X2 | R1 |
|---|---|---|---|
| 8-1 | O | O | 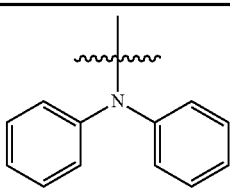 |
| 8-2 | O | O | 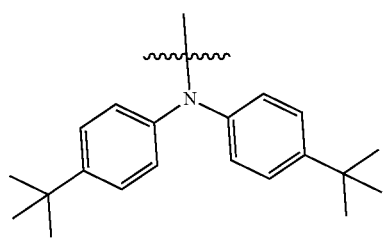 [SMILES: *N(c1ccc(C(C)(C)C)cc1)c1ccc(C(C)(C)C)cc1] |

-continued
| | | | |
|---|---|---|---|
| 8-3 | O | O | 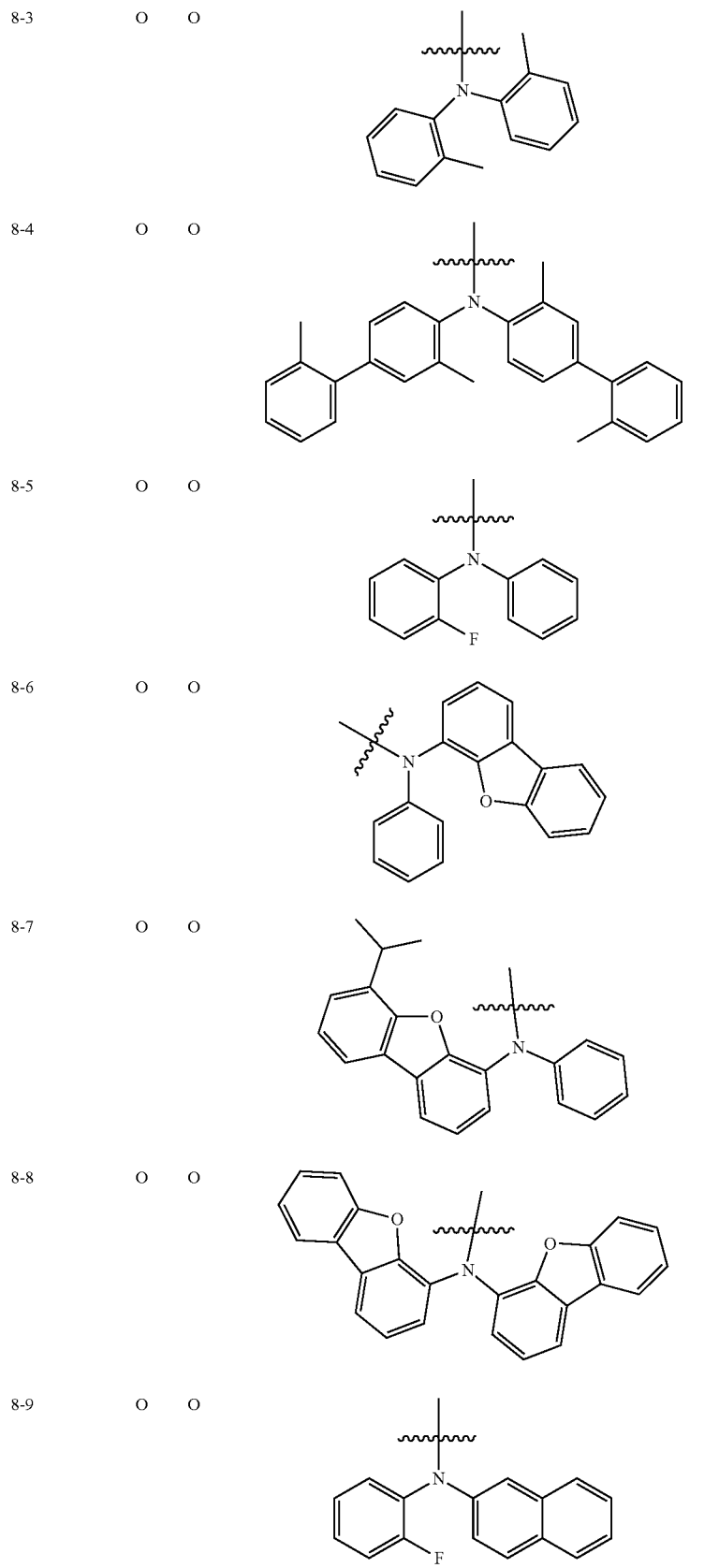 |
| 8-4 | O | O | |
| 8-5 | O | O | |
| 8-6 | O | O | |
| 8-7 | O | O | |
| 8-8 | O | O | |
| 8-9 | O | O | |

-continued
| | | | |
|---|---|---|---|
| 8-10 | O | O | 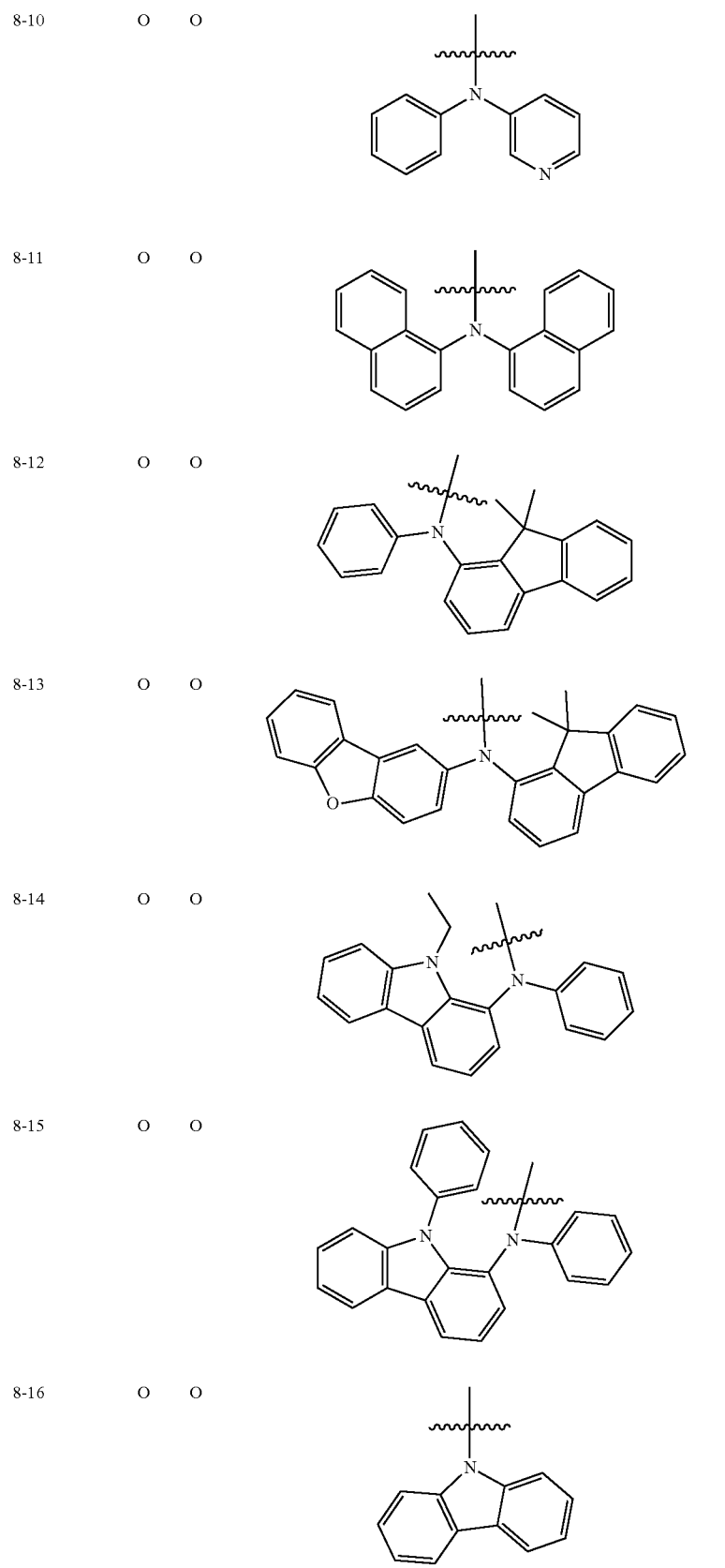 |
| 8-11 | O | O | |
| 8-12 | O | O | |
| 8-13 | O | O | |
| 8-14 | O | O | |
| 8-15 | O | O | |
| 8-16 | O | O | |

-continued
| | | | |
|---|---|---|---|
| 8-17 | O | O | 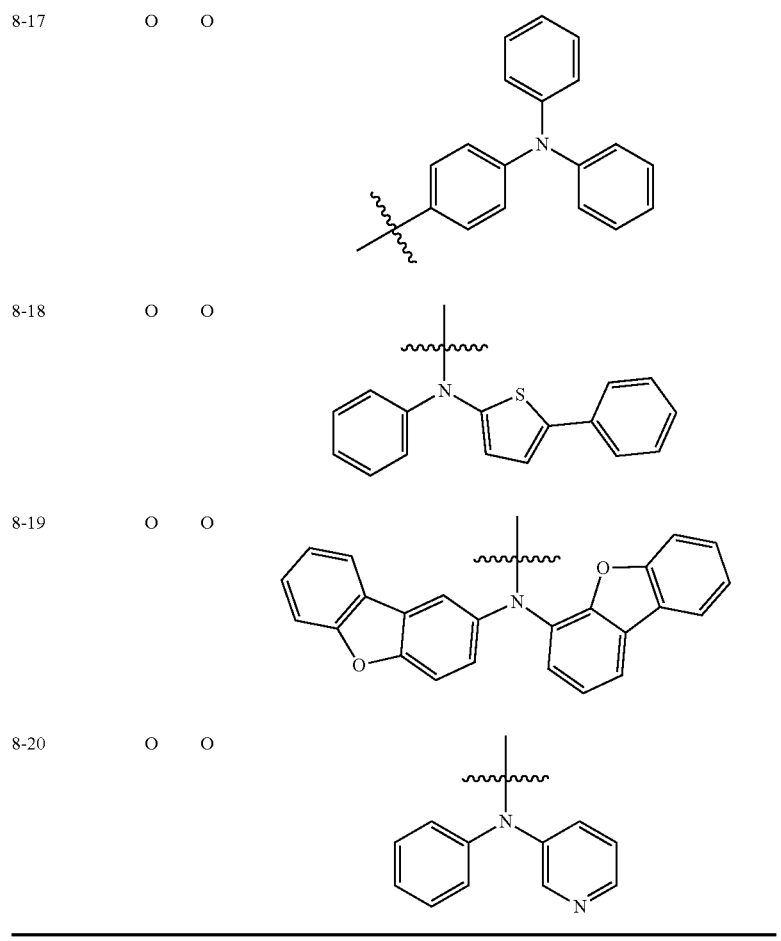 |
| 8-18 | O | O | |
| 8-19 | O | O | |
| 8-20 | O | O | |
| Compound | R2 | R3 to R6 |
|---|---|---|
| 8-1 | 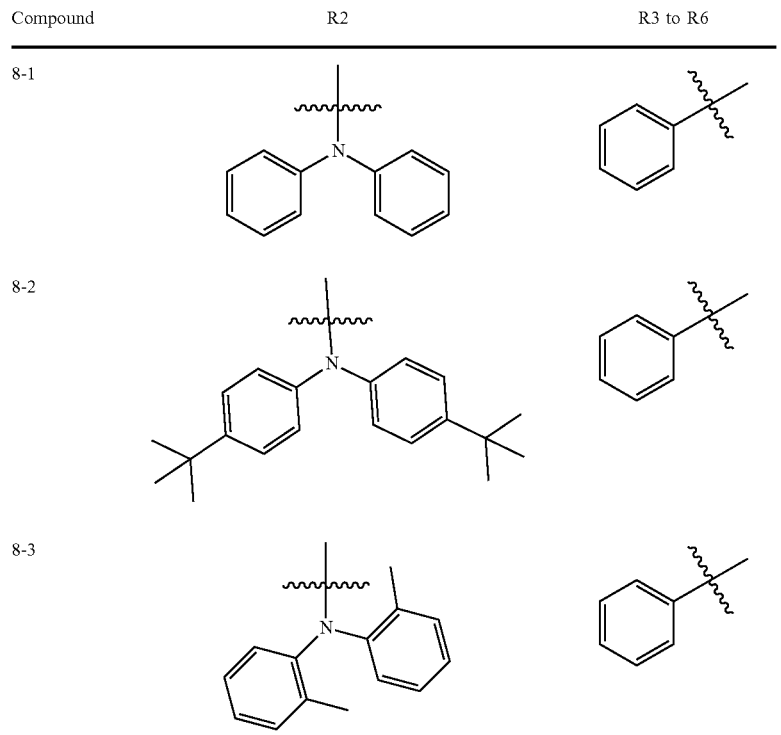 | |
| 8-2 | | |
| 8-3 | | |

8-4 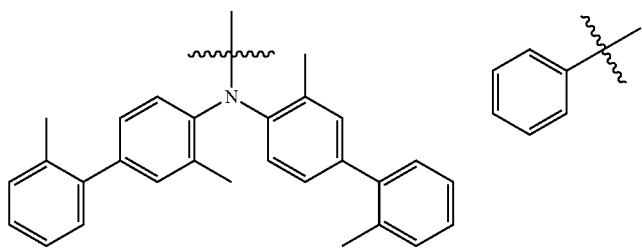
8-5 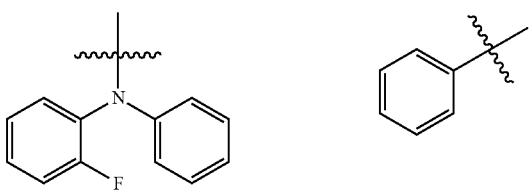
8-6 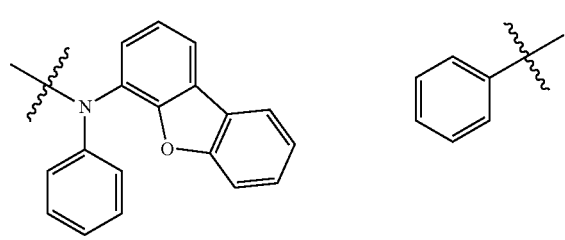
8-7 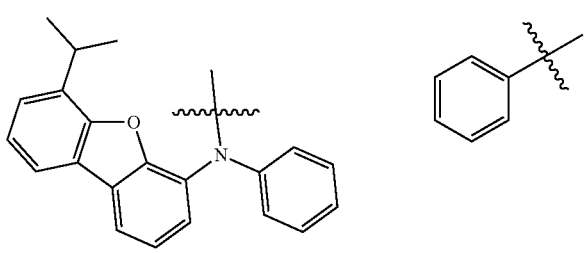
8-8 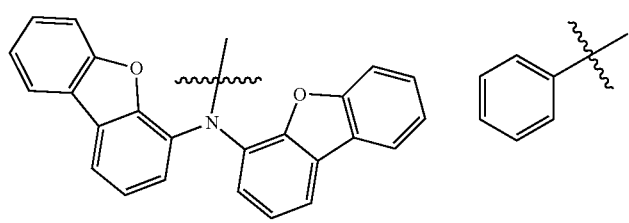
8-9 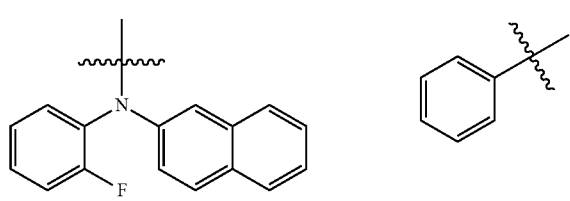
8-10 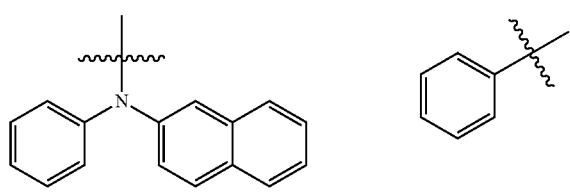

| | | |
|---|---|---|
| 8-11 | 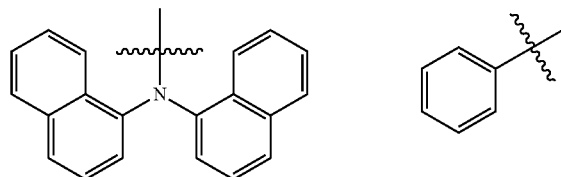 | 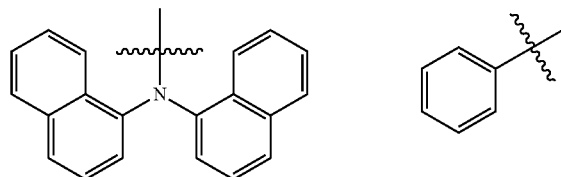 |
| 8-12 | 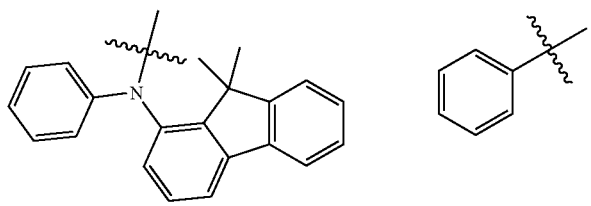 | |
| 8-13 | 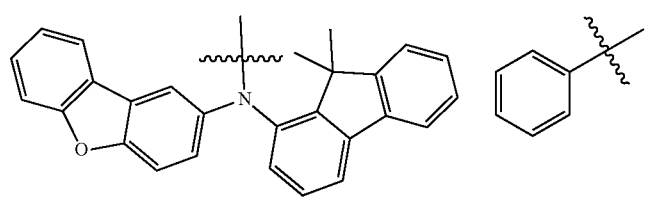 | |
| 8-14 | 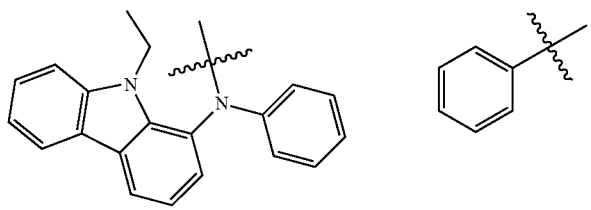 | |
| 8-15 | 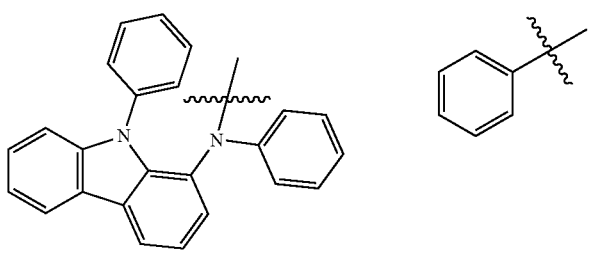 | |
| 8-16 | 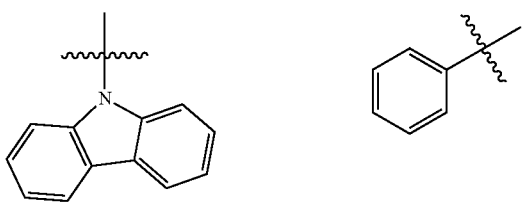 | |
| 8-17 | 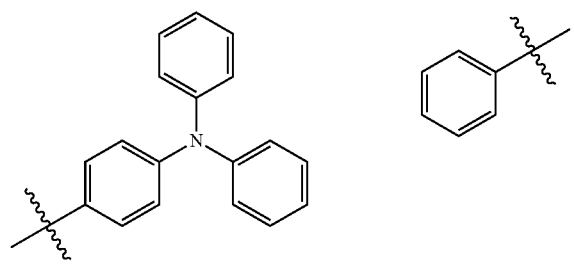 | |

-continued
8-18 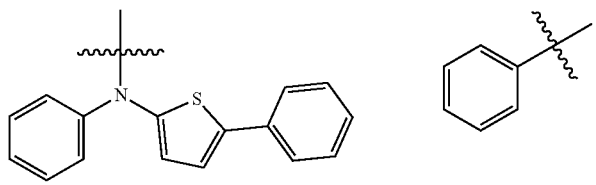
8-19 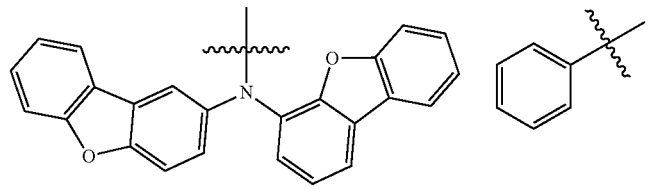
8-20 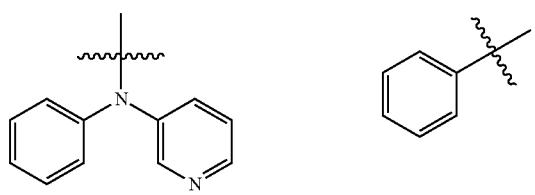
| Compound | X1 | X2 | R1 | R2 | R3 to R6 |
|---|---|---|---|---|---|
| 9-1 | S | S | 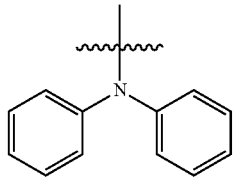 [SMILES: *N(c1ccccc1)c1ccccc1] | 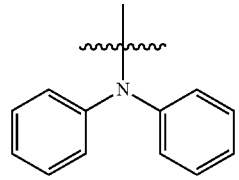 [SMILES: *N(c1ccccc1)c1ccccc1] | —CH$_3$ |
| 9-2 | S | S | 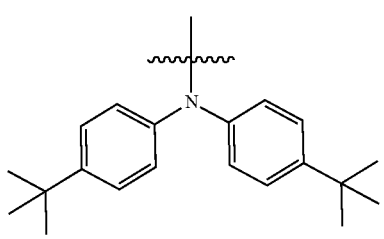 [SMILES: *N(c1ccc(C(C)(C)C)cc1)c1ccc(C(C)(C)C)cc1] | 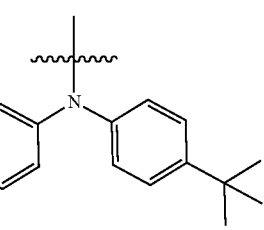 | —CH$_3$ |
| 9-3 | S | S | 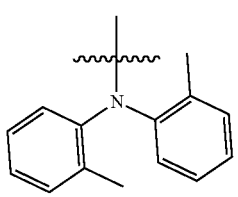 [SMILES: *N(c1ccccc1C)c1ccccc1C] | 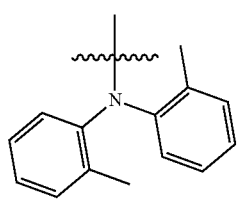 [SMILES: *N(c1ccccc1C)c1ccccc1C] | —CH$_3$ |
| 9-4 | S | S | 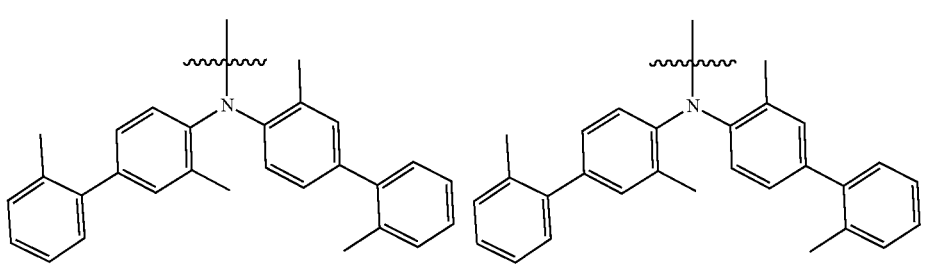 | | —CH$_3$ |

-continued

| Compound | X1 | X2 | R1 | R2 | R3 to R6 |
|---|---|---|---|---|---|
| 9-5 | S | S | 2-fluorophenyl(phenyl)amino | 2-fluorophenyl(phenyl)amino | —CH₃ |
| 9-6 | S | S | phenyl(dibenzofuran-1-yl)amino | phenyl(dibenzofuran-1-yl)amino | —CH₃ |
| 9-7 | S | S | phenyl(6-isopropyldibenzofuran-4-yl)amino | phenyl(6-isopropyldibenzofuran-4-yl)amino | —CH₃ |
| 9-8 | S | S | bis(dibenzofuran-4-yl)amino | bis(dibenzofuran-4-yl)amino | —CH₃ |
| 9-9 | S | S | 2-fluorophenyl(naphthalen-2-yl)amino | 2-fluorophenyl(naphthalen-2-yl)amino | —CH₃ |
| 9-10 | S | S | phenyl(pyridin-3-yl)amino | phenyl(naphthalen-2-yl)amino | —CH₃ |
| 9-11 | S | S | di(naphthalen-1-yl)amino | di(naphthalen-1-yl)amino | —CH₃ |

-continued

| Compound | X1 | X2 | R1 | R2 | R3 to R6 |
|---|---|---|---|---|---|
| 9-12 | S | S | (N-phenyl-N-(9,9-dimethylfluoren-1-yl)amino) | (N-phenyl-N-(9,9-dimethylfluoren-1-yl)amino) | —CH₃ |
| 9-13 | S | S | (N-(dibenzofuran-2-yl)-N-(9,9-dimethylfluoren-1-yl)amino) | (N-(dibenzofuran-2-yl)-N-(9,9-dimethylfluoren-1-yl)amino) | —CH₃ |
| 9-14 | S | S | (N-(9-ethylcarbazol-1-yl)-N-phenylamino) | (N-(9-ethylcarbazol-1-yl)-N-phenylamino) | —CH₃ |
| 9-15 | S | S | (N-(9-phenylcarbazol-1-yl)-N-phenylamino) | (N-(9-phenylcarbazol-1-yl)-N-phenylamino) | —CH₃ |
| 9-16 | S | S | (carbazol-9-yl) | (carbazol-9-yl) | —CH₃ |
| 9-17 | S | S | (4-(diphenylamino)phenyl) | (4-(diphenylamino)phenyl) | —CH₃ |
| 9-18 | S | S | (N-phenyl-N-(5-phenylthiophen-2-yl)amino) | (N-phenyl-N-(5-phenylthiophen-2-yl)amino) | —CH₃ |

-continued
| Compound | X1 | X2 | R1 | R2 | R3 to R6 |
|---|---|---|---|---|---|
| 9-19 | S | S | 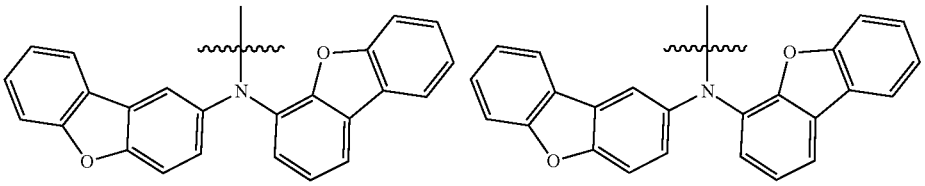 | 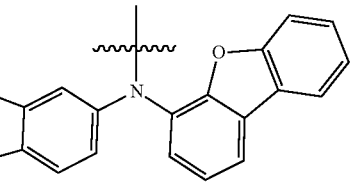 | —CH₃ |
| 9-20 | S | S | 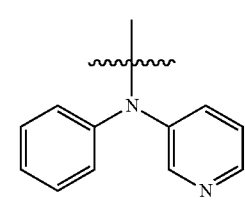 [SMILES: *N(c1ccccc1)c1cccnc1] | 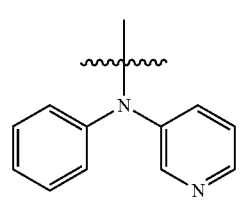 [SMILES: *N(c1ccccc1)c1cccnc1] | —CH₃ |
| Compound | X1 | X2 | R1 |
|---|---|---|---|
| 10-1 |  |  | 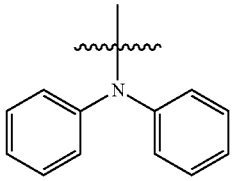 [SMILES: *N(c1ccccc1)c1ccccc1] |
| 10-2 |  |  | 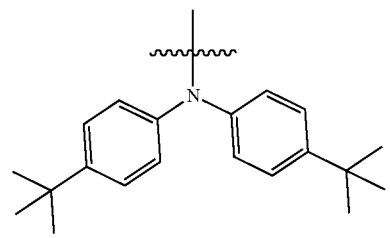 [SMILES: *N(c1ccc(C(C)(C)C)cc1)c1ccc(C(C)(C)C)cc1] |
| 10-3 |  |  | 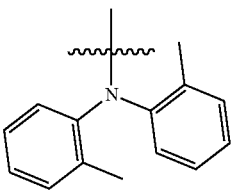 [SMILES: *N(c1ccccc1C)c1ccccc1C] |
| 10-4 | | | 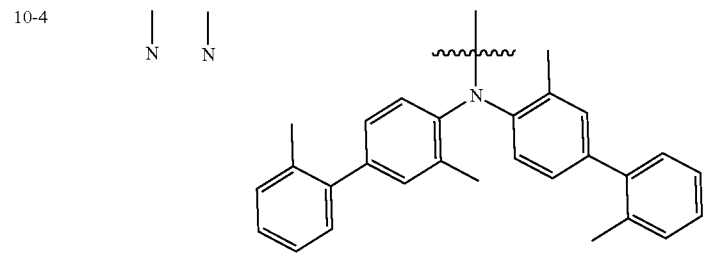 |

-continued
| | | |
|---|---|---|
| 10-5 | | 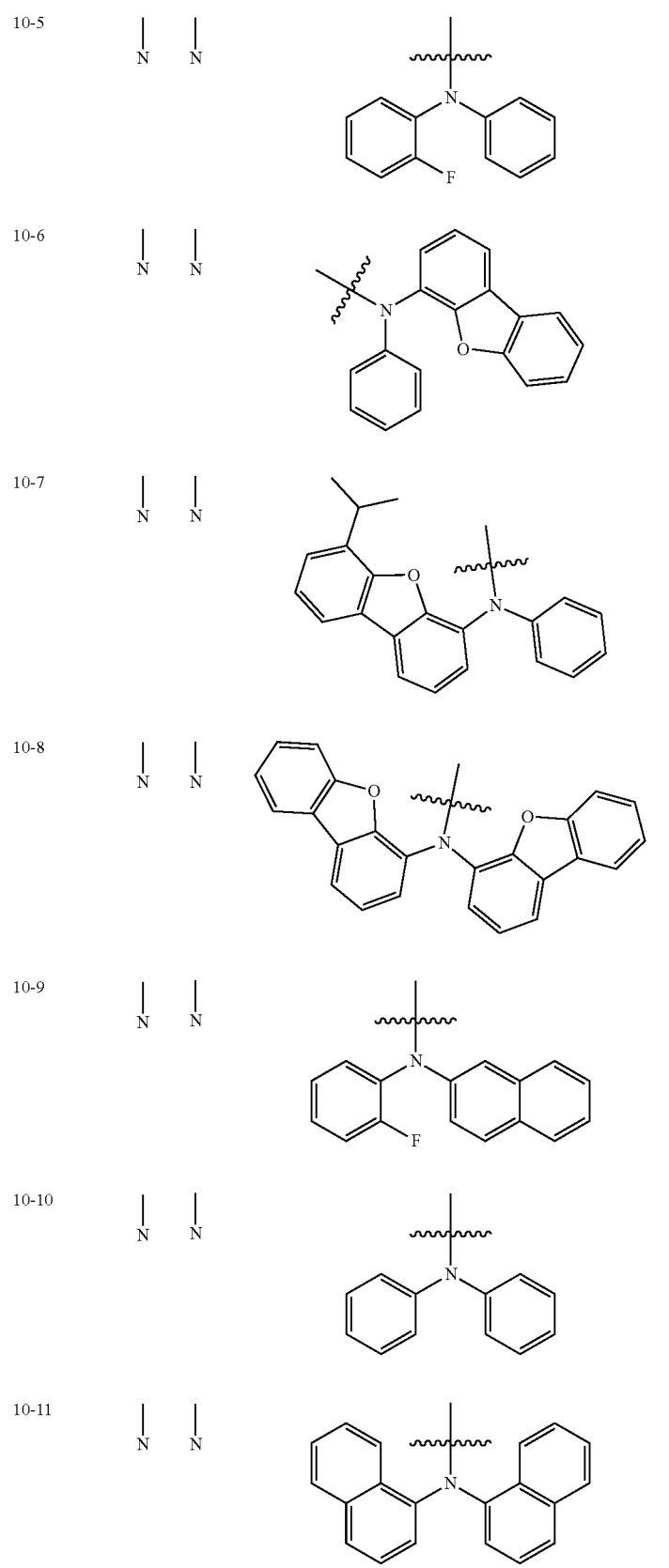 |
| 10-6 | | |
| 10-7 | | |
| 10-8 | | |
| 10-9 | | |
| 10-10 | | |
| 10-11 | | |

-continued
10-12 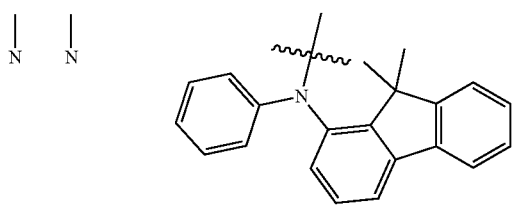
10-13 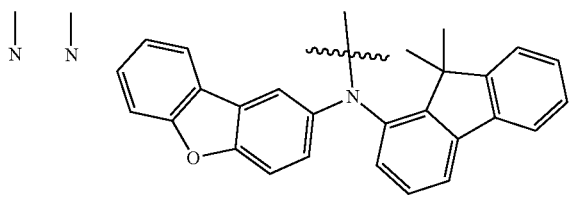
10-14 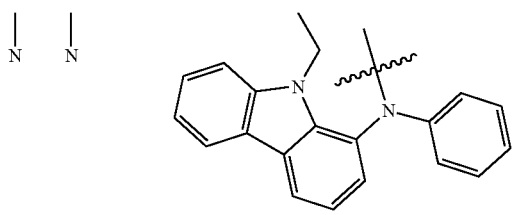
10-15 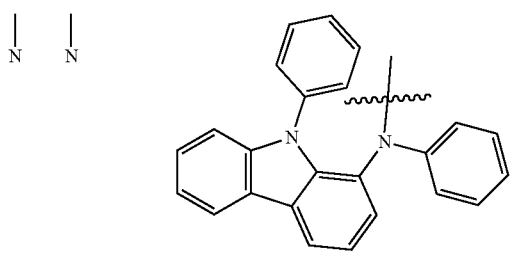
10-16 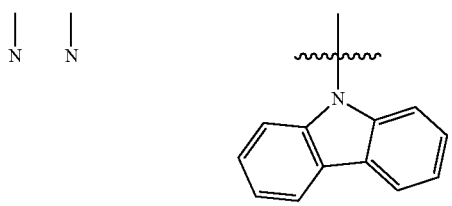
10-17 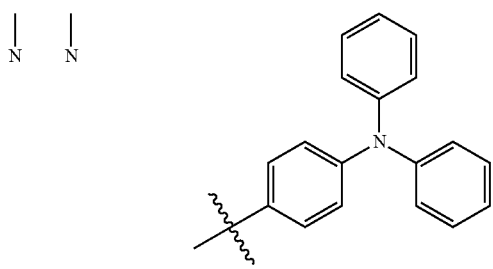
10-18 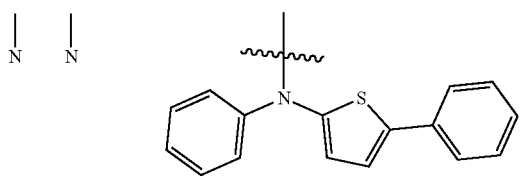

-continued
| | | |
|---|---|---|
| 10-19 | 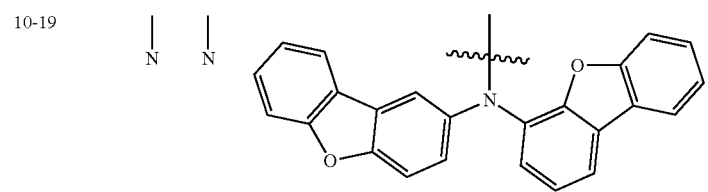 | |
| 10-20 | 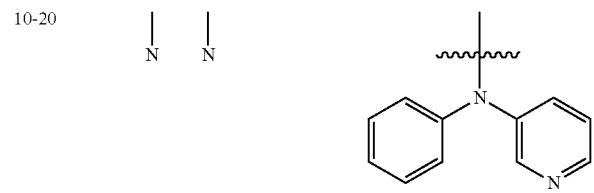 | |
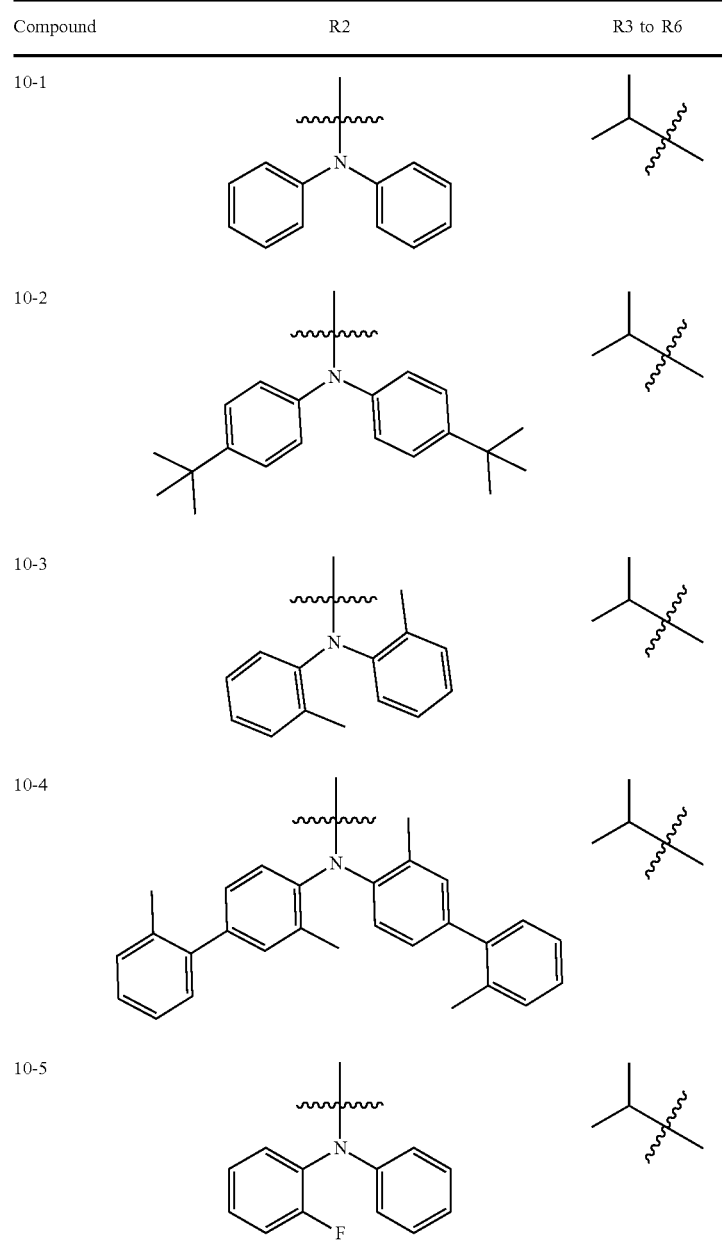
| Compound | R2 | R3 to R6 |
|---|---|---|
| 10-1 | | |
| 10-2 | | |
| 10-3 | | |
| 10-4 | | |
| 10-5 | | |

-continued
| | | |
|---|---|---|
| 10-6 | 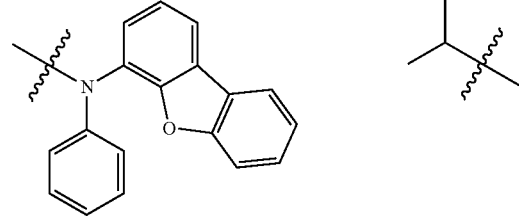 | 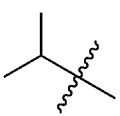 |
| 10-7 | 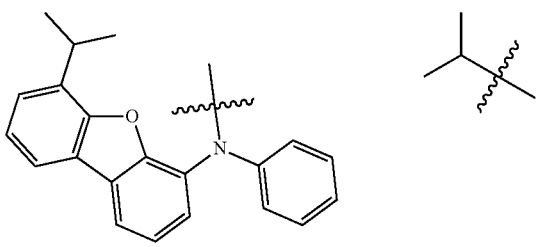 | 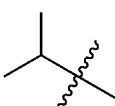 |
| 10-8 | 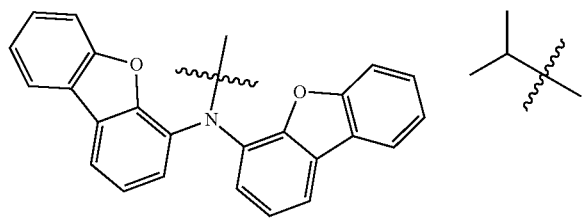 | 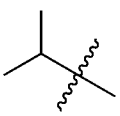 [SMILES: *C(C)C] |
| 10-9 | 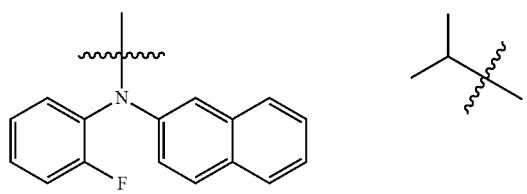 | 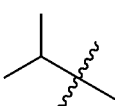 |
| 10-10 | 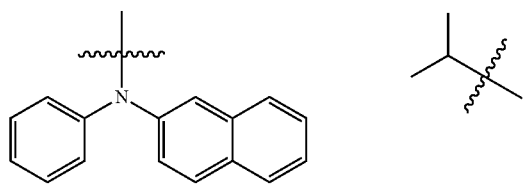 | 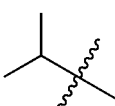 |
| 10-11 | 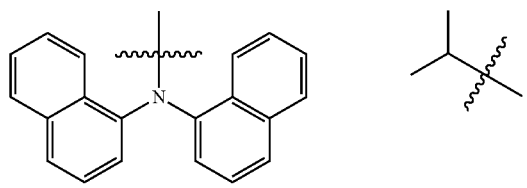 | 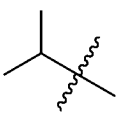 [SMILES: *C(C)C] |
| 10-12 | 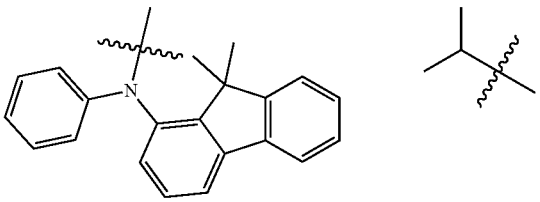 | 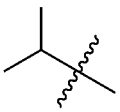 [SMILES: *C(C)C] |

-continued
| | | |
|---|---|---|
| 10-13 | 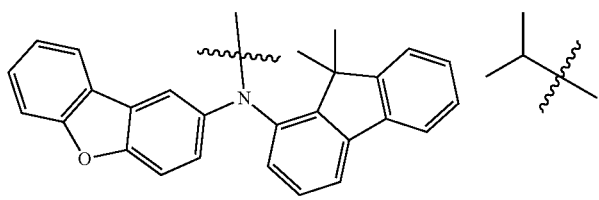 | |
| 10-14 | 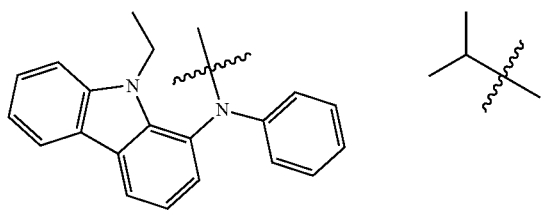 | |
| 10-15 | 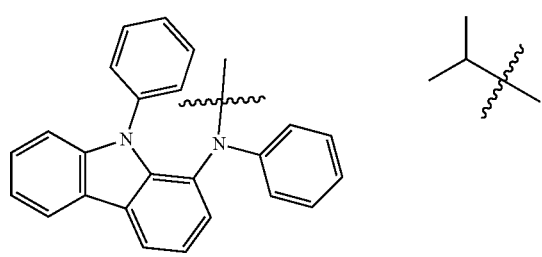 | |
| 10-16 | 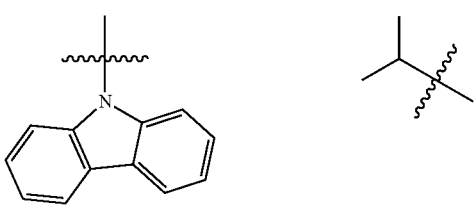 | |
| 10-17 | 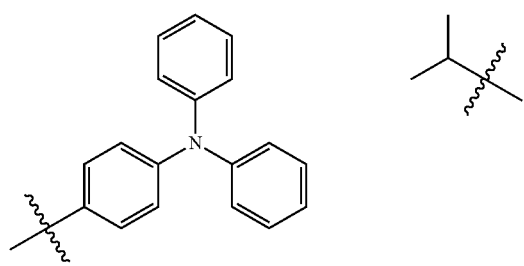 | |
| 10-18 | 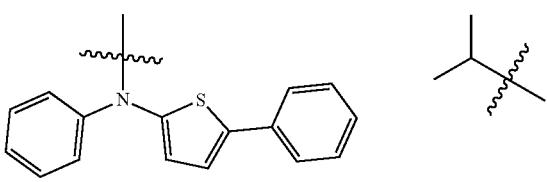 | |
| 10-19 | 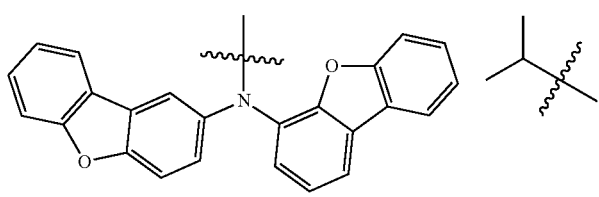 | |

-continued
| | | |
|---|---|---|
| 10-20 | 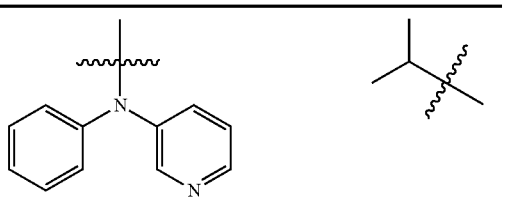 | |
| Compound | X1 | X2 | R1 |
|---|---|---|---|
| 11-1 | | | 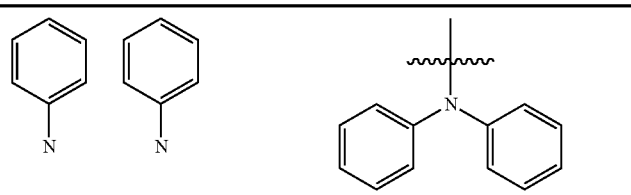 |
| 11-2 | | | 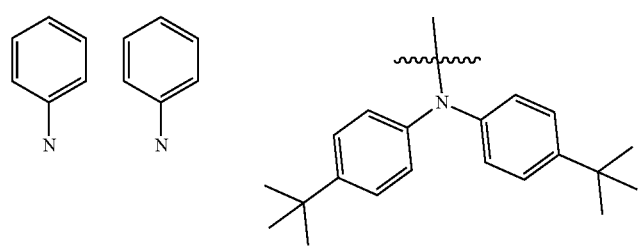 |
| 11-3 | | | 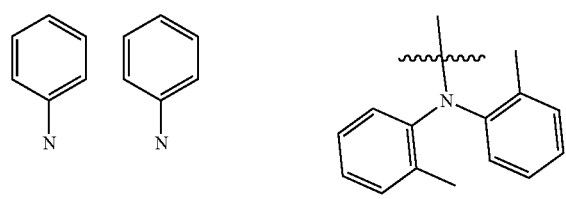 |
| 11-4 | | | 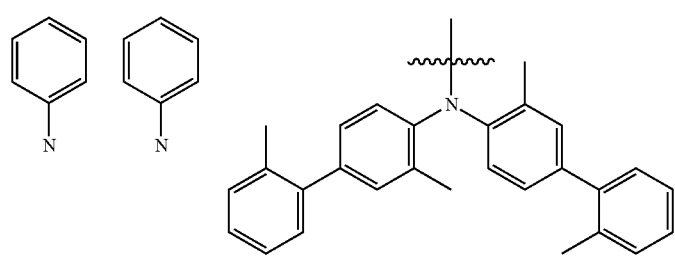 |
| 11-5 | | | 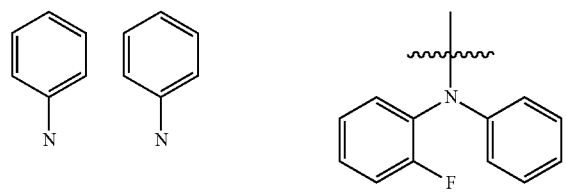 |
| 11-6 | | | 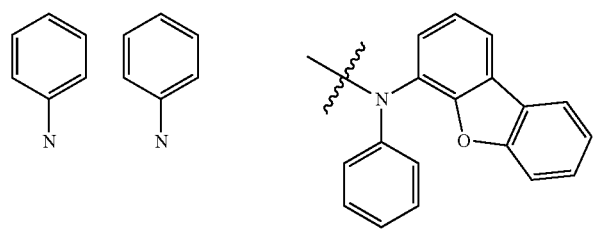 |

-continued
| | | | |
|---|---|---|---|
| 11-7 | 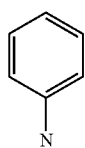 | 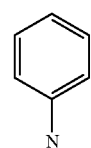 | 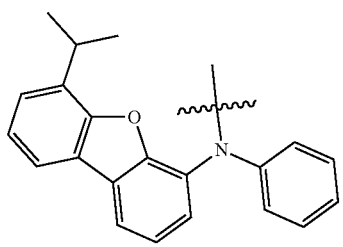 [SMILES: *N(c1ccccc1)c1cccc2c1oc1c(C(C)C)cccc12] |
| 11-8 | 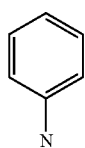 | 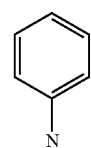 | 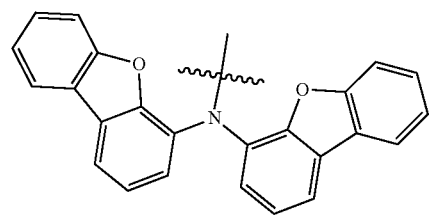 [SMILES: *N(c1cccc2c1oc1ccccc12)c1cccc2c1oc1ccccc12] |
| 11-9 | 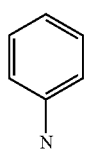 | 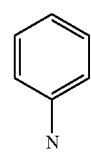 | 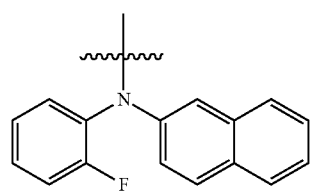 [SMILES: *N(c1ccc2ccccc2c1)c1ccccc1F] |
| 11-10 | 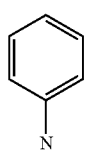 | 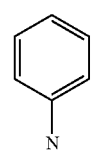 | 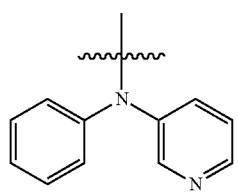 [SMILES: *N(c1ccccc1)c1cccnc1] |
| 11-11 | 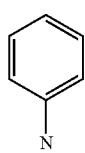 | 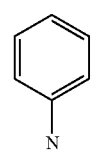 | 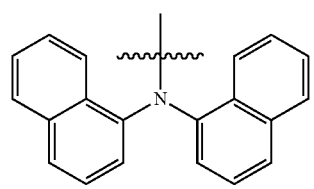 [SMILES: *N(c1cccc2ccccc12)c1cccc2ccccc12] |
| 11-12 | 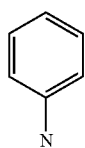 | 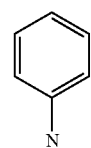 | 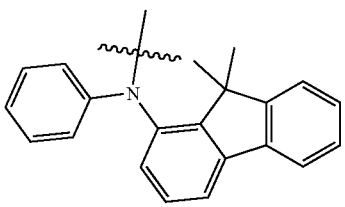 [SMILES: *N(c1ccccc1)c1cccc2c1C(C)(C)c1ccccc1-2] |
| 11-13 | 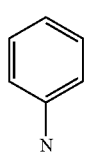 | 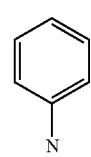 | 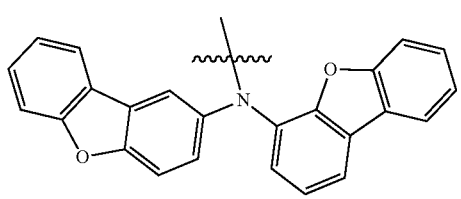 [SMILES: *N(c1ccc2oc3ccccc3c2c1)c1cccc2c1oc1ccccc12] |

-continued
| | | | |
|---|---|---|---|
| 11-14 | 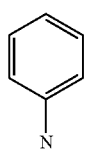 | 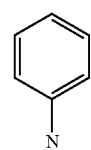 | 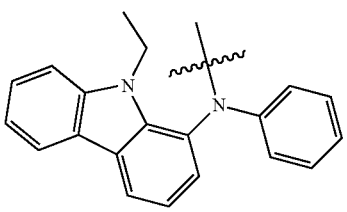 [SMILES: *N(c1ccccc1)c1cccc2c3ccccc3n(CC)c12] |
| 11-15 | 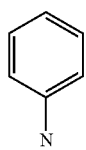 | 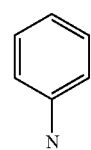 | 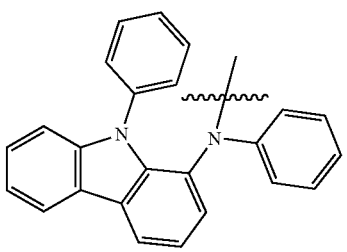 [SMILES: *N(c1ccccc1)c1cccc2c3ccccc3n(-c3ccccc3)c12] |
| 11-16 | 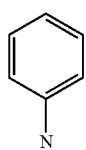 | 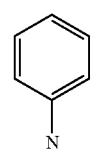 | 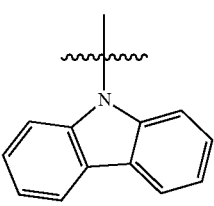 [SMILES: *n1c2ccccc2c2ccccc21] |
| 11-17 | 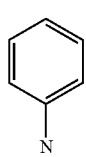 | 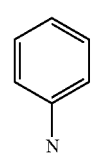 | 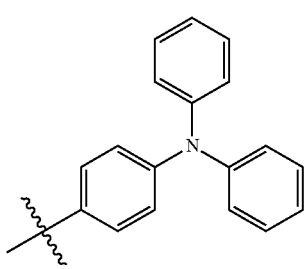 [SMILES: *c1ccc(N(c2ccccc2)c2ccccc2)cc1] |
| 11-18 | 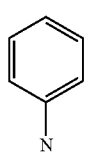 | 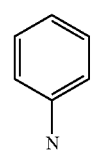 | 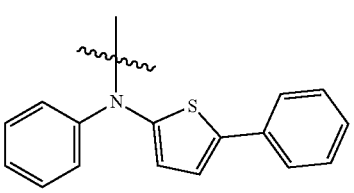 [SMILES: *N(c1ccccc1)c1ccc(-c2ccccc2)s1] |
| 11-19 | 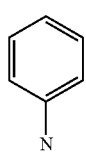 | 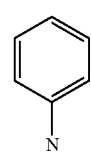 | 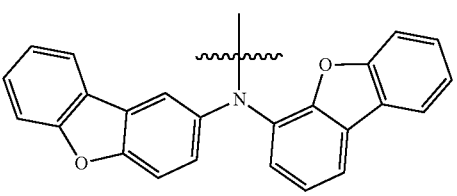 [SMILES: *N(c1ccc2oc3ccccc3c2c1)c1cccc2c1oc1ccccc12] |
| 11-20 | 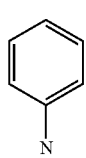 | 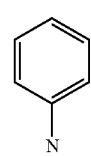 | 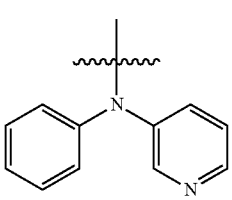 [SMILES: *N(c1ccccc1)c1cccnc1] |

-continued
| Compound | R2 | R3 to R6 |
|---|---|---|
| 11-1 | 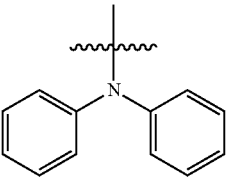 [SMILES: *N(c1ccccc1)c1ccccc1] | 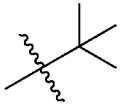 |
| 11-2 | 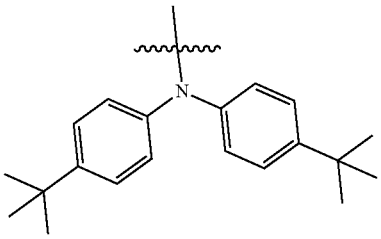 [SMILES: *N(c1ccc(C(C)(C)C)cc1)c1ccc(C(C)(C)C)cc1] | 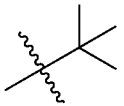 [SMILES: *C(C)(C)C] |
| 11-3 | 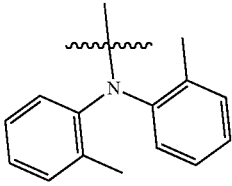 [SMILES: *N(c1ccccc1C)c1ccccc1C] | 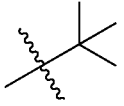 |
| 11-4 | 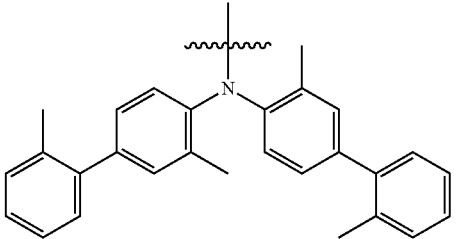 [SMILES: *N(c1ccc(-c2ccccc2C)cc1C)c1ccc(-c2ccccc2C)cc1C] | 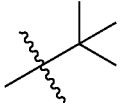 [SMILES: *C(C)(C)C] |
| 11-5 | 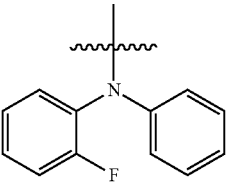 [SMILES: *N(c1ccccc1)c1ccccc1F] | 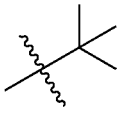 [SMILES: *C(C)(C)C] |
| 11-6 | 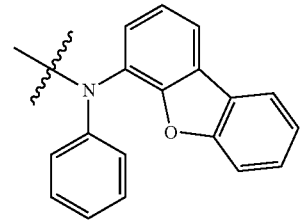 [SMILES: *N(c1ccccc1)c1cccc2c1oc1ccccc12] | 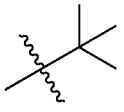 [SMILES: *C(C)(C)C] |
| 11-7 | 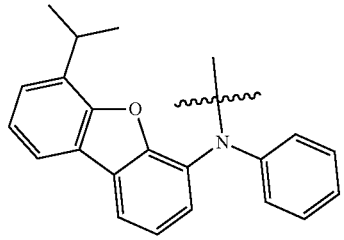 [SMILES: *N(c1ccccc1)c1cccc2c1oc1c(C(C)C)cccc12] | 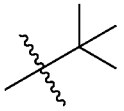 [SMILES: *C(C)(C)C] |

-continued
| | | |
|---|---|---|
| 11-8 | 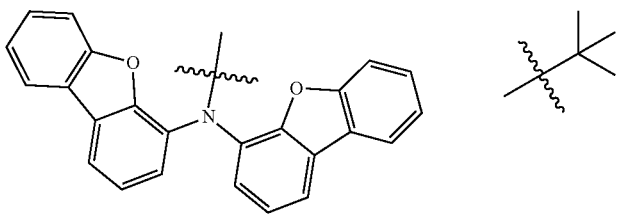 | |
| 11-9 | 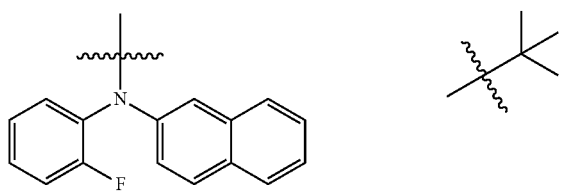 | |
| 11-10 | 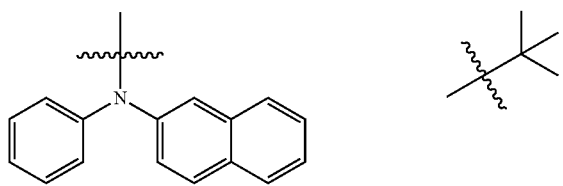 | |
| 11-11 | 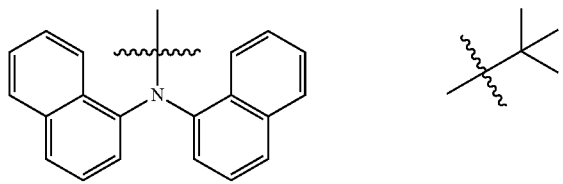 | |
| 11-12 | 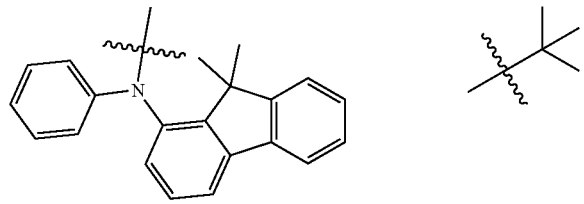 | |
| 11-13 | 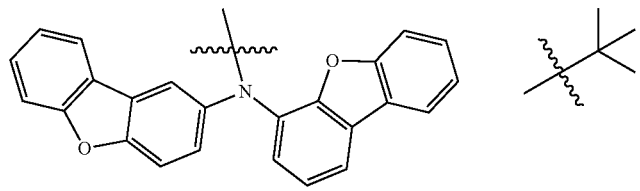 | |
| 11-14 | 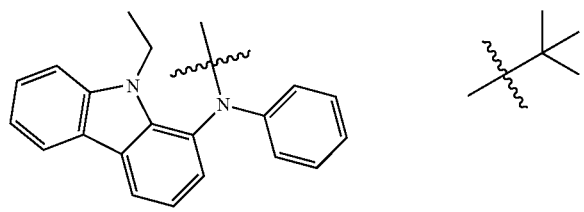 | |

-continued
| | | |
|---|---|---|
| 11-15 | 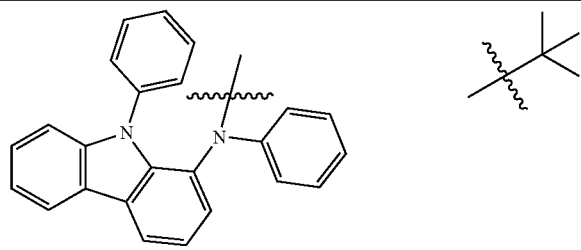 | |
| 11-16 | 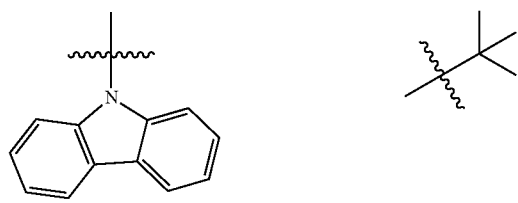 | |
| 11-17 | 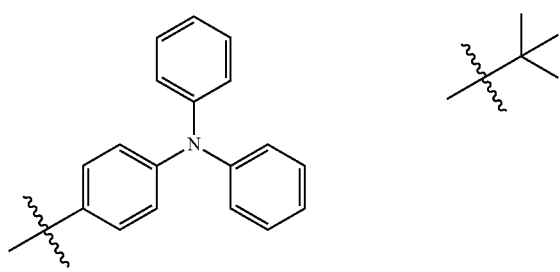 | |
| 11-18 | 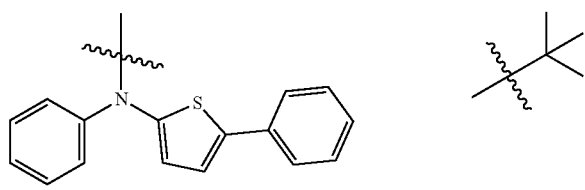 | |
| 11-19 | 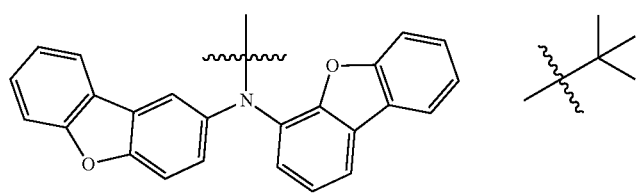 | |
| 11-20 | 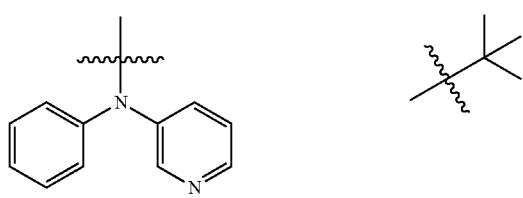 | |
| Compound | X | X | R1 |
|---|---|---|---|
| 12-1 | | | 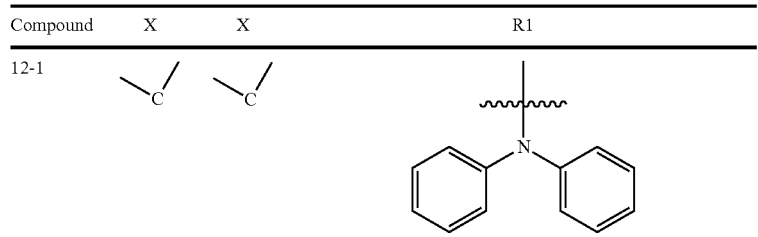 |

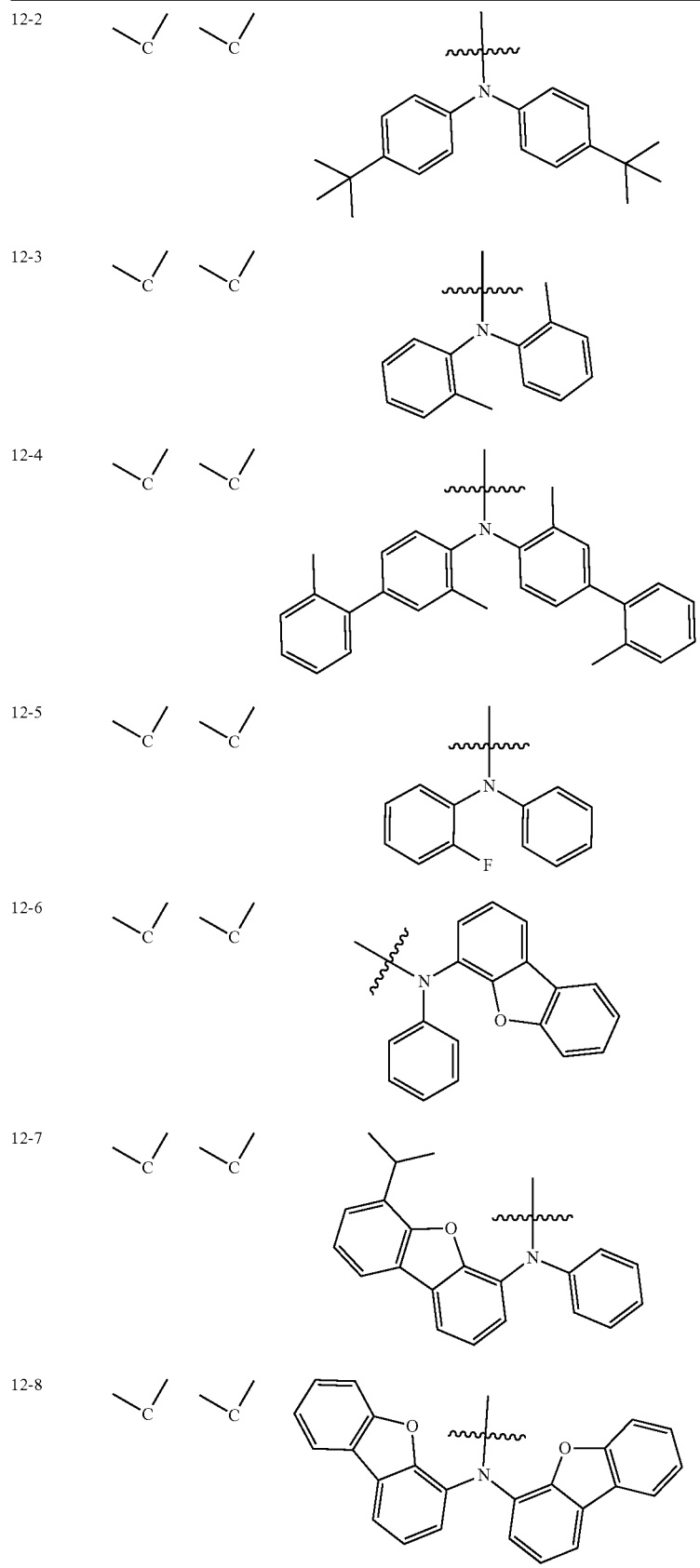

| | | |
|---|---|---|
| 12-9 | 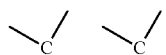 | 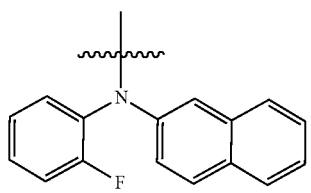 [SMILES: *N(c1ccc2ccccc2c1)c1ccccc1F] |
| 12-10 | 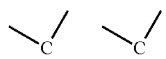 | 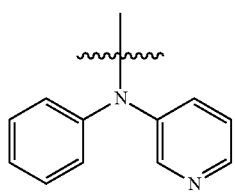 [SMILES: *N(c1ccccc1)c1cccnc1] |
| 12-11 | 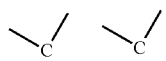 | 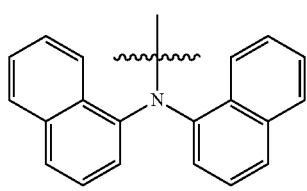 [SMILES: *N(c1cccc2ccccc12)c1cccc2ccccc12] |
| 12-12 | 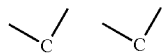 | 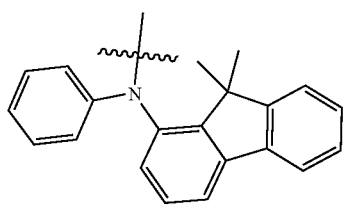 [SMILES: *N(c1ccccc1)c1cccc2c1C(C)(C)c1ccccc1-2] |
| 12-13 | 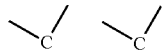 | 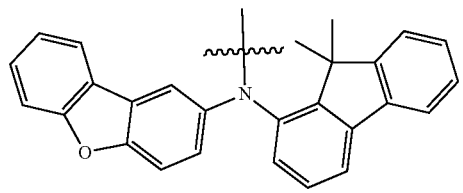 [SMILES: *N(c1ccc2oc3ccccc3c2c1)c1cccc2c1C(C)(C)c1ccccc1-2] |
| 12-14 | 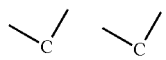 | 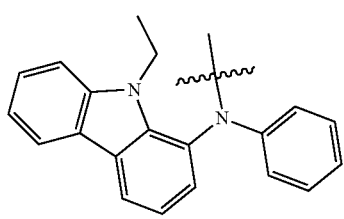 [SMILES: *N(c1ccccc1)c1cccc2c3ccccc3n(CC)c12] |
| 12-15 | 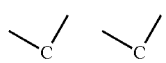 | 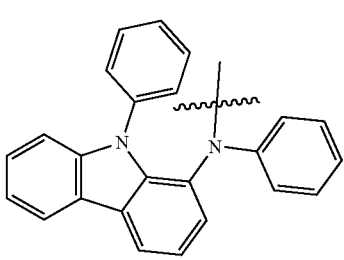 [SMILES: *N(c1ccccc1)c1cccc2c3ccccc3n(-c3ccccc3)c12] |

-continued
| Compound | | |
|---|---|---|
| 12-16 | | |
| 12-17 | | |
| 12-18 | | |
| 12-19 | | |
| 12-20 | | |
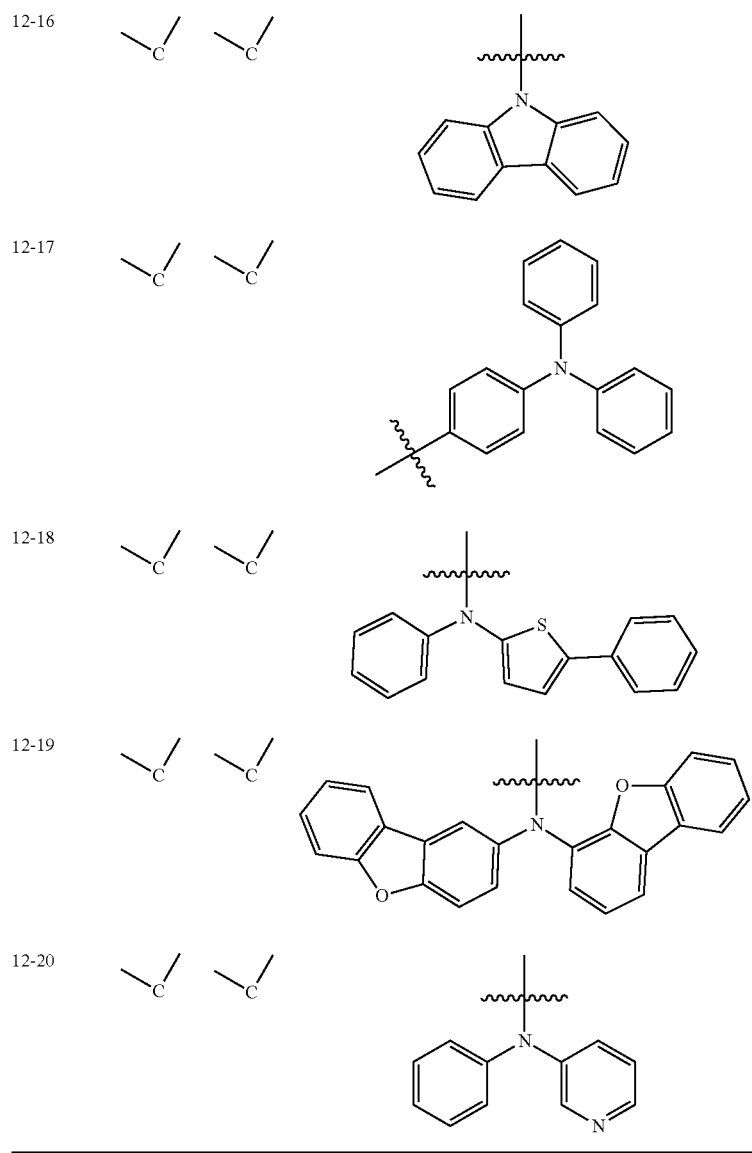
| Compound | R2 | R3 to R6 |
|---|---|---|
| 12-1 | | |
| 12-2 | | |
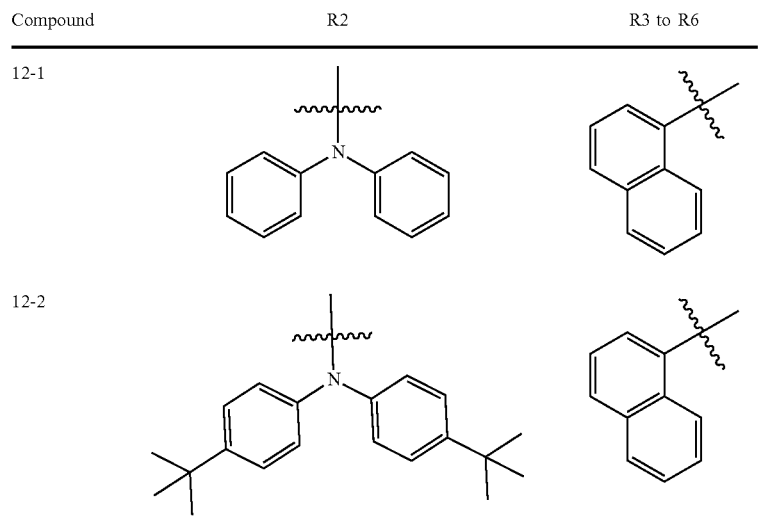

| | | |
|---|---|---|
| 12-3 | 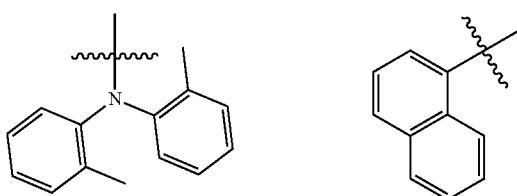 | |
| 12-4 | 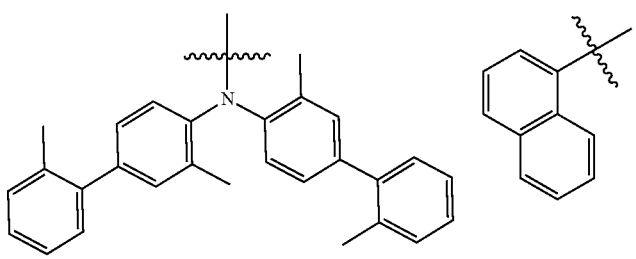 | |
| 12-5 | 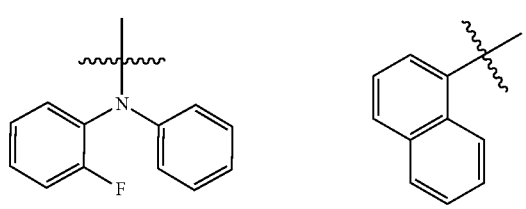 | |
| 12-6 | 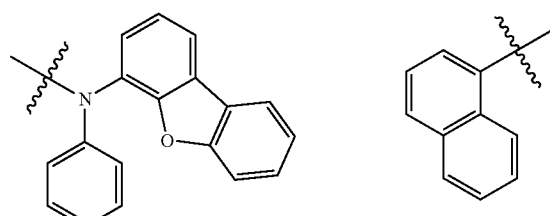 | |
| 12-7 | 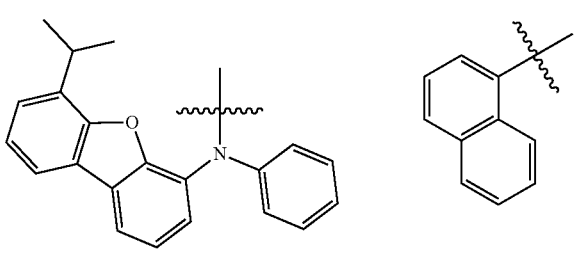 | |
| 12-8 | 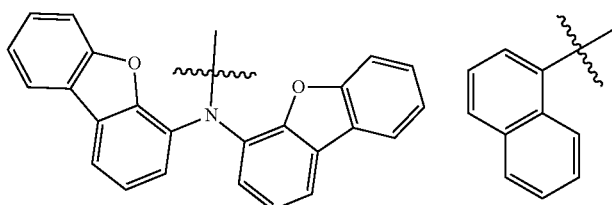 | |
| 12-9 | 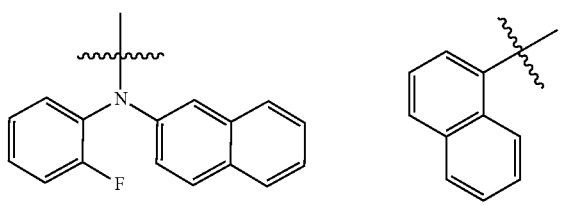 | |

-continued
12-10 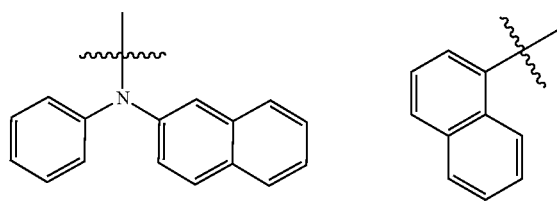
12-11 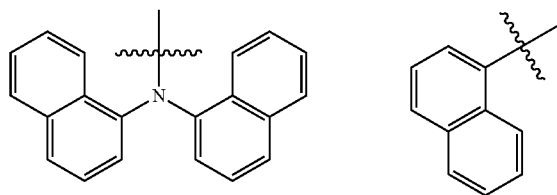
12-12 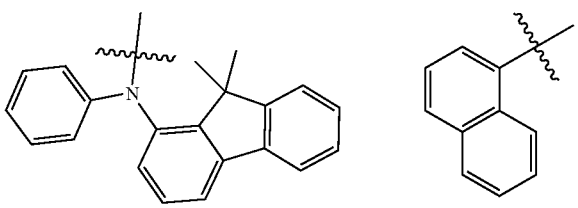
12-13 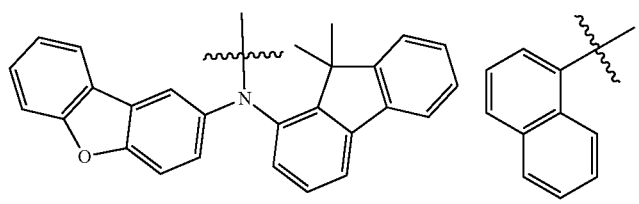
12-14 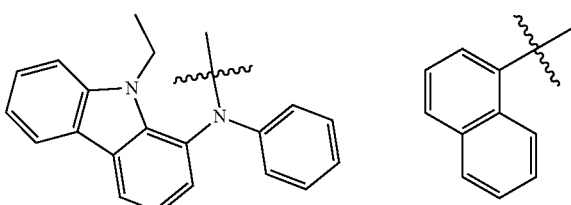
12-15 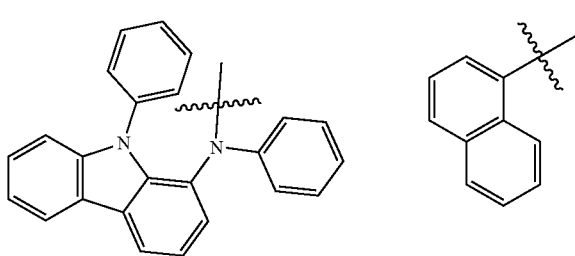
12-16 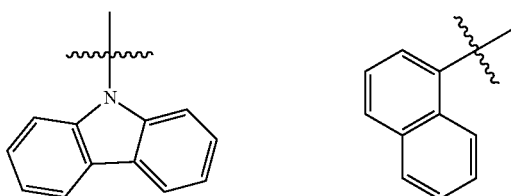

-continued
| | | |
|---|---|---|
| 12-17 | 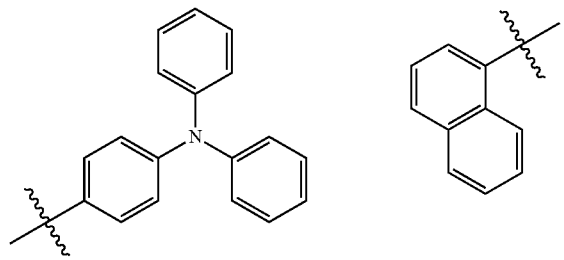 | |
| 12-18 | 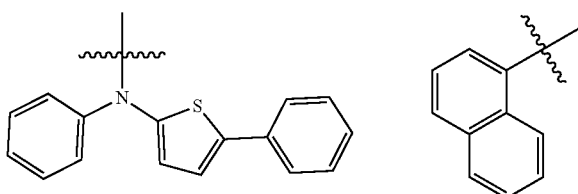 | |
| 12-19 | 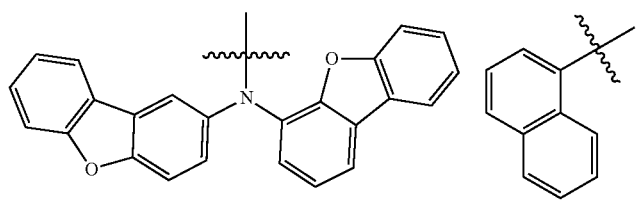 | |
| 12-20 | 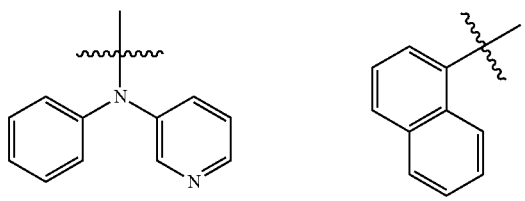 | |
| Compound | X | X | R1 |
|---|---|---|---|
| 13-1 | 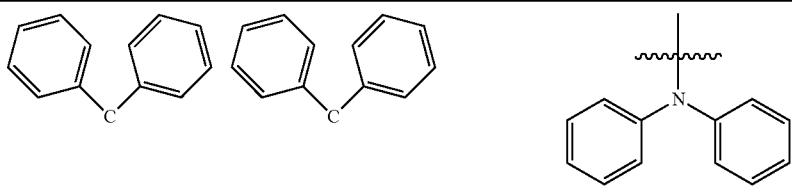 | | |
| 13-2 | 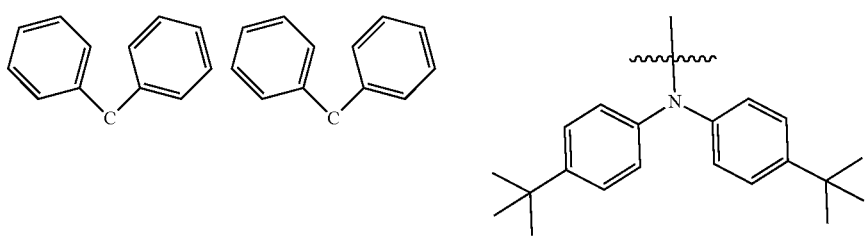 | | |
| 13-3 | 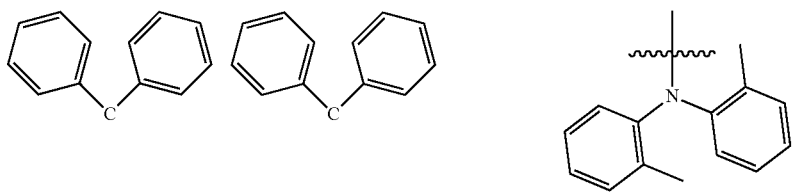 | | |

-continued
13-4 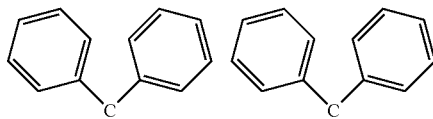 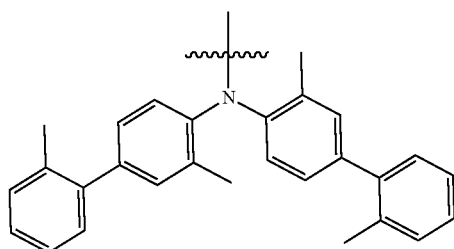
13-5 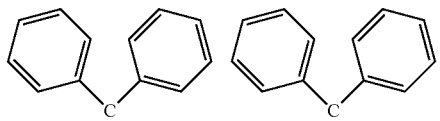 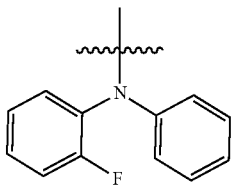 [SMILES: *N(c1ccccc1)c1ccccc1F]
13-6 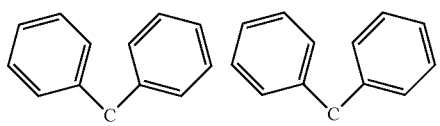 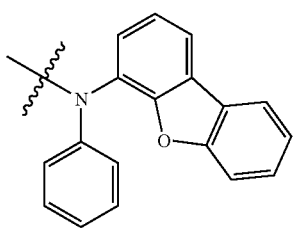 [SMILES: *N(c1ccccc1)c1cccc2c1oc1ccccc12]
13-7 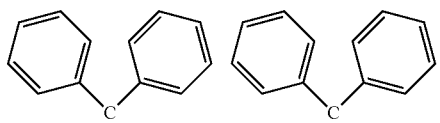 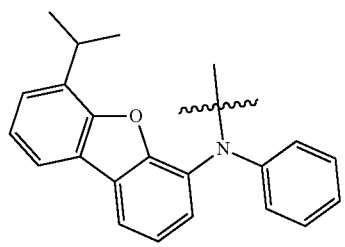 [SMILES: *N(c1ccccc1)c1cccc2c1oc1c(C(C)C)cccc12]
13-8 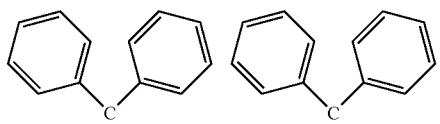 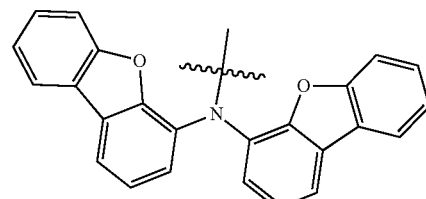
13-9 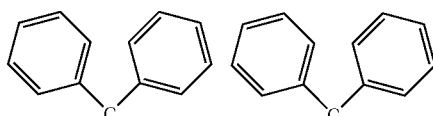 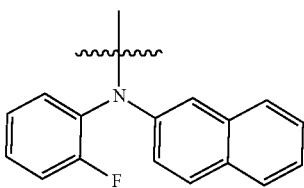 [SMILES: *N(c1ccc2ccccc2c1)c1ccccc1F]
13-10 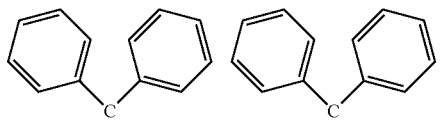 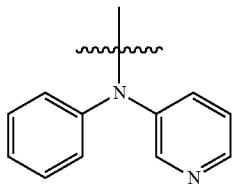 [SMILES: *N(c1ccccc1)c1cccnc1]

| | | |
|---|---|---|
| 13-11 | 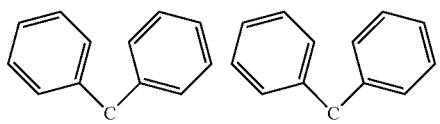 | 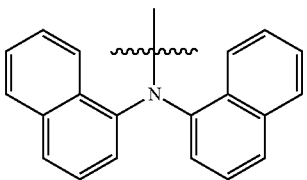 [SMILES: *N(c1cccc2ccccc12)c1cccc2ccccc12] |
| 13-12 | 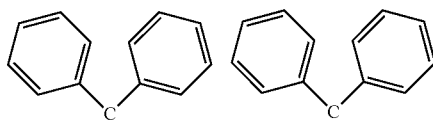 | 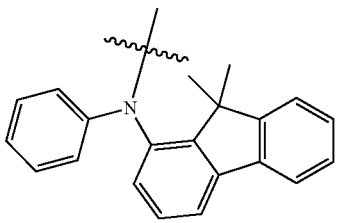 [SMILES: *N(c1ccccc1)c1cccc2c1C(C)(C)c1ccccc1-2] |
| 13-13 | 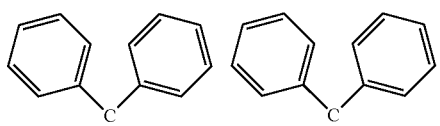 | 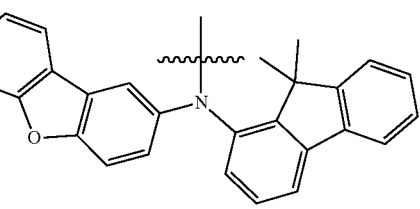 |
| 13-14 | 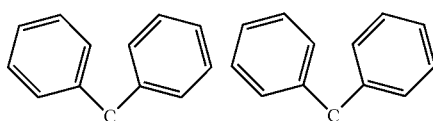 | 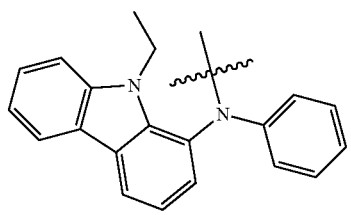 [SMILES: *N(c1ccccc1)c1cccc2c3ccccc3n(CC)c12] |
| 13-15 | 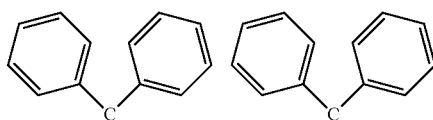 | 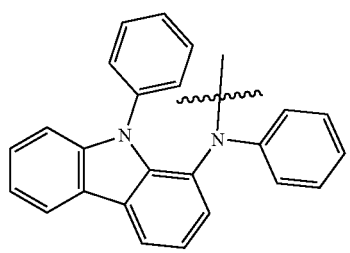 [SMILES: *N(c1ccccc1)c1cccc2c3ccccc3n(-c3ccccc3)c12] |
| 13-16 | 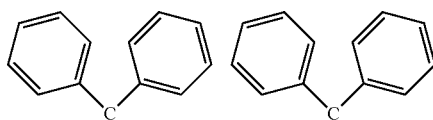 | 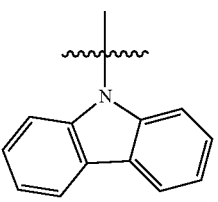 [SMILES: *n1c2ccccc2c2ccccc21] |
| 13-17 | 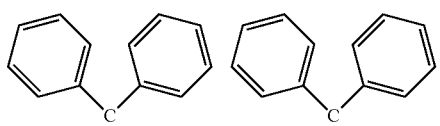 | 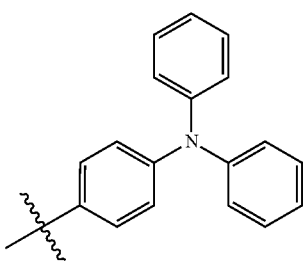 [SMILES: *c1ccc(N(c2ccccc2)c2ccccc2)cc1] |

-continued
| | | |
|---|---|---|
| 13-18 | 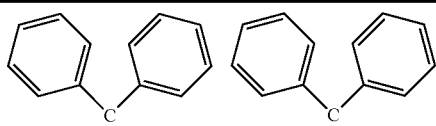 | 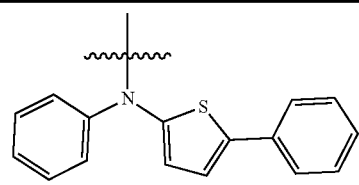 |
| 13-19 | 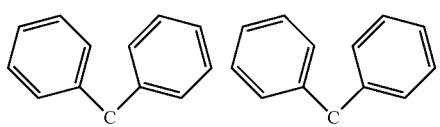 | 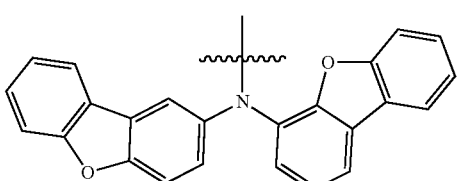 |
| 13-20 | 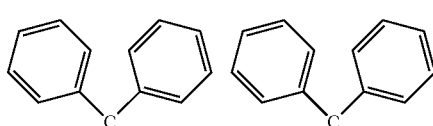 | 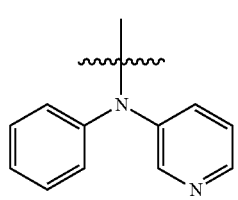 [SMILES: *N(c1ccccc1)c1cccnc1] |
| Compound | R2 | R3 to R6 |
|---|---|---|
| 13-1 | 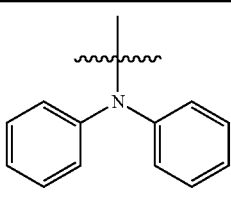 | 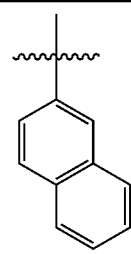 |
| 13-2 | 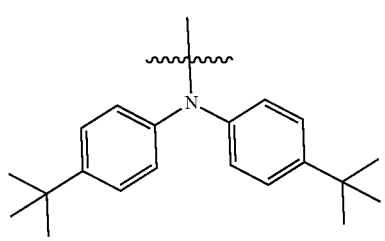 [SMILES: *N(c1ccc(C(C)(C)C)cc1)c1ccc(C(C)(C)C)cc1] | 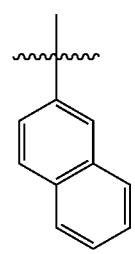 |
| 13-3 | 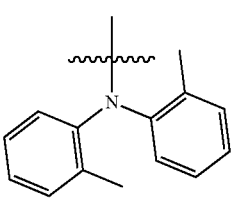 [SMILES: *N(c1ccccc1C)c1ccccc1C] | 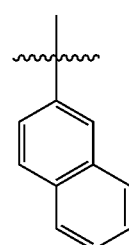 |
| 13-4 | 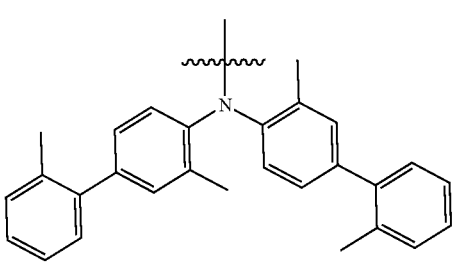 [SMILES: *N(c1ccc(-c2ccccc2C)cc1C)c1ccc(-c2ccccc2C)cc1C] | 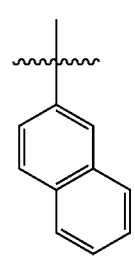 [SMILES: *c1ccc2ccccc2c1] |

| | | |
|---|---|---|
| 13-5 | 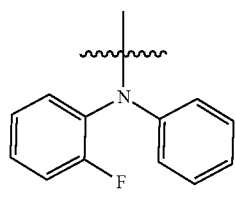 [SMILES: *N(c1ccccc1)c1ccccc1F] | 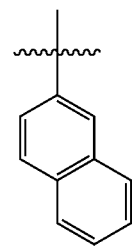 |
| 13-6 | 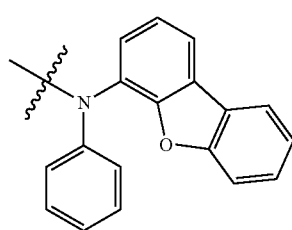 | 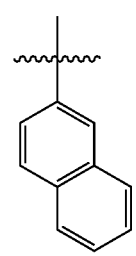 [SMILES: *c1ccc2ccccc2c1] |
| 13-7 | 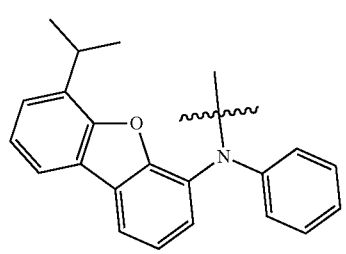 [SMILES: *N(c1ccccc1)c1cccc2c1oc1c(C(C)C)cccc12] | 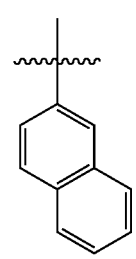 |
| 13-8 | 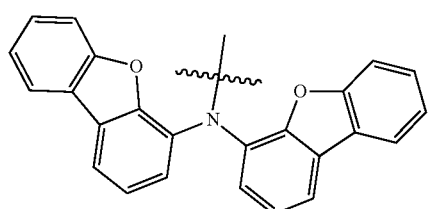 | 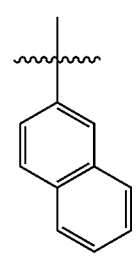 |
| 13-9 | 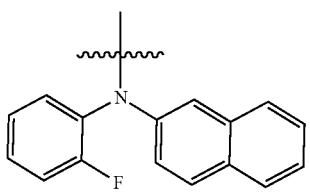 [SMILES: *N(c1ccc2ccccc2c1)c1ccccc1F] | 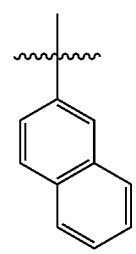 |
| 13-10 | 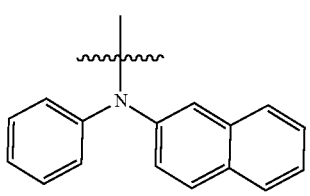 [SMILES: *N(c1ccccc1)c1ccc2ccccc2c1] | 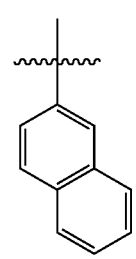 |

US 11,489,122 B1
353                                                                                        354
-continued
13-11   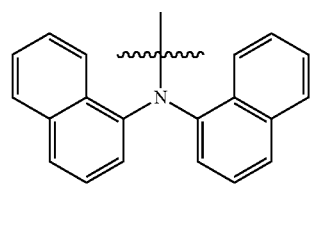                          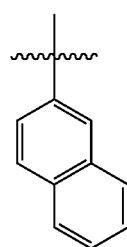
13-12   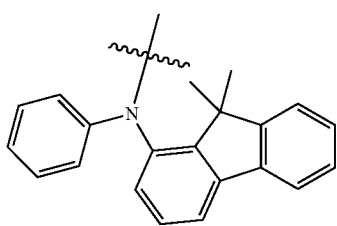 [SMILES: *N(c1ccccc1)c1cccc2c1C(C)(C)c1ccccc1-2]                          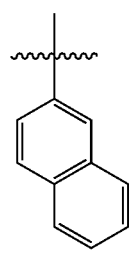
13-13   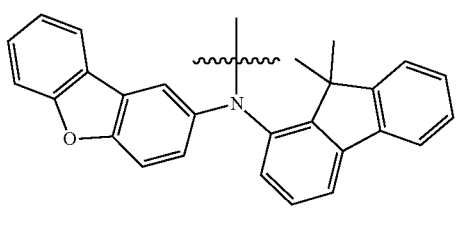 [SMILES: *N(c1ccc2oc3ccccc3c2c1)c1cccc2c1C(C)(C)c1ccccc1-2]                          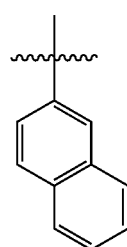
13-14   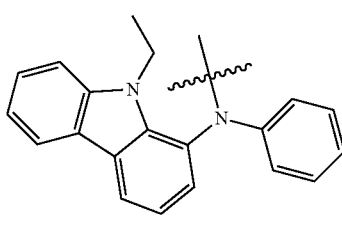                          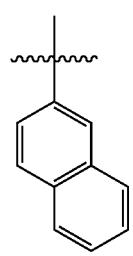
13-15   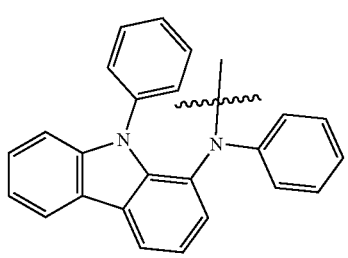 [SMILES: *N(c1ccccc1)c1cccc2c3ccccc3n(-c3ccccc3)c12]                          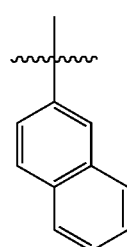
13-16   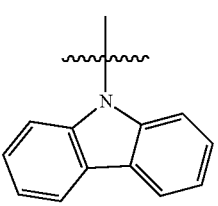 [SMILES: *n1c2ccccc2c2ccccc21]                         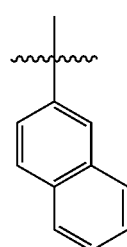

-continued
13-17 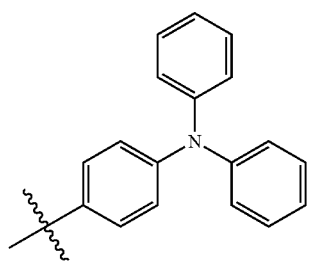 [SMILES: *c1ccc(N(c2ccccc2)c2ccccc2)cc1] 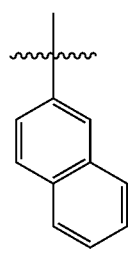
13-18 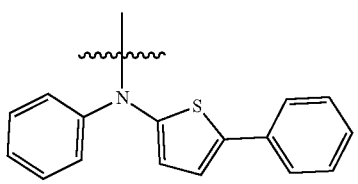 [SMILES: *N(c1ccccc1)c1ccc(-c2ccccc2)s1] 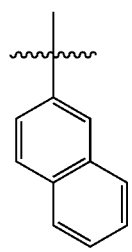
13-19 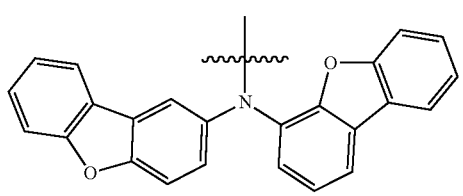 [SMILES: *N(c1ccc2oc3ccccc3c2c1)c1cccc2c1oc1ccccc12] 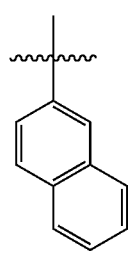 [SMILES: *c1ccc2ccccc2c1]
13-20 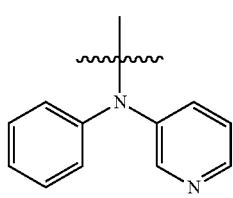 [SMILES: *N(c1ccccc1)c1cccnc1] 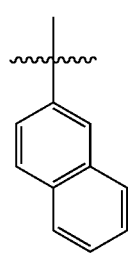
| Compound | X | X | R1 |
|---|---|---|---|
| 14-1 | O | S | 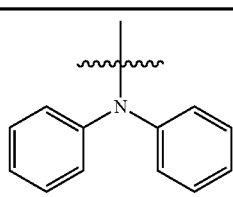 |
| 14-2 | O | N | 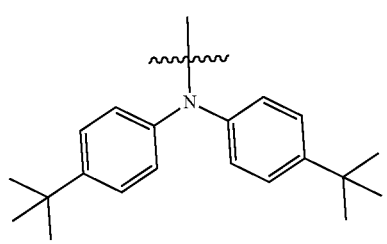 [SMILES: *N(c1ccc(C(C)(C)C)cc1)c1ccc(C(C)(C)C)cc1] |

| | | | |
|---|---|---|---|
| 14-3 | O | 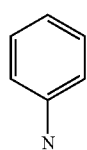 | 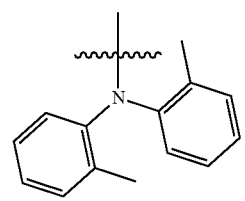 [SMILES: *N(c1ccccc1C)c1ccccc1C] |
| 14-4 | O |  | 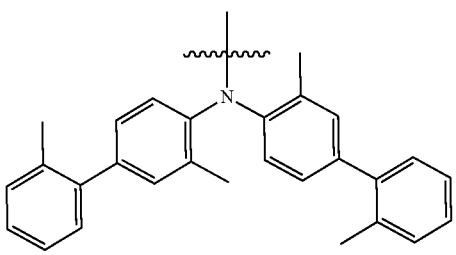 [SMILES: *N(c1ccc(-c2ccccc2C)cc1C)c1ccc(-c2ccccc2C)cc1C] |
| 14-5 | O | 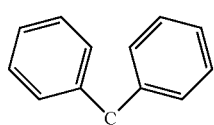 | 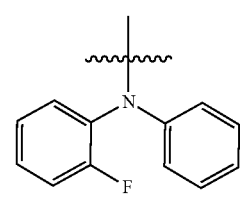 [SMILES: *N(c1ccccc1)c1ccccc1F] |
| 14-6 | S |  | 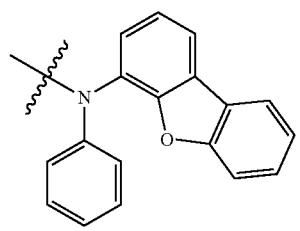 [SMILES: *N(c1ccccc1)c1cccc2c1oc1ccccc12] |
| 14-7 | S | 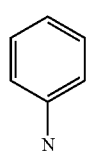 | 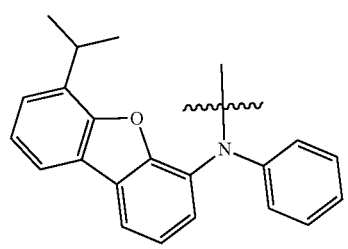 [SMILES: *N(c1ccccc1)c1cccc2c1oc1c(C(C)C)cccc12] |
| 14-8 | S |  | 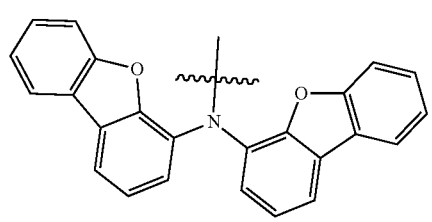 [SMILES: *N(c1cccc2c1oc1ccccc12)c1cccc2c1oc1ccccc12] |
| 14-9 | S | 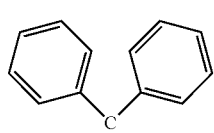 | 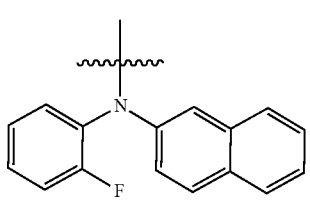 [SMILES: *N(c1ccc2ccccc2c1)c1ccccc1F] |

| | | | |
|---|---|---|---|
| 14-10 | 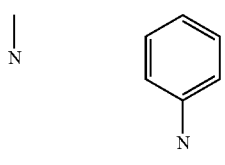 | 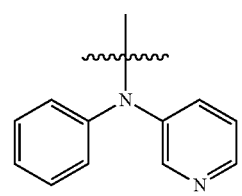 [SMILES: *N(c1ccccc1)c1cccnc1] | |
| 14-11 |  | 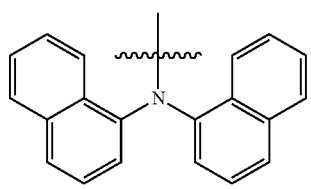 [SMILES: *N(c1cccc2ccccc12)c1cccc2ccccc12] | |
| 14-12 | 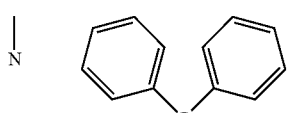 | 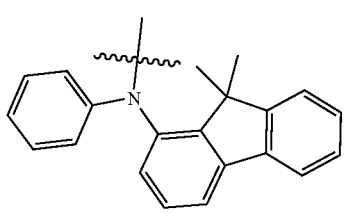 [SMILES: *N(c1ccccc1)c1cccc2c1C(C)(C)c1ccccc1-2] | |
| 14-13 | 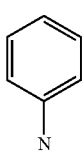 | 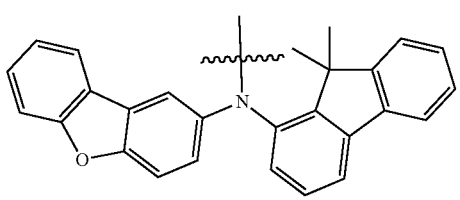 [SMILES: *N(c1ccc2oc3ccccc3c2c1)c1cccc2c1C(C)(C)c1ccccc1-2] | |
| 14-14 | 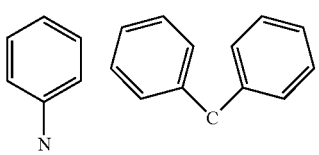 | 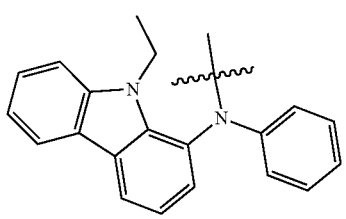 [SMILES: *N(c1ccccc1)c1cccc2c3ccccc3n(CC)c12] | |
| 14-15 | 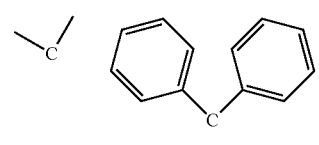 | 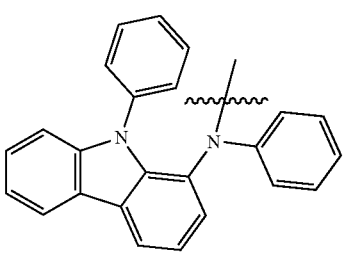 [SMILES: *N(c1ccccc1)c1cccc2c3ccccc3n(-c3ccccc3)c12] | |
| 14-16 | O  | S  | 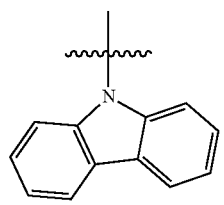 [SMILES: *n1c2ccccc2c2ccccc21] |

US 11,489,122 B1
361                                                                  362
-continued
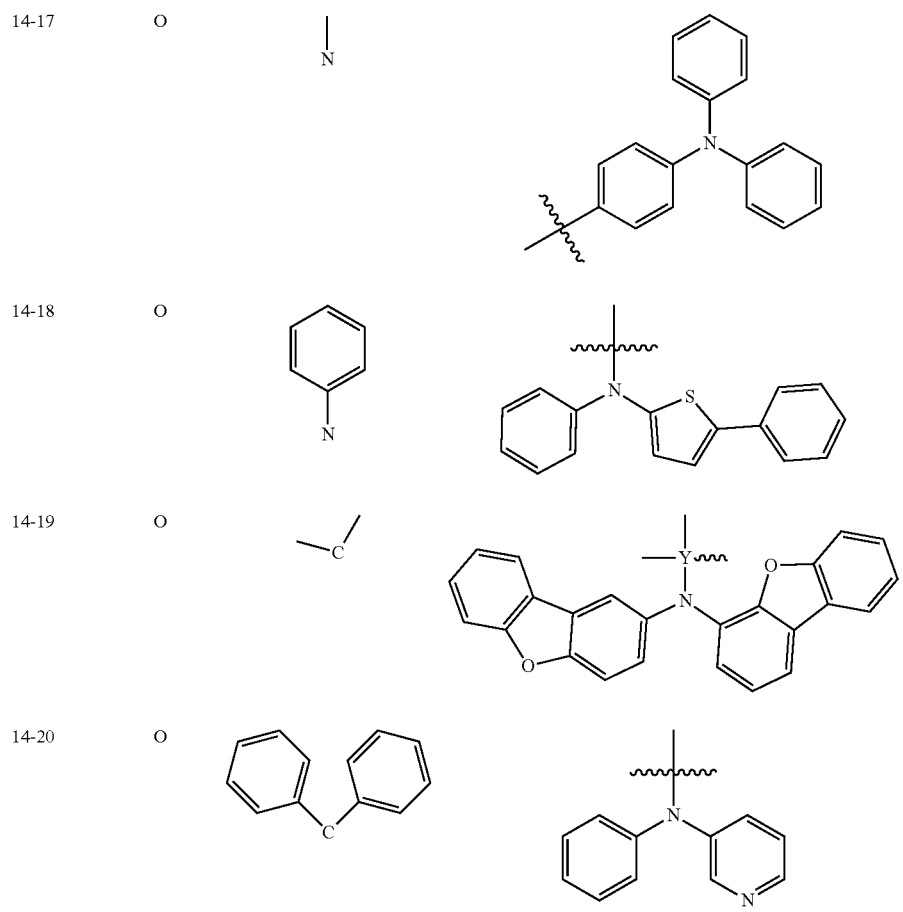
| Compound | R2 | R3 to R6 |
|---|---|---|
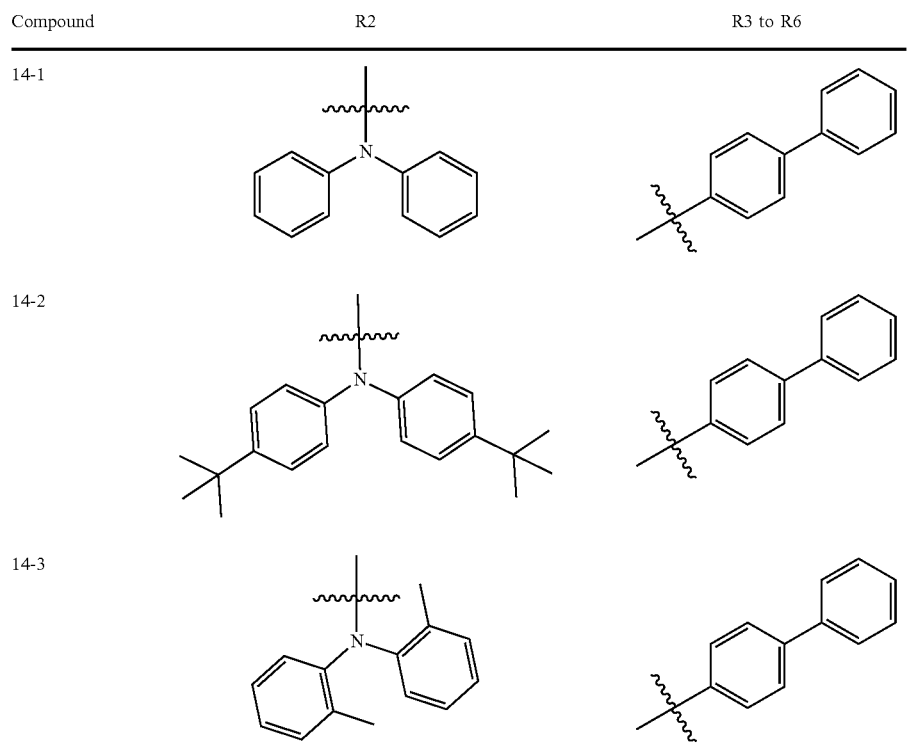

| | | |
|---|---|---|
| 14-4 | 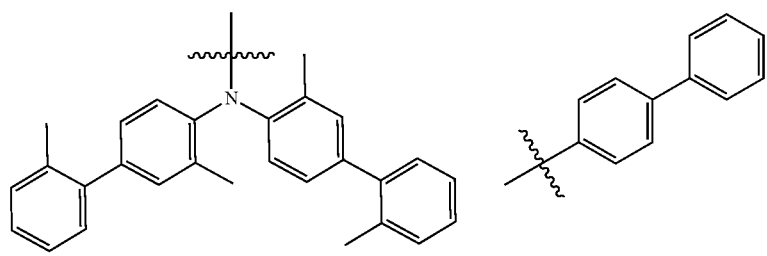 | |
| 14-5 | 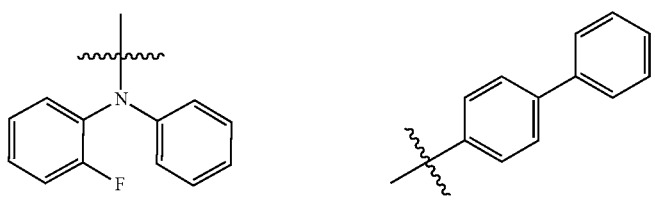 | |
| 14-6 | 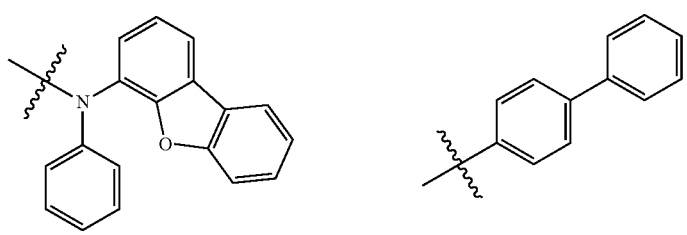 | |
| 14-7 | 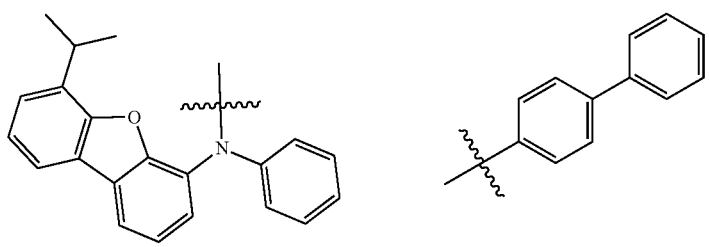 | |
| 14-8 | 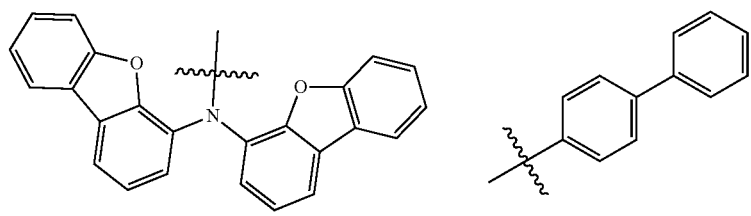 | |
| 14-9 | 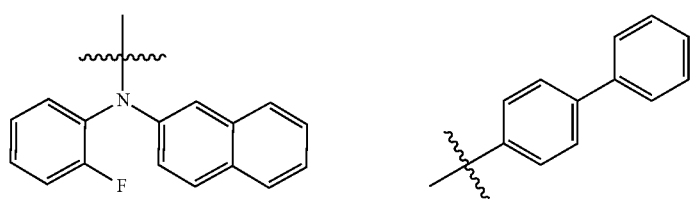 | |
| 14-10 | 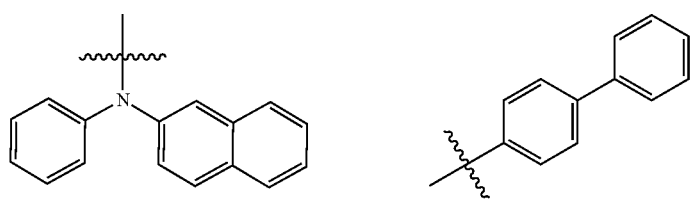 | |

-continued
14-11 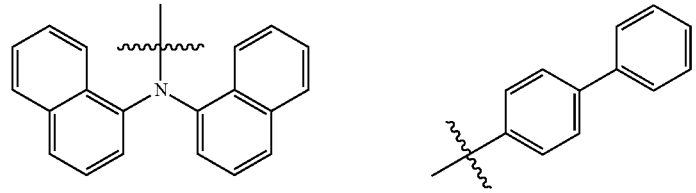 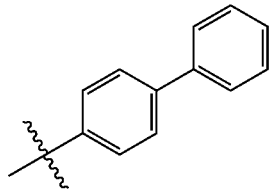 [SMILES: *c1ccc(-c2ccccc2)cc1]
14-12 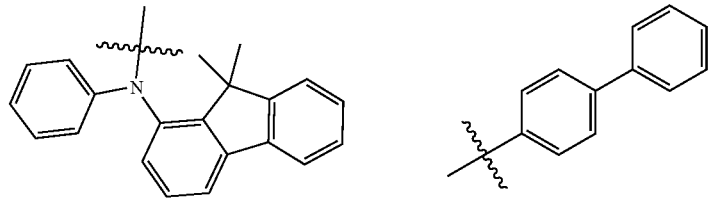 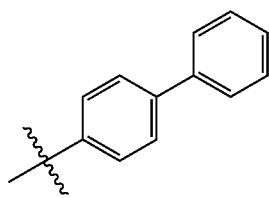 [SMILES: *c1ccc(-c2ccccc2)cc1]
14-13 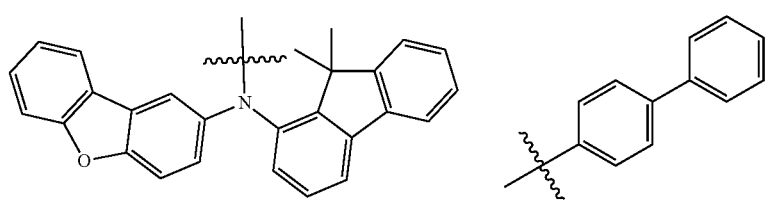 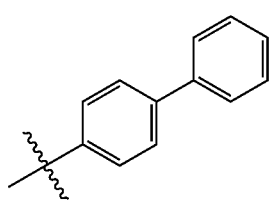 [SMILES: *c1ccc(-c2ccccc2)cc1]
14-14 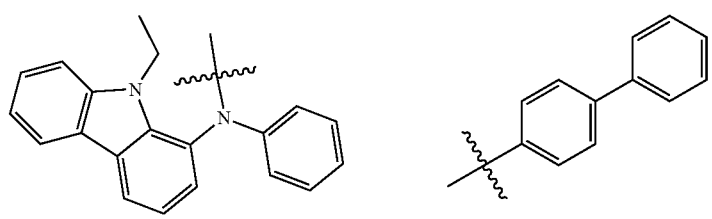 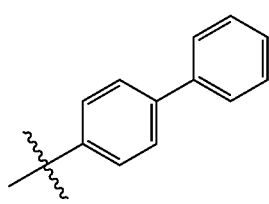 [SMILES: *c1ccc(-c2ccccc2)cc1]
14-15 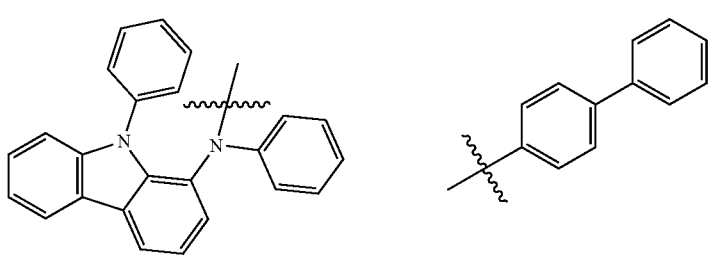 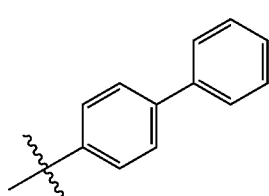
14-16 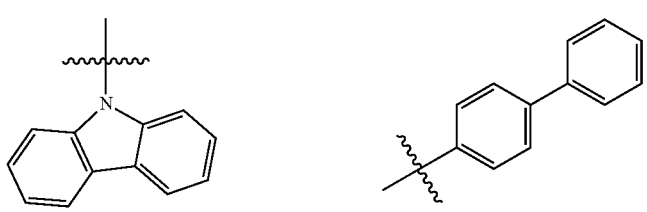 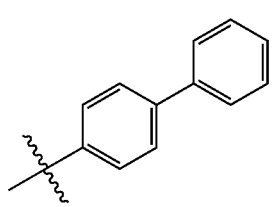 [SMILES: *c1ccc(-c2ccccc2)cc1]
14-17 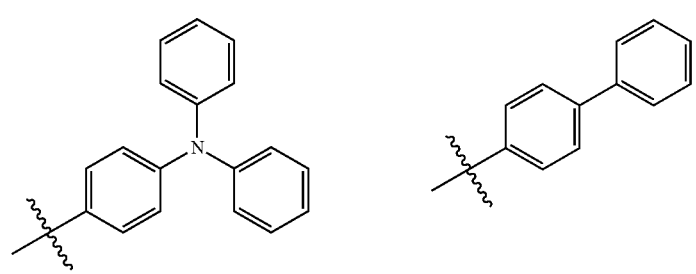 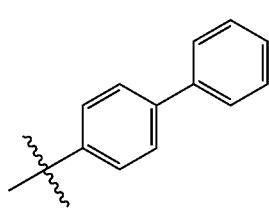 [SMILES: *c1ccc(-c2ccccc2)cc1]

-continued 14-18

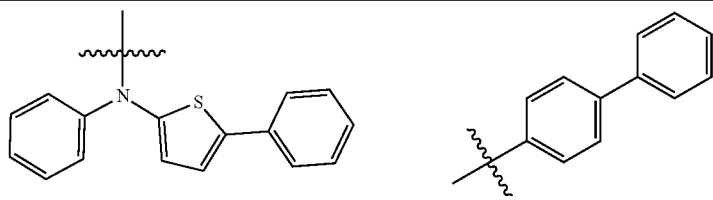

14-19

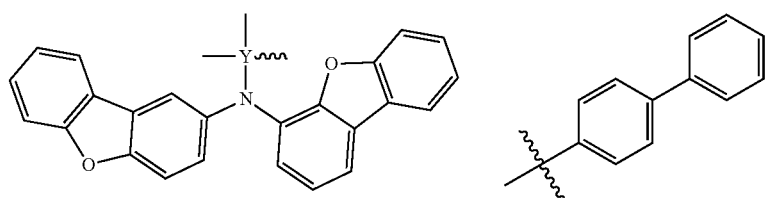

14-20

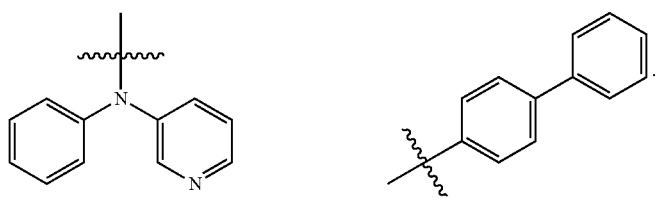

8. An organic light emitting device comprising:
a first electrode;
a second electrode provided to face the first electrode; and
an organic material layer having one or more layers provided between the first electrode and the second electrode,
wherein one or more layers of the organic material layer comprise the compound of claim 1.

9. The organic light emitting device of claim 8, wherein the organic material layer comprises a light emitting layer, and the light emitting layer comprises the compound.

10. The organic light emitting device of claim 8, wherein the organic material layer comprises a hole injection layer or a hole transport layer, and the hole injection layer or the hole transport layer comprises the compound.

11. The organic light emitting device of claim 8, wherein the organic material layer comprises an electron injection layer, an electron transport layer, or a layer which injects and transports electrons simultaneously, and the electron injection layer, the electron transport layer, or the layer which injects and transports electrons simultaneously comprises the compound.

12. The organic light emitting device of claim 8, wherein the organic material layer comprises an electron blocking layer or a hole blocking layer, and the electron blocking layer or the hole blocking layer comprises the compound.

13. The organic light emitting device of claim 8, wherein the organic material layer comprises a light emitting layer, and the light emitting layer comprises a compound of Formula 1A:

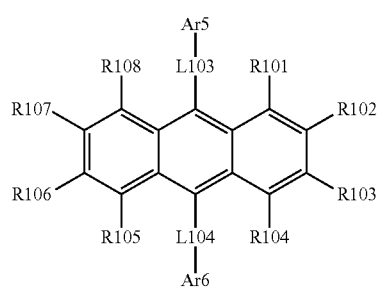

[Formula 1A]

wherein in Formula 1A:
L103 and L104 are the same as or different from each other, and are each independently a direct bond, a substituted or unsubstituted arylene group, or a substituted or unsubstituted heteroarylene group;
Ar5 and Ar6 are the same as or different from each other, and are each independently a substituted or unsubstituted aryl group or a substituted or unsubstituted heteroaryl group; and
R101 to R108 are the same as or different from each other, and are each independently hydrogen, deuterium, a halogen group, a nitrile group, a nitro group, a substituted or unsubstituted alkyl group, a substituted or unsubstituted cycloalkyl group, a substituted or unsubstituted silyl group, a substituted or unsubstituted phosphine oxide group, a substituted or unsubstituted aryl group, or a substituted or unsubstituted heteroaryl group.

14. The organic light emitting device of claim 13, wherein L103 and L104 are the same as or different from each other, and are each independently selected from the substituents in the following Table 1, and Ar5 and Ar6 are the same as or different from each other, and are each independently selected from the substituents in the following Table 2:
TABLE 1
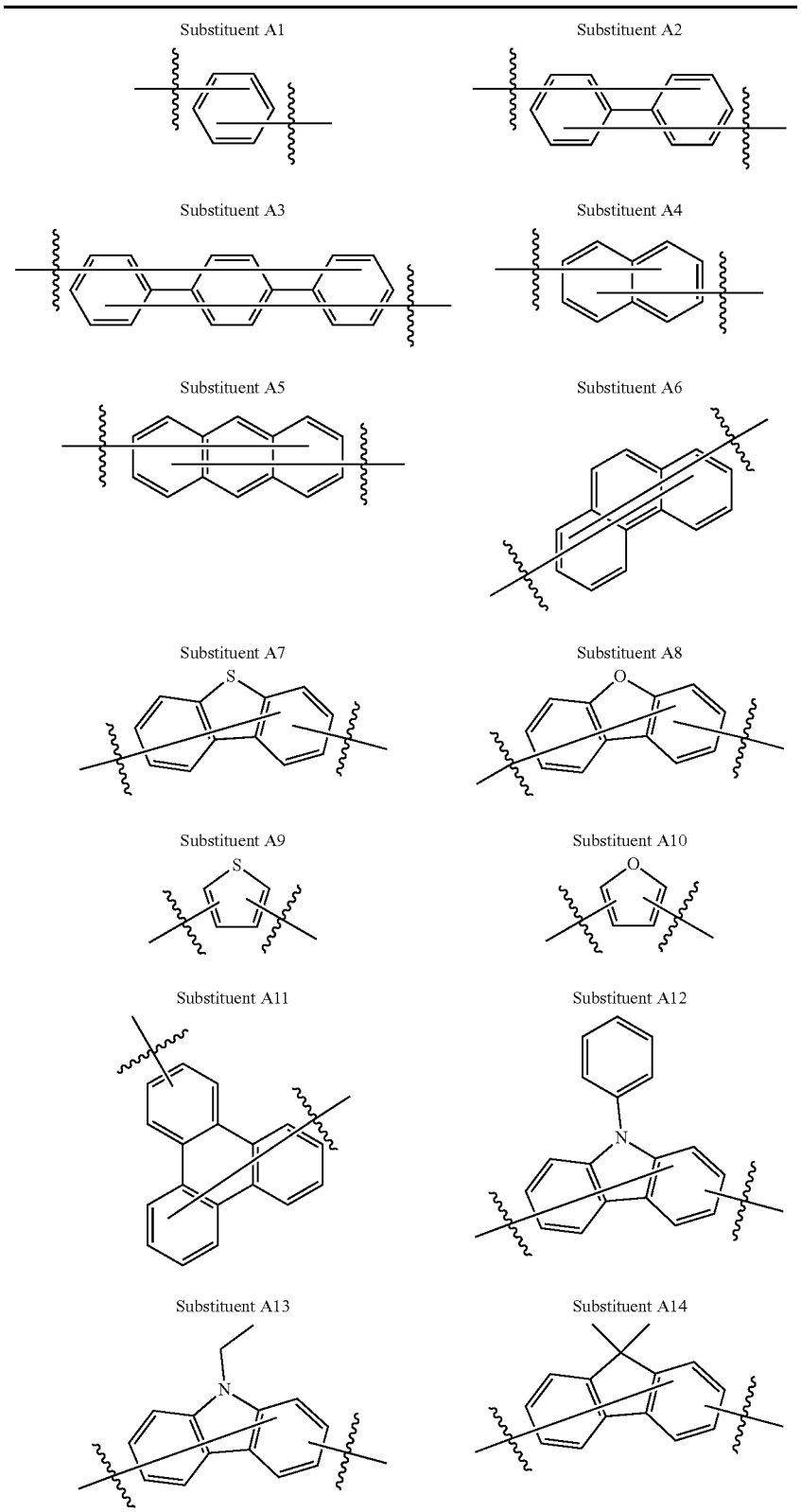

TABLE 1-continued
Substituent A15
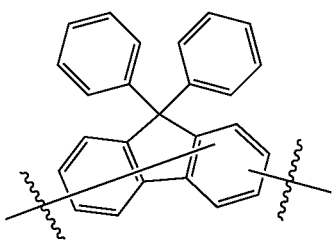
TABLE 2
| Substituent B1 | Substituent B2 |
|---|---|
| 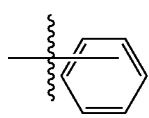 | 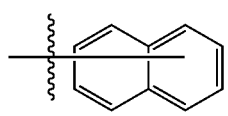 |
| Substituent B3 | Substituent B4 |
| 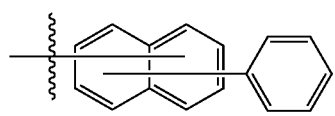 | 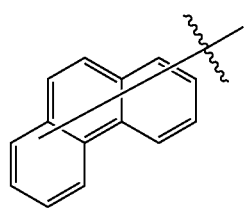 |
| Substituent B5 | Substituent B6 |
| 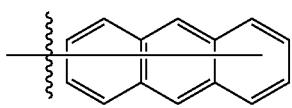 | 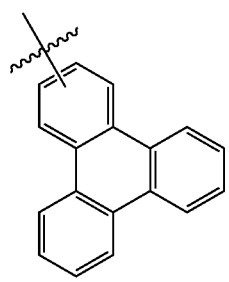 |
| Substituent B7 | Substituent B8 |
| 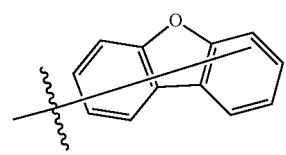 | 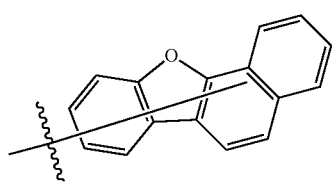 |
| Substituent B9 | Substituent B10 |
| 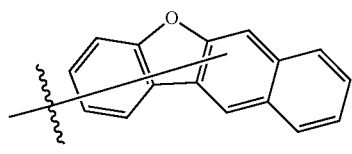 | 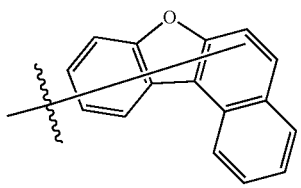 |

TABLE 2-continued
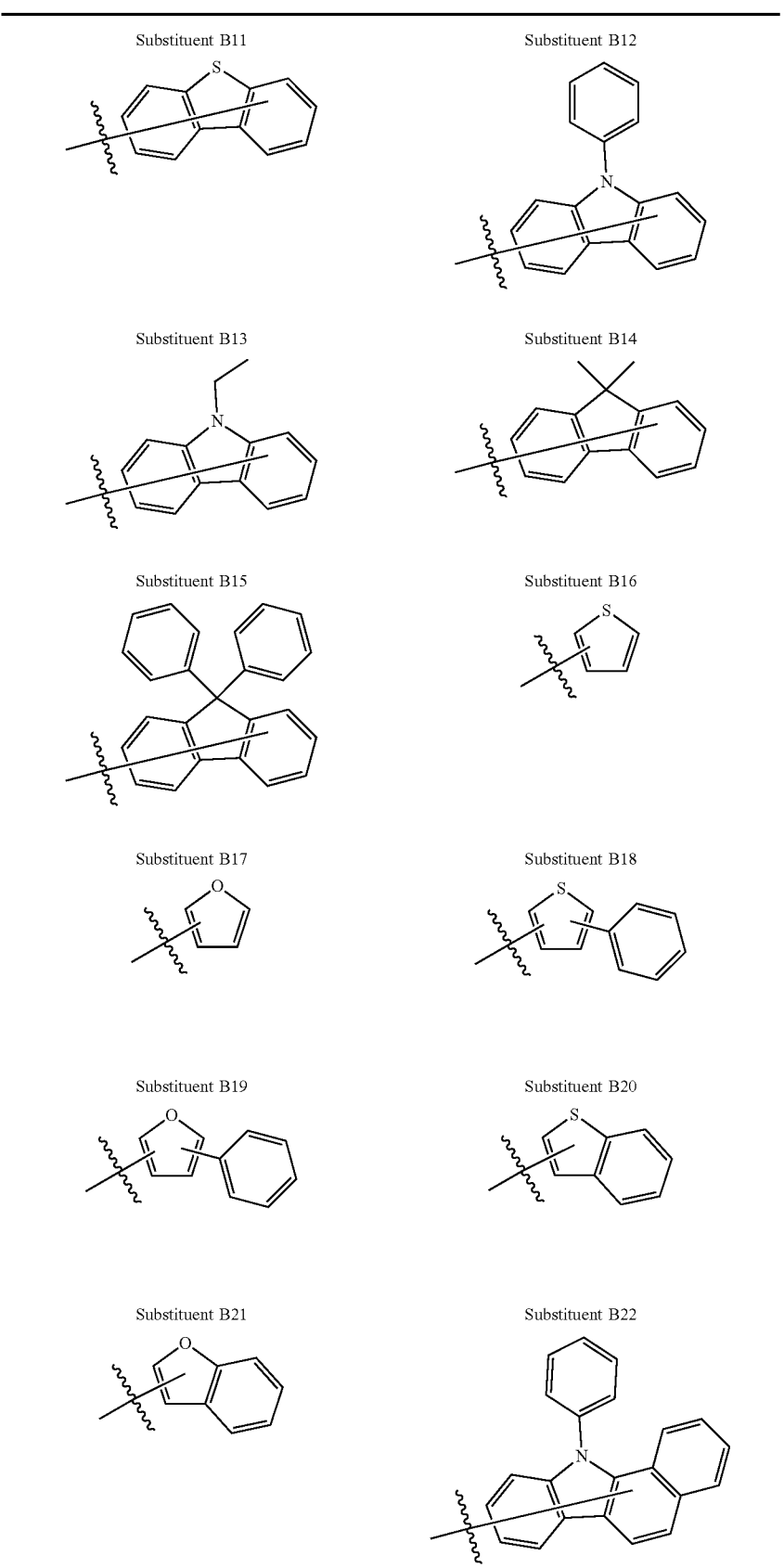

TABLE 2-continued
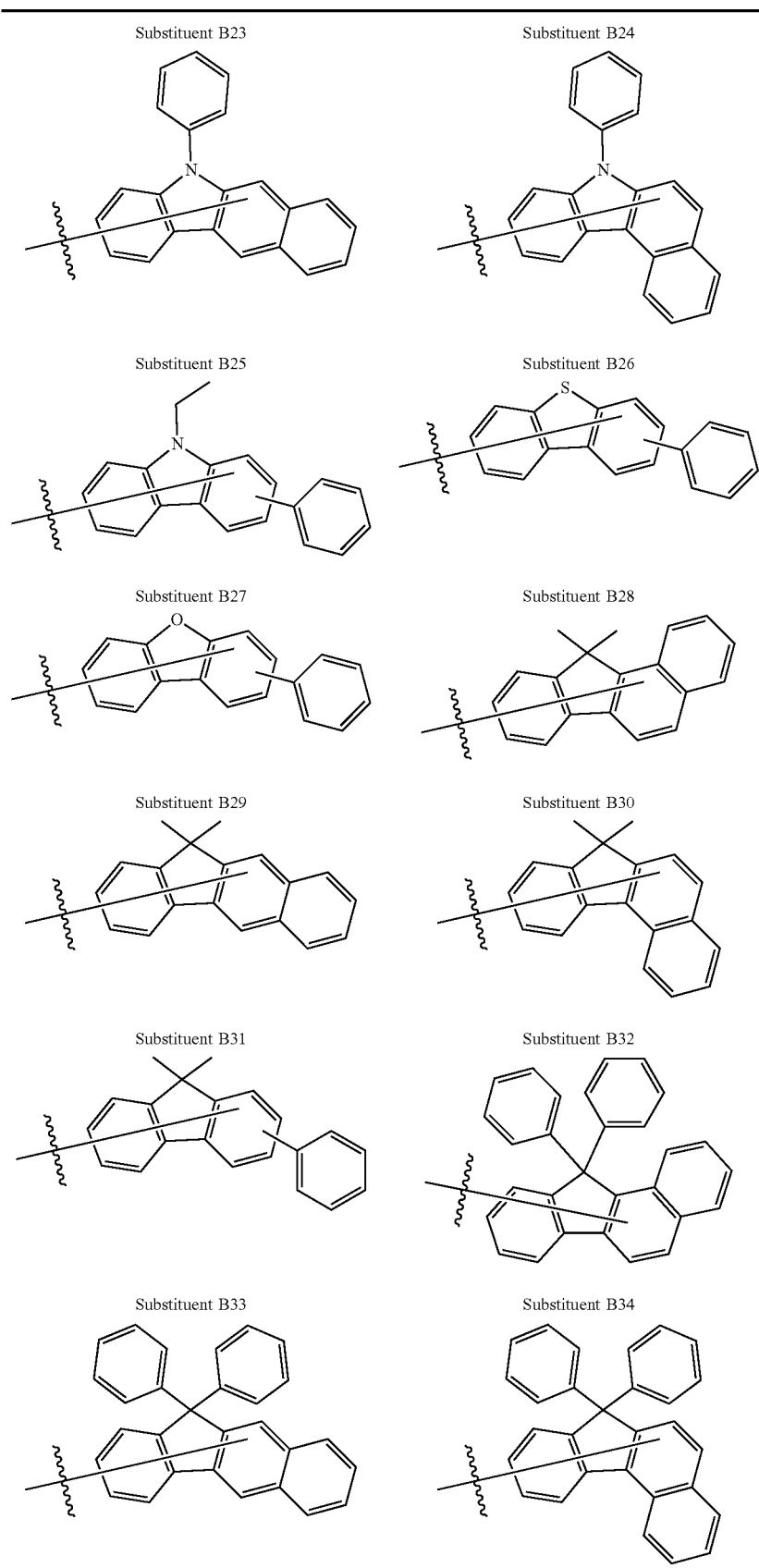

TABLE 2-continued
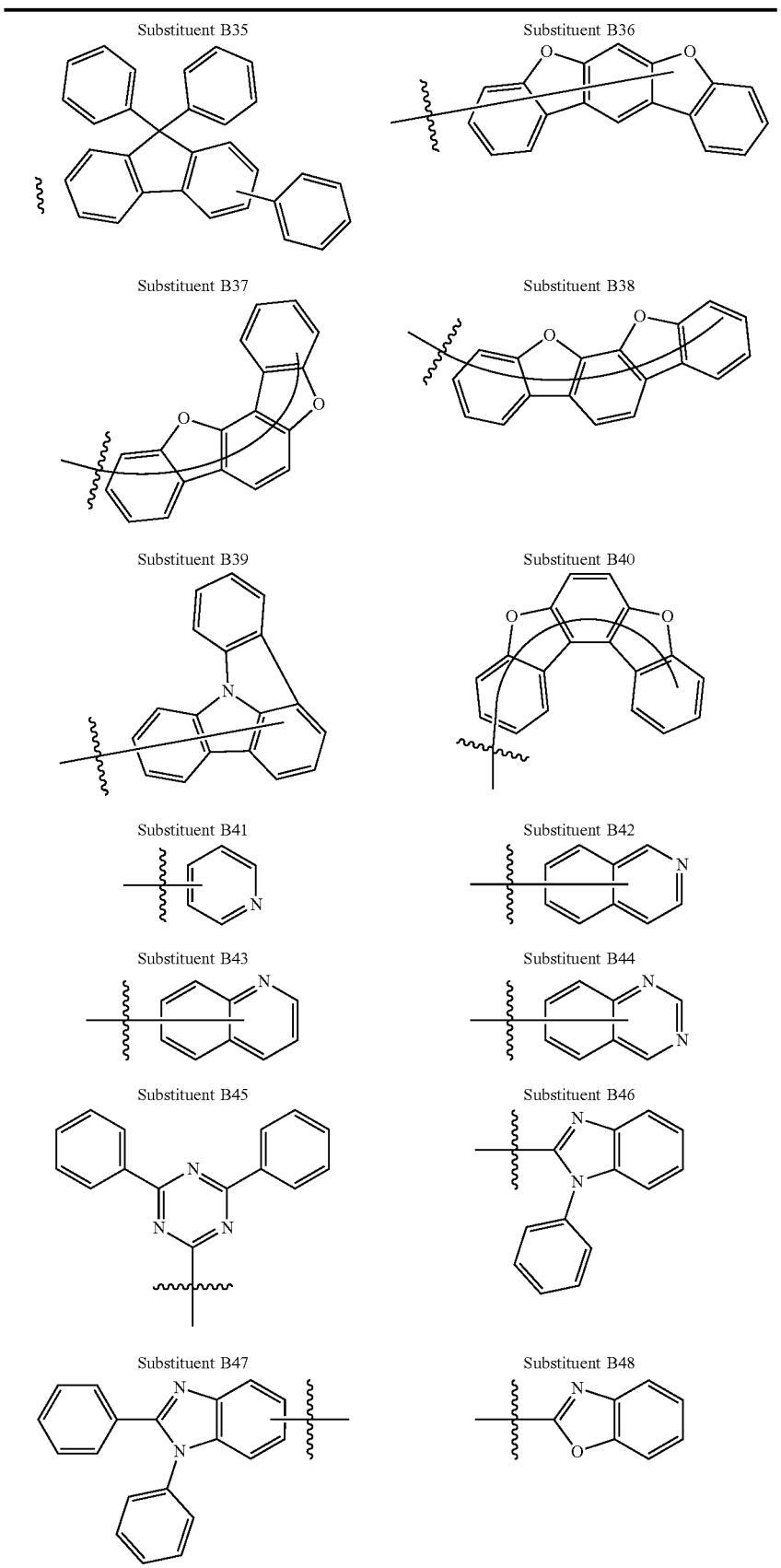

TABLE 2-continued

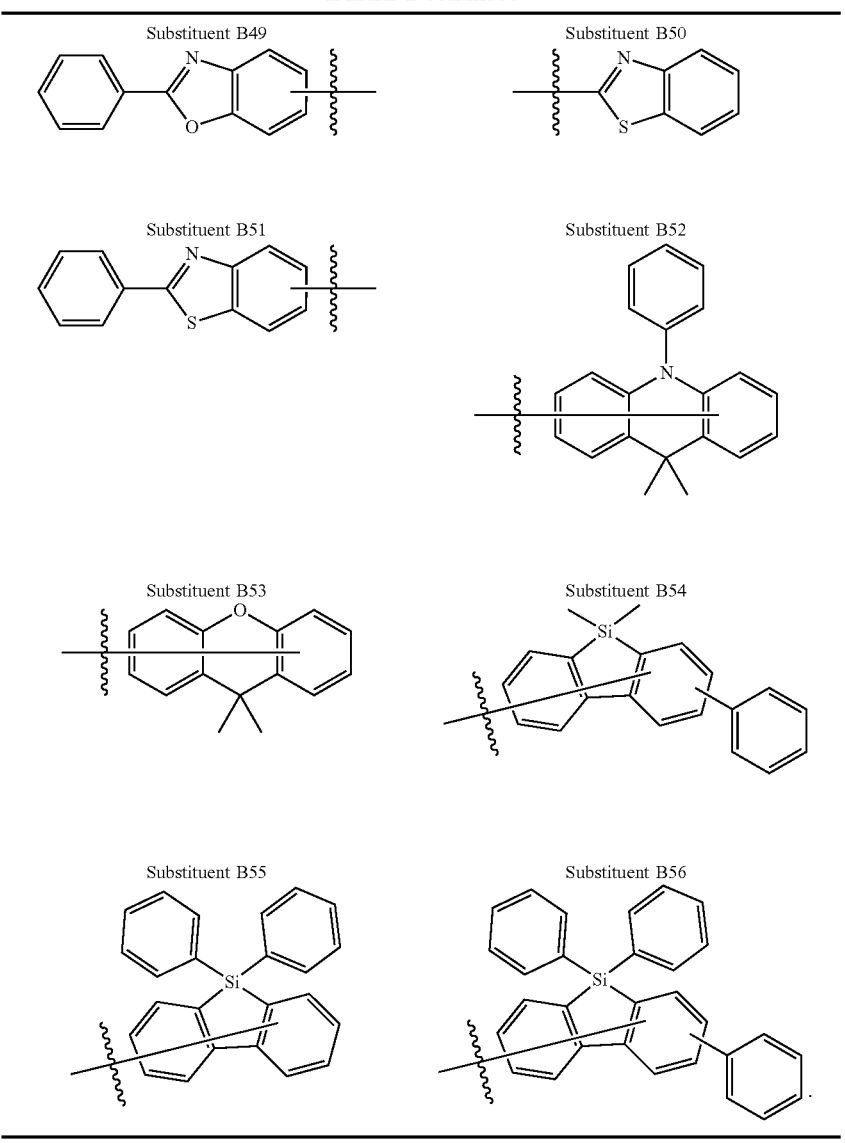

15. The organic light emitting device of claim 8, wherein the organic material layer comprises a light emitting layer, and the light emitting layer comprises a compound of Formula 1B:

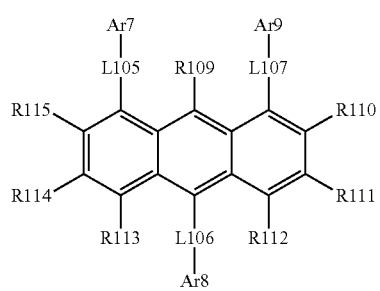

[Formula 1B]

wherein in Formula 1B:

L105 to L107 are the same as or different from each other, and are each independently a direct bond, a substituted or unsubstituted arylene group, or a substituted or unsubstituted heteroarylene group;

Ar7 to Ar9 are the same as or different from each other, and are each independently a substituted or unsubstituted aryl group or a substituted or unsubstituted heteroaryl group; and R109 to R115 are the same as or different from each other, and are each independently hydrogen, deuterium, a halogen group, a nitrile group, a nitro group, a substituted or unsubstituted alkyl group, a substituted or unsubstituted cycloalkyl group, a substituted or unsubstituted silyl group, a substituted or unsubstituted phosphine oxide group, a substituted or unsubstituted aryl group, or a substituted or unsubstituted heteroaryl group.

16. The organic light emitting device of claim 15, wherein L105 to L107 are the same as or different from each other, and are each independently selected from the substituents in the following Table 3, and Ar7 to Ar9 are the same as or different from each other, and are each independently selected from the substituents in the following Table 4:

TABLE 3
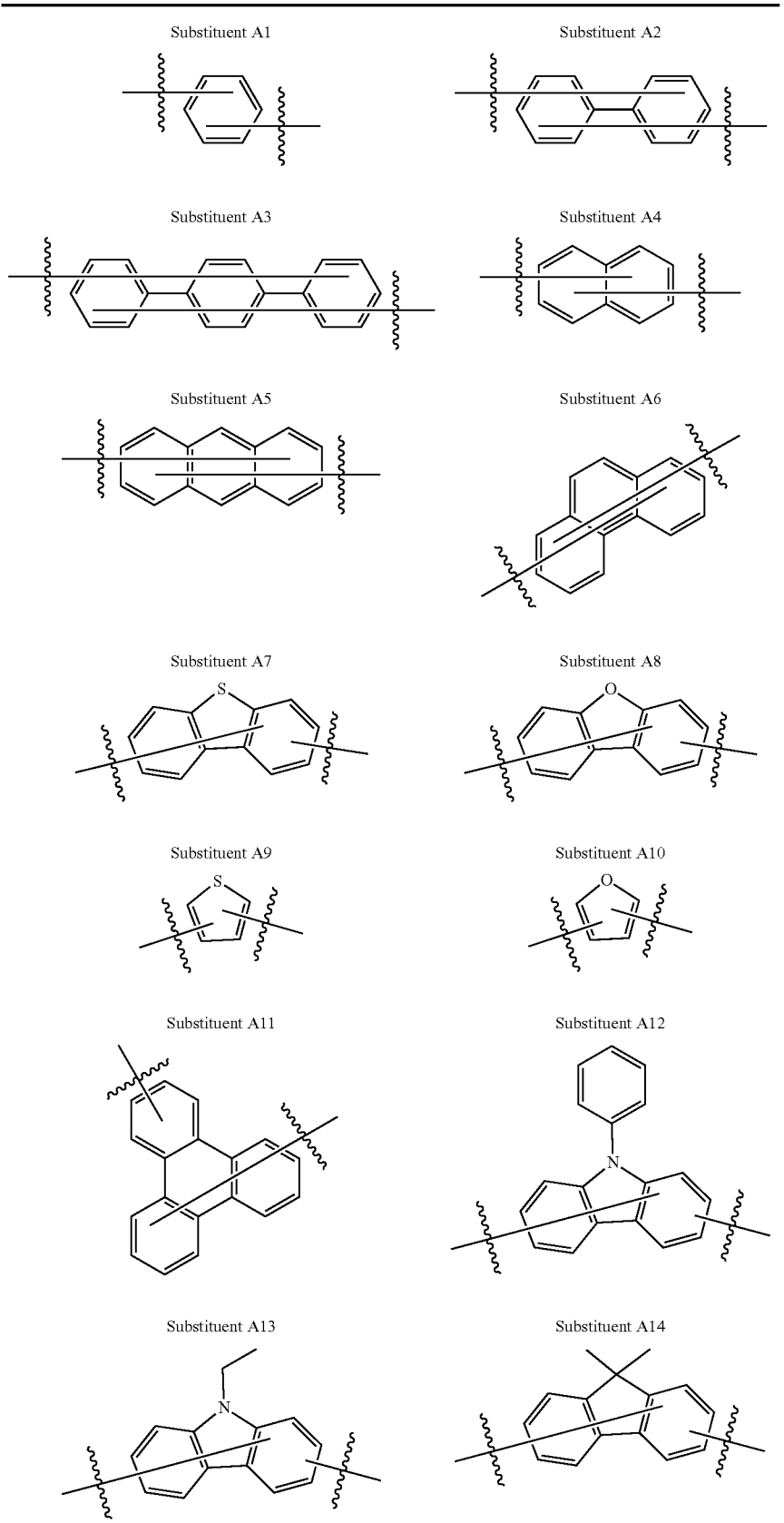

TABLE 3-continued
Substituent A15
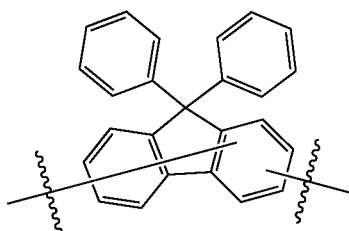
TABLE 4
| Substituent B1 | Substituent B2 |
|---|---|
| 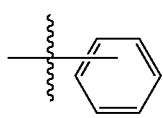 | 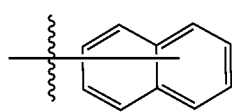 |
| Substituent B3 | Substituent B4 |
| 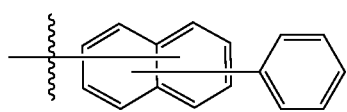 | 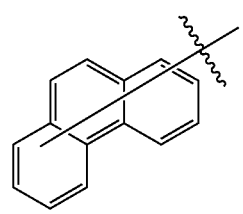 |
| Substituent B5 | Substituent B6 |
| 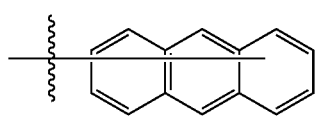 | 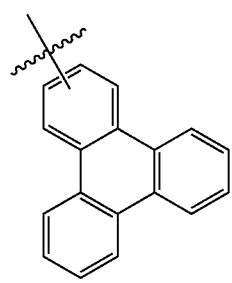 |
| Substituent B7 | Substituent B8 |
| 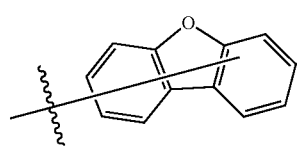 | 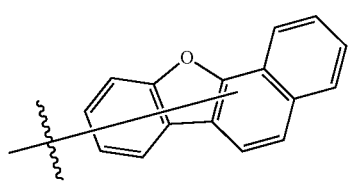 |
| Substituent B9 | Substituent B10 |
| 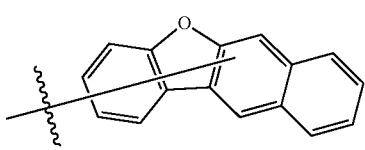 | 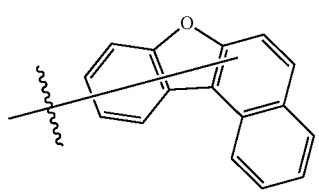 |

TABLE 4-continued
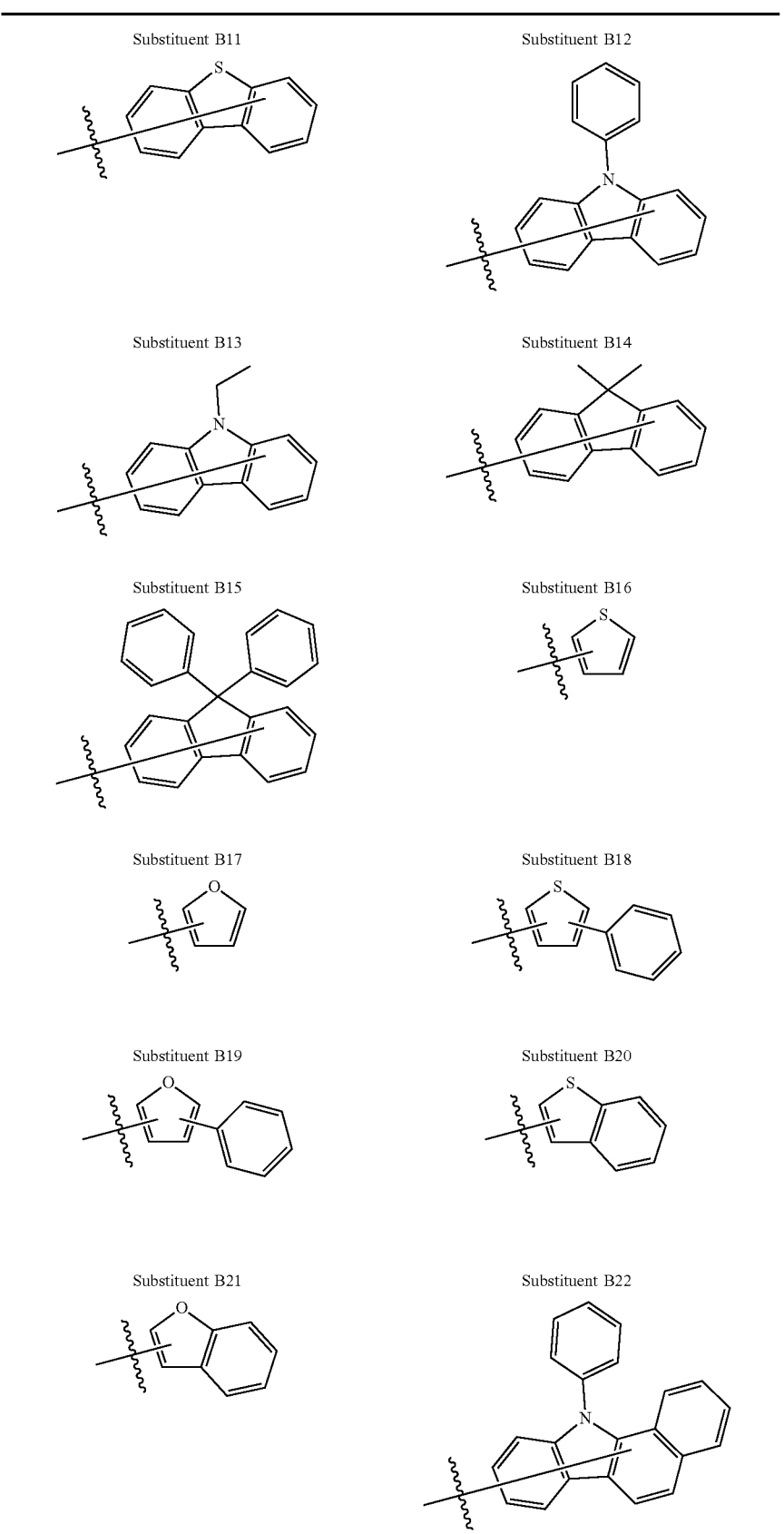

TABLE 4-continued
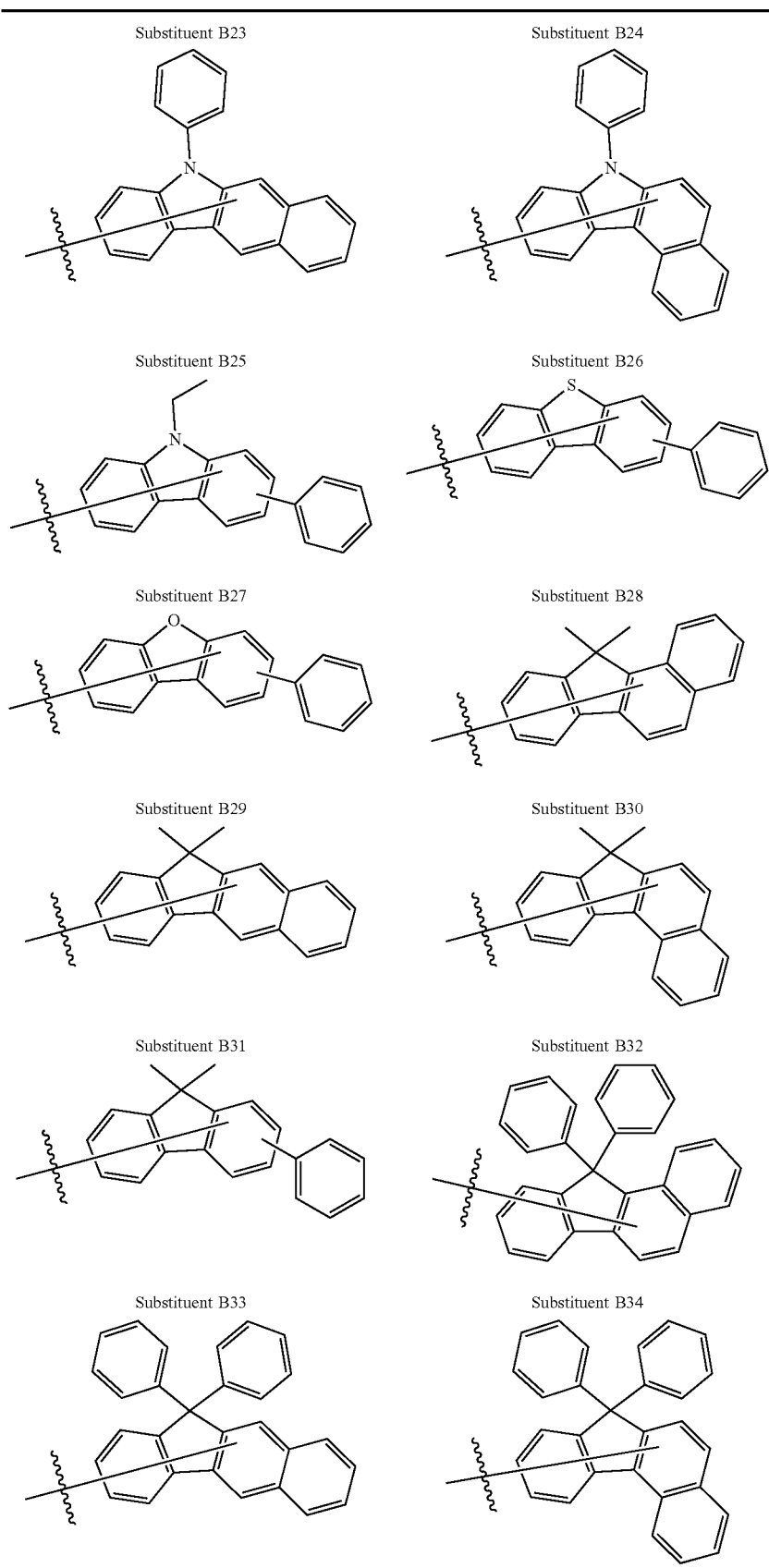

TABLE 4-continued
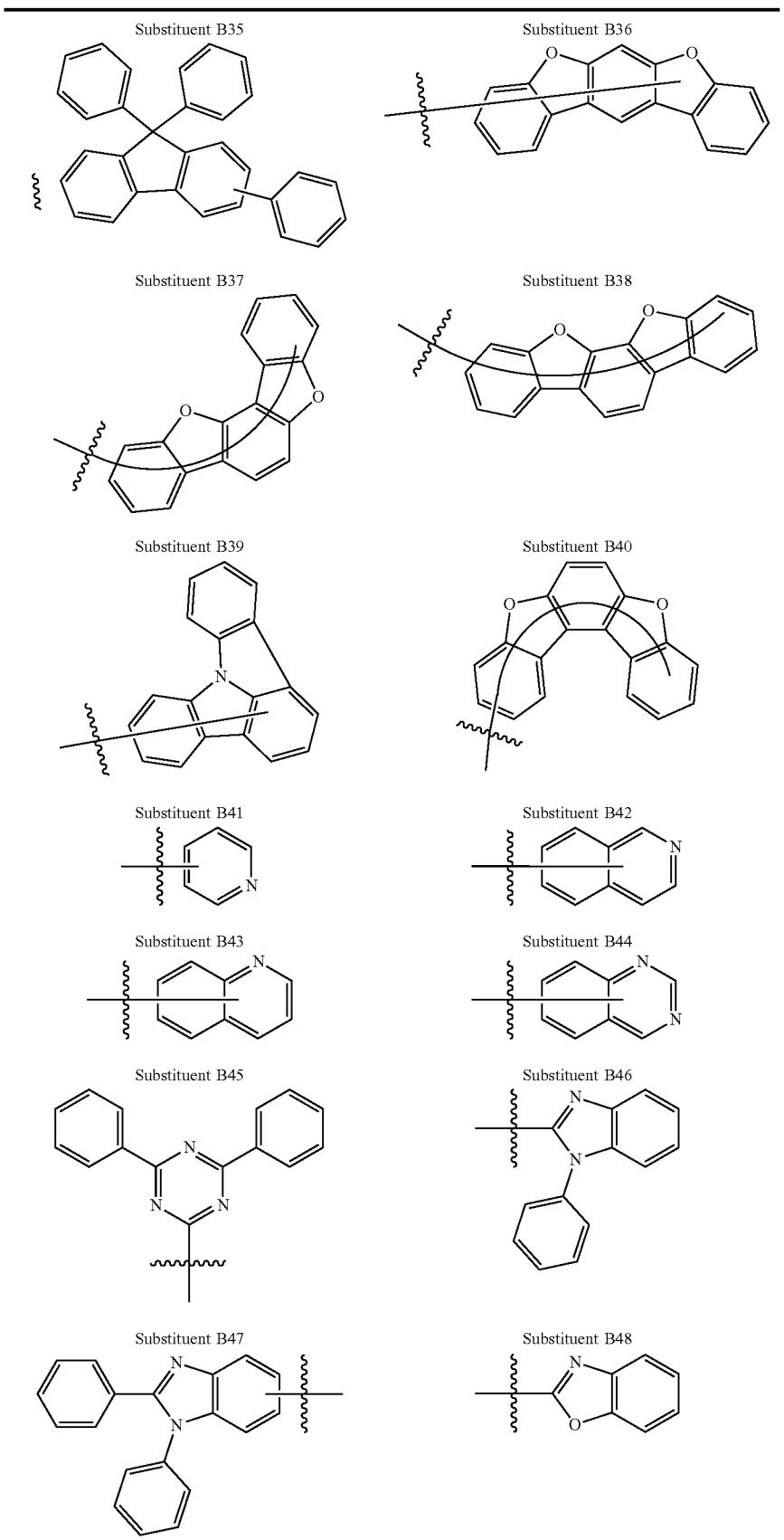

TABLE 4-continued
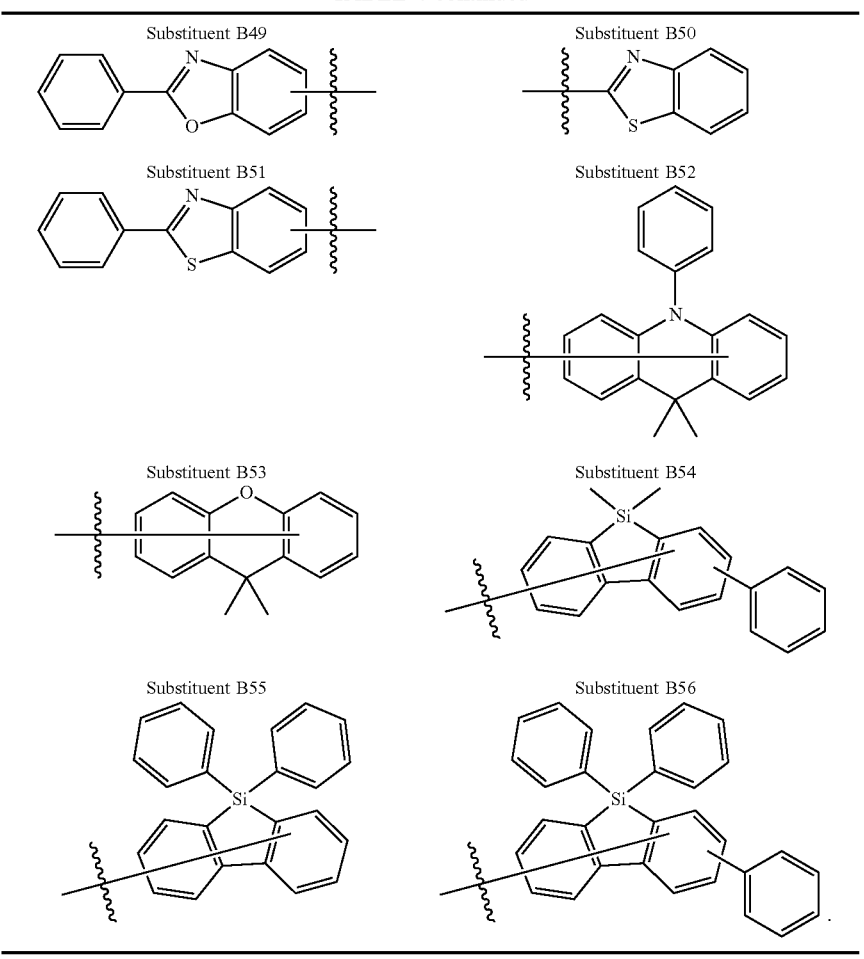
17. The organic light emitting device of claim 8, wherein the organic light emitting device further comprises one or more layers selected from the group consisting of a light emitting layer, a hole injection layer, a hole transport layer, an electron injection layer, an electron transport layer, an electron blocking layer, and a hole blocking layer.
* * * * *

UNITED STATES PATENT AND TRADEMARK OFFICE
CERTIFICATE OF CORRECTION

PATENT NO.         : 11,489,122 B1                                         Page 1 of 2
APPLICATION NO.    : 16/630331
DATED              : November 1, 2022
INVENTOR(S)        : Woochul Lee et al.

It is certified that error appears in the above-identified patent and that said Letters Patent is hereby corrected as shown below:

In the Specification

At Column 12, Lines 43-53, please replace Chemical Formula 1-7 with the following Chemical Formula 1-7:

Chemical Formula 1-7

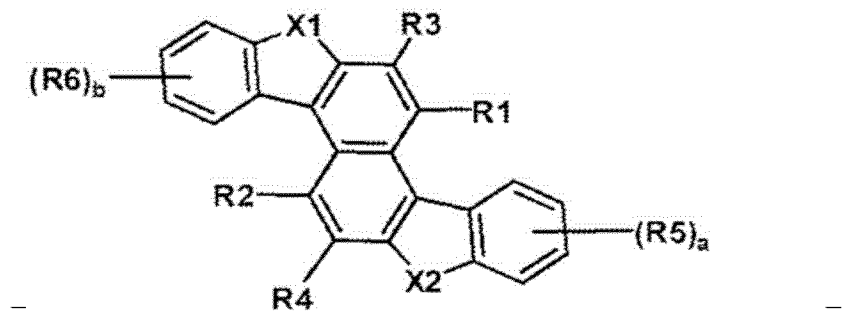

In the Claims

In Claim 3, at Column 223, at Lines 40-50, please replace Chemical Formula 1-7 with the following Chemical Formula 1-7:

Chemical Formula 1-7

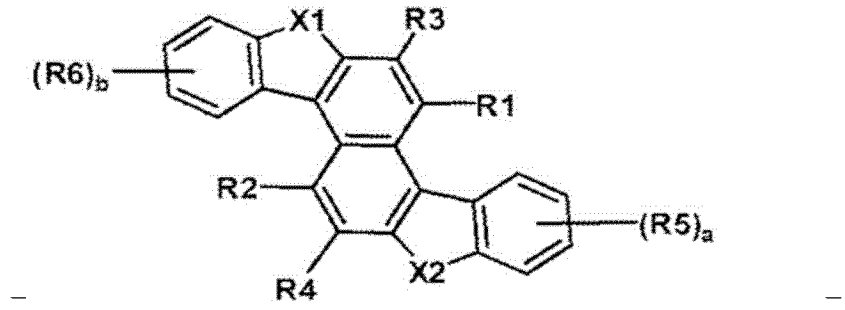

Signed and Sealed this
Tenth Day of January, 2023

Katherine Kelly Vidal
*Director of the United States Patent and Trademark Office*

CERTIFICATE OF CORRECTION (continued)
U.S. Pat. No. 11,489,122 B1

In Claim 4, at Column 224, Lines 52-53, please replace:
"the definitions of X1, X2, R5, R6, a, and b are the same as those defined in Formula"

With:
— the definitions of X1, X2, R5, R6, a, and b are the same as those defined in Formula 1; —

In Claim 7, at Column 362, for Chemical Compound 14-19, please replace R1 with:

14-19  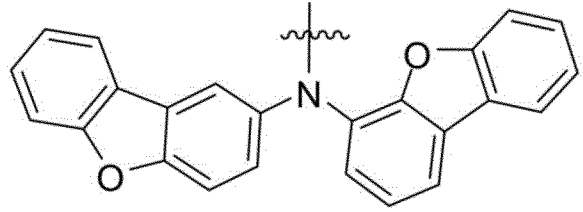

In Claim 7, at Column 368, for Chemical Compound 14-19, please replace R2 with: